US011986165B1

(12) United States Patent
Linard et al.

(10) Patent No.: US 11,986,165 B1
(45) Date of Patent: May 21, 2024

(54) CO-MANIPULATION SURGICAL SYSTEM FOR USE WITH SURGICAL INSTRUMENTS FOR PERFORMING LAPAROSCOPIC SURGERY WHILE ESTIMATING HOLD FORCE

(71) Applicant: Moon Surgical SAS, Paris (FR)

(72) Inventors: Nicolas Linard, Montrouge (FR); Ehsan Basafa, Redwood City, CA (US); David Paul Noonan, San Francisco, CA (US)

(73) Assignee: Moon Surgical SAS, Paris (FR)

( * ) Notice: Subject to any disclaimer, the term of this patent is extended or adjusted under 35 U.S.C. 154(b) by 0 days.

(21) Appl. No.: 18/535,991

(22) Filed: Dec. 11, 2023

Related U.S. Application Data

(63) Continuation-in-part of application No. 18/331,073, filed on Jun. 7, 2023, now Pat. No. 11,839,442.
(Continued)

(30) Foreign Application Priority Data

Jan. 9, 2023 (EP) .................... 23305026

(51) Int. Cl.
*A61B 1/313* (2006.01)
*A61B 1/00* (2006.01)
(52) U.S. Cl.
CPC ........ *A61B 1/3132* (2013.01); *A61B 1/00039* (2013.01); *A61B 1/00149* (2013.01); *A61B 1/0016* (2013.01)
(58) Field of Classification Search
CPC .............. A61B 1/3132; A61B 1/00039; A61B 1/00149; A61B 1/0016
(Continued)

(56) References Cited

U.S. PATENT DOCUMENTS 1,058,297 A 4/1913 Grant et al.
5,836,869 A 11/1998 Kudo et al.
(Continued)

FOREIGN PATENT DOCUMENTS

CN 111618857 A 9/2020
EP 2298218 A2 3/2011
(Continued)

OTHER PUBLICATIONS

Andronic Devices 510(k):ENDEX Endoscopic Positioning System, K936308 (Mar. 31, 1994).
(Continued)

*Primary Examiner* — Aaron F Roane
(74) *Attorney, Agent, or Firm* — Eversheds Sutherland (US) LLP; Christopher C. Bolten; Albert K. Heng

(57) ABSTRACT

Co-manipulation robotic systems are described herein that may be used for assisting with laparoscopic surgical procedures. The co-manipulation robotic systems allow a surgeon to use commercially-available surgical tools while providing benefits associated with surgical robotics. Advantageously, the surgical tools may be seamlessly coupled to the robot arms using a disposable coupler while the reusable portions of the robot arm remain in a sterile drape. Further, the co-manipulation robotic system may operate in multiple modes to enhance usability and safety, while allowing the surgeon to position the instrument directly with the instrument handle and further maintain the desired position of the instrument using the robot arm.

22 Claims, 82 Drawing Sheets

Related U.S. Application Data

(60) Provisional application No. 63/495,527, filed on Apr. 11, 2023, provisional application No. 63/479,142, filed on Jan. 9, 2023.

(58) Field of Classification Search
USPC .......................................................... 600/118
See application file for complete search history.

(56) References Cited

U.S. PATENT DOCUMENTS

| | | |
|---|---|---|
| 5,887,121 A | 3/1999 | Funda et al. |
| 6,246,200 B1 | 6/2001 | Blumenkranz et al. |
| 6,346,072 B1 | 2/2002 | Cooper |
| 6,491,701 B2 | 12/2002 | Tierney et al. |
| 6,496,756 B1 | 12/2002 | Nishizawa et al. |
| 6,522,906 B1 | 2/2003 | Salisbury, Jr. et al. |
| 6,714,841 B1 | 3/2004 | Wright et al. |
| 6,786,896 B1 | 9/2004 | Madhani et al. |
| 6,800,056 B2 | 10/2004 | Tartaglia et al. |
| 6,850,794 B2 | 2/2005 | Shahidi |
| 6,913,613 B2 | 7/2005 | Schwarz et al. |
| 7,048,745 B2 | 5/2006 | Tierney et al. |
| 7,198,630 B2 | 4/2007 | Lipow |
| 7,524,320 B2 | 4/2009 | Tierney et al. |
| 7,741,802 B2 | 6/2010 | Prisco et al. |
| 7,747,311 B2 | 6/2010 | Quaid, III |
| 7,831,292 B2 | 11/2010 | Quaid et al. |
| 7,833,156 B2 | 11/2010 | Williams et al. |
| 7,907,166 B2 | 3/2011 | Lamprecht et al. |
| 7,996,110 B2 | 8/2011 | Lipow et al. |
| 8,004,229 B2 | 8/2011 | Nowlin et al. |
| 8,095,237 B2 | 1/2012 | Habibi et al. |
| 8,100,133 B2 | 1/2012 | Mintz et al. |
| 8,142,447 B2 | 3/2012 | Cooper et al. |
| 8,246,617 B2 | 8/2012 | Welt et al. |
| 8,273,076 B2 | 9/2012 | Devengenzo et al. |
| 8,287,522 B2 | 10/2012 | Moses et al. |
| 8,343,096 B2 | 1/2013 | Kirschenman et al. |
| 8,374,677 B2 | 2/2013 | Piferi et al. |
| 8,398,541 B2 | 3/2013 | DiMaio et al. |
| 8,449,552 B2 | 5/2013 | Sanders |
| 8,457,790 B2 | 6/2013 | Blondel et al. |
| 8,489,235 B2 | 7/2013 | Moll et al. |
| 8,498,744 B2 | 7/2013 | Odermatt et al. |
| 8,515,576 B2 | 8/2013 | Lipow et al. |
| 8,518,024 B2 | 8/2013 | Williams et al. |
| 8,600,134 B2 | 12/2013 | Vercauteren et al. |
| 8,608,773 B2 | 12/2013 | Tierney et al. |
| 8,649,905 B2 | 2/2014 | Ortmaier |
| 8,668,638 B2 | 3/2014 | Donhowe et al. |
| 8,746,533 B2 | 6/2014 | Whitman et al. |
| 8,749,190 B2 | 6/2014 | Nowlin et al. |
| 8,808,164 B2 | 8/2014 | Hoffman et al. |
| 8,827,135 B2 | 9/2014 | Amid et al. |
| 8,845,622 B2 | 9/2014 | Paik et al. |
| 8,870,049 B2 | 10/2014 | Amid et al. |
| 8,894,634 B2 | 11/2014 | Devengenzo et al. |
| 8,911,429 B2 | 12/2014 | Olds et al. |
| 8,919,348 B2 | 12/2014 | Williams et al. |
| 8,961,499 B2 | 2/2015 | Paik et al. |
| 8,969,777 B2 | 3/2015 | Savoire et al. |
| 8,972,057 B1 | 3/2015 | Freeman et al. |
| 8,992,542 B2 | 3/2015 | Hagag et al. |
| 8,996,173 B2 | 3/2015 | Itkowitz et al. |
| 9,039,608 B2 | 5/2015 | Donhowe et al. |
| 9,066,751 B2 | 6/2015 | Sasso |
| 9,095,681 B2 | 8/2015 | Wenderow et al. |
| 9,125,669 B2 | 9/2015 | Ranawat et al. |
| 9,265,587 B2 | 2/2016 | Vancamberg et al. |
| 9,266,239 B2 | 2/2016 | Miller |
| 9,283,048 B2 | 3/2016 | Kostrzewski et al. |
| 9,295,379 B2 | 3/2016 | Sholev |
| 9,333,040 B2 | 5/2016 | Shellenberger et al. |
| 9,339,346 B2 | 5/2016 | Malackowski |
| 9,345,545 B2 | 5/2016 | Shellenberger et al. |
| 9,360,934 B2 | 6/2016 | Ruiz Morales et al. |
| 9,486,272 B2 | 11/2016 | Bonyak et al. |
| 9,532,838 B2 | 1/2017 | Coste-Maniere et al. |
| 9,549,781 B2 | 1/2017 | He et al. |
| 9,566,122 B2 | 2/2017 | Bowling et al. |
| 9,586,327 B2 | 3/2017 | Schena |
| 9,592,096 B2 | 3/2017 | Maillet et al. |
| 9,603,672 B2 | 3/2017 | Shellenberger et al. |
| 9,622,831 B2 | 4/2017 | Azizian et al. |
| 9,636,185 B2 | 5/2017 | Quaid et al. |
| 9,652,591 B2 | 5/2017 | Moctezuma et al. |
| 9,662,174 B2 | 5/2017 | Taylor et al. |
| 9,681,920 B2 | 6/2017 | Bowling et al. |
| 9,687,310 B2 | 6/2017 | Nowlin et al. |
| 9,699,445 B2 | 7/2017 | Hoffman et al. |
| 9,707,684 B2 | 7/2017 | Ruiz et al. |
| 9,739,674 B2 | 8/2017 | Malackowski et al. |
| 9,775,681 B2 | 10/2017 | Quaid et al. |
| 9,775,682 B2 | 10/2017 | Quaid et al. |
| 9,782,261 B2 | 10/2017 | Collazo et al. |
| 9,788,903 B2 | 10/2017 | Kim et al. |
| 9,795,361 B2 | 10/2017 | Marx et al. |
| 9,795,446 B2 | 10/2017 | DiMaio et al. |
| 9,802,323 B2 | 10/2017 | Louveau |
| 9,814,392 B2 | 11/2017 | Balicki et al. |
| 9,820,818 B2 | 11/2017 | Malackowski et al. |
| 9,827,059 B2 | 11/2017 | Robinson et al. |
| 9,895,197 B2 | 2/2018 | Poquet et al. |
| 9,901,411 B2 | 2/2018 | Gombert et al. |
| 9,937,058 B2 | 4/2018 | Axelson, Jr. et al. |
| 9,943,964 B2 | 4/2018 | Hares |
| 9,948,852 B2 | 4/2018 | Lilagan et al. |
| 9,993,309 B2 | 6/2018 | Bowling |
| 9,993,313 B2 | 6/2018 | Schuh et al. |
| 10,002,427 B2 | 6/2018 | Linard et al. |
| 10,010,377 B2 | 7/2018 | Iorgulescu et al. |
| 10,034,719 B2 | 7/2018 | Richmond et al. |
| 10,039,605 B2 | 8/2018 | Kostrzewski et al. |
| 10,098,704 B2 | 10/2018 | Bowling et al. |
| 10,118,289 B2 | 11/2018 | Louveau |
| 10,123,844 B2 | 11/2018 | Nowlin et al. |
| 10,136,949 B2 | 11/2018 | Felder et al. |
| 10,159,534 B2 | 12/2018 | Maillet et al. |
| 10,178,368 B2 | 1/2019 | Zhao et al. |
| 10,201,392 B2 | 2/2019 | Frimer et al. |
| 10,247,545 B2 | 4/2019 | Elliot |
| 10,251,713 B2 | 4/2019 | Ruiz et al. |
| 10,251,714 B2 | 4/2019 | Carnes et al. |
| 10,258,416 B2 | 4/2019 | Mintz et al. |
| 10,258,419 B2 | 4/2019 | Auld et al. |
| 10,265,057 B2 | 4/2019 | Herzlinger et al. |
| 10,265,129 B2 | 4/2019 | Beira |
| 10,278,782 B2 | 5/2019 | Jarc et al. |
| 10,299,773 B2 | 5/2019 | Frimer et al. |
| 10,299,868 B2 | 5/2019 | Tsuboi et al. |
| 10,314,661 B2 | 6/2019 | Bowling et al. |
| 10,334,227 B2 | 6/2019 | Panescu et al. |
| 10,335,242 B2 | 7/2019 | Devengenzo et al. |
| 10,357,320 B2 | 7/2019 | Beira |
| 10,357,324 B2 | 7/2019 | Flatt et al. |
| 10,363,055 B2 | 7/2019 | Beira et al. |
| 10,365,554 B1 | 7/2019 | McDowall et al. |
| 10,390,737 B2 | 8/2019 | Malackowski et al. |
| 10,398,519 B2 | 9/2019 | Kim et al. |
| 10,410,746 B2 | 9/2019 | Moctezuma et al. |
| 10,413,374 B2 | 9/2019 | Chassot et al. |
| 10,420,625 B2 | 9/2019 | Suzuki et al. |
| 10,426,321 B2 | 10/2019 | Sholev |
| 10,441,372 B2 | 10/2019 | Devengenzo et al. |
| 10,464,209 B2 | 11/2019 | Ho et al. |
| 10,485,616 B2 | 11/2019 | Auld et al. |
| 10,512,509 B2 | 12/2019 | Bowling et al. |
| 10,512,512 B2 | 12/2019 | Richmond et al. |
| 10,517,681 B2 | 12/2019 | Roh et al. |
| 10,537,441 B2 | 1/2020 | Axelson, Jr. et al. |
| 10,548,680 B2 | 2/2020 | Beira |
| 10,568,709 B2 | 2/2020 | Beira |
| 10,582,977 B2 | 3/2020 | Morel et al. |
| 10,603,127 B2 | 3/2020 | Hasser et al. |

(56) References Cited

U.S. PATENT DOCUMENTS

| | | |
|---|---|---|
| 10,607,346 B2 | 3/2020 | Linard et al. |
| 10,609,291 B2 | 3/2020 | Festy et al. |
| 10,610,310 B2 | 4/2020 | Todd et al. |
| 10,636,147 B2 | 4/2020 | Linard et al. |
| 10,638,918 B2 | 5/2020 | Atarot et al. |
| 10,646,291 B2 | 5/2020 | Turner |
| 10,646,293 B2 | 5/2020 | Hasser et al. |
| 10,646,294 B2 | 5/2020 | Beira |
| 10,660,712 B2 | 5/2020 | Kostrzewski et al. |
| 10,660,724 B2 | 5/2020 | Hufnagel et al. |
| 10,667,868 B2 | 6/2020 | Malackowski |
| 10,667,876 B2 | 6/2020 | Maillet et al. |
| 10,674,900 B2 | 6/2020 | Hoffman et al. |
| 10,675,106 B2 | 6/2020 | Tsuboi et al. |
| 10,751,139 B2 | 8/2020 | Frimer et al. |
| 10,754,241 B2 | 8/2020 | McDowall et al. |
| 10,776,920 B2 | 9/2020 | Linard et al. |
| 10,782,501 B2 | 9/2020 | Hirose et al. |
| 10,786,272 B2 | 9/2020 | Beira |
| 10,786,317 B2 | 9/2020 | Zhou et al. |
| 10,786,323 B2 | 9/2020 | Ang et al. |
| 10,802,597 B2 | 10/2020 | Von Wendorff et al. |
| 10,813,704 B2 | 10/2020 | Kostrzewski et al. |
| 10,828,120 B2 | 11/2020 | Kostrzewski et al. |
| 10,864,049 B2 | 12/2020 | Beira |
| 10,864,052 B2 | 12/2020 | Beira |
| 10,869,659 B2 | 12/2020 | Thommen et al. |
| 10,874,464 B2 | 12/2020 | Roh et al. |
| 10,888,996 B2 | 1/2021 | Tabandeh et al. |
| 10,918,450 B2 | 2/2021 | Martin |
| 10,925,586 B2 | 2/2021 | Herzlinger et al. |
| 10,939,968 B2 | 3/2021 | Kostrzewski et al. |
| 11,007,020 B2 | 5/2021 | Ziraknejad et al. |
| 11,007,031 B2 | 5/2021 | Fuerst et al. |
| 11,019,329 B2 | 5/2021 | Hoffman et al. |
| 11,027,432 B2 | 6/2021 | Bowling et al. |
| 11,039,820 B2 | 6/2021 | Beira |
| 11,039,893 B2 | 6/2021 | Kostrzewski |
| 11,045,077 B2 | 6/2021 | Stern et al. |
| 11,045,276 B2 | 6/2021 | Nowatschin et al. |
| 11,058,503 B2 | 7/2021 | Chassot et al. |
| 11,103,315 B2 | 8/2021 | Malackowski |
| 11,109,917 B2 | 9/2021 | Abovitz et al. |
| 11,119,105 B2 | 9/2021 | Penny et al. |
| 11,141,230 B2 | 10/2021 | Zhou et al. |
| 11,148,297 B2 | 10/2021 | Maret |
| 11,172,997 B2 | 11/2021 | Kostrzewski et al. |
| 11,183,297 B2 | 11/2021 | Moctezuma et al. |
| 11,185,315 B2 | 11/2021 | Frimer et al. |
| 11,191,598 B2 | 12/2021 | Crawford et al. |
| 11,197,731 B2 | 12/2021 | Hoffman et al. |
| 11,504,197 B1 | 11/2022 | Noonan et al. |
| 11,622,826 B2 | 4/2023 | Basafa et al. |
| 2002/0128552 A1 | 9/2002 | Nowlin et al. |
| 2004/0034282 A1 | 2/2004 | Quaid |
| 2004/0236352 A1 | 11/2004 | Wang et al. |
| 2006/0142657 A1 | 6/2006 | Quaid et al. |
| 2007/0021738 A1 | 1/2007 | Hasser et al. |
| 2007/0044365 A1 | 3/2007 | Deken |
| 2007/0142823 A1 | 6/2007 | Prisco et al. |
| 2008/0033240 A1 | 2/2008 | Hoffman et al. |
| 2008/0039867 A1 | 2/2008 | Feussner et al. |
| 2009/0157076 A1 | 6/2009 | Athas et al. |
| 2010/0076310 A1 | 3/2010 | Wenderow et al. |
| 2010/0249507 A1 | 9/2010 | Prisco et al. |
| 2010/0274087 A1 | 10/2010 | Diolaiti et al. |
| 2010/0298636 A1 | 11/2010 | Castro et al. |
| 2010/0298839 A1 | 11/2010 | Castro |
| 2011/0060183 A1 | 3/2011 | Castro et al. |
| 2011/0066173 A1 | 3/2011 | Williams et al. |
| 2011/0092963 A1 | 4/2011 | Castro |
| 2011/0118545 A1 | 5/2011 | Williams et al. |
| 2011/0184231 A1 | 7/2011 | Page et al. |
| 2011/0196418 A1 | 8/2011 | Castro |
| 2011/0230723 A1 | 9/2011 | Castro et al. |
| 2011/0251599 A1 | 10/2011 | Shellenberger et al. |
| 2012/0143084 A1 | 6/2012 | Shoham |
| 2012/0265214 A1 | 10/2012 | Bender et al. |
| 2013/0041372 A1 | 2/2013 | Welt et al. |
| 2013/0096377 A1 | 4/2013 | Duindam et al. |
| 2013/0253313 A1 | 9/2013 | Kang et al. |
| 2013/0281924 A1 | 10/2013 | Shellenberger |
| 2014/0052154 A1 | 2/2014 | Griffiths et al. |
| 2014/0222020 A1 | 8/2014 | Bender et al. |
| 2014/0222023 A1 | 8/2014 | Kim et al. |
| 2014/0276667 A1 | 9/2014 | Shellenberger et al. |
| 2014/0276950 A1 | 9/2014 | Smaby et al. |
| 2014/0314538 A1 | 10/2014 | Carter et al. |
| 2015/0001273 A1 | 1/2015 | Amid et al. |
| 2015/0066050 A1 | 3/2015 | Jardine et al. |
| 2015/0100066 A1 | 4/2015 | Kostrzewski et al. |
| 2015/0105629 A1 | 4/2015 | Williams et al. |
| 2015/0133960 A1 | 5/2015 | Lohmeier et al. |
| 2015/0238181 A1 | 8/2015 | Sanders et al. |
| 2015/0374446 A1 | 12/2015 | Malackowski et al. |
| 2016/0058513 A1 | 3/2016 | Giorgi |
| 2016/0089212 A1 | 3/2016 | Balicki et al. |
| 2016/0235496 A1 | 8/2016 | Hoffman et al. |
| 2016/0271385 A1 | 9/2016 | Sterlina et al. |
| 2016/0361125 A1 | 12/2016 | Balicki et al. |
| 2017/0014018 A1 | 1/2017 | Cash |
| 2017/0027654 A1 | 2/2017 | Frimer et al. |
| 2017/0119480 A9 | 5/2017 | Sholev et al. |
| 2017/0165019 A1 | 6/2017 | Penny et al. |
| 2017/0165834 A1 | 6/2017 | Hares |
| 2017/0212723 A1 | 7/2017 | Atarot et al. |
| 2017/0304007 A1 | 10/2017 | Piron et al. |
| 2018/0042680 A1 | 2/2018 | DiMaio et al. |
| 2018/0042684 A1 | 2/2018 | Kostrzewski et al. |
| 2018/0169854 A1 | 6/2018 | Shiratsuchi |
| 2018/0214221 A1 | 8/2018 | Crawford et al. |
| 2018/0296284 A1 | 10/2018 | Miller et al. |
| 2018/0297206 A1 | 10/2018 | Larkin et al. |
| 2018/0325604 A1 | 11/2018 | Atarot et al. |
| 2018/0368930 A1 | 12/2018 | Esterberg et al. |
| 2019/0008598 A1 | 1/2019 | Frimer et al. |
| 2019/0022857 A1 | 1/2019 | Conus et al. |
| 2019/0060019 A1 | 2/2019 | Maret |
| 2019/0069962 A1 | 3/2019 | Tabandeh et al. |
| 2019/0133699 A1 | 5/2019 | Pomati |
| 2019/0159848 A1 | 5/2019 | Quaid et al. |
| 2019/0199915 A1 | 6/2019 | Coiseur |
| 2019/0231456 A1 | 8/2019 | Ruiz Morales et al. |
| 2019/0239968 A1 | 8/2019 | Beira |
| 2019/0254757 A1 | 8/2019 | Piron et al. |
| 2019/0269390 A1 | 9/2019 | Frimer et al. |
| 2019/0282323 A1 | 9/2019 | Petrucci et al. |
| 2019/0328475 A1 | 10/2019 | Arai et al. |
| 2019/0365481 A1 | 12/2019 | Otto et al. |
| 2019/0374293 A1 | 12/2019 | Larkin et al. |
| 2020/0030040 A1 | 1/2020 | Kostrzewski et al. |
| 2020/0038124 A1 | 2/2020 | Lin et al. |
| 2020/0038126 A1 | 2/2020 | Cau |
| 2020/0039085 A1 | 2/2020 | Yen et al. |
| 2020/0039086 A1 | 2/2020 | Meyer et al. |
| 2020/0046394 A1 | 2/2020 | Cau |
| 2020/0046439 A1 | 2/2020 | Tekiela et al. |
| 2020/0054401 A1 | 2/2020 | Yu et al. |
| 2020/0121404 A1 | 4/2020 | Morard et al. |
| 2020/0155244 A1 | 5/2020 | Sevimli et al. |
| 2020/0156259 A1 | 5/2020 | Ruiz Morales et al. |
| 2020/0167930 A1 | 5/2020 | Wang et al. |
| 2020/0187928 A1 | 6/2020 | Couture |
| 2020/0222138 A1 | 7/2020 | Diolaiti |
| 2020/0237448 A1 | 7/2020 | Kostrzewski et al. |
| 2020/0253678 A1 | 8/2020 | Hulford et al. |
| 2020/0254757 A1 | 8/2020 | Oya et al. |
| 2020/0268460 A1 | 8/2020 | Tse et al. |
| 2020/0268464 A1 | 8/2020 | Beira |
| 2020/0268472 A1 | 8/2020 | Wolf et al. |
| 2020/0279394 A1 | 9/2020 | Hong et al. |
| 2020/0281667 A1 | 9/2020 | Blondel et al. |
| 2020/0305984 A1 | 10/2020 | Zhao et al. |
| 2020/0322526 A1 | 10/2020 | Lilagan et al. |

(56) References Cited

U.S. PATENT DOCUMENTS

| | | |
|---|---|---|
| 2020/0324408 A1 | 10/2020 | Bourlion et al. |
| 2020/0330166 A1 | 10/2020 | Meglan et al. |
| 2020/0383736 A1 | 12/2020 | Frimer et al. |
| 2020/0397515 A1 | 12/2020 | Frimer et al. |
| 2020/0397520 A1 | 12/2020 | Penny et al. |
| 2020/0405375 A1 | 12/2020 | Shelton, IV et al. |
| 2020/0405414 A1 | 12/2020 | Shelton, IV et al. |
| 2021/0000554 A1 | 1/2021 | Penny et al. |
| 2021/0038313 A1 | 2/2021 | Sholev et al. |
| 2021/0039262 A1 | 2/2021 | Maillet et al. |
| 2021/0106348 A1 | 4/2021 | Beira |
| 2021/0137624 A1 | 5/2021 | Maret |
| 2021/0228289 A1 | 7/2021 | Rohr Daniel et al. |
| 2021/0282862 A1 | 9/2021 | Bourlion et al. |
| 2021/0307737 A1 | 10/2021 | Beira |
| 2021/0307848 A1 | 10/2021 | Kostrzewski |
| 2021/0315645 A1 | 10/2021 | Hares et al. |
| 2021/0323147 A1 | 10/2021 | Oaki et al. |
| 2021/0330408 A1 | 10/2021 | Chassot et al. |
| 2021/0369354 A1 | 12/2021 | Hares et al. |
| 2021/0405052 A1 | 12/2021 | Penny et al. |
| 2022/0000568 A1 | 1/2022 | Hufford et al. |
| 2022/0032473 A1 | 2/2022 | Maret |
| 2022/0152821 A1 | 5/2022 | Wang et al. |
| 2022/0192765 A1 | 6/2022 | Brasset et al. |
| 2023/0049155 A1 | 2/2023 | Koenke |
| 2023/0114137 A1 | 4/2023 | Wu et al. |
| 2023/0157770 A1 | 5/2023 | Deane |

FOREIGN PATENT DOCUMENTS

| | | |
|---|---|---|
| EP | 2413818 A1 | 2/2012 |
| EP | 2413819 A1 | 2/2012 |
| EP | 2760361 A1 | 8/2014 |
| EP | 2814644 A1 | 12/2014 |
| EP | 3175810 A1 | 6/2017 |
| EP | 3363401 A1 | 8/2018 |
| EP | 3366255 A1 | 8/2018 |
| EP | 3585297 B1 | 6/2020 |
| EP | 3582706 B1 | 7/2020 |
| EP | 3706656 A1 | 9/2020 |
| EP | 3538006 B1 | 4/2021 |
| FR | 3032346 A1 | 8/2016 |
| KR | 102188334 B1 | 12/2020 |
| WO | WO-02060653 A2 | 8/2002 |
| WO | WO-2006124390 A2 | 11/2006 |
| WO | WO-2016124752 A2 | 8/2016 |
| WO | WO-2019092372 A1 | 5/2019 |
| WO | WO-2021011533 A1 | 1/2021 |
| WO | WO-2023203491 A1 | 10/2023 |

OTHER PUBLICATIONS

Cadiere, et al., First human surgery using a surgical assistance robotics device for laparoscopic cholecystectomies, Surgical Endoscopy, available at, https://doi.org/10.1007/s00464-023-10296-3, 7 pages (Published online: Aug. 21, 2023).

EP Partial Search Report dated Jun. 17, 2022 in EP Patent Application Serial No. EP22305572.4 (01EP5).

Extended EP Search Report dated Apr. 21, 2022 in EP Patent Application Serial No. 21305929.8 (01EP2).

Extended EP Search Report dated Jun. 13, 2022 in EP Patent Application Serial No. 21306904.0 (01EP4).

Extended EP Search Report dated Jun. 14, 2022 in EP Patent Application Serial No. 21306905.7 (01EP3).

Extended EP Search Report dated Sep. 19, 2022 in EP Patent Application Serial No. 22305572.4 (02EP).

Extended EP Search Report dated Sep. 29, 2021 in EP Patent Application Serial No. 21305417.4 (01EP1).

International Search Report & Written Opinion dated Feb. 9, 2023 in Int'l PCT Patent Appl. Serial No. PCT/IB2022/056159 (0210).

International Search Report & Written Opinion dated Jul. 25, 2022 in Int'l PCT Patent Appl. Serial No. PCT/IB2022/052989 (0110).

International Search Report & Written Opinion dated Aug. 8, 2023 in Int'l PCT Patent Appl. Serial No. PCT/IB2023/053972 (0410).

Lefkovich, Charlotte, "The Use of Predicates in FDA Regulation of Medical Devices: A Case Study of Robotic Surgical Devices," Thesis. Rochester Institute of Technology (2018).

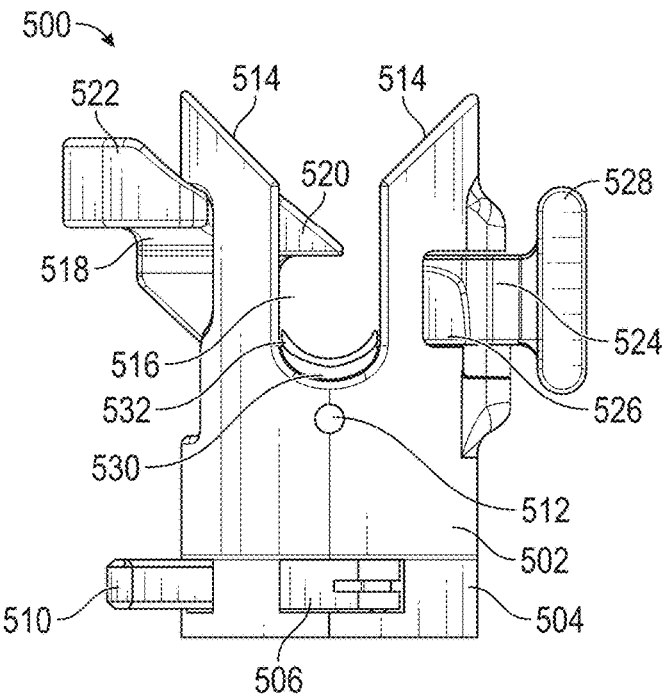
FIG. 7A
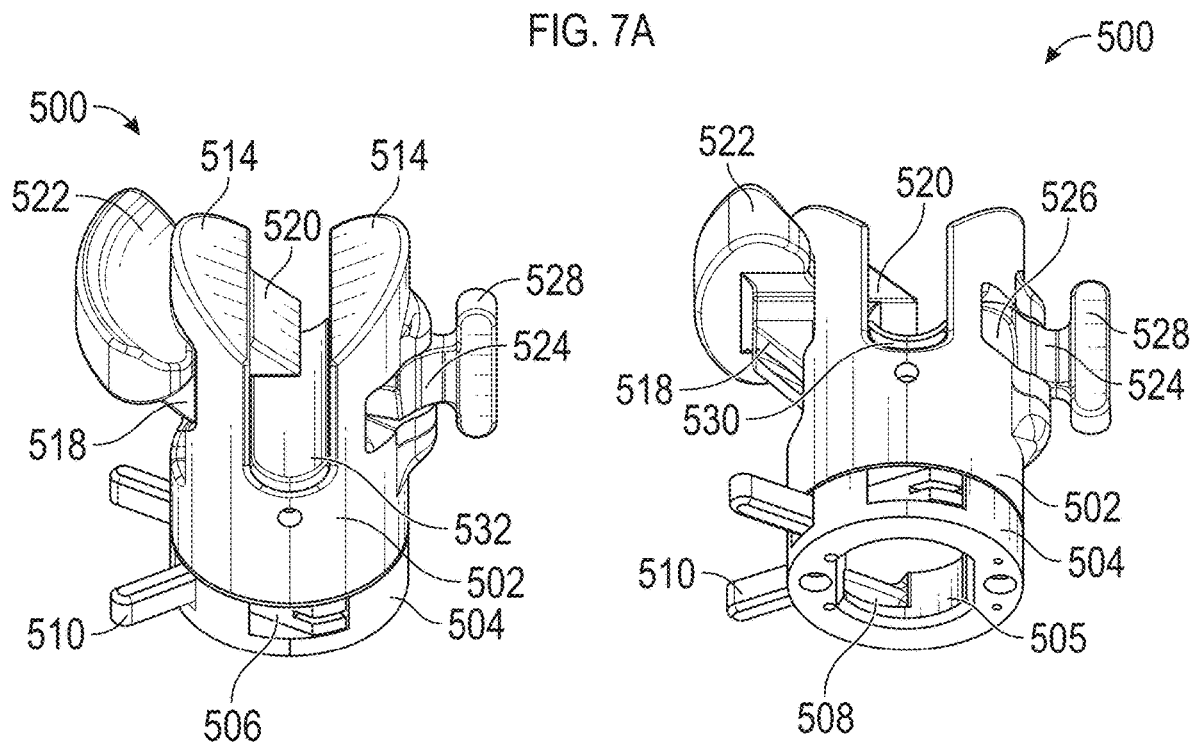
FIG. 7B
FIG. 7C

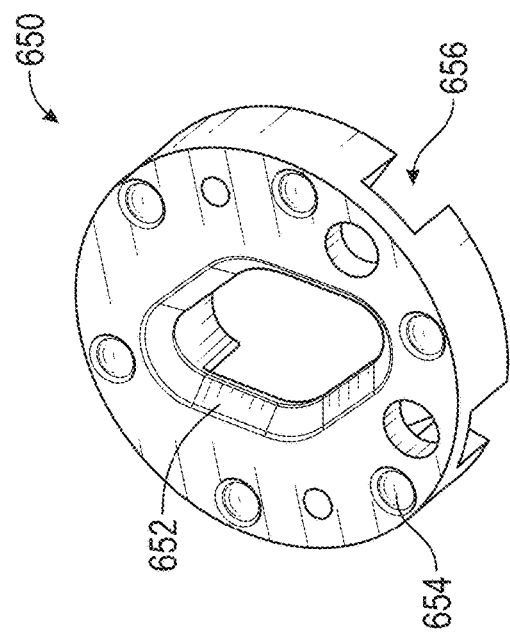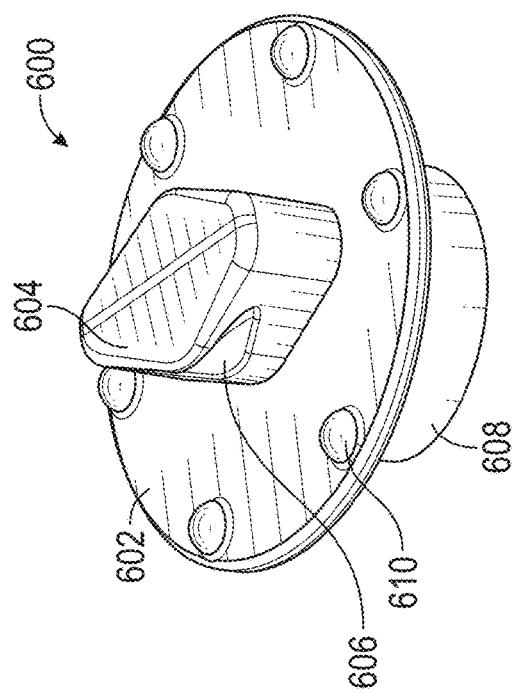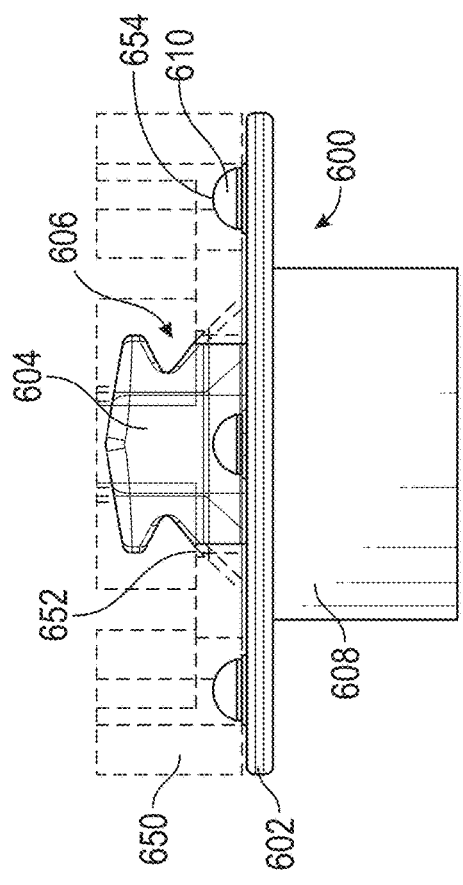
FIG. 7E
FIG. 7D
FIG. 7F

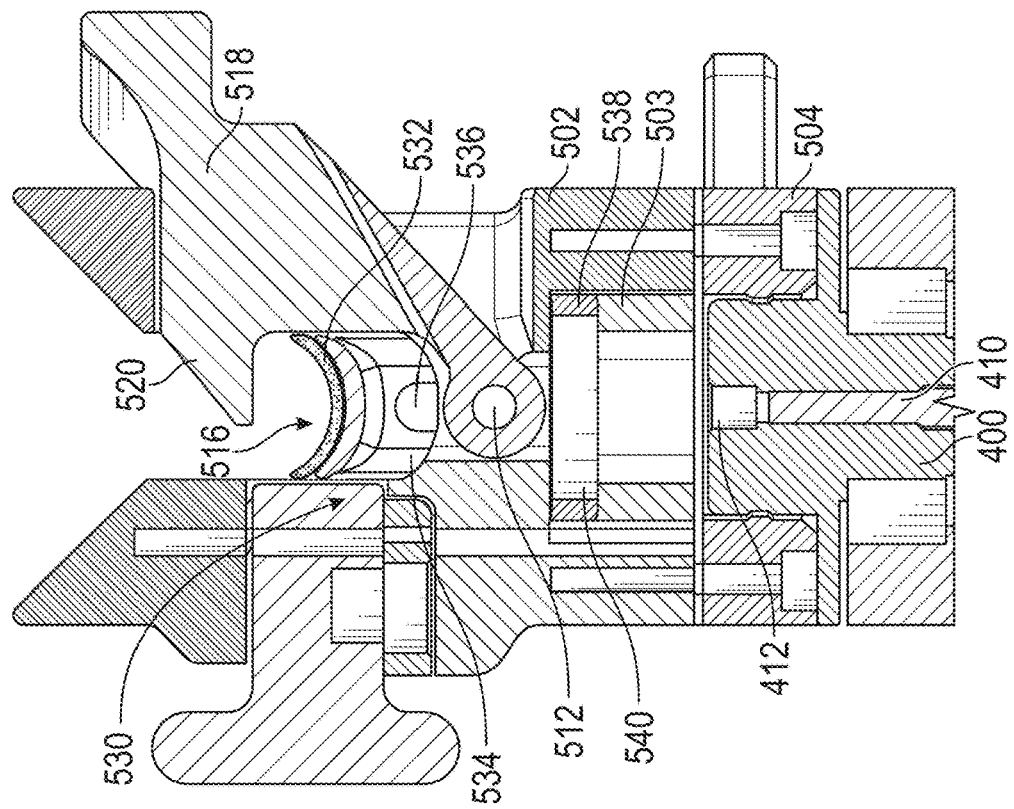
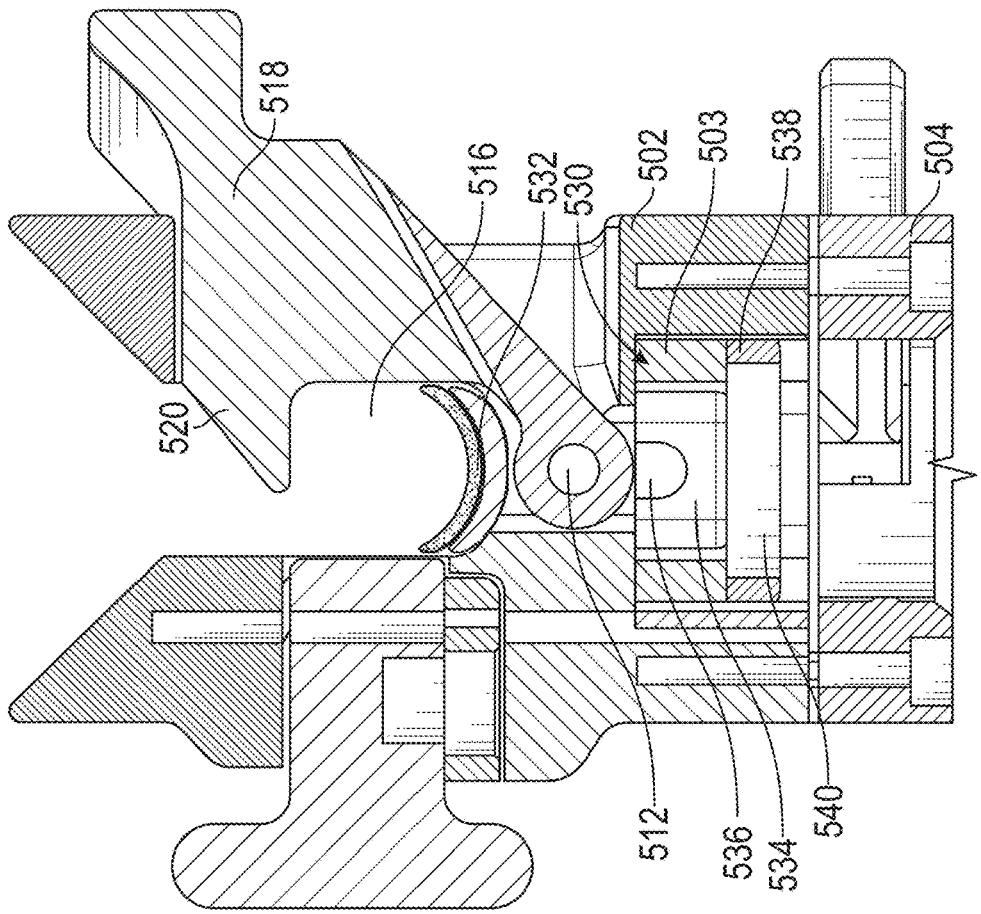

| Instrument Type | Optional Predefined Threshold Release Force | Optional Viscosity Level | Optional Threshold Dwell Time | Optional Dwell Speed |
|---|---|---|---|---|
| Scope (e.g., without limitation, 5mm or 10mm) | Medium (e.g., without limitation, 7 N, or approximately 7 N) | Variable* | Low (0.25 second) | Medium (5 mm/second or approximately 5 mm/second) |
| Tissue manipulation instruments (e.g., without limitation, grasper/retractor) | Variable due to potential for external forces on surgical instrument from tissue (e.g., without limitation, 7 N or approximately 7 N to 15 N or approximately 15 N) | Low (0 N) | Low (0.25 second) | Medium (5 mm/second or approximately 5 mm/second) |
| Suturing instruments (e.g., without limitation, needle driver) | Medium (e.g., without limitation, 7 N, or approximately 7 N) | Variable* | Low (0.25 second) | Low (1 mm/second or approximately 1 mm/second) |
| High force instruments (e.g., without limitation, stapler/clip applier) | High (e.g., without limitation, 10 N, or approximately 10 N) | Variable* | Low (0.25 second) | Low (1 mm/second or approximately 1 mm/second) |

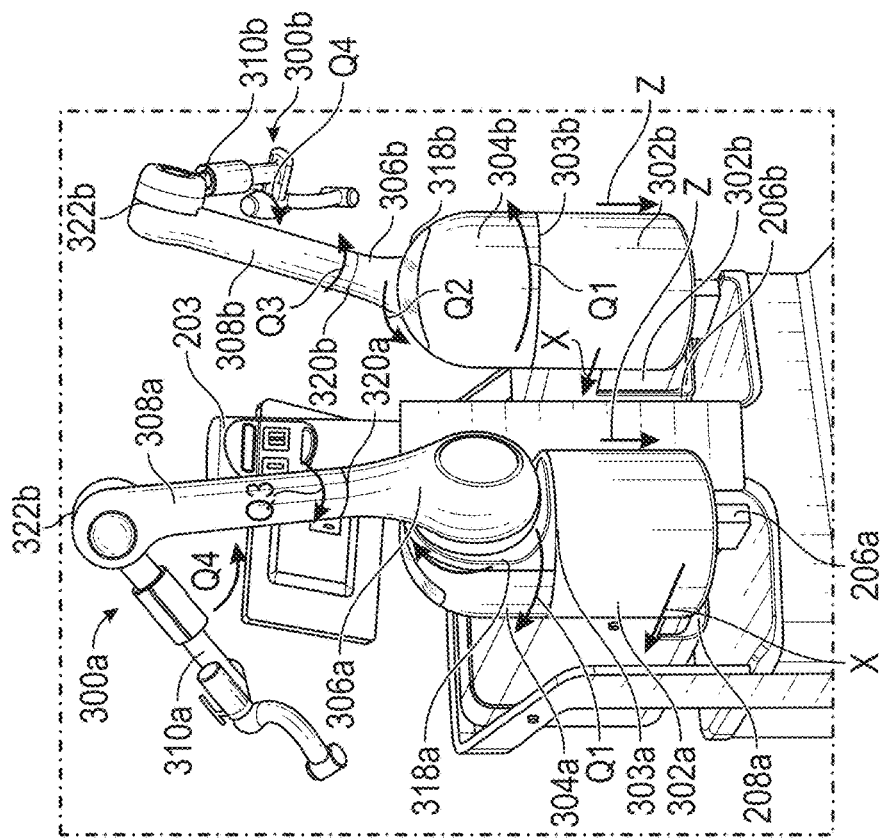
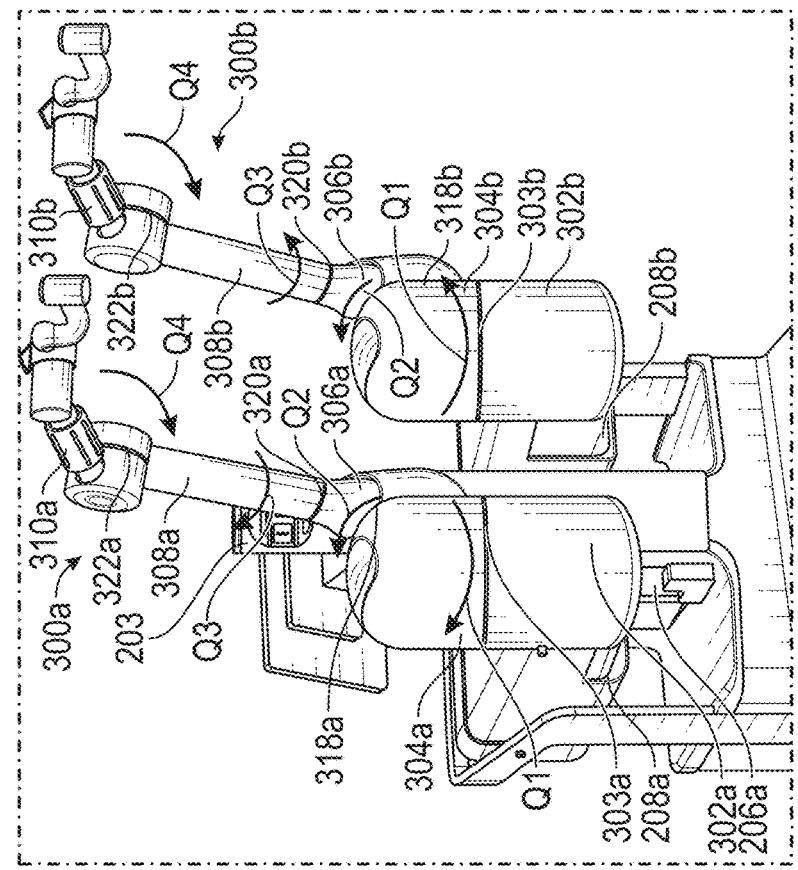
FIG. 44

CO-MANIPULATION SURGICAL SYSTEM FOR USE WITH SURGICAL INSTRUMENTS FOR PERFORMING LAPAROSCOPIC SURGERY WHILE ESTIMATING HOLD FORCE

CROSS-REFERENCE TO RELATED APPLICATIONS

This application is a continuation-in-part application of U.S. patent application Ser. No. 18/331,073, filed Jun. 7, 2023, now U.S. Pat. No. 11,839,442, which claims the benefit of priority of U.S. Provisional Patent Appl. No. 63/495,527, filed Apr. 11, 2023, U.S. Provisional Patent Appl. No. 63/479,142, filed Jan. 9, 2023, and EP Patent Appl. No. 23305026.9, filed Jan. 9, 2023, the entire contents of each of which are incorporated herein by reference.

FIELD OF USE

This technology relates to co-manipulation robotic systems, such as those designed to be coupled to clinician-selected surgical instruments to permit movement of the robot arm(s) via movement at the handle of the surgical instrument(s), along with enhanced features for setup and automatic intraoperative movements.

BACKGROUND

Managing vision and access during a laparoscopic procedure is a challenge. The surgical assistant paradigm is inherently imperfect, as the assistant is being asked to anticipate and see with the surgeon's eyes, without standing where the surgeon stands, and similarly to anticipate and adjust how the surgeon wants the tissue of interest exposed, throughout the procedure. For example, during a laparoscopic procedure, one assistant may be required to hold a retractor device to expose tissue for the surgeon, while another assistant may be required to hold a laparoscope device to provide a field of view of the surgical space within the patient to the surgeon during the procedure, either one of which may be required to hold the respective tools in an impractical position, e.g., from between the arms of the surgeon while the surgeon is actively operating additional surgical instruments.

Various attempts have been made at solving this issue. For example, a rail-mounted orthopedic retractor, which is a purely mechanical device that is mounted to the patient bed/table, may be used to hold a laparoscope device in position during a laparoscopic procedure, and another rail-mounted orthopedic retractor may be used to hold a retractor device in position during the laparoscopic procedure. However, the rail-mounted orthopedic retractor requires extensive manual interaction to unlock, reposition, and lock the tool in position.

Complex robot-assisted systems such as the Da Vinci Surgical System (made available by Intuitive Surgical, Sunnyvale, California) have been used by surgeons to enhance laparoscopic surgical procedures by permitting the surgeon to tele-operatively perform the procedure from a surgeon console remote from the patient console holding the surgical instruments. Such complex robot-assisted systems are very expensive, and have a very large footprint and take up a lot of space in the operating room. Moreover, such robot-assisted systems typically require unique system-specific surgical instruments that are compatible with the system, and thus surgeons may not use standard off-the-shelf surgical instruments that they are used to. As such, the surgeon is required to learn an entirely different way of performing the laparoscopic procedure.

In view of the foregoing drawbacks of previously known systems and methods, there exists a need for a system that provides the surgeon with the ability to seamlessly position and manipulate various surgical instruments as needed, thus avoiding the workflow limitations inherent to both human and mechanical solutions.

SUMMARY

The present disclosure overcomes the drawbacks of previously-known systems and methods by providing a co-manipulation surgical system to assist with laparoscopic surgery performed using a surgical instrument having a handle, an operating end, and an elongated shaft therebetween. The co-manipulation surgical system may include a robot arm having a proximal end, a distal end that may be removably coupled to the surgical instrument, a plurality of links, and a plurality of joints between the proximal end and the distal end. The co-manipulation surgical system further may include a controller operatively coupled the robot arm. The controller may be programmed to cause the robot arm to automatically switch between: a passive mode responsive to determining that movement of the robot arm due to movement at the handle of the surgical instrument is less than a predetermined amount for at least a predetermined dwell time period, wherein the controller may be programmed to cause the robot arm to maintain a static position in the passive mode; and a co-manipulation mode responsive to determining that force applied at the robot arm due to force applied at the handle of the surgical instrument exceeds a predetermined threshold, wherein the controller may be programmed to permit the robot arm to be freely moveable in the co-manipulation mode responsive to movement at the handle of the surgical instrument for performing laparoscopic surgery using the surgical instrument, and wherein the controller may be programmed to apply a first impedance to the robot arm in the co-manipulation mode to account for weight of the surgical instrument and the robot arm. The controller further may be programmed to cause the robot arm to automatically switch to a haptic mode responsive to determining that at least a portion of the robot arm is outside a predefined haptic barrier, wherein the controller may be programmed to apply a second impedance to the robot arm in the haptic mode greater than the first impedance, thereby making movement of the robot arm responsive to movement at the handle of the surgical instrument more viscous in the haptic mode than in the co-manipulation mode.

In accordance with one aspect of the present disclosure, a co-manipulation surgical system to assist with laparoscopic surgery performed using a surgical instrument having a handle, an operating end, and an elongated shaft therebetween is provided. The co-manipulation surgical system may include a robot arm comprising a proximal end, a distal end configured to be removably coupled to the surgical instrument, a plurality of links, and a plurality of joints between the proximal end and the distal end, and a controller operatively coupled to the robot arm and configured to permit the robot arm to be freely moveable responsive to movement at the handle of the surgical instrument for performing laparoscopic surgery. The controller programmed to: cause the robot arm to maintain a static position in a passive mode responsive to determining that movement of the robot arm due to movement at the handle of the surgical instrument is less than a predetermined amount for at least a predetermined dwell time period; identify, when the surgical instrument comprises a laparoscope having a field of view, a target surgical instrument within the field of view of the laparoscope based on image data from the laparoscope; and cause the robot arm to switch to an instrument centering mode where the robot arm moves the laparoscope to maintain the target surgical instrument within the field of view of the laparoscope.

The controller may be configured to cause the robot arm to automatically switch to a co-manipulation mode responsive to determining that force applied at the robot arm due to force applied at the handle of the surgical instrument exceeds a predetermined threshold. Accordingly, the controller may be configured to permit the robot arm to be freely moveable in the co-manipulation mode responsive to movement at the handle of the surgical instrument, while applying an impedance to the robot arm in the co-manipulation mode to account for weight of the surgical instrument and the robot arm. In addition, the controller may be configured to identify the target surgical instrument within the field of view of the laparoscope by detecting a predefined gestural pattern by the target surgical instrument within the field of view of the laparoscope. The predefined gestural pattern may comprise positioning of the target surgical instrument within a center portion of the field of view of the laparoscope and maintaining the position of the target surgical instrument within the center portion for at least a predetermined hold period. In some embodiments, the controller may be configured to identify the target surgical instrument within the field of view of the laparoscope based on user input identifying the target surgical instrument. Moreover, the controller may be configured to distinguish the target surgical instrument from one or more other surgical instruments within the field of view of the laparoscope. In the instrument centering mode, the controller may cause the robot arm to move the laparoscope to maintain the target surgical instrument within a predefined boundary region within the field of view of the laparoscope, such that the robot arm does not move the laparoscope unless the target surgical instrument moves outside of the predefined boundary region.

Moreover, in the instrument centering mode, the controller may cause the robot arm to move the laparoscope by executing a trajectory generation algorithm to generate a trajectory from a current position of the laparoscope to a desired position of the laparoscope, and causing the robot arm to move the laparoscope along the trajectory to maintain the target surgical instrument within the field of view of the laparoscope. Accordingly, the controller may be configured to: permit the robot arm to be freely moveable in a co-manipulation mode responsive to determining that force applied at the robot arm due to force applied at the laparoscope exceeds a predetermined threshold, while applying an impedance to the robot arm in the co-manipulation mode to account for weight of the laparoscope and the robot arm; record a trajectory of the freely moving robot arm when the movement of the robot arm deviates from the generated trajectory; and update the trajectory generation algorithm based the recorded trajectory. The generated trajectory may comprise moving the robot arm along a longitudinal axis of the laparoscope to maintain the target surgical instrument within the field of view of the laparoscope and within a predetermined resolution threshold. In addition, the generated trajectory may comprise moving the robot arm along at least one of a longitudinal axis of the laparoscope or an axis perpendicular to the longitudinal axis of the laparoscope to maintain the target surgical instrument within the field of view of the laparoscope.

The trajectory may be generated by: measuring a current position of the distal end of the robot arm; determining a point of entry of the laparoscope into the patient; and calculating a distance required to move the distal end of the robot arm from its current position to a second position that causes a distal end of the laparoscope to move from its current position to the desired position based on the point of entry and a known length between the distal end of the robot arm and the distal end of the laparoscope. The controller may cause the robot arm to move the laparoscope along the trajectory by: calculating a force required to move the distal end of the robot arm the distance from its current position to the second position; and applying torque to the at least some joints of the plurality of joints of the robot arm based on the calculated force to move the distal end of the robot arm the distance from its current position to the second position to thereby move the distal end of the laparoscope from its current position to the desired position. Further, the controller may be configured to: detect an offset angle between a camera head of the laparoscope and the laparoscope; and calibrate the trajectory to correct the offset angle such that movement of the laparoscope along the calibrated trajectory maintains the target surgical instrument within the field of view of the laparoscope. For example, the controller may be configured to detect the offset angle by: causing the robot arm to move along a predetermined trajectory in a known direction in a robot arm coordinate frame; measuring an actual movement of a static object within the field of view of the laparoscope responsive to movement of the robot arm along the predetermined trajectory; and comparing the actual movement of the static object with an expected movement of the static object associated with the predetermined trajectory.

The controller further may be configured to cause the robot arm to switch to the instrument centering mode responsive to user input. In addition, the controller may be configured to: determine a phase of the laparoscopic surgery; estimate the target surgical instrument based on the phase of the laparoscopic surgery; and identify the target surgical instrument within the field of view of the laparoscope based on the estimation and the image data from the laparoscope. Moreover, the controller may be configured to: determine a phase of the laparoscopic surgery; and automatically switch to the instrument centering mode responsive to the phase of the laparoscopic surgery. Accordingly, the controller may be configured to: identify one or more anatomical structures within the field of view of the laparoscope based on image data from the laparoscope; determine the phase of the laparoscope surgery based on the identified one or more anatomical structures; and cause the robot arm, in the instrument centering mode, to move the laparoscope to maintain the identified one or more anatomical structures within the field of view of the laparoscope. Additionally, the controller may be configured to: generate an overlay indicative of the target surgical instrument; and cause the overlay to be displayed over the image data from the laparoscope via a graphical user interface.

The controller may be configured to: cause the robot arm to move the laparoscope in a predetermined trajectory; and compare an actual trajectory of the image data from the laparoscope during movement along the predetermined trajectory with an expected trajectory of the image data associated with the predetermined trajectory to determine an angle of a distal tip of the laparoscope. For example, the predetermined trajectory may comprise a circular pattern in a single plane. Moreover, the controller may be configured to identify the target surgical instrument within the field of view of the laparoscope based on image data from the laparoscope using machine learning algorithms executed at the controller. For example, the machine learning algorithms may be trained with a database of annotated image data of associated surgical instruments. Accordingly, the machine learning algorithms may be configured to evaluate pixels of the image data from the laparoscope and indicate if the pixels correspond to the target surgical instrument to identify the target surgical instrument. The controller may be configured to identify the target surgical instrument within the field of view of the laparoscope in real time. The controller may be configured to cause, in the instrument centering mode, the robot arm to move the laparoscope to track the target surgical instrument that is being manually held by a surgeon. In some embodiments, the system may include a second robot arm configured to be removably coupled to the target surgical instrument that is being manually held by the surgeon.

In accordance with another aspect of the present disclosure, a method for assisting with laparoscopic surgery is provided. The method may include: providing a robot arm comprising a proximal end, a distal end configured to be removably coupled a laparoscope, a plurality of links, and a plurality of joints between the proximal end and the distal end; permitting, via a controller operatively coupled to the robot arm, the robot arm to be freely moveable responsive to movement at the handle of the laparoscope for performing laparoscopic surgery; automatically causing, via the controller, the robot arm to maintain a static position in a passive mode responsive to determining that movement of the robot arm due to movement at the handle of the laparoscope is less than a predetermined amount for at least a predetermined dwell time period; identifying, via the controller, a target surgical instrument within a field of view of the laparoscope based on image data from the laparoscope; switching, via the controller, the robot arm to an instrument centering mode; and automatically causing, via the controller while in the instrument centering mode, the robot arm to move the laparoscope to maintain the target surgical instrument within the field of view of the laparoscope. For example, identifying the target surgical instrument within the field of view of the laparoscope may comprise detecting, via the controller, a predefined gestural pattern by the target surgical instrument within the field of view of the laparoscope, the predefined gestural pattern comprising positioning of the target surgical instrument within a center portion of the field of view of the laparoscope and maintaining the position of the target surgical instrument within the center portion for at least a predetermined hold period.

In accordance with another aspect of the present disclosure, a co-manipulation surgical system to assist with laparoscopic surgery performed using a surgical instrument is provided. The co-manipulation surgical system may include a robot arm comprising a plurality of links, a plurality of joints, a proximal end operatively coupled to a base of the robot arm, and a distal region having a distal end configured to be removably coupled to the surgical instrument, and a platform coupled to the base of the robot arm. The platform may comprise a stage assembly configured to independently move the base of the robot arm in at least two degrees of freedom relative to the platform. Accordingly, in a user guided setup mode, application of a force at the distal region of the robot arm in a first direction may cause the stage assembly to move the base of the robot arm in a first degree of freedom of the at least two degrees of freedom relative to the platform.

For example, in the user guided setup mode, the stage assembly may be configured to move the base of the robot arm in the first degree of freedom when the force applied at the distal region of the robot arm in the first direction exceeds a predetermined force threshold. Further, in the user guided setup mode, the stage assembly may be configured to stop moving the base of the robot arm in the first degree of freedom when the force applied at the distal region of the robot arm in the first direction falls below a predetermined release threshold. Moreover, in the user guided setup mode, the stage assembly may be configured to stop moving the base of the robot arm in the first degree of freedom upon application of a counter force at the robot arm in a second direction opposite to the first direction. In addition, in the user guided setup mode, application of a force at the distal region of the robot arm in a second direction may cause the stage assembly to move the base of the robot arm in a second degree of freedom of the at least two degrees of freedom relative to the platform. The system further may include an actuator configured to be actuated to switch the system to the user guided setup mode. In some embodiments, the system remains in the user guided setup mode only while the actuator is actuated. The actuator may be disposed on a collar rotatably coupled to a link of the plurality of links, such that actuation of the actuator permits rotation of the collar in a first direction to cause rotation of a distal link of the plurality of links adjacent to a setup joint of the plurality of joints in a corresponding first direction relative to a proximal link of the plurality of links adjacent to the setup joint, and permits rotation of the collar in a second direction to cause rotation of the distal link adjacent to the setup joint in a corresponding second direction relative to the proximal link adjacent to the setup joint.

The system further may include a graphical user interface operatively coupled to the stage assembly. The graphical user interface may be configured to display an actuator configured to be actuated to cause the stage assembly to move the base of the robot arm in at least one of the at least two degrees of freedom relative to the platform. For example, the actuator may comprise a slidable cursor configured to be moved relative to a neutral center point of a cursor pad, such that movement of the slidable cursor in a direction relative to the neutral center point within the cursor pad may cause the stage assembly to move the base of the robot arm in a corresponding direction relative to the platform. The stage assembly may be configured to move the base of the robot arm in the corresponding direction relative to the platform at a velocity that correlates with a distance of the slidable cursor from the neutral center point. In addition, the graphical user interface may be configured to display one or more indicators, the one or more indicators indicative of a configuration of the robot arm relative to the platform in real-time responsive to actuation of the actuator. Moreover, in a co-manipulation mode, the robot arm may be permitted to be freely moveable responsive to movement at the handle of the surgical instrument for performing laparoscopic surgery.

The system further may include a plurality of motors disposed within the base, the plurality of motors operatively coupled to at least some joints of the plurality of joints, and a controller operatively coupled to the plurality of motors. The controller may be programmed to: measure current of the plurality of motors, the measured current indicative of force applied at the distal region of the robot arm; and cause, in the user guided setup mode, the stage assembly to move the base of the robot arm in at least one of the at least two degrees of freedom based on the measured current. The controller further may be operatively coupled to a setup joint of the plurality of joints of the robot arm, such that the controller may be programmed to: determine if one or more objects are within a predetermined proximity threshold of the robot arm; and automatically rotate a distal link of the plurality of links adjacent to the setup joint relative to a proximal link of the plurality of links adjacent to the setup joint to avoid a collision with the one or more objects as the stage assembly moves the base of the robot arm in at least one of the at least two degrees of freedom relative to the platform in the user guided setup mode.

The system further may include one or more depth sensors configured to detect the one or more objects adjacent to the robot arm, and generate one or more signals indicative of a proximity of the one or more objects to the robot arm. Accordingly, the controller may be configured to determine if the one or more objects are within the predetermined proximity threshold of the robot arm based on the one or more signals. For example, the one or more depth sensors may comprise one or more proximity sensors disposed within the base of the robot arm, the one or more proximity sensors comprising at least one of electromagnetic, capacitive, ultrasonic, or infrared proximity sensors. Additionally, or alternatively, the one or more depth sensors may comprise one or more depth cameras. Accordingly, the controller may be configured to stop movement of the base of the robot arm via the stage assembly if the one or more objects are within the predetermined proximity threshold. The co-manipulation surgical system may not be teleoperated via user input received at a remote surgeon console.

In accordance with another aspect of the present disclosure, a method for assisting with laparoscopic surgery using a robot arm comprising a plurality of links, and a plurality of joints, a proximal end operatively coupled to a base of the robot arm, and a distal region having a distal end configured to be removably coupled to a surgical instrument is provided. The method may include: switching, via a controller operatively coupled to a stage assembly operatively coupled to the base of the robot arm, the system to a user guided setup mode; and causing, via the controller in the user guided setup mode, the stage assembly to move the base of the robot arm in a first degree of freedom of at least two degrees of freedom relative to a platform coupled to the stage assembly upon application of a force at the distal region of the robot arm in a first direction. For example, causing the stage assembly to move the base of the robot arm in the first degree of freedom may comprise causing, via the controller in the user guided setup mode, the stage assembly to move the base of the robot arm in the first degree of freedom when the force applied at the distal region of the robot arm in the first direction exceeds a predetermined force threshold.

The method further may include causing, via the controller in the user guided setup mode, the stage assembly to stop moving the base of the robot arm in the first degree of freedom when the force applied at the distal region of the robot arm in the first direction falls below a predetermined release threshold. In addition, the method may include causing, via the controller in the user guided setup mode, the stage assembly to stop moving the base of the robot arm in the first degree of freedom upon application of a counter force at the robot arm in a second direction opposite to the first direction. Further, the method may include causing, via the controller in the user guided setup mode, the stage assembly to move the base of the robot arm in a second degree of freedom of the at least two degrees of freedom relative to the platform upon application of a force at the distal region of the robot arm in a second direction. Moreover, switching the system to the user guided setup mode may comprise switching the system to the user guided setup mode responsive to actuation of an actuator operatively coupled to the controller, such that the system may remain in the user guided setup mode only while the actuator is actuated.

The method further may include causing, via the controller in the user guided setup mode, the stage assembly to move the base of the robot arm in at least one of the at least two degrees of freedom relative to the platform responsive to actuation of an actuator displayed on a graphical user interface operatively coupled to the controller. Accordingly, the method further may include causing, via the controller in the user guided setup mode, the graphical user interface to display one or more indicators indicative of a configuration of the robot arm relative to the platform in real-time responsive to actuation of the actuator. The method further may include determining, via the controller in the user guided setup mode, if one or more objects are within a predetermined proximity threshold of the robot arm; and stopping, via the controller if the one or more objects are within the predetermined proximity threshold, movement of the base of the robot arm via the stage assembly to avoid a collision with the one or more objects as the stage assembly moves the base of the robot arm in at least one of the at least two degrees of freedom relative to the platform. Moreover, the method may include switching, via the controller, the system to a co-manipulation mode; and permitting, via the controller in the co-manipulation mode, the robot arm to be freely moveable responsive to movement at a handle of the surgical instrument for performing laparoscopic surgery.

In accordance with another aspect of the present disclosure, a co-manipulation surgical system to assist with laparoscopic surgery performed using a surgical instrument having a handle, an operating end, and an elongated shaft therebetween is provided. The co-manipulation surgical system may include a robot arm comprising a plurality of links, a plurality of joints comprising one or more motorized joints, a setup joint, and one or more passive joints, a proximal end operatively coupled to a base of the robot arm, and a distal region having a distal end configured to be removably coupled to the surgical instrument, and a plurality of motors operatively coupled to the one or more motorized joints and to the setup joint. In addition, the system may include an actuator operatively coupled to the setup joint and configured to be actuated to cause rotation of a distal link of the plurality of links adjacent to the setup joint relative to a proximal link of the plurality of links adjacent to the setup joint from a first setup configuration to a second setup configuration responsive to actuation of the actuator. Accordingly, when the actuator is in an unactuated state, the robot arm may be permitted to be freely moveable responsive to movement at the handle of the surgical instrument for performing laparoscopic surgery via the one or more motorized joints and the one or more passive joints while the distal link adjacent to the setup joint and the proximal link adjacent to the setup joint remain in the second setup configuration.

The actuator may comprise a collar rotatably coupled to a link of the plurality of links, the collar configured to be rotated in a first direction relative to the link of the plurality of links to cause rotation of the distal link adjacent to the setup joint in a corresponding first direction relative to the proximal link adjacent to the setup joint, and rotated in a second direction relative to the link of the plurality of links to cause rotation of the distal link adjacent to the setup joint in a corresponding second direction relative to the proximal link adjacent to the setup joint. Moreover, the collar may comprise a setup mode actuator, the setup mode actuator configured to be actuated to permit the rotation of the distal link adjacent to the setup joint in the corresponding first and second directions relative to the proximal link adjacent to the setup joint responsive to rotation of the collar. The collar may be spring-enforced such that upon release of the collar in any position, the collar is configured to return to a neutral position relative to the link of the plurality of links.

The system further may include a graphical user interface operatively coupled to the setup joint, such that the actuator may be configured to be displayed on the graphical user interface. For example, the actuator may comprise a slidable cursor configured to be moved relative to a neutral center point, such that movement of the slidable cursor in a first direction relative to the neutral center point causes rotation of the distal link adjacent to the setup joint in a first direction relative to the proximal link adjacent to the setup joint, and movement of the slidable cursor in a second direction relative to the neutral center point causes rotation of the distal link adjacent to the setup joint in a second direction relative to the proximal link adjacent to the setup joint. In some embodiments, the distal link adjacent to the setup joint may be configured to rotate in the corresponding direction relative to the proximal link adjacent to the setup joint a velocity that correlates with a distance of the slidable cursor from the neutral center point. In addition, the graphical user interface may be configured to display an indicator, the indicator indicative of a configuration of the distal link adjacent to the setup joint relative to the proximal link adjacent to the setup joint in real-time responsive to actuation of the actuator. Additionally, the graphical user interface may be configured to display graphical representations of a plurality of configurations of the distal link adjacent to the setup joint relative to the proximal link adjacent to the setup joint, such that a position of the indicator relative to the graphical representations of the plurality of configurations may be indicative of the configuration of the distal link adjacent to the setup joint relative to the proximal link adjacent to the setup joint in real-time responsive to actuation of the actuator.

The system further may include a controller operatively coupled to the robot arm, the controller programmed to cause the robot arm to be freely moveably responsive to movement at the handle of the surgical instrument for performing laparoscopic surgery during an operating stage. The controller may be configured to switch from the operating stage to a setup stage upon actuation of a setup mode actuator, such that actuation of the actuator only causes rotation of the distal link adjacent to the setup joint relative to the proximal link adjacent to the setup joint when the setup mode actuator is in an actuated state. When the actuator is in an actuated state, application of a force at the distal region of the robot arm in a first direction may cause rotation of the distal link adjacent to the setup joint in a first direction relative to the proximal link adjacent to the setup joint, and application of a force at the distal region of the robot arm in a second direction causes rotation of the distal link adjacent to the setup joint in a second direction relative to the proximal link adjacent to the setup joint. Moreover, when the actuator is in the unactuated state, the setup joint may be configured to cause the distal and proximal links adjacent to the setup joint to be fixed relative to each other in the second setup configuration. In addition, all motors of the plurality of motors operatively coupled to the one or more motorized joints may be disposed within the base of the robot arm. Moreover, a shoulder link of the plurality of links may comprise a distal shoulder link rotatably coupled to a proximal shoulder link via the setup joint, and the motor of the plurality of motors operatively coupled to the setup joint may not back-drivable. For example, the motor of the plurality of motors operatively coupled to the setup joint may be disposed on the shoulder link adjacent to the setup joint.

The system further may include a platform operatively coupled to the base of the robot arm, the platform comprising a stage assembly configured to independently move the base of the robot arm in a horizontal direction and in a vertical direction relative to the platform. Accordingly, in a user guided setup mode, application of a force at the distal region of the robot arm in a first direction may cause the stage assembly to move the base of the robot arm in the horizontal direction relative to the platform, and application of a force at the distal region of the robot arm in a second direction may cause the stage assembly to move the base of the robot arm in the vertical direction relative to the platform. The system further may include a setup mode actuator configured to be actuated to switch the system to the user guided setup mode, such that the system may remain in the user guided setup mode only while the setup mode actuator is actuated. In some embodiments, the actuator may comprise a collar rotatably coupled to a link of the plurality of links, such that the setup mode actuator may be disposed on the collar. Accordingly, actuation of the setup mode actuator may permit rotation of the collar in a first direction to cause rotation of the distal link adjacent to the setup joint in a corresponding first direction relative to the proximal link adjacent to the setup joint, and may permit rotation of the collar in a second direction to cause rotation of the distal link adjacent to the setup joint in a corresponding second direction relative to the proximal link adjacent to the setup joint. The co-manipulation surgical system may not be teleoperated via user input received at a remote surgeon console.

In accordance with another aspect of the present disclosure, a method for assisting with laparoscopic surgery using a robot arm comprising a plurality of links, a plurality of joints comprising one or more motorized joints, a setup joint, and one or more passive joints, a proximal end operatively coupled to a base of the robot arm, and a distal region having a distal end configured to be removably coupled to a surgical instrument is provided. The method may include: actuating an actuator operatively coupled to a motor operatively coupled to the setup joint to cause rotation of a distal link of the plurality of links adjacent to the setup joint relative to a proximal link of the plurality of links adjacent to the setup joint from a first setup configuration to a second setup configuration responsive to actuation of the actuator; and moving, when the actuator is in an unactuated state, the robot arm responsive to movement at the handle of the surgical instrument for performing laparoscopic surgery via the one or more motorized joints and the one or more passive joints while the distal link adjacent to the setup joint and proximal link adjacent to the setup joint remain in the second setup configuration. For example, actuating the actuator to cause rotation of the distal link adjacent to the setup joint relative to the proximal link adjacent to the setup joint may comprise rotating a collar rotatably coupled to a link of the plurality of links in a first direction to cause rotation of the distal link adjacent to the setup joint in a corresponding first direction relative to the proximal link adjacent to the setup joint, and rotating the collar in a second direction to cause rotation of the distal link adjacent to the setup joint in a corresponding second direction relative to the proximal link adjacent to the setup joint. Moreover, actuating the actuator to cause rotation of the distal link adjacent to the setup joint relative to the proximal link adjacent to the setup joint further may comprise actuating a setup mode actuator disposed on the collar to permit the rotation of the distal link adjacent to the setup joint in the corresponding first and second directions relative to the proximal link adjacent to the setup joint responsive to rotation of the collar.

In addition, actuating the actuator to cause rotation of the link distal to the setup joint relative to the link proximal to the setup joint may comprise actuating the actuator displayed on a graphical user interface. For example, actuating the actuator displayed on the graphical user interface may comprise moving a slidable cursor relative to a neutral center point, such that movement of the slidable cursor in a first direction relative to the neutral center point causes rotation of the distal link adjacent to the setup joint in a first direction relative to the proximal link adjacent to the setup joint, and movement of the slidable cursor in a second direction relative to the neutral center point causes rotation of the distal link adjacent to the setup joint in a second direction relative to the proximal link adjacent to the setup joint. Accordingly, the method further may include displaying, via the graphical user interface, an indicator indicative of a configuration of the distal link adjacent to the setup joint relative to the proximal link adjacent to the setup joint in real-time responsive to actuation of the actuator.

In addition, the method may include displaying, via the graphical user interface, graphical representations of a plurality of configurations of the distal link adjacent to the setup joint relative to the proximal link adjacent to the setup joint, such that a position of the indicator relative to the graphical representations of the plurality of configurations is indicative of the configuration of the distal link adjacent to the setup joint relative to the proximal link adjacent to the setup joint in real-time responsive to actuation of the actuator. Moreover, actuating the actuator to cause rotation of the link distal to the setup joint relative to the link proximal to the setup joint may comprise applying, when the actuator is in an actuated state, a force at the distal region of the robot arm in a direction to cause rotation of the distal link adjacent to the setup joint in a corresponding direction relative to the proximal link adjacent to the setup joint. The method further may include applying, in a user guided setup mode, a force at the distal region of the robot arm in a direction to cause a stage assembly operatively coupled to the base of the robot arm to move the base of the robot arm in a corresponding direction relative to a platform coupled to the stage assembly.

In accordance with another aspect of the present disclosure, a co-manipulation surgical system for providing adaptive gravity compensation to a robot arm comprising a plurality of links, a plurality of joints, and a distal end configured to be removably coupled to a surgical instrument is provided. The co-manipulation surgical system may comprise at least one processor configured to: apply an initial gravity compensation to the robot arm to compensate for gravity of the surgical instrument based on an estimated instrument parameter associated with the surgical instrument; calculate, during application of the initial gravity compensation, a hold force required to maintain the distal end of the robot arm in a static position in a passive mode; and determine a calibrated instrument parameter for the surgical instrument based on the hold force, the calibrated instrument parameter selected to adjust the hold force required to maintain the distal end of the robot arm in the static position in the passive mode during application of an adjusted gravity compensation to the robot arm based on the calibrated instrument parameter.

The at least one processor further may be configured to apply torque to one or more motorized joints of the plurality of joints of the robot arm to apply the initial gravity compensation to the robot arm to compensate for gravity of the surgical instrument. The estimated instrument parameter and the calibrated instrument parameter may comprise at least one of a mass or a center of mass associated with the surgical instrument. In addition, the at least one processor may be configured to: load a calibration file associated with a known parameter of the surgical instrument, such that the calibration file may comprise the estimated instrument parameter. For example, the known parameter may comprise a diameter of an elongated shaft of the surgical instrument. Moreover, the at least one processor may be configured to determine the known parameter upon coupling of the surgical instrument to the distal end of the robot arm via a coupler body removably coupled to the surgical instrument and to the distal end of the robot arm. In some embodiments, the at least one processor may be configured to determine the known parameter based on the coupler body. The system further may include an optical sensor configured to collect depth data, such that the at least one processor may be configured to determine the known parameter based on the depth data. Additionally, or alternatively, the system may include a user interface operatively coupled to the at least one processor, such that the at least one processor is configured to determine the known parameter via user input received by the user interface.

The calibrated instrument parameter may be selected to adjust the hold force during application of the adjusted gravity compensation based on the calibrated instrument parameter within a predetermined range associated with a known parameter of the surgical instrument. Moreover, when the distal end of the robot arm is not subjected to any external forces other than gravity on the robot arm and the surgical instrument in the static position, the calibrated instrument parameter may be selected to adjust the hold force to or near zero upon application of the adjusted gravity compensation based on the calibrated instrument parameter. In addition, when the distal end of the robot arm is subjected to one or more external forces in addition to gravity on the robot arm and the surgical instrument in the static position, the calibrated instrument parameter may be selected to adjust the hold force within a predetermined range associated with a known parameter of the surgical instrument.

The at least one processor further may be configured to: calculate the adjusted gravity compensation of the surgical instrument based on the calibrated instrument parameter; and apply the adjusted gravity compensation to the robot arm to compensate for gravity of the surgical instrument. For example, the at least one processor may be configured to apply torque to one or more motorized joints of the plurality of joints of the robot arm to apply the adjusted gravity compensation to the robot arm to compensate for gravity of the surgical instrument. Moreover, the at least one processor may be configured to cause the robot arm to automatically switch to a co-manipulation mode responsive to determining that force applied at the robot arm due to force applied at a handle of the surgical instrument exceeds a predetermined force threshold. Additionally, the at least one processor may be configured to permit the robot arm to be freely moveable in the co-manipulation mode responsive to movement at the handle of the surgical instrument, while applying the adjusted gravity compensation to the robot arm to compensate for gravity of the surgical instrument in the co-manipulation mode.

The at least one processor further may be configured to calculate the adjusted hold force to maintain the distal end of the robot arm in the static position in the passive mode upon application of the adjusted gravity compensation. Accordingly, the at least one processor may be configured to: establish a baseline hold force based on the adjusted hold force after a predetermined time period upon initiation of the passive mode; and apply a predetermined constant breakaway force threshold to the robot arm based on the baseline hold force, such that the at least one processor may not maintain the distal end of the robot arm in the static position if the hold force exceeds the predetermined constant breakaway force threshold. In addition, the at least one processor may be configured to apply a predetermined high breakaway force threshold during the predetermined time period, such that the at least one processor may not maintain the distal end of the robot arm in the static position if the hold force exceeds the predetermined high breakaway force threshold during the predetermined time period. Moreover, the at least one processor may be configured to cause the robot arm to automatically switch to the passive mode responsive to determining that movement of the robot arm due to movement at a handle of the surgical instrument is less than a predetermined amount for at least a predetermined dwell time period. The at least one processor further may be configured to record the calibrated instrument parameter in a calibration file associated with the surgical instrument.

In accordance with another aspect of the present disclosure, a method for assisting with laparoscopic surgery using a robot arm comprising a proximal end, a distal end configured to be removably coupled to a surgical instrument, a plurality of links, and a plurality of joints between the proximal end and the distal end is provided. The method may include: applying, via a controller operatively coupled to the robot arm, an initial gravity compensation to the robot arm to compensate for gravity of the surgical instrument when the surgical instrument is coupled to the distal end of the robot arm based on an estimated instrument parameter associated with the surgical instrument; calculating, via the controller during application of the initial gravity compensation, a hold force required to maintain the distal end of the robot arm in a static position in a passive mode; and determining, via the controller, a calibrated instrument parameter for the surgical instrument based on the hold force, the calibrated instrument parameter selected to adjust the hold force required to maintain the distal end of the robot arm in the static position in the passive mode during application of an adjusted gravity compensation to the robot arm based on the calibrated instrument parameter. The estimated instrument parameter and the calibrated instrument parameter may comprise at least one of a mass or a center of mass associated with the surgical instrument.

The method further may include loading, via the controller, a calibration file associated with a known parameter of the surgical instrument, such that the calibration file may comprise the estimated instrument parameter. For example, the known parameter may comprise a diameter of an elongated shaft of the surgical instrument. In addition, the method may include: coupling the surgical instrument to the distal end of the robot arm via a coupler body removably coupled to the surgical instrument; and determining, via the controller, the known parameter based on the coupler body. Additionally, the method may include determining, via the controller, the known parameter via user input received by a user interface operatively coupled to the controller. Moreover, determining the calibrated instrument parameter based on the hold force may comprise determining the calibrated instrument parameter selected to adjust the hold force upon application of the adjusted gravity compensation within a predetermined range associated with a known parameter of the surgical instrument. The method further may include: calculating, via the controller, the adjusted gravity compensation of the surgical instrument based on the calibrated instrument parameter; and applying, via the controller, torque to one or more motorized joints of the plurality of joints of the robot arm to apply the adjusted gravity compensation to the robot arm to compensate for gravity of the surgical instrument.

In addition, the method may include: automatically switching, via the controller, to a co-manipulation mode responsive to determining that force applied at the robot arm due to force applied at the handle of the surgical instrument exceeds a predetermined force threshold; and permitting, via the controller, the robot arm to be freely moveable in the co-manipulation mode responsive to movement at the handle of the surgical instrument, while applying the adjusted gravity compensation to the robot arm to compensate for gravity of the surgical instrument in the co-manipulation mode. The method further may include: calculating, via the controller, the adjusted hold force to maintain the distal end of the robot arm in the static position in the passive mode upon application of the adjusted gravity compensation; establishing, via the controller, a baseline hold force based on the adjusted hold force after a predetermined time period upon initiation of the passive mode; and applying, via the controller, a predetermined constant breakaway force threshold to the robot arm based on the baseline hold force, wherein the controller does not maintain the distal end of the robot arm in the static position if the hold force exceeds the predetermined constant breakaway force threshold.

In accordance with another aspect of the present disclosure, a co-manipulation surgical system for operating a robot arm comprising a plurality of links, a plurality of joints, and a distal end configured to be removably coupled to a surgical instrument is provided. The co-manipulation surgical system may comprise at least one processor configured to: cause the robot arm to switch to a passive mode responsive to determining that movement of the robot arm due to movement at a handle of the surgical instrument is less than a predetermined amount for at least a predetermined dwell time period, the at least one processor configured to cause the robot arm to maintain a static position in the passive mode; apply gravity compensation to the robot arm to compensate for gravity of the surgical instrument; calculate, during application of the gravity compensation, a hold force required to maintain the distal end of the robot arm in the static position in the passive mode; establish a baseline hold force based on the hold force; and apply a breakaway force threshold to the robot arm based on the baseline hold force, the breakaway force threshold being a predetermined amount of force required to be applied to the robot arm to cause the robot arm to exit the passive mode. A magnitude of the breakaway force threshold may be equal in every direction relative to the baseline hold force. For example, a total amount of force required to be applied to the robot arm in a direction to cause the robot arm to exit the passive mode may be a sum of the baseline hold force and the breakaway force threshold in the direction.

The hold force required to maintain the distal end of the robot arm in the static position may be continuously calculated in the passive mode. Accordingly, the at least one processor may be configured to determine that the surgical instrument is in contact with one or more anatomical structures in the passive mode if the hold force gradually increases over time. In addition, the at least one processor may be configured to calculate the hold force required to maintain the distal end of the robot arm in the static position in the passive mode when one or more external forces are applied to the surgical instrument by one or more anatomical structures having an unknown mass. Moreover, the at least one processor may be configured to determine a force required to be applied to the distal end of the robot arm to move the distal end of the robot arm from a current position to the static position to calculate the hold force required to maintain the distal end of the robot arm in the static position in the passive mode. The at least one processor may further be configured to cause the robot arm to automatically switch to a co-manipulation mode responsive to determining that the hold force required to maintain the distal end of the robot arm in the static position exceeds the breakaway force threshold, such that the at least one processor may be configured to permit the robot arm to be freely moveable in the co-manipulation mode responsive to movement at the handle of the surgical instrument, while applying the gravity compensation to the robot arm to compensate for gravity of the surgical instrument in the co-manipulation mode.

The at least one processor may be configured to sense a force applied at the distal end of the robot arm to calculate the hold force required to maintain the distal end of the robot arm in the static position in the passive mode. For example, the at least one processor may be configured to measure current of a plurality of motors operatively coupled to at least some joints of the plurality of joints to sense the force applied at the distal end of the robot arm. Moreover, the at least one processor may be configured to apply torque to at least some joints of the plurality of joints of the robot arm to apply the gravity compensation to the robot arm to compensate for gravity of the surgical instrument.

In addition, the at least one processor may be configured to establish the baseline hold force after a predetermined time period upon initiation of the passive mode. Accordingly, the at least one processor may be configured to: apply a high breakaway force threshold to the robot arm during the predetermined time period, the high breakaway force threshold greater than the breakaway force threshold, such that the at least one processor may be configured to cause, if the hold force required to maintain the distal end of the robot arm in the static position exceeds the high breakaway force threshold during the predetermined time period, the robot arm to exit the passive mode. For example, the high breakaway force threshold may be selected to prevent inadvertent disengagement of the robot arm from passive mode in response to inadvertent forces applied at the distal end of the robot arm during the predetermined time period. The at least one processor may further be configured to: apply an initial breakaway force threshold to the robot arm during the predetermined time period; and apply, if force applied at the distal end of the robot arm exceeds the initial breakaway force threshold during the predetermined time period, a high breakaway force threshold during the predetermined time period, the high breakaway force threshold greater than the breakaway force threshold, such that the at least one processor may be configured to cause, if the hold force required to maintain the distal end of the robot arm in the static position exceeds the high breakaway force threshold during the predetermined time period, the robot arm to exit the passive mode.

Moreover, the at least one processor may be configured to: apply, if the hold force fluctuates after the predetermined time period upon initiation of the passive mode such that the baseline hold force cannot be established based on the calculated hold force, a default breakaway force threshold to the robot arm, such that the at least one processor may be configured to cause, if the hold force required to maintain the distal end of the robot arm in the static position exceeds the default breakaway force threshold, the robot arm to exit the passive mode. For example, the at least one processor may be configured to select the default breakaway force threshold from between a default high breakaway force threshold and a default low breakaway force threshold based on user input via a graphical user interface operatively coupled to the at least one processor. Additionally, the at least one processor may be configured to adjust at least one of the default high breakaway force threshold or the default low breakaway force threshold based on user input via the graphical user interface.

The at least one processor may further be configured to: apply the gravity compensation to the robot arm to compensate for gravity of the surgical instrument based on an estimated instrument parameter associated with the surgical instrument; determine a calibrated instrument parameter for the surgical instrument based on the hold force; and apply an adjusted gravity compensation to the robot arm based on the calibrated instrument parameter, such that the baseline hold force may be established based on the hold force required to maintain the distal end of the robot arm in the static position in the passive mode upon application of the adjusted gravity compensation to the robot arm. Moreover, the calibrated instrument parameter may be selected such that, during application of the adjusted gravity compensation, the hold force is adjusted within a predetermined range associated with a known parameter of the surgical instrument.

In accordance with another aspect of the present disclosure, a method for assisting with laparoscopic surgery using a robot arm comprising a proximal end, a distal end configured to be removably coupled a surgical instrument, a plurality of links, and a plurality of joints between the proximal end and the distal end is provided. The method may include: causing, via a controller operatively coupled to the robot arm, the robot arm to switch to a passive mode responsive to determining that movement of the robot arm due to movement at a handle of the surgical instrument is less than a predetermined amount for at least a predetermined dwell time period, the controller configured to cause the robot arm to maintain a static position in the passive mode; applying, via the controller, gravity compensation to the robot arm to compensate for gravity of the surgical instrument; calculating, via the controller during application of the gravity compensation, a hold force required to maintain the distal end of the robot arm in a static position in the passive mode; establishing, via the controller, a baseline hold force based on the hold force; and applying, via the controller, a breakaway force threshold to the robot arm based on the baseline hold force, the breakaway force threshold being a predetermined amount of force required to be applied to the robot arm to cause the robot arm to exit the passive mode. A magnitude of the breakaway force threshold may be equal in every direction relative to the baseline hold force, and a total amount of force required to be applied to the robot arm in a direction to cause the robot arm to exit the passive mode may be a sum of the baseline hold force and the breakaway force threshold in the direction.

Calculating the hold force required to maintain the distal end of the robot arm in the static position in the passive mode may comprise continuously calculating, via the controller, the hold force required to maintain the distal end of the robot arm in the static position in the passive mode. Moreover, the method may include determining, via the controller, that the surgical instrument is in contact with one or more anatomical structures in the passive mode if the hold force gradually increases over time. In addition, calculating the hold force required to maintain the distal end of the robot arm in the static position in the passive mode may comprise calculating, via the controller, the hold force required to maintain the distal end of the robot arm in the static position in the passive mode when one or more external forces are applied to the surgical instrument by one or more anatomical structures having an unknown mass. Additionally or alternatively, calculating the hold force required to maintain the distal end of the robot arm in the static position in the passive mode may comprise determining, via the controller, a force required to be applied to the distal end of the robot arm to move the distal end of the robot arm from a current position to the static position. The method further may include causing, via the controller, the robot arm to automatically switch to a co-manipulation mode responsive to determining that the hold force required to maintain the distal end of the robot arm in the static position exceeds the breakaway force threshold, such that the robot arm may be permitted to be freely moveable in the co-manipulation mode responsive to movement at the handle of the surgical instrument, while the gravity compensation is applied to the robot arm to compensate for gravity of the surgical instrument in the co-manipulation mode.

Moreover, calculating the hold force required to maintain the distal end of the robot arm in the static position in the passive mode may comprise sensing, via the controller, a force applied at the distal end of the robot arm. For example, sensing the force applied at the distal end of the robot arm may comprise measuring, via the controller, current of a plurality of motors operatively coupled to at least some joints of the plurality of joints. Additionally, applying gravity compensation to the robot arm to compensate for gravity of the surgical instrument may comprise applying, via the controller, torque to at least some joints of the plurality of joints of the robot arm. Establishing the baseline hold force based on the hold force may comprise establishing, via the controller, the baseline hold force after a predetermined time period upon initiation of the passive mode. Accordingly, the method further may include: applying, via the controller, a high breakaway force threshold to the robot arm during the predetermined time period, the high breakaway force threshold greater than the breakaway force threshold; and causing, via the controller if the hold force required to maintain the distal end of the robot arm in the static position exceeds the high breakaway force threshold during the predetermined time period, the robot arm to exit the passive mode. For example, the high breakaway force threshold may be selected to prevent inadvertent disengagement of the robot arm from passive mode in response to inadvertent forces applied at the distal end of the robot arm during the predetermined time period.

The method further may include: applying, via the controller, an initial breakaway force threshold to the robot arm during the predetermined time period; applying, via the controller if force applied at the distal end of the robot arm exceeds the initial breakaway force threshold during the predetermined time period, a high breakaway force threshold during the predetermined time period, the high breakaway force threshold greater than the breakaway force threshold; and causing, via the controller if the hold force required to maintain the distal end of the robot arm in the static position exceeds the high breakaway force threshold during the predetermined time period, the robot arm to exit the passive mode. The method further may include: applying, via the controller, if the hold force fluctuates after the predetermined time period upon initiation of the passive mode such that the baseline hold force cannot be established based on the calculated hold force, a default breakaway force threshold to the robot arm; and causing, via the controller if the hold force required to maintain the distal end of the robot arm in the static position exceeds the default breakaway force threshold, the robot arm to exit the passive mode. In addition, the method may include selecting, via the controller, the default breakaway force threshold from between a default high breakaway force threshold and a default low breakaway force threshold based on user input via a graphical user interface operatively coupled to the controller. The method further may include adjusting, via the controller, at least one of the default high breakaway force threshold or the default low breakaway force threshold based on user input via the graphical user interface.

Moreover, applying gravity compensation to the robot arm to compensate for gravity of the surgical instrument may comprise applying, via the controller, the gravity compensation to the robot arm to compensate for gravity of the surgical instrument based on an estimated instrument parameter associated with the surgical instrument. Accordingly, the method further may include: determining, via the controller, a calibrated instrument parameter for the surgical instrument based on the hold force; and applying, via the controller, an adjusted gravity compensation to the robot arm based on the calibrated instrument parameter, such that establishing the baseline hold force based on the hold force may comprise establishing, via the controller, the baseline hold force based on the hold force required to maintain the distal end of the robot arm in the static position in the passive mode upon application of the adjusted gravity compensation to the robot arm. For example, the calibrated instrument parameter may be selected such that, during application of the adjusted gravity compensation, the hold force is adjusted within a predetermined range associated with a known parameter of the surgical instrument.

In accordance with another aspect of the present disclosure, another co-manipulation surgical system to assist with laparoscopic surgery performed using a surgical instrument having a handle, an operating end, and an elongated shaft therebetween is provided. The system may include a robot arm comprising a proximal end, a distal end configured to be removably coupled to the surgical instrument, a plurality of links, and a plurality of joints, and a controller operatively coupled to the robot arm and configured to permit the robot arm to be freely moveable responsive to movement at the handle of the surgical instrument for performing the surgical procedure using the surgical instrument. The controller may be programmed to: identify a type of the surgical instrument coupled to the distal end of the robot arm; apply a first impedance to the robot arm to account for weight of the surgical instrument and the robot arm; and apply a second impedance to the robot arm based on the type of the surgical instrument to adjust viscosity at the distal end of the robot arm to thereby guide a movement of the surgical instrument by the user during a predetermined phase of the surgical procedure.

For example, the identified type of the surgical instrument may comprise a suturing device, and the predetermined phase of the surgical procedure may comprise a suturing phase, such that the second impedance may be sufficient to provide more viscous control of the suturing device during the suturing phase of the surgical procedure. Additionally, or alternatively, the identified type of the surgical instrument may comprise a stapling device, and the predetermined phase of the surgical procedure may comprise a stapling phase, such that the second impedance may be sufficient to provide stiff grounding to facilitate force application of the stapling device during the stapling phase of the surgical procedure. The controller may further be configured to identify the predetermined phase of the surgical procedure based on the type of the surgical instrument. Moreover, the type of the surgical instrument may be selected from a list comprising at least one of a wristed instrument, a stapling device, a dissection device, a suturing device, a retraction device, a tissue removal device, or a clip applier device. The controller may be configured to apply the second impedance to the robot arm based on the type of the surgical instrument to adjust viscosity at the distal end of the robot arm to thereby guide the movement of the surgical instrument by the user during the predetermined phase of the surgical procedure without actively causing movement of the robot arm.

In accordance with another aspect of the present disclosure, a computer implemented system for providing image registration to a robot arm comprising a plurality of links, a plurality of joints, and a distal end configured to be removably coupled to a laparoscope having a rotatable camera sensor module is provided. The system may comprise at least one processor configured to: retrieve a plurality of images from the laparoscope during movement of a field of view of the laparoscope; compute motion of individual pixels between consecutive images of the plurality of images via a computer vision technique, the motion of individual pixels indicative of image motion; calculate an average of the motion of individual pixels in an x and y direction of the plurality of images to obtain an image motion direction; and compute an angular offset between the camera sensor module and the distal end of the robot arm based on the image motion direction.

The at least one processor further may be configured to: synchronize the image motion and movement of the distal end of the robot arm associated with the movement of the field of view of the laparoscope; and compare the image motion direction with the movement of the distal end of the robot arm to compute the angular offset between the camera sensor module and the distal end of the robot arm. Moreover, the at least one processor may be configured to cause, in a foreground mode, the robot arm to move the laparoscope along a predetermined trajectory, such that the image motion may be synchronized with movement of the distal end of the robot arm associated with movement of the laparoscope along the predetermined trajectory. Additionally, or alternatively, in a background mode, the image motion may be synchronized with movement of the distal end of the robot arm responsive to movement of the field of view of the laparoscope by a user. The at least one processor may be configured to retrieve data indicative of the movement of the distal end of the robot arm via one or more sensors operatively coupled to at least some joints of the plurality of joints of the robot arm.

Moreover, the at least one processor may be configured to validate the image motion direction. For example, the at least one processor may be configured to: calculate a norm of a vector of the image motion direction to determine a magnitude of the image motion; and compare the magnitude of the image motion with a magnitude threshold. Accordingly, the image motion direction may be validated if the magnitude of the image motion exceeds the magnitude threshold. Additionally, or alternatively, the at least one processor may be configured to: calculate a percentage of image pixels that moved between consecutive images based on the motion of individual pixels; and compare the percentage with a percentage threshold. Accordingly, the image motion direction may be validated if the percentage exceeds the percentage threshold. The at least one processor may be configured to determine whether the image motion is due to at least one of movement of the field of view of the laparoscope or local motion of one or more tools or tissue within the plurality of images based on the comparison of the percentage with the percentage threshold. Additionally, or alternatively, the at least one processor may be configured to: calculate a relative angle between each motion of the individual pixels and the image motion direction to determine whether each motion of the individual pixels are in agreement with the image motion direction; and compare a percentage of individual pixels motion that are in agreement with the image motion direction with an agreement threshold. Accordingly, the image motion direction may be validated if the percentage exceeds the agreement threshold.

The at least one processor further may be configured to: cause the robot arm to move the laparoscope along a predetermined axial trajectory; compare the image motion direction with a direction threshold; and determine whether the laparoscope has a flat or angled tip based on the comparison of the image motion direction with the direction threshold. In some embodiments, movement of the field of view of the laparoscope may be due to zooming of the camera sensor module, such that the at least one processor may be configured to: compare the image motion direction with a direction threshold; and determine whether the laparoscope has a flat or angled tip based on the comparison of the image motion direction with the direction threshold. The controller further may be configured to cause the robot arm to automatically switch to a co-manipulation mode responsive to determining that force applied at the robot arm due to force applied at the laparoscope exceeds a predetermined threshold. Accordingly, the controller may be configured to permit the robot arm to be freely moveable in the co-manipulation mode responsive to movement at the laparoscope, while applying an impedance to the robot arm in the co-manipulation mode to account for weight of the laparoscope and the robot arm.

In accordance with another aspect of the present disclosure, a system for robotic surgery is provided. The system may include a robot arm comprising a proximal end operatively coupled to a base of the robot arm, a distal end, a plurality of links, and a plurality of joints between the proximal end and the distal end, and the robot arm may be configured to be positioned adjacent to a bed for holding a patient during surgery. The system further may include a platform coupled to the base of the robot arm, and the platform may comprise a stage assembly configured to independently move the base of the robot arm in at least two degrees of freedom relative to the platform. In addition, the system may include a graphical user interface comprising a plurality of predetermined, selectable surgical procedures, and a controller operatively coupled to the robot arm. The controller may be programmed to: during a surgery setup phase, automatically position the robot arm in a first position specific to a first surgical procedure relative to the bed in response to selection of the first surgical procedure of the plurality of predetermined, selectable surgical procedures; and during the surgery setup phase, automatically position the robot arm in a second position specific to a second surgical procedure relative to the bed in response to selection of the second surgical procedure of the plurality of predetermined, selectable surgical procedures. For example, the first position specific to the first surgical procedure may be different than the second position specific to the second surgical procedure.

Moreover, the controller may be configured to, upon selection of the cholecystectomy: cause a shoulder link of the plurality of links of the robot arm to rotate in a leftward direction relative to the platform; and cause the stage assembly to move the base of the robot arm in a downward direction of a first degree of freedom of the at least two degrees of freedom and in an outward direction of a second degree of freedom of the at least two degrees of freedom. In addition, the system may include a second robot arm, such that the controller may be configured to, upon selection of the cholecystectomy, cause a stage assembly of the second robot arm to move a base of the second robot arm in an upward direction of a first degree of freedom of at least two degrees of freedom and in an inward direction of a second degree of freedom of the at least two degrees of freedom. At least one of the first or second surgical procedures may comprise a cholecystectomy, gastric sleeve, hiatal hernia repair, Nissen fundoplication, inguinal hernia repair (TEP), right, left, and/or complete colectomy, gastric bypass, sigmoid colectomy, umbilical hernia repair, or incisional hernia repair.

In accordance with another aspect of the present disclosure, a co-manipulation surgical system to assist with laparoscopic surgery performed using a surgical instrument is provided. The system may include a plurality of robot arms, each robot arm comprising a plurality of links, a plurality of joints, a proximal region operatively coupled to a base, and a distal region configured to be removably coupled to the surgical instrument. The system further may include a platform coupled to the base of each robot arm, wherein, in a surgical mode, each of the robot arms may be configured to extend away from the platform and towards a surgical site, and a controller configured to, upon actuation of a stow mode, cause each of the robot arms to transition to a retracted stow configuration via the robot arm's respective plurality of links and joints and rotate about the robot arm's respective base such that each of the robot arms is within a footprint of the platform in the retracted stow configuration. For example, in the retracted stow configuration, each of the robot arms may be entirely within the footprint of the platform.

Upon actuation of the stow mode, the controller may cause a first robot arm of the plurality of robot arms to rotate in a first direction about its base, and may cause a second robot arm of the plurality of robot arms to rotate in a second direction about its base, the second direction opposite to the first direction. Alternatively, the second direction may be the same as the first direction. In the retracted stow configuration, a first robot arm of the plurality of robot arms may have a same configuration and orientation as a second robot arm of the plurality of robot arms relative to the platform. In addition, in the retracted stow configuration, each of the robot arms may extend in a direction towards a rear of the platform. Upon actuation of the stow mode, the controller may cause at least one robot arm of the plurality of robot arms to move to a position via the at least one robot arm's respective plurality of links and joints, such that, upon rotation of the at least one robot arm about the at least one robot arm's respective base, collision between the at least one robot arm and the platform is avoided.

The platform may comprise a stage assembly configured to independently move the base of each robot arm in at least two degrees of freedom relative to the platform. Accordingly, upon actuation of the stow mode, the controller may cause the stage assembly to move the base of each robot arm in an inward direction along a first degree of freedom of the at least two degrees of freedom, such that, upon rotation of each of the robot arms about the robot arm's respective base, each of the robot arms is within the footprint of the platform in the retracted stow configuration. In addition, upon actuation of the stow mode, the controller may cause the stage assembly to move the base of each robot arm in a downward direction along a second degree of freedom of the at least two degrees of freedom, such that the robot arms have a minimal height relative to the platform for transportation and/or storage of the co-manipulation surgical system in the retracted stow configuration. Moreover, upon actuation of the stow mode, the controller may cause the stage assembly to move the base of each robot arm in a downward direction along a second degree of freedom of the at least two degrees of freedom, such that the robot arms have a minimal height relative to the platform for transportation and/or storage of the co-manipulation surgical system in the retracted stow configuration. Additionally, upon actuation of the stow mode, the controller may cause the stage assembly to move the base of at least one robot arm in an outward direction along a first degree of freedom of the at least two degrees of freedom and/or an upward direction along a second degree of freedom of the at least two degrees of freedom, such that, upon rotation of at least one robot arm of the plurality of robot arms about the at least one robot arm's respective base, collision between the at least one robot arm and the platform is avoided. In some embodiments, upon actuation of the stow mode, the controller may cause the stage assembly to rotate the base of each robot arm in a direction towards one another along a horizontal plane relative to the platform, such that, upon rotation of each of the robot arms about the robot arm's respective base, each of the robot arms is within the footprint of the platform in the retracted stow configuration.

The system further may include a graphical user interface operatively coupled to the controller. The graphical user interface may be configured to display a stow mode actuator configured to be actuated by a user to actuate the stow mode. Moreover, upon actuation of a compact mode, the controller may cause each of the robot arms to transition to a semi-retracted configuration via the robot arm's respective plurality of links and joints and rotate about the robot arm's respective base such that each of the robot arms extend away from the platform to facilitate transportation of the co-manipulation surgical system, wherein the semi-retracted configuration is less retracted than the retracted stow configuration of stow mode. In addition, upon actuation of a drape mode, the controller may cause each of the robot arms to transition to an extended configuration via the robot arm's respective plurality of links and joints and rotate about the robot arm's respective base such that each of the robot arms extend away from the platform to facilitate draping of the robot arms. In the extended configuration, distal links of the plurality of links of each robot arm may be substantially parallel to the ground.

In accordance with another aspect of the present disclosure, a method for assisting with laparoscopic surgery is provided. The method may include providing a plurality of robot arms, each robot arm comprising a plurality of links, a plurality of joints, a proximal region operatively coupled to a base, and a distal region configured to be removably coupled to a surgical instrument, each base coupled to a platform such that, in a surgical mode, each of the robot arms may be configured to extend away from the platform and towards a surgical site; and automatically causing, upon actuation of a stow mode, each of the robot arms to transition to a retracted stow configuration via the robot arm's respective plurality of links and joints and rotate about the robot arm's respective base such that each of the robot arms is within a footprint of the platform in the retracted stow configuration. Automatically causing each of the robot arms to transition to the retracted stow configuration may comprise automatically rotating a first robot arm of the plurality of robot arms in a first direction about its base, and automatically rotating a second robot arm of the plurality of robot arms in a second direction about its base, the second direction opposite to the first direction. Alternatively, the second direction may be the same as the first direction. In addition, automatically causing each of the robot arms to transition to the retracted stow configuration may comprise automatically causing at least one robot arm of the plurality of robot arms to move to a position via the at least one robot arm's respective plurality of links and joints, such that, upon rotation of the at least one robot arm about the at least one robot arm's respective base, collision between the at least one robot arm and the platform is avoided.

The platform may comprise a stage assembly configured to independently move the base of each robot arm in at least two degrees of freedom relative to the platform. Accordingly, automatically causing each of the robot arms to transition to the retracted stow configuration may comprise automatically causing the stage assembly to move the base of each robot arm in an inward direction along a first degree of freedom of the at least two degrees of freedom, such that, upon rotation of each of the robot arms about the robot arm's respective base, each of the robot arms is within the footprint of the platform in the retracted stow configuration. Automatically causing each of the robot arms to transition to the retracted stow configuration may comprise automatically causing the stage assembly to move the base of each robot arm in a downward direction along a second degree of freedom of the at least two degrees of freedom, such that the robot arms have a minimal height relative to the platform for transportation and/or storage in the retracted stow configuration. In addition, automatically causing each of the robot arms to transition to the retracted stow configuration may comprise automatically causing the stage assembly to move the base of at least one robot arm in an outward direction along a first degree of freedom of the at least two degrees of freedom and/or an upward direction along a second degree of freedom of the at least two degrees of freedom, such that, upon rotation of at least one robot arm of the plurality of robot arms about the at least one robot arm's respective base, collision between the at least one robot arm and the platform is avoided.

The method further may include displaying, via a graphical user interface, a stow mode actuator configured to be actuated by a user to actuate the stow mode. Moreover, the method may include automatically causing, upon actuation of a compact mode, each of the robot arms to transition to a semi-retracted configuration via the robot arm's respective plurality of links and joints and rotate about the robot arm's respective base such that each of the robot arms extend away from the platform to facilitate transportation of the platform, wherein the semi-retracted configuration is less retracted than the retracted stow configuration of stow mode. In addition, the method may include automatically causing, upon actuation of a drape mode, each of the robot arms to transition to an extended configuration via the robot arm's respective plurality of links and joints and rotate about the robot arm's respective base such that each of the robot arms extend away from the platform to facilitate draping of the robot arms. In the extended configuration, distal links of the plurality of links of each robot arm may be substantially parallel to the ground. The method further may include covering the plurality of robot arms with a sterile drape in the extended configuration.

In accordance with another aspect of the present disclosure, a co-manipulation surgical system to assist with laparoscopic surgery performed using a surgical instrument is provided. The co-manipulation surgical system may comprise a robot arm comprising a proximal region having a base, a plurality of links, an elbow joint, a shoulder joint coupled to the base, and a distal region having a distal end configured to be removably coupled to the surgical instrument, and a platform coupled to the base of the robot arm, the platform configured to be moveable on a floor. Accordingly, in a drape mode, a link of the plurality of links between the elbow joint and the shoulder joint may be configured to extend away from the base at a first angle and a link of the plurality of links distal to the elbow joint may be configured to extend away from the base at a second angle so as to be more aligned with the floor, to thereby facilitate draping of the robot arm. For example, the first angle may be selected such that the link between the elbow joint and the shoulder joint is configured to be substantially vertical in the drape mode. In addition, the second angle may be selected such that the link distal to the elbow joint is configured to be substantially horizontal in the drape mode. Additionally or alternatively, the second angle may be selected such that the link distal to the elbow joint is configured to be substantially parallel with the floor in the drape mode.

The platform may comprise a plurality of wheels configured to permit mobility of the platform on the floor. In addition, the robot arm may not be teleoperated via user input received at a remote surgeon console. The co-manipulation surgical system further may comprise a controller operatively coupled to the robot arm. The controller may be configured to, upon actuation of the drape mode, automatically cause the link between the elbow joint and the shoulder joint to extend away from the base at the first angle and the link distal to the elbow joint to extend away from the base at the second angle. For example, upon actuation of the drape mode, the controller may automatically cause the robot arm to rotate about the base such that the link between the elbow joint and the shoulder joint extends away from the platform at the first angle and the link distal to the elbow joint extends away from the platform at the second angle. The controller may further be configured to apply a virtual haptic boundary about the robot arm such that, when the robot arm is within the virtual haptic boundary, the controller applies a high level of impedance to the robot arm such that movement of the robot arm is more viscous within the virtual haptic boundary. Additionally or alternatively, the controller may further be configured to apply a temporary localized virtual haptic boundary at the distal region of the robot arm in the drape mode such that movement of the robot arm is more viscous, thereby stabilizing the robot arm in the drape mode.

The co-manipulation surgical system further may comprise a coupler configured to be removably coupled to the distal end of the robot arm after application of a sterile drape over the robot arm, the coupler configured to be removably coupled to the surgical instrument, e.g., to thereby removably couple the surgical instrument to the distal end of the robot arm. Accordingly, the controller may further be configured to remove the temporary localized virtual haptic boundary at the distal region of the robot arm upon detection of the coupler being removably coupled to the distal end of the robot arm. Moreover, the platform may be configured to move the base of the robot arm in at least two degrees of freedom relative to the floor, such that, upon actuation of the drape mode, the controller may automatically cause the platform to move the base of the robot arm in at least one of the at least two degrees of freedom relative to the floor to align the link distal to the elbow joint with a height of a user to facilitate draping of the robot arm by the user. Accordingly, the controller may further be configured to store data indicative of the height of the user in a user-specific profile, and execute the user-specific profile responsive to user input received at a user interface operatively coupled to the controller. Additionally or alternatively, the co-manipulation surgical system further may comprise an optical sensor operatively coupled to the controller and configured to collect depth data, such that the controller may be configured to determine the height of the user based on depth data collected by the optical sensor.

In some embodiments, the co-manipulation surgical system further may comprise a second robot arm having a second base coupled to the platform, such that, in the drape mode, a plurality of links of the second robot arm may be parallel with the corresponding plurality of links of the robot arm. The co-manipulation surgical system further may comprise a sterile drape having a first portion sized and shaped to cover at least the robot arm and a second portion sized and shaped to cover at least the second robot arm. For example, the first and second portions of the sterile drape may each comprise seal end portions configured to contact distal ends of the respective robot arms, such that the robot arms are fully enclosed within the sterile drape. Moreover, a proximal end of the sterile drape may comprise an opening sized and shaped to receive at least a portion of the platform therethrough. The proximal end of the sterile drape may comprise an elastic band along the opening configured to facilitate wrapping of the sterile drape over the at least the portion of the platform. In addition, the sterile drape may comprise one or more straps configured to secure the first and second portions of the sterile drape to the respective robot arm. Further, the sterile drape may comprise one or more rigid guides configured to be grabbed by a user to guide the sterile drape over the robot arms. The co-manipulation surgical system further may comprise first and second couplers configured to be removably coupled to the distal ends of the respective robot arms after application of the sterile drape over the robot arms, the first and second couplers each configured to be removably coupled to a surgical instrument. Accordingly, the controller may further be configured to apply a temporary localized virtual haptic boundary at the distal regions of the robot arms in the drape mode such that movement of the robot arms are more viscous, thereby stabilizing the robot arms in the drape mode, and remove the temporary localized virtual haptic boundary at the distal regions of the robot arms upon detection that both the first and second couplers are removably coupled to the distal ends of the robot arms.

In accordance with another aspect of the present disclosure, a method for assisting with laparoscopic surgery is provided. The method may comprise: providing a robot arm comprising a proximal region having a base coupled to a platform configured to be moveable on a floor, a plurality of links, an elbow joint, a shoulder joint coupled to the base, and a distal region having a distal end configured to be removably coupled to the surgical instrument; and transitioning the robot arm to a drape mode where a link of the plurality of links between the elbow joint and the shoulder joint extends away from the base at a first angle and a link of the plurality of links distal to the elbow joint extends away from the base at a second angle so as to be more aligned with the floor, to thereby facilitate draping of the robot arm. For example, when the link distal to the elbow joint extends away from the base at the second angle, the link distal to the elbow joint may be substantially horizontal.

Transitioning the robot arm to the drape mode may comprise automatically causing, upon actuation of the drape mode via a controller operatively coupled to the robot arm, the link between the elbow joint and the shoulder joint to extend away from the base at the first angle and the link distal to the elbow joint to extend away from the base at the second angle. Moreover, transitioning the robot arm to the drape mode further may comprise automatically causing, upon actuation of the drape mode via the controller, the robot arm to rotate about the base such that the link between the elbow joint and the shoulder joint extends away from the platform at the first angle and the link distal to the elbow joint extends away from the platform at the second angle. The method further may comprise applying, via the controller, a temporary localized virtual haptic boundary at the distal region of the robot arm in the drape mode such that movement of the robot arm is more viscous, thereby stabilizing the robot arm in the drape mode. Additionally, the method may comprise: applying a sterile drape over the robot arm; removably coupling a coupler to the distal end of the robot arm such that the sterile drape is disposed between the sterile drape and the distal end of the robot arm; and removably coupling the surgical instrument to the coupler. Moreover, the method may comprise: providing a second robot arm having a second base coupled to the platform; and transitioning the second robot arm to the drape mode where a plurality of links of the second robot arm are parallel with the corresponding plurality of links of the robot arm in the drape mode.

BRIEF DESCRIPTION OF THE DRAWINGS

FIGS. 7A-7C illustrate an exemplary coupler body of the surgical instrument coupling mechanism of FIGS. 5A and 5B.

FIGS. 7D-7H illustrate an alternative exemplary surgical instrument coupling mechanism constructed in accordance with the principles of the present disclosure.

FIG. 8A is a cross-sectional view of the coupler body of FIG. 7A when the coupler body is detached from the coupler interface.

FIG. 8B is a cross-sectional view of the surgical instrument coupling mechanism of FIG. 5A when the coupler body is coupled to the coupler interface.

FIG. 16 is a table of example values related to some arrangements of a passive mode of the robot arm in accordance with the principles of the present disclosure.

FIGS. 40A-40C illustrate an exemplary graphical user interface of the co-manipulation surgical system displaying a virtual map in accordance with the principles of the present disclosure.

FIG. 44 illustrates movement of the shoulder portion and the stages of the co-manipulation surgical system for the preset stow configuration of FIGS. 43A-43D.

DETAILED DESCRIPTION

Figure 1A:
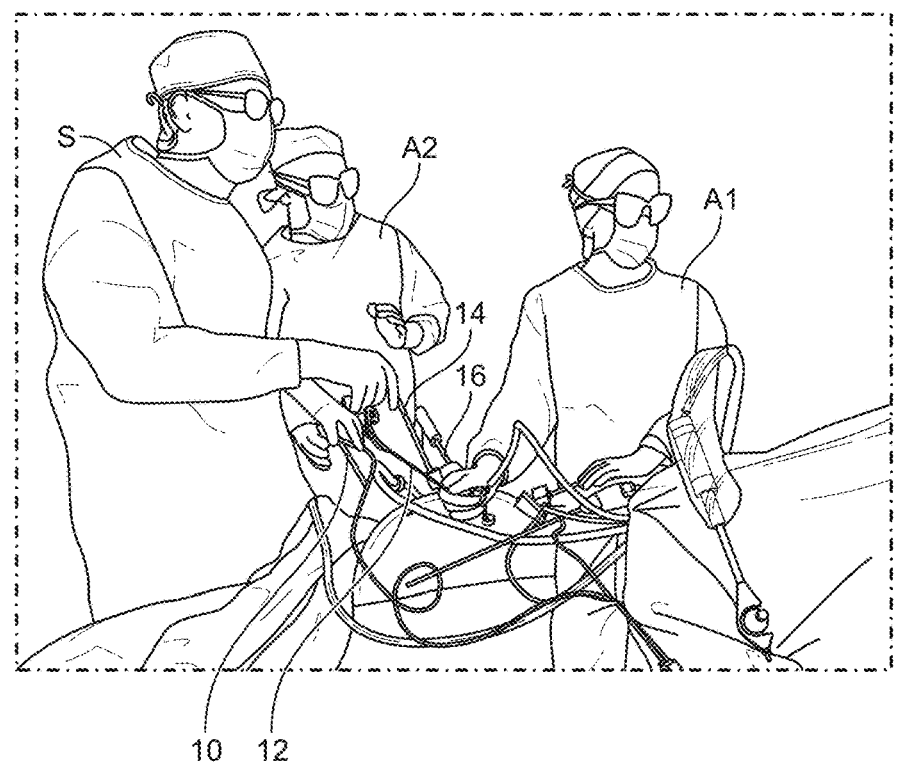
FIGS. 1A and 1B illustrate a traditional laparoscopic procedure performed by a surgeon and one or more assistants.

Disclosed herein are co-manipulation surgical robot systems for assisting an operator, e.g., a surgeon, in performing a surgical procedure, e.g., a laparoscopic procedure, and methods of use thereof. Currently, laparoscopic procedures typically require a surgeon and one or more assistants. For example, as shown in FIG. 1A, during a laparoscopic procedure assistant A1 may be required to hold retractor device 12 to expose tissue for surgeon S, while another assistant A2 may be required to hold laparoscope device 10 to provide a field of view of the surgical space within the patient to surgeon S via a display (not shown) during the procedure. As shown in FIG. 1A, assistant A2 may be required to hold laparoscope device 10 in an impractical position, e.g., from between the arms of surgeon S while the surgeon actively operates additional surgical instruments, e.g., surgical instruments 14 and 16. As further shown in FIG. 1A, surgeon S may need to let go of surgical instrument 16 in order to guide/reposition laparoscope device 10 held by assistant A2 in order to achieve the field of view desired by the surgeon.

Figure 1B:
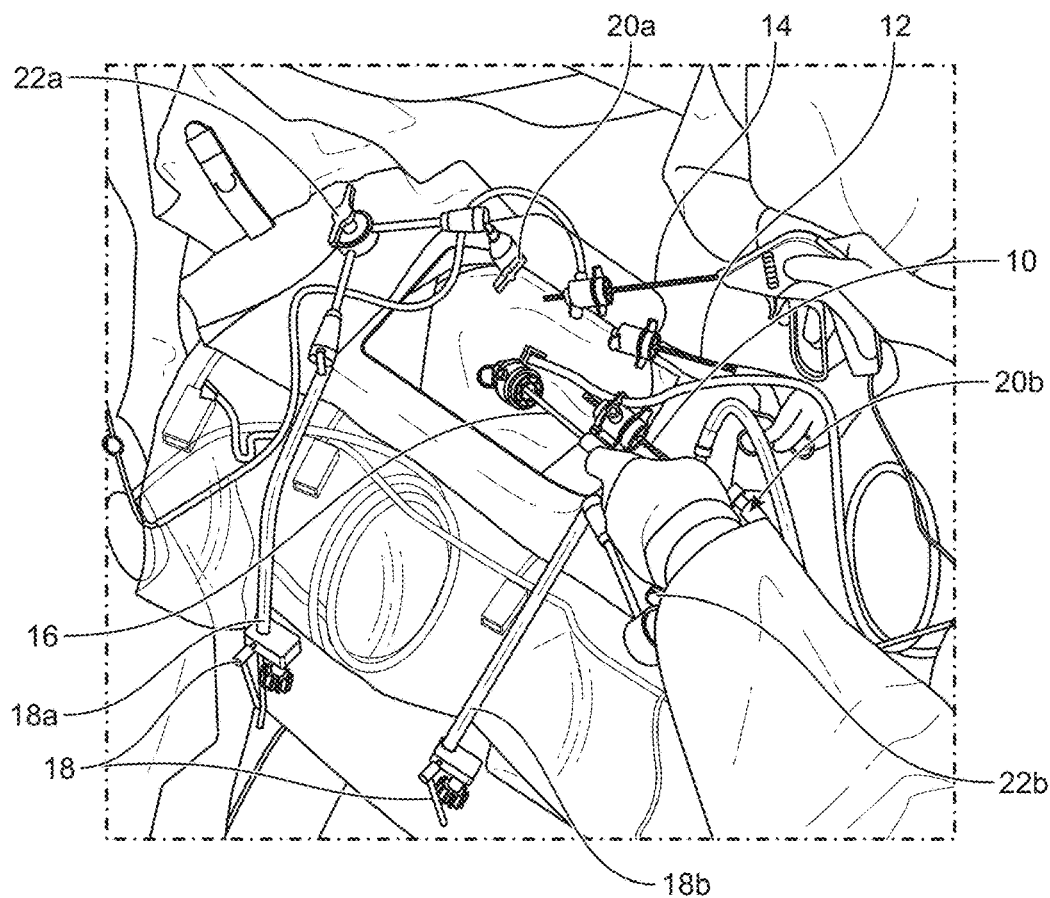

As shown in FIG. 1B, rail-mounted orthopedic retractors 18 may be used to hold one or more surgical instruments in position during the laparoscopic procedure, in attempt to free hands of the surgeon and/or assistant for other tasks, as well as for stability. As shown in FIG. 1B, first rail-mounted orthopedic retractor 18a may include retractor end 20a for engaging with and holding laparoscope device 10 in position upon actuation of lock 22a. For example, lock 22a may be disengaged such that retractor 18a may be manually positioned at a desired location relative to the patient, and re-engaged to lock retractor 18a, and accordingly laparoscopic device 10 coupled thereto, in the desired position. As shown in FIG. 1B, second rail-mounted orthopedic retractor 18b having retractor end 20b may be used during the procedure to engage with and hold another surgical instrument in position upon actuation of lock 22b. Thus, retractors 18a and 18b require extensive manual interaction with locks 22a and 22b, and with retractors 18a and 18b themselves, to reposition and lock the respective tools in position.

The co-manipulation surgical robot systems described herein provide superior control and stability such that the surgeon and/or assistant may seamlessly position various off-the-shelf surgical instruments as needed, thus avoiding the workflow limitations inherent to both human and mechanical solutions. For example, the robot arms of the co-manipulation surgical robot system may provide surgical assistance by holding a first surgical instrument, e.g., a laparoscope, via a first robot arm, and a second surgical instrument, e.g., a retractor, via a second robot arm, stable throughout the procedure to provide an optimum view of the surgical site and reduce the variability of force applied by the surgical instruments to the body wall at the trocar point. As will be understood by a person having ordinary skill in the art, the robots arms of the co-manipulation surgical robot systems described herein may hold any surgical instrument, preferably having a long and thin instrument shaft, used for surgical procedures such as laparoscopic procedures including, e.g., endoscopes/laparoscopes, retractors, graspers, surgical scissors, needle holders, needle drivers, clamps, suturing instruments, cautery tools, staplers, clip appliers, hooks, etc.

The co-manipulation surgical robot system further allows the surgeon to easily maneuver both tools when necessary, providing superior control and stability over the procedure and overall safety. Any implementations of the systems described herein enable a surgeon to directly co-manipulate instruments while remaining sterile at the patient bedside. For example, the system may include two robot arms that may be used by the surgeon to hold both a laparoscope and a retractor. During a surgical procedure, the system may seamlessly reposition either instrument to provide optimal visualization and exposure of the surgical field. Both instruments may be directly coupled to the robot arms of the system and the system may constantly monitor and record the position of the two instruments and/or the two robot arms throughout the procedure. Moreover, the system may record information such as the position and orientation of surgical instruments attached to the robot arms, sensor readings related to force(s) applied at proximal and distal ends of the surgical instruments attached to robot arms, force required to hold each instrument in position, endoscopic video streams, algorithm parameters, operating room 3D stream captured with an optical scanning device, including, e.g., position(s) of surgical entry port(s), position and movements of the surgeon's hands, surgical instrument(s) position and orientation, whether or not attached to robot arms, patient position, and patient table orientation and height.

Such data may be used to develop a database of historical data that may be used to develop the algorithms used in some implementations to control one or more aspects of an operation of the system. In addition, such data may be used during a procedure to control of one or more aspects of an operation of the system per one or more algorithms of the system. For example, the data may be used to assess a level of fatigue of a user of the system as described in U.S. Pat. No. 11,504,197, the entire contents of which is incorporated herein by reference.

As the operator manipulates a robot arm of the co-manipulation surgical robot system by applying movement to the surgical instrument coupled to the robot arm, the system may automatically transition the robot arm between various operational modes upon determination of predefined conditions. For example, the system may transition the robot arm to a passive mode responsive to determining that movement of the robot arm due to movement at the handle of the surgical instrument is less than a predetermined amount for at least a predetermined dwell time period, such that in the passive mode, the robot arm maintains a static position, e.g., to prevent damage to the equipment and/or injury to the patient. Additionally, the system may transition the robot arm to a co-manipulation mode responsive to determining that force applied at the robot arm due to force applied at the handle of the surgical instrument exceeds a predetermined threshold, such that in the co-manipulation mode, the robot arm is permitted to be freely moveable responsive to movement at the handle of the surgical instrument for performing laparoscopic surgery using the surgical instrument, while a first impedance is applied to the robot arm in the co-manipulation mode to account for weight of the surgical instrument and the robot arm. Moreover, the system may transition the robot arm to a haptic mode responsive to determining that at least a portion of the robot arm is outside a predefined haptic barrier, such that in the haptic mode, a second impedance greater than the first impedance is applied to the robot arm, thereby making movement of the robot arm responsive to movement at the handle of the surgical instrument more viscous in the haptic mode than in the co-manipulation mode. The system further may transition the robot arm to a robotic assist mode responsive to detecting various conditions that warrant automated movement of the robot arm to guide the surgical instrument attached thereto, e.g., along a planned trajectory or to avoid a collision with another object or person in the surgical space. For example, in an instrument centering mode of the robotic assist mode, a robot arm coupled to a laparoscope may automatically move the laparoscope along a planned trajectory to track an identified surgical instrument and maintain the instrument within the field of view of the laparoscope to provide assisted instrument centering. As described in further detail below, the system further may transition the robot arm to one or more setup modes for manual and/or automatic reconfiguration of the robot arm to an optimized position for a given surgical procedure.

Figure 2A:
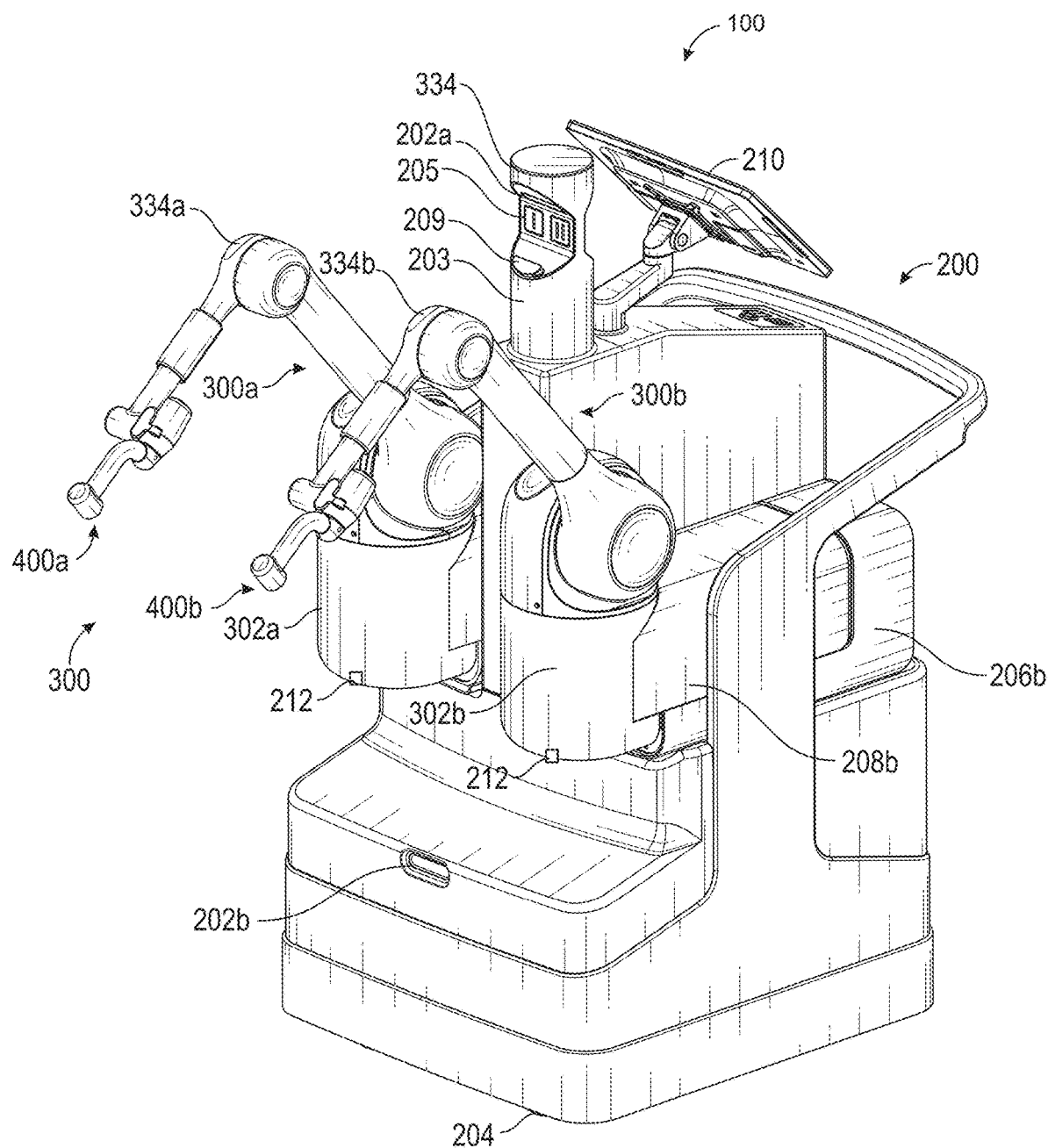
FIGS. 2A and 2B illustrate an exemplary co-manipulation surgical system constructed in accordance with the principles of the present disclosure.
Figure 2B:
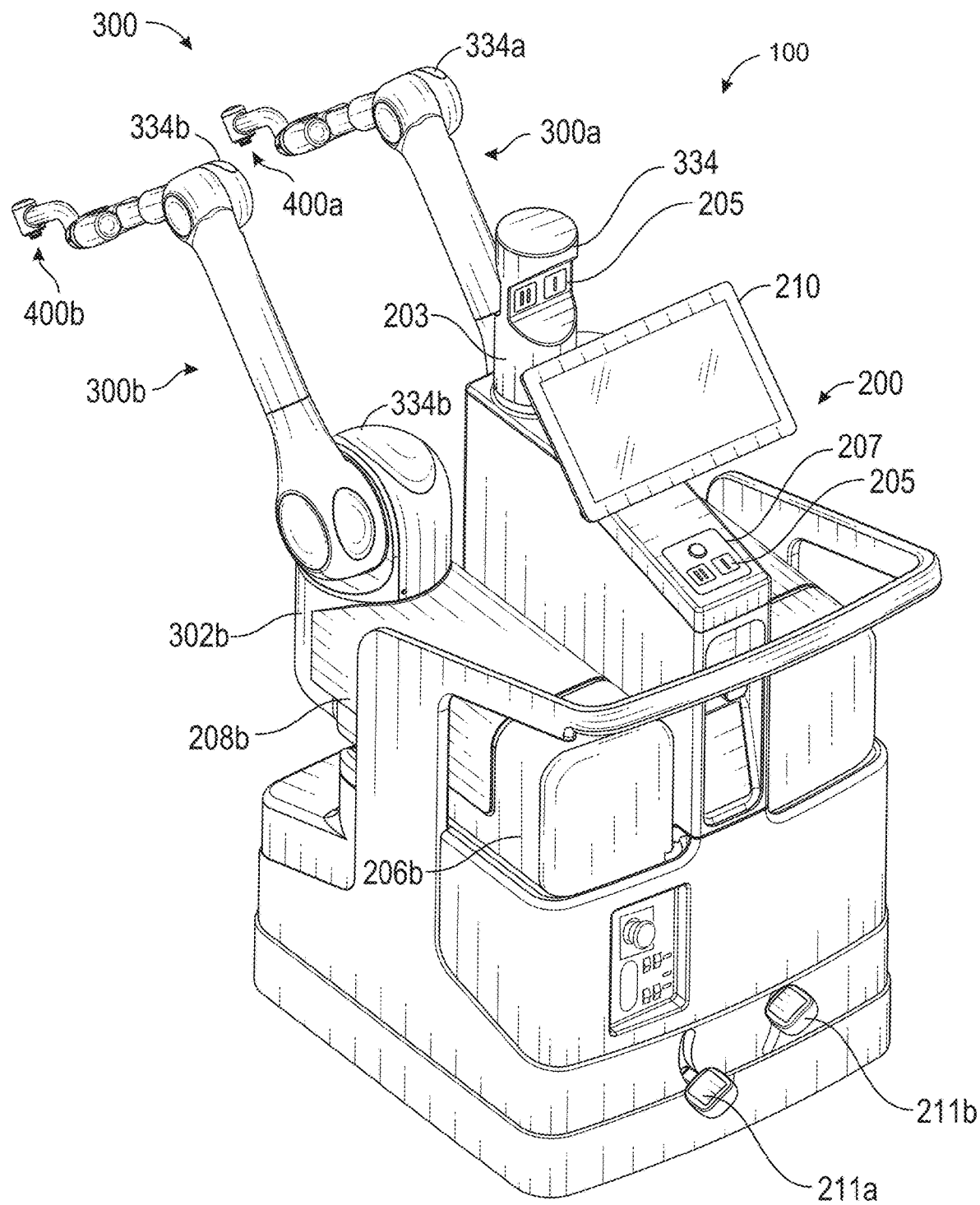

Referring now to FIGS. 2A and 2B, co-manipulation surgical robot system 100 is provided. As shown in FIGS. 2A and 2B, system 100 may include platform 200, e.g., a surgical cart, sized and shaped to support one or more robot arms, e.g., robot arm 300a and robot arm 300b (collectively referred to herein as robot arms 300), each of robot arms 300 having a surgical instrument coupler interface, e.g., coupler interface 400a and coupler interface 400b, for removably coupling to a surgical instrument, and a computing system operatively coupled to platform 200 and robot arms 300. As shown in FIG. 2A, system 100 further may include one or more optical scanners, e.g., optical scanner 202a and optical scanner 202b, for capturing depth data, and graphical user interface display 210 for displaying operational information as well as receiving user input.

Figure 2C:
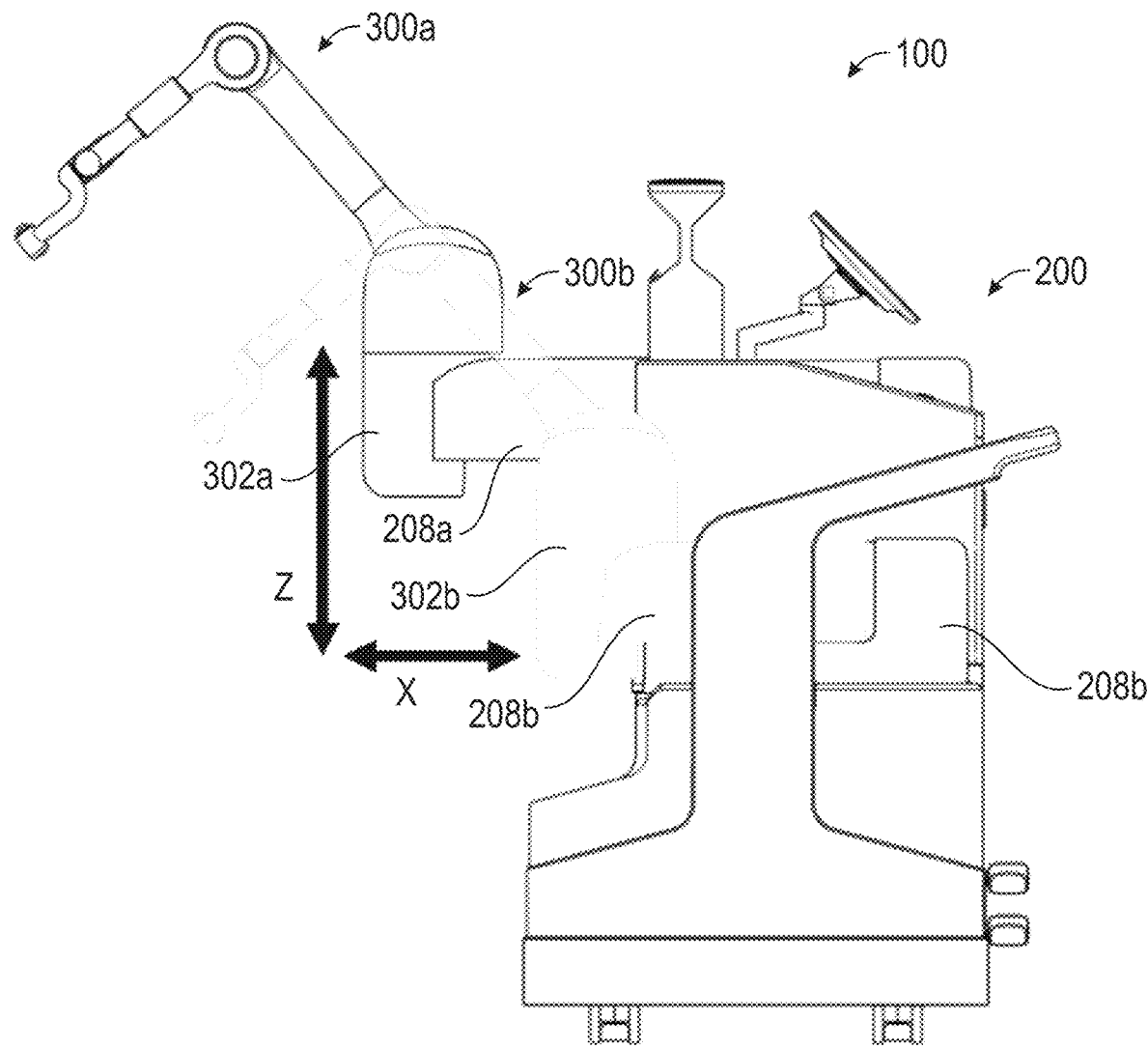
FIG. 2C illustrates movement of an exemplary stage assembly of the platform of FIGS. 2A and 2B in accordance with the principles of the present disclosure.

As shown in FIGS. 2A and 2B, platform 200 may include a stage assembly, e.g., one or more stages coupled to the base portion of one or more robot arms, e.g., base portion 302a of robot arm 300a and base portion 302b of robot arm 300b, for providing movement to the respective robot arm, e.g., in at least the horizontal and vertical directions relative to platform 200. Each stage may include vertical extenders, e.g., vertical extender 206a and vertical extender 206b, for independently moving robot arm 300a and robot arm 300b, respectively, vertically relative to platform 200, and horizontal extenders, e.g., horizontal extender 208a and horizontal extender 208b, for independently moving robot arm 300a and robot arm 300b, respectively, horizontally relative to platform 200, to thereby permit the operator flexibility in positioning robot arms 300 relative to the patient. Accordingly, platform 200 may independently move each of robot arm 300a and robot arm 300b in any direction, including a first or vertical direction toward and away from the floor (e.g., along the z-axis), and/or a second or horizontal direction toward and away from the patient (e.g., along the x-axis), as shown in FIG. 2C, and/or a third direction or horizontal direction along a length of the patient (e.g., along the y-axis).

In some embodiments, platform 200 may move robot arm 300a and robot arm 300b in the same direction simultaneously, and/or further may cause rotational movement of robot arm 300a and robot arm 300b. For example, the stages may be rotatable relative to platform 200 to thereby cause robot arm 300a and robot arm 300b to rotate towards or away from each other, e.g., along a horizontal plane defined by the x-axis and the y-axis. The center of rotation of each stage may be spaced apart from one another or, alternatively, may be coaxial with one another. Accordingly, in some embodiments, platform 200 may have a smaller footprint, such that robot arms 300a, 300b may be entirely within the footprint of platform 200 in a stow mode, and the stages may rotate and extend base portions 302a, 302b of robot arms 300a, 300b away from each other along the horizontal plane to achieve a spaced apart configuration generally provided by a wider footprint platform, as described in further detail below with regard to FIGS. 46A and 46B.

Referring again to FIG. 2A, platform 200 may include a plurality of wheels 204, e.g., castor wheels, to provide mobility of platform 200, and accordingly, robot arms 300, within the operating room. Wheels 204 may each include a braking mechanism which may be actuated to prevent movement of platform 200 via wheels 204. Preferably, wheels 204 may be manually actuated by an operator to mechanically engage/disengage the respective braking mechanism. For example, as shown in FIG. 2B, platform 200 may include locking pedal 211a configured to be actuated, e.g., stepped on by a user, to engage the braking mechanism, and unlocking pedal 211b configured to be actuated, e.g., stepped on by a user, to disengage the braking mechanism. Locking pedal 211a and unlocking pedal 211b may be configured such that movement of locking pedal 211a in a first direction causes movement of unlocking pedal 211b in a second direction opposite to the first, and vice versa.

Additionally or alternatively, wheels 104 may be electrically powered such that they may be actuated to electrically engage/disengage the respective braking mechanism. When ready for operation, platform 200 may be moved to a desired position at the side of the patient bed and locked in place via wheels 204, and the vertical and horizontal positions of robot arms 300a and 300b may be adjusted to an optimum position relative to the patient for the procedure via vertical extenders 206a, 206b and horizontal extenders 208a, 208b, responsive to user input received by graphical user interface display 210, and/or via user guided stage control as described in further detail below. As described in further detail below, platform 200 may automatically move robot arm 300a and robot arm 300b responsive to detection of, e.g., potential collisions with other objects and/or persons within the operating room and/or user input applied via the robot arms, during a laparoscopic procedure and/or during setup of the robot arms.

Figure 2D:
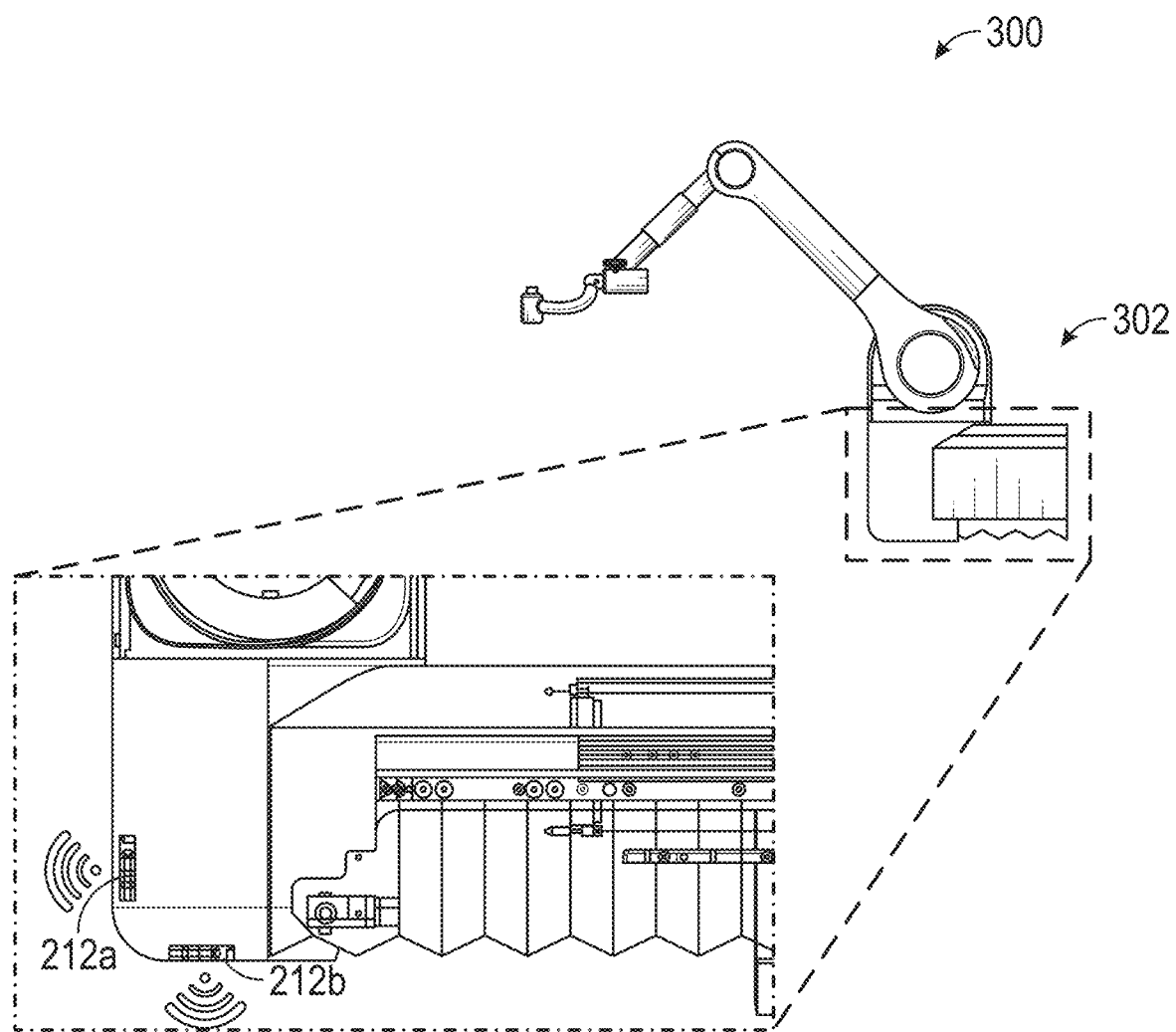
FIG. 2D illustrates proximity sensors within a base of a robot arm of the system of FIGS. 2A and 2B.

Moreover, system 100 may include a plurality of depth sensors, e.g., proximity sensors 212, disposed on platform 100. Proximity sensors 212 may be, e.g., a depth camera, a stereo RGB camera, a LIDAR device, and/or an electromagnetic, capacitive, ultrasound, or infrared proximity sensor, etc. For example, a first set of proximity sensors 212 may be positioned on robot arm 300a, e.g., at a lower portion of base portion 302a, and a second set of proximity sensors 212 may be positioned on robot arm 300b, e.g., at a lower portion of base portion 302b, to thereby enhance detection of objects approaching the vicinity of robot arms 300a, 300b. For example, as shown in FIG. 2D, each base portion 302 may include a set of proximity sensors, e.g., forward proximity sensor 212a for detecting and determining the proximity of objects in front of and around base portion 302 and bottom proximity sensor 212b for detecting and determining the proximity of objects in beneath and around base portion 302. As will be understood by a person having ordinary skill in the art, each base portion may have less or more than two proximity sensors. In some embodiments, proximity sensors 212 may only be active during movement of the stages of platform 200, as described in further detail below, and when the system is unlocked. Alternatively, proximity sensors 212 may be active during movement of platform 200, e.g., when the braking mechanism of wheels 204 are disengaged.

As base portions 302a, 302b are generally lower than the more distal components of robot arms 300a, 300b, they may be more prone to collision with, e.g., the patient bed, as the stages of platform 200 move robot arms 300a, 300b horizontally and vertically relative to platform 200. Accordingly, the system may generate an alert, e.g., via indicators 334 as described in further detail below, when the proximity sensors detect that the proximity between the robot arms and one or more objects within the operating room falls below a predetermined distance threshold. For example, indicators 334 may illuminate in a predetermined color and/or pattern, e.g., blinking, to indicate proximity with the one or more objects, and the frequency of the blinking may increase as the proximity gets closer. Moreover, the system may cause the stage assembly of platform 200 to stop movement of robot arms relative to platform 200 when the proximity between the robot arms and the one or more objects within the operating room falls below the predetermined distance threshold. In addition, the system further may display, e.g., via GUI 210, an indication that an object is within a predetermined proximity of the robot arm, as determined by forward proximity sensors 212a and/or bottom proximity sensors 212b.

Surgical robot system 100 is configured for co-manipulation, such that system 100 may assist the user or operator, e.g., a surgeon and/or surgical assistant, by permitting the user to freely move robot arm 300a and/or robot arm 300b due to manipulation of one or more surgical instruments coupled with the robot arms in response to force applied by the user to the surgical instruments. Accordingly, system 100 may be configured so that it is not controlled remotely, such that robot arms 300 move directly responsive to movement of the surgical instrument coupled thereto by the operator, while compensating for the mass of the surgical instrument and of the respective robot arm and providing localized impedance along the robot arm, thereby increasing the accuracy of the movements or actions of the operator as the operator manipulates the surgical instrument.

System 100 may be particularly useful in laparoscopic surgical procedures and/or other surgical procedures that utilize long and thin instruments that may be inserted, e.g., via cannulas, into the body of a patient to allow surgical intervention. As will be understood by a person having ordinary skill in the art, system 100 may be used for any desired or suitable surgical operation. Moreover, system 100 may be used in conjunction or cooperation with video monitoring provided by one or more cameras and/or one or more endoscopes so that an operator of system 100 may view and monitor the use of the instrument coupled with robot arms 300a, 300b via respective coupler interfaces 400a, 400b. For example, robot arm 300a may be removeably coupled with and manipulate an endoscope, while robot arm 300b may be may be removeably coupled with and manipulate a surgical instrument.

As shown in FIG. 2A, system 100 further may include one or more optical scanners, e.g., optical scanners 202a, 202b (collectively referred to herein as optical scanners 202), e.g., a LiDAR scanner or other suitable optical scanning device such as an RGBD camera or sensor, RGB camera with machine learning, a time-of-flight depth camera, structured light, multiple projection cameras, a stereo camera, ultrasound sensors, laser scanner, other type of coordinate measuring area scanner, or any combination of the foregoing, for providing a video stream of the surgical scene, e.g., via streaming, for monitoring and analysis. For example, the LiDAR camera/scanner may be capable of recording both color (RGB) and the Depth (D) of the surgical field, and may include, for example, an Intel RealSense LiDAR Camera L515 or an Intel RealSense Depth Camera D435i (made available by Intel, Santa Clara, California) or other LiDAR or depth cameras having similar or suitable specifications including, without limitation, any of the following specifications: (i) range: 25 cm to 500 cm; depth accuracy: 5 mm or approximately 5 mm; depth field of view: 70×55 or approximately 70×55 (degrees); depth output resolution: 1024×768 pixels or approximately 1024×768 pixels; depth/RGB frame rate: 30 frames per second; RGB frame resolution: 1920×1080; and/or RGB field of view: 70×43 degrees or approximately 70×43 degrees. The LiDAR scanner or optical scanner further may include both a ¼-20 UNC thread or 2×M3 thread mounting points.

Optical scanners 202, and any other electronics, wiring, or other components of the system, may be supported via platform 200 such that optical scanners 202 are mounted in a fixed location relative to the other objects in the surgical space, and the position and orientation of optical scanners 202 are known or may be determined with respect to the global coordinate system of the system, and accordingly, the robot arms. This allows all data streams to be transformed into a single coordinate system for development purposes. Moreover, telemetry data captured by optical scanners 202, e.g., indicative of the movements of the surgeon's hands, other body parts, the patient bed, the cut-out in a sterile drape over the patient on the surgical bed, the exposed skin through the cut-out in the sterile drape, the trocar(s), the surgical instruments, and other components of the system, may be recorded to provide a rich and detailed dataset describing the precise movements and forces applied by the surgeon throughout the procedure.

As shown in FIG. 2A, a first optical scanner, e.g., optical scanner 202a, may be supported on an upper portion of platform 200, e.g., via lighthouse 203, and may be adjusted, e.g., up/down, in/out, right/left, to adjust the field of view of optical scanner 202a to allow optical scanner 202a to gain an optimum field of view or position relative to the other components of the system, for example, robot arms 300a, 300b, the surgical instruments attached thereto, the surgeon, and/or surgical assistant. For example, optical scanner 202a may collect depth data indicative of, e.g., the height of the surgical bed, the angle of the surgical bed (cranial to caudal, and medial to lateral), the plane of the surgical bed, the cranial end of the surgical bed, the position and orientation of the surgical bed, the location of one or more trocar ports, movement of a surgical instrument coupled to the distal end of the robot arm, movement of a handheld surgical instrument not coupled to the robot arm, e.g., held by a user, attachment and detachment of a surgical instrument to the distal end of the robot arm, etc.

As shown in FIG. 2A, lighthouse 203 may include indicator 334, e.g., an LED ring, disposed thereon for displaying visual alerts, as described in further detail below. In addition, system 100 may include one or more robot arm markers, e.g., markers 205, configured to indicate which robot arm, e.g., robot arm 300a, 300b, is in operation/active. For example, markers 205 may include a visual representation associated with each robot arm, e.g., Roman numeral I associated with robot arm 300a and Roman numeral II associated with robot arm 300b, each of which may illuminate to indicate that the respective robot arm is in operation, e.g., being moved by the operator and/or system. Markers 205 may be disposed on the front side of lighthouse 203, as shown in FIG. 2A, and further may be disposed on, e.g., the rear side of lighthouse 203 and/or on power button panel 207, as shown in FIG. 2B, such that markers 205 may be visible to a user standing behind platform 200. As shown in FIG. 2A, lighthouse 203 further may include drape hook 209, e.g., below markers 205 on the front side of lighthouse 203, sized and shaped to support a sterile drape, as described in further detail below with regard to FIG. 10F.

As shown in FIG. 2A, a second optical scanner, e.g., optical scanner 202b, may be supported on a lower portion of platform 200 to allow optical scanner 202b to provide the system a more complete field of view of the operating room that may not be captured by first optical scanner 202a, e.g., the patient table and objects on the floor of the operating room such as electrical cables. For example, optical scanner 202a may collect depth data indicative of, e.g., the distance/proximity between system 100 and a surgical bed, the relative angle between system 100 and the surgical bed, closest feature on and edge of the surgical bed, the cranial and caudal ends of the surgical bed, one or more objects/persons between system 100 and the surgical bed, one or more objects/persons on the other side of the surgical bed, etc. As will be understood by a person having ordinary skill in the art, more than two optical scanners may be used to further enhance the field of view of the system.

The data obtained by the optical scanners may be used to optimize the procedures performed by the system including, e.g., automatic servoing (i.e., moving) of one or more portions of robot arms 300. By tracking the tendency of the surgeon to keep the tools in a particular region of interest and/or the tendency of the surgeon to avoid moving the tools into a particular region of interest, the system may optimize the automatic servoing algorithm to provide more stability in the particular region of interest. In addition, the data obtained may be used to optimize the procedures performed by the system including, e.g., automatic re-centering of the field of view of the optical scanning devices of the system. For example, if the system detects that the surgeon has moved or predicts that the surgeon might move out of the field of view, the system may cause the robot arm supporting the optical scanning device, e.g., a laparoscope, to automatically adjust the laparoscope to track the desired location of the image as the surgeon performs the desired procedure, as described in further detail below. This behavior may be surgeon-specific and may require an understanding of a particular surgeon's preference for an operating region of interest. Additionally or alternatively, this behavior may be procedure-specific. Thus, the system may control the robot arms pursuant to specific operating requirements and/or preferences of a particular surgeon. Moreover, if the system detects that the robot arms are in an extended position for a period of time exceeding a predetermined threshold, the system may cause the stages coupled to the base portions of the robot arms to move the robot arms in a manner to case extension of the robot arms, and thereby provide additional range for extension of the robot arms by the user.

Figure 3:
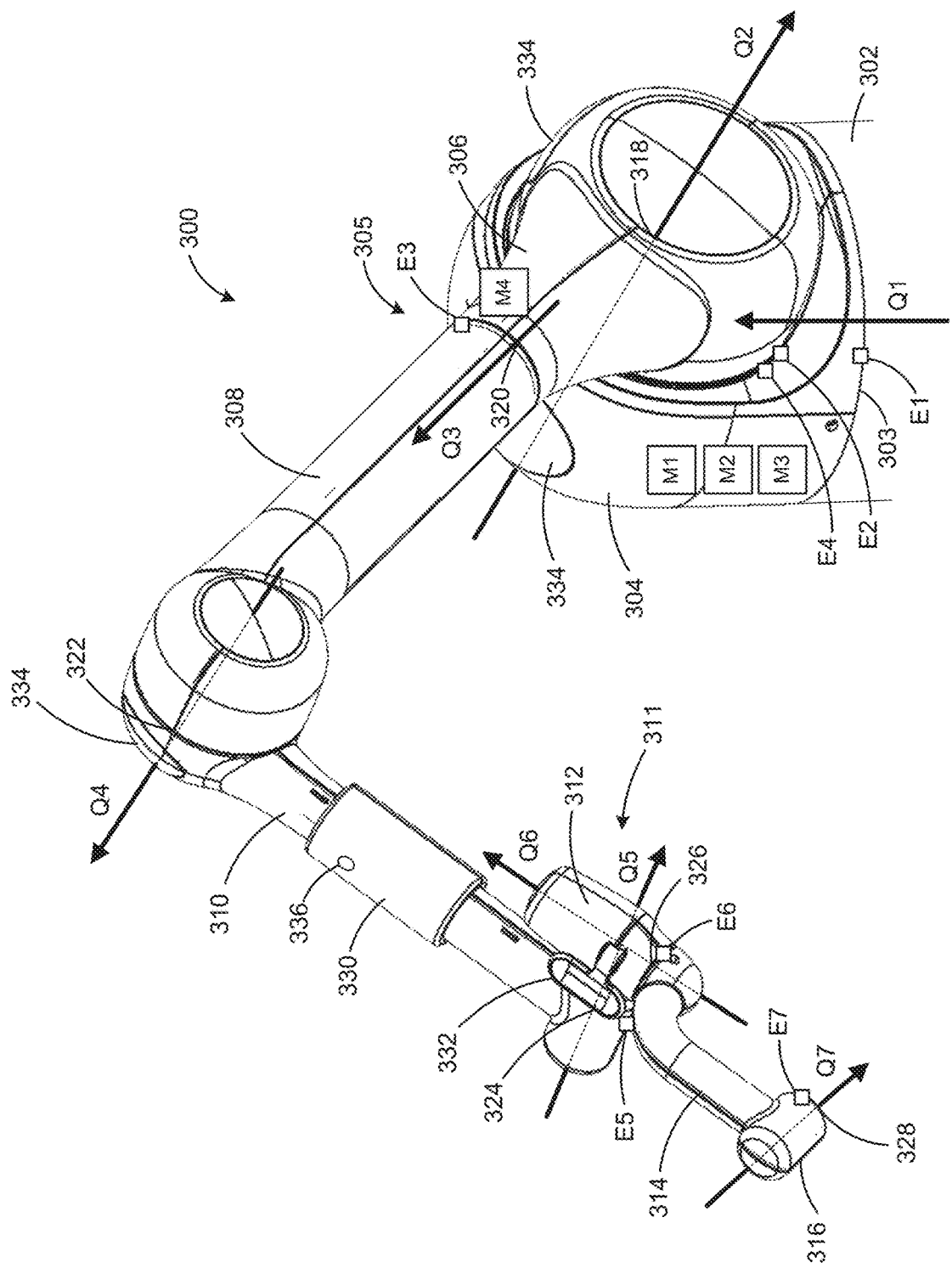
FIG. 3 illustrates an exemplary robot arm of the system of FIGS. 2A and 2B constructed in accordance with the principles of the present disclosure.

Referring now to FIG. 3, a surgical support arm is provided. As described above, system 100 may include a plurality of robot arms, e.g., robot arm 300a and robot arm 300b; however, as each robot arm may be constructed identically, only a single robot arm, e.g., robot arm 300, is described with regard to FIG. 3 for brevity, collectively as robot arm 300. Aspects of the robot arms described herein may utilize structures from U.S. Pat. No. 10,118,289 to Louveau, U.S. Pat. No. 11,504,197 to Noonan, U.S. Pat. No. 11,622,826 to Basafa, and U.S. Patent Appl. Publ. No. 2023/0114137 to Wu, the entire contents of each of which are incorporated herein by reference. Robot arm 300 may include a plurality of arm segments/links and a plurality of articulation joints extending from a base portion. For example, robot arm 300 may include a base portion, a shoulder portion, an elbow portion, and a wrist portion, thereby mimicking the kinematics of a human arm. As shown in FIG. 3, robot arm 300 may include a base, which includes base portion 302 rotatably coupled to shoulder portion 304 at base joint 303. For example, shoulder portion 304 may sit on top of base portion 302, and may be rotated relative to base portion 302 about axis Q1 at base joint 303. In some embodiments, robot arm 300 may be interchanged, swapped, or coupled with the base in any desired arrangement.

Robot arm 300 further may include shoulder link 305, which includes proximal shoulder link 306 rotatably coupled to distal shoulder link 308. A proximal end of proximal shoulder link 306 may be rotatably coupled to shoulder portion 304 of the base at shoulder joint 318, such that proximal shoulder link 306 may be rotated relative to shoulder portion 304 about axis Q2 at shoulder joint 318. As shown in FIG. 3, axis Q2 may be perpendicular to axis Q1. The distal end of proximal shoulder link 306 may be rotatably coupled to the proximal end of distal shoulder link 308 at joint 320, such that distal shoulder link 308 may be rotated relative to proximal shoulder link 306 about axis Q3 at joint 320. As shown in FIG. 3, axis Q3 may be parallel to the longitudinal axis of shoulder link 305.

In addition, robot arm 300 may include actuator 330, e.g., a collar, lever, button, or switch, operatively coupled to a motor operatively coupled to distal shoulder link 308 and/or proximal shoulder link 306 at joint 320, such that distal shoulder link 308 may only be rotated relative to proximal should link 306 upon actuation of actuator 330. Actuator 330 may be configured to permit dual actuation, e.g., a first actuation to cause distal shoulder link 308 to rotate in a first direction relative to shoulder link 306, and a second actuation to cause distal shoulder link 308 to rotate in a second direction opposite to the first direction. For example, as shown in FIG. 3, actuator 330 may be a collar rotatably coupled to a link of robot arm 300, e.g., elbow link 310 described below, such that rotation of collar 330 in a first direction about the longitudinal axis of link 310 causes distal shoulder link 308 to rotate in a corresponding first direction relative to proximal shoulder link 306, and rotation of collar 330 in a second direction about the longitudinal axis of link 310 opposite to the first direction causes distal shoulder link 308 to rotate in a corresponding second direction relative to proximal shoulder link 306 opposite to the corresponding first direction.

As shown in FIG. 3, collar 330 may include setup mode actuator 336 disposed thereon, e.g., a button, which the system may require to be actuated to permit a rotation of collar 330 to cause a corresponding rotation of distal shoulder link 308 relative to proximal shoulder link 306. For example, the user may be required to actuate setup actuator 336 to switch the system to the user guided setup mode, and maintain setup actuator 336 in an actuated state while collar 330 is rotated to cause a corresponding rotation of distal shoulder link 308 relative to proximal shoulder link 306. In addition, collar 330 may be spring-enforced such that upon release of collar 330 in any position, collar 330 returns to a neutral position relative to link 310 whereby distal shoulder link 308 does not rotate relative to proximal shoulder link 306. Alternatively or additionally, instead of actuating collar 330 to cause rotation of distal shoulder link 308 relative to proximal shoulder link 306, in some embodiments, upon actuation of setup actuator 336, application of a force to the distal end of the robot arm, e.g., a left/right force, may cause distal shoulder link 308 to rotate in a corresponding direction relative to proximal shoulder link 306. Distal shoulder link 308 may continue to be rotated relative to proximal shoulder link 306 until the applied force is released and/or a counter force in an opposite direction is applied to the distal end of the robot arm, and/or until a maximum rotation is reached.

Figure 11A:
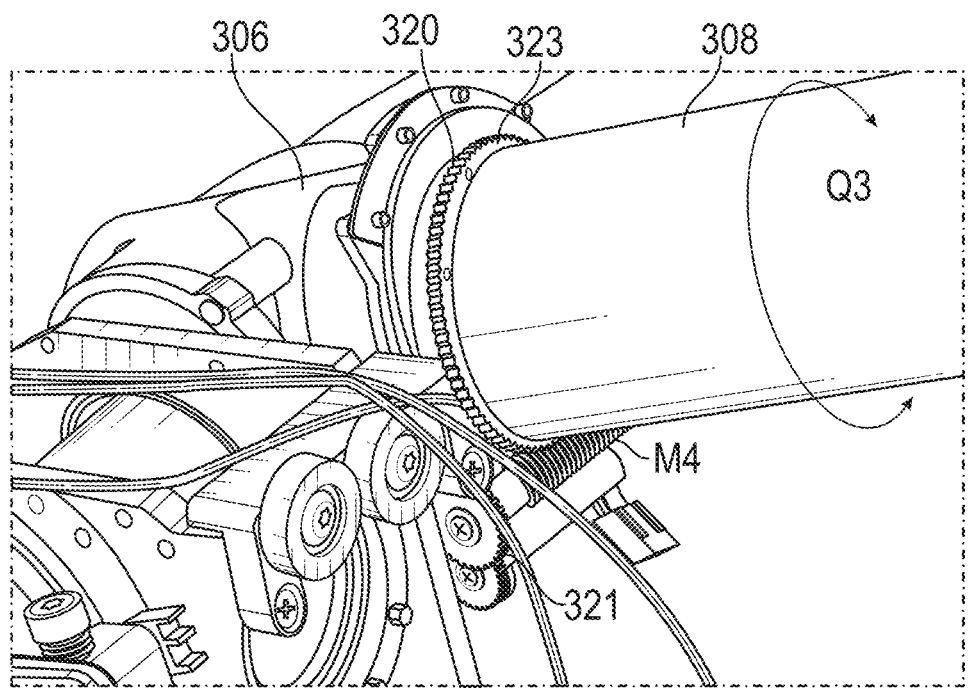
FIGS. 11A and 11B illustrate rotation of the shoulder link of the robot arm in accordance with the principles of the present disclosure.
Figure 11B:
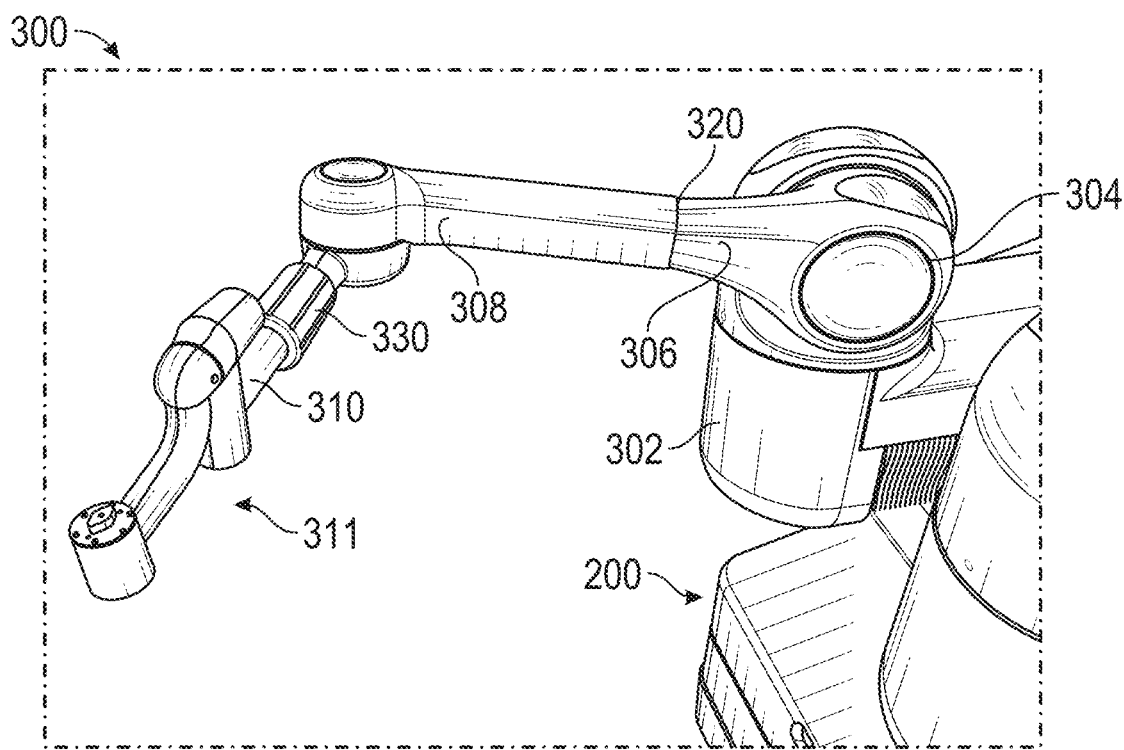

Accordingly, axis Q3 may be a "setup" axis, such distal shoulder link 308 may be rotated and fixed relative to proximal shoulder link 306 during a setup stage prior to an operating stage where robot arm 300 is used in a surgical procedure, as described in further detail with regard to FIGS. 11A and 11B. In addition, the system may switch between the operating stage and the setup stage during a surgical procedure to permit reconfiguration of the robot arm via the setup joints as needed. When actuator 330 is in an unactuated state, setup joint 320 prevents relative movement between distal shoulder link 308 and proximal shoulder link 306, such that distal shoulder link 308 is fixed relative to proximal shoulder link 306. Upon actuation of actuator 330, distal shoulder link 308 may be automatically rotated relative to proximal shoulder link 306 until actuator 330 is released. Alternatively, actuator 330 may be operatively coupled to distal shoulder link 308 and/or proximal shoulder link 306, such that upon actuation of actuator 330, distal shoulder link 308 may be manually rotated in predefined increments relative to proximal shoulder link 306.

Robot arm 300 further may include elbow link 310. A proximal end of elbow link 310 may be rotatably coupled to a distal end of distal shoulder link 308 at elbow joint 322, such that elbow link 310 may be rotated relative to distal shoulder link 308 about axis Q4 at elbow joint 322. Robot arm 300 further may include wrist portion 311, which may include proximal wrist link 312 rotatably coupled to the distal end of elbow link 310 at wrist joint 324, middle wrist link 314 rotatably coupled to proximal wrist link 312 at joint 326, and distal wrist link 316 coupled to/extending from middle wrist link 314, which may be rotatably coupled to surgical instrument coupler interface 400 (not shown) at joint 328, as further shown in FIGS. 5A and 5B. Accordingly, wrist portion 311 may be rotated relative to elbow link 310 about axis Q5 at wrist joint 324, middle wrist portion 314 may be rotated relative to proximal wrist link 312 about axis Q6 at joint 326, and surgical instrument coupler interface 400 may be rotated relative to distal wrist link 316, and accordingly middle wrist link 314, about axis Q7 at joint 328.

Referring again to FIG. 3, robot arm 300 may include actuator 332, e.g., a lever, button, or switch, operatively coupled to elbow link 310 and/or proximal wrist link 312 at joint 324, such that proximal wrist link 312 may only be rotated relative to elbow link 310 upon actuation of actuator 332. Accordingly, axis Q5 may be a "setup" axis, such proximal wrist link 312 may be rotated and fixed relative to elbow link 310 during a setup stage, upon actuation of actuator 332, prior to the operating stage where robot arm 300 is used in a surgical procedure. When actuator 332 is in an unactuated state, setup joint 324 prevents relative movement between proximal wrist link 312 and elbow link 310, such that proximal wrist link 312 is fixed relative to elbow link 310. In some preferred embodiments, upon actuation of actuator 332, proximal wrist link 312 may be manually rotated in predefined increments relative to elbow link 310, thereby removing the necessity of having additional motors and/or electronics at the distal region of robot arm 300. Alternatively, upon actuation of actuator 332, proximal wrist link 312 may be automatically rotated relative to elbow link 310 until actuator 332 is released, e.g., via a motor operatively coupled to proximal wrist link 312 and/or elbow link 310 at joint 324.

As shown in FIG. 3, robot arm 300 may include a plurality of motors, e.g., motors M1, M2, M3, which may all be disposed within the base of robot arm 300, and M4, which preferably may be disposed adjacent to joint 320. Alternatively, motor M4 also may be disposed within the base of robot arm 300. Each of motors M1, M2, M3, may be operatively coupled to a respective motorized joint of robot arm 300, e.g., base joint 303, shoulder joint 318, and elbow joint 322, to thereby apply a localized impedance at the respective joint. For example, motors M1, M2, M3 may produce an impedance/torque at any of base joint 303, shoulder joint 318, and elbow joint 322, respectively, to thereby effectively apply an impedance at the distal end of robot arm, e.g., at the attachment point with the surgical instrument, to improve the sensations experienced by the operator during manipulation of the surgical instrument as well as the actions of the operator during surgical procedures. For example, impedance may be applied to the distal end of robot arm 300, and accordingly the surgical instrument coupled thereto, to provide a sensation of a viscosity, a stiffness, and/or an inertia to the operator manipulating the surgical instrument. Moreover, applied impedances may simulate a tissue density or stiffness, communicate surgical boundaries to the operator, and may be used to direct a surgical instrument along a desired path, or otherwise. In some embodiments, the motors may actuate the respective joints to thereby cause movement of robot arm 300 about the respective joints. Accordingly, axis Q1, axis Q2, and axis Q4 may each be a "motorized" axis, such that motors M1, M2, M3 may apply an impedance/torque to base joint 303, shoulder joint 318, and elbow joint 322, respectively, to inhibit or actuate rotation about the respective axis. As described in further detail below, motors M1, M2, M3 may be controlled by a processor of the co-manipulation robot platform. With three motorized axes, some implementations of robot arm 300 may apply force/torque at the distal end of robot arm 300 in three directions to thereby move the surgical instrument coupled to the distal end of robot arm 300 in three degrees of freedom.

Motor M4 may be operatively coupled to setup joint 320 to thereby apply a torque to joint 320 to actuate rotation of distal shoulder link 308 relative to proximal shoulder link 306 about axis Q3. Unlike the other motorized joints described herein, e.g., base joint 303, shoulder joint 318, and elbow joint 322, motorized joint 320 is preferably not "back-drivable," in that the user cannot actuate motorized joint 320, e.g., via movement of the surgical instrument coupled to the robot arm when the system is in co-manipulation mode. Instead, as described above, actuation of motorized joint 320 may be conducted via one or more actuators, e.g., actuator 330 and/or an actuator displayed on GUI 210, that may be actuated to automatically cause rotation of distal shoulder link 308 relative to proximal shoulder link 306.

Figure 5A:
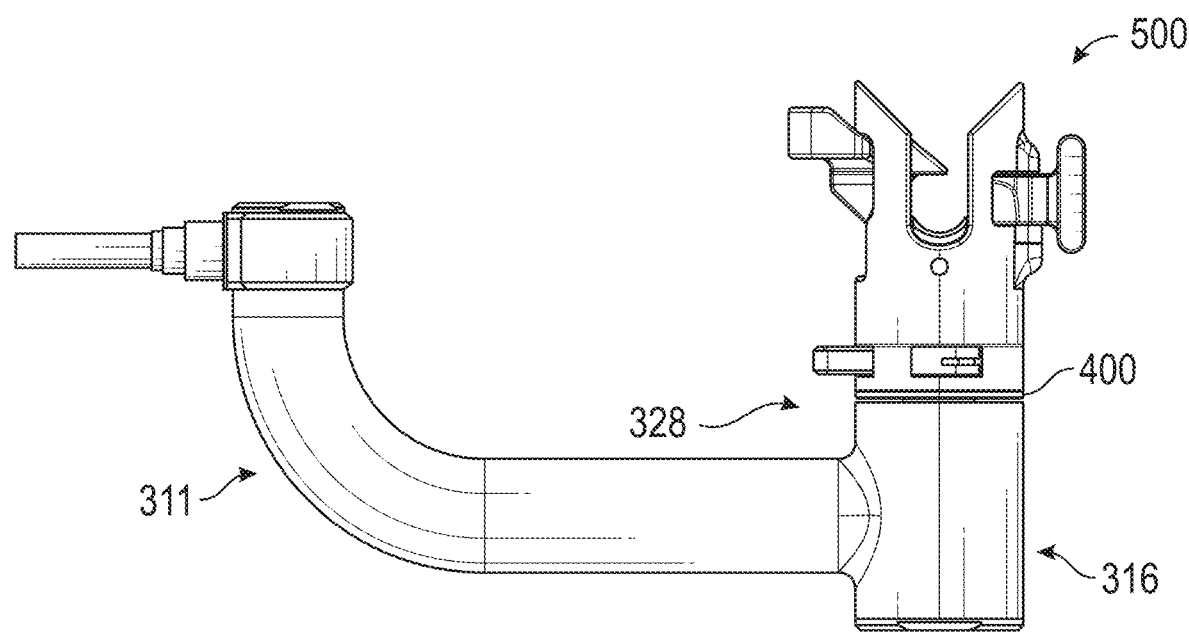
FIGS. 5A and 5B illustrate an exemplary surgical instrument coupling mechanism at the distal end of the robot arm of FIG. 3 constructed in accordance with the principles of the present disclosure.
Figure 5B:
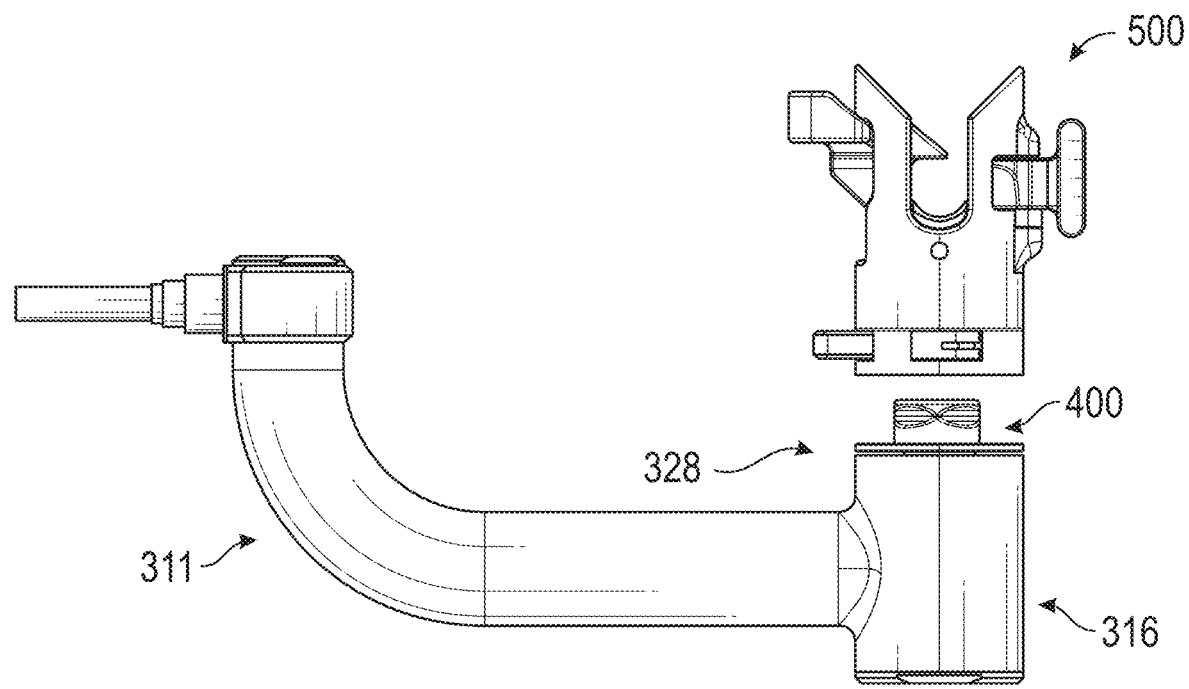

Axis Q6 and axis Q7 may each be a "passive" axis, such that middle wrist link 314 may be rotated relative to proximal wrist link 312 at passive joint 326 without any applied impedance from system 100, and surgical instrument coupler interface 400 may be rotated relative to distal wrist link 316 at passive joint 328 without any applied impedance from system 100. The distal end of distal wrist link 316 may be rotatably coupled to surgical instrument coupler interface 400 for removably coupling with a surgical instrument, e.g., via coupler body 500 as shown in FIGS. 5A and 5B, which may be removeably coupled to the surgical instrument and to coupler interface 400, as described in further detail below. Alternatively, wrist portion 311 may include a passive ball joint at the attachment point with the surgical instrument, as described in U.S. Pat. No. 10,582,977, the entire disclosure of which is incorporated herein by reference.

Referring again to FIG. 3, robot arm 300 further may include a plurality of encoders, e.g., encoders E1-E7, disposed on at least some of the plurality of joints of robot arm 300. For example, encoder E1 for measuring angulation between base portion 302 and shoulder portion 304 may be disposed on or adjacent to base joint 303 within the base, encoder E2 for measuring angulation between shoulder portion 304 and proximal shoulder link 306 may be disposed on or adjacent to shoulder joint 318 within the base, encoder E3 for measuring angular rotation between proximal shoulder link 306 and distal shoulder link 308 may be disposed on or adjacent to joint 320, encoder E4 for measuring angulation between distal shoulder link 308 and elbow link 310 may be disposed adjacent to motor M3 operatively coupled to elbow joint 322 within the base as transmission of rotational motion at elbow joint 322 is achieved via a connection rod extending from the base to elbow joint 322, encoder E5 for measuring angular rotation between elbow link 310 and proximal wrist link 312 may be disposed on or adjacent to wrist joint 324, encoder E6 for measuring angulation between proximal wrist link 312 and middle wrist link 314 may be disposed on or adjacent to joint 326, and encoder E7 for measuring angulation of between distal wrist link 316 and surgical instrument coupler interface 400 may be disposed on or adjacent to joint 328. Alternatively, encoder E4 may be disposed on or adjacent to elbow joint 322. The encoders may be absolute encoders or other position/angulation sensors configured to generate data for accurately determining the position and/or angulation of corresponding links at the respective joint and/or the exact position of the surgical instrument coupled to the distal end of robot arm 300. Accordingly, the exact position of each link, joint, and the distal end of robot 300 may be determined based on measurements obtained from the plurality of encoders. Preferably, a redundant encoder is disposed at each location along robot arm 300 where an encoder is placed, to provide more accurate position data, as well as, to detect a fault condition, as described in further detail below.

Prior to attachment with a surgical instrument, robot arm 300 may be manually manipulated by a user, e.g., to position robot arm 300 is a desired position for coupling with the surgical instrument. For example, the user may manually manipulate robot arm 300 via wrist portion 311, actuator 330, and/or actuator 332. Upon actuation of actuator 330, the user may automatically rotate distal shoulder link 308, and upon actuation of actuator 332, the user may manually manipulate proximal wrist portion 312. Moreover, robot arm 300 may further be manually moved by application of a force directly on the other links and/or joints of robot arm 300.

In some embodiments, in a user guided setup mode, responsive to force applied to a distal region of robot arm 300, e.g., at any location distal to Q4 such as at wrist portion 311, wrist joint 324, elbow link 310, the surgical instrument, etc., by the user, e.g., exceeding a predetermined force threshold or in a predetermined pattern, in a given direction, e.g., in/out and/or up/down, the processor of the co-manipulation robot platform may cause the stages of platform 200 coupled to base portion 302 of robot arm 300 to move robot arm 300 in the same/corresponding direction, e.g., via vertical extenders 206a, 206b and horizontal extenders 208a, 208b, until the force applied to robot arm 300 by the user is detected by the system to drop below a predetermined threshold, e.g., when the user releases robot arm 300. Due to the lever arm effect, forces applied to robot arm 300 farther from Q4 will be greater than forces applied closer to Q4, and therefore may be preferable during user guided setup mode to move the stages of platform 200. In some embodiments, the system may cause movement of the base of the robot arm via the stage assembly upon application of force at the distal region of the robot arm in the user guided setup mode at a velocity corresponding to the amount of force applied at the distal region of the robot arm. Accordingly, the velocity of movement of the stage assembly may be controlled by adjusting the amount of force applied to the distal region of the robot arm in the user guided setup mode, and further may slow down as the stage assembly reaches or nears its maximum extension range.

As described above, in some embodiments, the processor of the co-manipulation robot platform also may cause the distal shoulder link to rotate relative to the proximal shoulder link responsive to force applied to the distal region of robot arm 300 by the user, e.g., exceeding a predetermined force threshold or in a predetermined pattern, in a given direction, e.g., left/right. In some embodiments, the system may stop movement of robot arm 300 in the same direction as the force applied by the user when the user applies a counter force to robot arm 300, e.g., in a direction opposite to the direction of movement of robot arm 300, to facilitate setup of robot arm 300 relative to the patient. This feature may be initiated/stopped via user actuation, e.g., by actuating actuator 336 on collar 330, voice command, etc. In a preferred embodiment, the system only switches to the user guided setup mode when actuator 336 is in an actuated state, e.g., actively being pressed by a user. Accordingly, the user may actuate actuator 336 with one hand, while simultaneously applying force to the distal region of the robot arm with the other hand to cause movement of the stages of platform 200 while actuator 336 is actuated.

For example, upon actuation of the user guided setup mode, the user may apply a force that exceeds a predetermined force threshold on wrist portion 311 in a first direction, e.g., by applying a pulling or pushing force, which causes the stages of platform 200 to move robot arm 300 in that same direction until the user stops movement of wrist portion 311, e.g., by letting go of robot arm 300 or by applying a counter force to robot arm 300, and/or a maximum extension of the stage assembly is reached, such that the system stops movement of the stages of platform 200. For example, a subsequent pushing force may be counter to an initial pulling force, and a subsequent pulling force may be counter to an initial pushing force. Moreover, the stages of platform 200 may stop moving robot arm 300 when force applied at the distal region of robot arm 300 falls below a predetermined release threshold, which may include letting go of robot arm 300. Accordingly, force applied at the distal region of the robot arm, e.g., wrist portion 311, wrist joint 324, elbow link 310, etc., may serve as an input for motion generated in particular directions of the robot arms via the stages coupled thereto. Such automated movement of the stages of platform 200 responsive to force applied to the distal end of robot arm 300 by the user may be limited to when the system is in a predefined operating mode, e.g., a user guided setup mode, which may be entered in during setup and/or during a surgical procedure, e.g., upon actuation of actuator 336, GUI 210, and/or via voice control.

Similarly, when the user applies a counter force exceeding a predetermined threshold in a predefined direction distinct from the directions that cause horizontal (x-axis) and vertical (z-axis) movement of the stages of platform 200, the system may automatically actuate motorized joint 320 to cause rotation of distal shoulder link 308 relative to proximal shoulder link 306 to facilitate movement of robot arm 300 in the predefined direction. For example, similar to how the system may cause the stages of platform 200 to move robot arm 300 responsive to movement of the distal region of robot arm 300 by the user, e.g., back/forth along the x-axis or up/down along the z-axis, as described above, the system may cause motorized joint 320 to rotate distal shoulder link 308 relative to proximal shoulder link 306 to move robot arm 300 along the y-axis responsive to movement of the distal end of robot arm 300 by the user along the y-axis. Accordingly, the system may stop actuation of motorized joint 320 when the force applied by the user to the distal region of robot arm 300 drops below a predetermined threshold. M4 may be controlled by a processor of the co-manipulation robot platform.

Upon attachment to the surgical instrument, robot arm 300 may still be manipulated manually by the user exerting force, e.g., one or more linear forces and/or one or more torques, directly to robot arm 300; however, during the laparoscopic procedure, the operator preferably manipulates robot arm 300 only via the handle of the surgical instrument, which applies force/torque to the distal end of the robot arm 300, and accordingly the links and joints of robot arm 300. As the operator applies a force to the surgical instrument attached to robot arm 300, thereby causing movement of the surgical instrument, robot arm 300 will move responsive to the movement of the surgical instrument to provide the operator the ability to freely move surgical instrument relative to the patient. As described in further detail below, robot arm 300 may apply an impedance to account for weight of the surgical instrument and of robot arm 300 itself, e.g., gravity compensation, as the operator moves the surgical instrument, thereby making it easier for the operator to move the instrument despite gravitational forces and/or inertial forces being exerted on the robot arm and/or the surgical instrument. As will be understood by a person having ordinary skill in the art, robot arm 300 may include less or more articulation joints than is shown in FIG. 3, as well as a corresponding number of motors and encoders/sensors.

Figure 4:
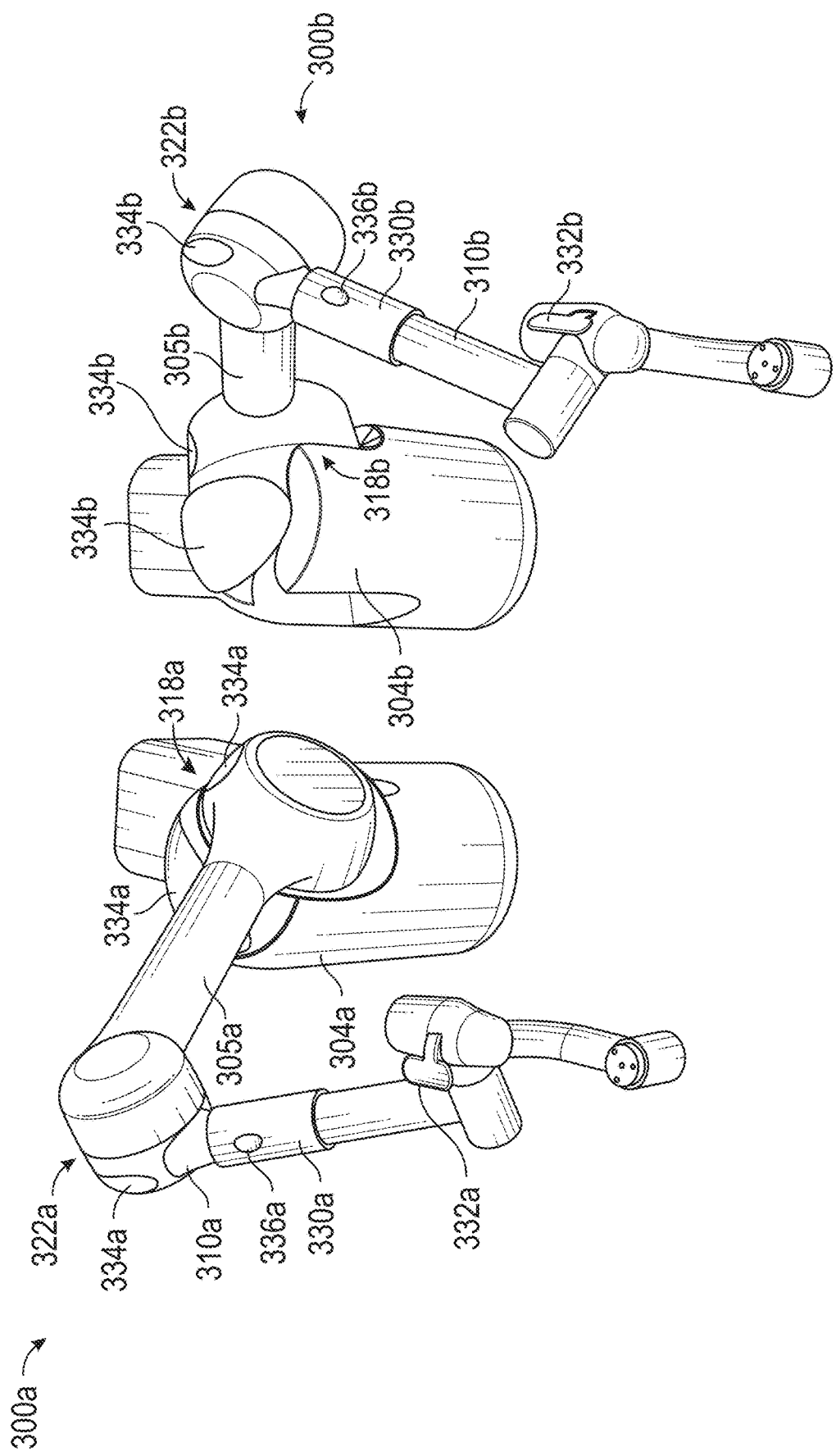
FIG. 4 illustrates exemplary robot arms of the system of FIGS. 2A and 2B constructed in accordance with the principles of the present disclosure.

In addition, each of robot arms 300 further may include indicators 334 for visually indicating the operational mode associated with the respective robot arm in real-time. For example, indicators 334 may be positioned on at least one of shoulder portion 304, shoulder link 305, elbow link 310, platform 200, lighthouse 203, display 210, etc. As shown in FIG. 4, robot arm 300*a* may include indicators 334*a* on shoulder portion 304*a*, e.g., adjacent to shoulder joint 318*a*, on shoulder link 305*a*, e.g., adjacent to shoulder joint 318*a*, and on elbow link 310*a*, e.g., adjacent to elbow joint 322*a*, and robot arm 300*b* may include indicators 334*b* on shoulder portion 304*b*, e.g., adjacent to shoulder joint 318*b*, on shoulder link 305*b*, e.g., adjacent to shoulder joint 318*b*, and on elbow link 310*b*, e.g., adjacent to elbow joint 322*b*. In some embodiments, the status of the system conveyed by the indicator on lighthouse 203 may be different from the status of the system/robot arms conveyed by the indicators elsewhere on the system, e.g., on the shoulder portion, on the base portion, on the elbow link, etc. For example, the indicator on lighthouse 203 may be programmed to illuminate in a predetermined amount of colors that is less than the predetermined amount of colors illuminated by the other indicators of the system, to thereby convey predetermined statuses of the overall system, whereas the other indicators of the system may be illuminated in various colors to convey specific statuses of the system and the robot arm, e.g., when a coupler is mounted on the robot arm, the current operational mode of the robot arm, etc.

Moreover, indicators 334, 334*a*, 334*b* may include lights, e.g., LED lights, that may illuminate in a variety of distinct colors and in distinct patterns, e.g., solid on or blinking. For example, each operational mode of system 100 may be associated with a uniquely colored light, such as red, yellow, blue, green, purple, white, orange, etc., as described in, for example, U.S. Pat. No. 11,504,197, the contents of which are incorporated herein by reference. Accordingly, indicators 334, 334*a*, 334*b* may indicate a transition from one operational mode to another operational mode. Additionally or alternatively, transitions from one operational mode to another operational mode may be indicated to a user via haptic feedback, e.g., a vibration delivered to the distal end of the robot arm, and accordingly to the surgical instrument coupled thereto. For example, the distal end of the robot arm may vibrate as the robot arm transitions from co-manipulation mode to static mode to assure the user that the robot arm is in static/passive mode and will remain in position upon release by the user and/or after the system identifies a hold as part of the instrument detection phase of the instrument centering mode described below. Additionally or alternatively, an audible alert may be emitted to indicate to the user when the robot arm transitions from one operational mode to another operational mode.

Referring now to FIGS. 5A and 5B, a close-up view of the coupling mechanism of coupler interface 400 and coupler body 500 is provided. The coupling mechanism may be constructed as described in U.S. Patent Appl. Publ. No. 2023/0114137. For example, the coupling mechanism may include coupler interface 400 at the distal end of the distal-most link of the robot arm (illustratively, link 316), and coupler body 500, which may be configured to be removably coupled to a surgical instrument and to coupler interface 400, such that a sterile drape may be placed between coupler interface 400 and coupler body 500. Accordingly, coupler body 500 may be disposable, or alternatively, sterilizable between surgical procedures. Moreover, the coupling mechanism may be operatively coupled to one or more sensors for detecting when coupler body 500 is coupled to coupler interface 400, and when a surgical instrument is coupled to coupler body 500 when coupler body 500 is coupled to coupler interface 400, as well as the type/size/make of the surgical instrument coupled to coupler body 500, as described in further detail below.

Figure 6:
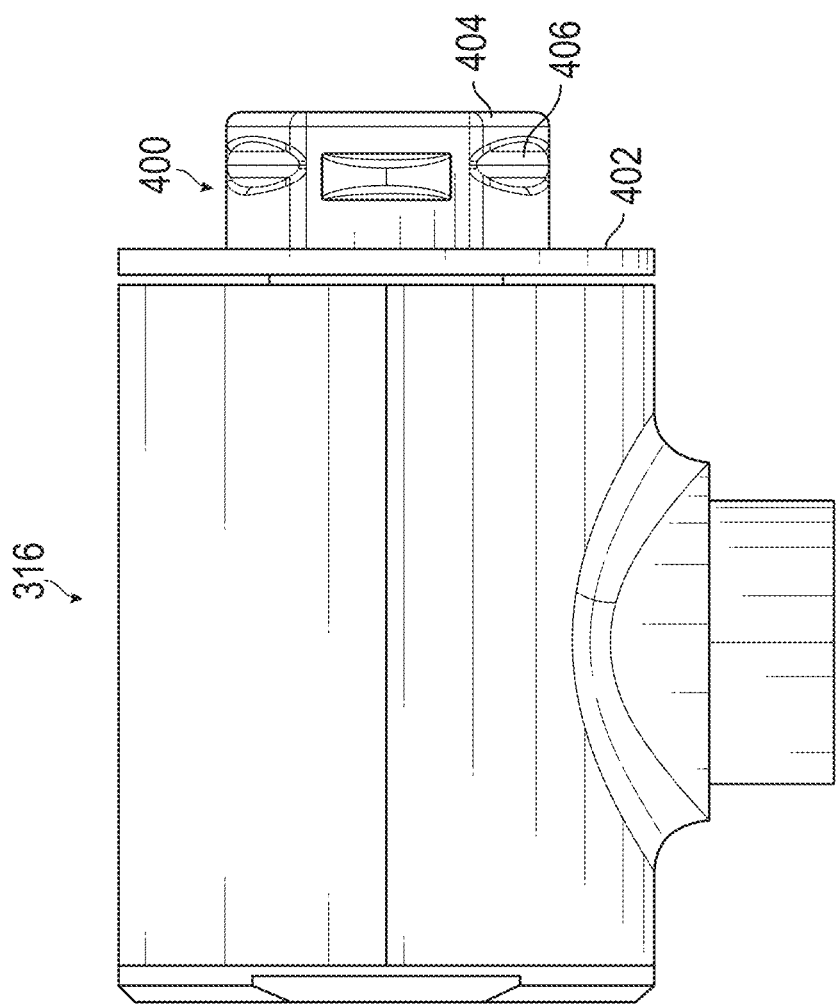
FIG. 6 illustrate an exemplary coupler interface of the surgical instrument coupling mechanism of FIGS. 5A and 5B.

FIG. 6 illustrate coupler interface 400 at the distal end of link 316 of the robot arm. As shown in FIG. 6, coupler interface 400 may include protrusion 404 extending from flat portion 402. Flat portion 402 may have an outer diameter that coincides with the outer diameter of link 316. Protrusion 404 may have a non-circular profile, which corresponds to the geometry of groove 505 of coupler body 500, as described in further detail below. Moreover, protrusion 404 may include one or more locking portions 406 disposed on the outer surface of the sidewall of protrusion 404. For example, locking portions 406 may be indentations/grooves extending along the outer surface of protrusion 404, and sized and shaped to engage with locking arms 506 of coupler body 500, as described in further detail below, for securing coupler body 500 to coupler interface 400, and for securing the sterile drape between coupler body 500 and coupler interface 400. Preferably, protrusion 404 includes at least a pair of locking portions 406, such that coupler body 500 may be securely coupled to coupler interface 400 in two orientations.

Moreover, coupler interface 400 may include an extended portion configured to be inserted within link 316. Coupler interface 400 may be rotatably coupled to the distal end of distal wrist link 316 using any suitable fasteners or connectors, e.g., magnets, screws, pins, clamps, welds, adhesive, rivets, and/or any other suitable faster or any combination of the foregoing. In addition, as described in U.S. Patent Appl. Publ. No. 2023/0114137, coupler interface 400 may include a repulsion magnet disposed within protrusion 404. The repulsion magnet is configured to apply a magnetic force to a magnet slidably disposed within coupler body 500 to facilitate determination of when coupler body 500 is coupled to coupler interface 400 and no surgical instrument is coupled to coupler body 500, e.g., by causing the magnet to move to a position within coupler body 500 with a maximum distance from coupler interface 400, and/or to facilitate coupling of the surgical instrument to coupler body 500, as described in further detail below. Moreover, as described above, robot arm 300 may include one or more encoders E7 for measuring angulation of between distal wrist link 316 and surgical instrument coupler interface 400 may be disposed on or adjacent to joint 328, e.g., within link 316. For example, encoders E7 may include two or more encoders positioned circumferentially around the extended portion of coupler interface 400.

Referring now to 7A to 7C, coupler body 500 is provided. Coupler body 500 may be configured to be removably coupled to a surgical instrument having a predefined shaft diameter, e.g., a 10 mm surgical instrument. Coupler body 500 is preferably designed to be locked to the distal end of the robot arm with a sterile drape therebetween such that the robot arm remains covered and sterile throughout a procedure. Further, coupler body 500 also has a separate portion for locking to a surgical instrument (e.g., a commercially available laparoscopic instrument) to permit the clinician to perform the surgeries with the robot arm(s) as described herein. As shown in FIGS. 7A to 7C, coupler body 500 may include coupler interface connection portion 504 and surgical instrument connection portion 502. As shown in FIG. 7C, coupler interface connection portion 504 may include groove 505 extending inward from a bottom surface of coupler body 500. Groove 505 may have a geometry that corresponds with the profile shape of protrusion 404 of coupler interface 400, such that protrusion 404 may be received by groove 505 while limiting rotational movement between coupler body 500 and coupler interface 400. The sterile drape may be positioned between protrusion 404 and groove 505 when protrusion 404 is disposed within groove 505. Preferably, the profile of protrusion 404 and the corresponding geometry of groove 505 are symmetrical such that protrusion 404 may be received by groove 505 in at least two orientations. For example, in some embodiments, the profiles of protrusion 404 and groove 505 may comprise a diamond, rectangular, or oval shape. Moreover, the profile of protrusion 404 and the corresponding geometry of groove 505 may guide the coupling of coupler body 500 to coupler interface 400 by the user.

Additionally, coupler interface connection portion 504 may include a pair of locking arms 506 configured to facilitate securing of coupler body 500 to coupler interface 400 when protrusion 404 is disposed within groove 505. Each of locking arms 506 may include handle portion 510 sized and shaped to be actuated by the user's fingers, and connection portion 508 sized and shaped to engage with locking portions 406 of protrusion 404. For example, connection portion 508 may have a tapered profile for securely engaging with locking portion 406. Locking arms 506 may be pivotally coupled to coupler interface connection portion 504, such that locking arms 506 may be transitionable between an unlocked state and a locked state. Moreover, locking arms 506 may be pivotally coupled to coupler interface connection portion 504 via a spring, e.g., a torsion spring, an extension spring, a compression spring, etc., such that locking arms 506 are biased toward the locked state. Accordingly, handle 510 may be actuated to transition locking arms 506 from the locked state to the unlocked state.

Accordingly, prior to coupling coupler body 500 to coupler interface 400, a sterile drape may be positioned between coupler body 500 and coupler interface 400, such that the sterile drape may be draped over robot arm 300, as described above. Moreover, an elastic band of the sterile drape may be hooked onto a hook disposed on lighthouse 203 to secure the drape over lighthouse 203. The sterile drape may be marked and secured with, e.g., peel-off labels, to facilitate efficient application of the drape. The user may then apply a force to handle portions 510 of locking arms 506, e.g., pinch handle portions 510 toward each other, to thereby cause connection portions 508 to move away from each other towards the unlocked state and out of groove 505, and provide clearance for protrusion 404 to be received within groove 505. When locking arms 506 are in their unlocked state, coupler body 500 may be coupled to coupler interface 400 such that protrusion 404 is disposed within groove 505. Once protrusion 404 is disposed within groove 505, the user may release handle portions 510, such that locking arms 506 move back towards their locked state and connection portion 508 engages with locking portion 406 of protrusion 406. Accordingly, the engagement of connection portion 508 and locking portion 406 due to the corresponding geometries of connection portion 508 and locking portion 406 may prevent movement between coupler body 500 and coupler interface 400, to thereby securely couple coupler body 500 to coupler interface 400.

As shown in FIGS. 7A to 7C, surgical instrument connection portion 502 may include opening 516 extending therethrough, sized and shaped to receive the shaft of a surgical instrument. For example, opening 516 may be sized and shaped to receive a 10 mm surgical instrument shaft. Opening 516 may be defined by a channel extending downward from an upper surface of surgical instrument connection portion 502 such that a surgical instrument may be inserted into opening 516 via the channel. As shown in FIGS. 7A and 7B, the upper surface of surgical instrument connection portion 502 may include tapered portions 514 that angle downward towards opening 516, thereby defining the channel into opening 516. Accordingly, tapered portions 514 ensure that the shaft of the surgical instrument is properly inserted into opening 516 in one of two orientations by rotating coupler body 500 and accordingly distal wrist link 316 to align with the longitudinal axis of the surgical instrument in one of two orientations. For example, tapered portions 514 may facilitate in "self-alignment" of the distal end of robot arm 300, e.g., by causing coupler interface 400 which is coupled to coupler body 500 to automatically rotate relative to distal wrist link 316 about axis Q7 at passive joint 328 as the instrument shaft is guided down tapered portions 514, such that the longitudinal axis of opening 516 aligns with the longitudinal axis of the surgical instrument. Accordingly, the user does not need to align the instrument shaft to opening 516, but rather, opening 516 rotates via rotation of coupler body 500 and surgical instrument coupler interface 400 relative to distal wrist link 316 to align with the longitudinal axis of the instrument shaft.

In addition, surgical instrument connection portion 502 may include clamp 518 pivotally coupled to surgical instrument connection portion 502 about axis 512, such that clamp 518 may be transitionable between an unlocked state and a locked state. Moreover, clamp 518 may be pivotally coupled to surgical instrument connection portion 502 via a torsion spring, such that clamp 518 is biased toward the locked state. Clamp 518 may include locking portion 520 configured to secure the surgical instrument within opening 516 when clamp 518 is in its locked state. For example, a lower surface of locking portion 520 may define the upper surface of opening 516 when clamp 518 is in its locked state, such that locking portion 520 prevents upward movement of the surgical instrument when the surgical instrument is positioned within opening 516 and clamp 518 is in its locked state.

The upper surface of locking portion 520 may be tapered to facilitate guidance of the surgical instrument into opening 516 along with tapered portions 514. Accordingly, the tapered angle of locking portion 520 may be alone sufficient to permit a surgical instrument to be inserted into opening 516, such that insertion of the surgical instrument towards opening 516 applies a force against the tapered upper surface of locking portion 520, thereby causing clamp 518 to rotate about axis 512 from the locked state to the unlocked state to permit the surgical instrument to be received by opening 516. Clamp 518 further may include handle 522 sized and shaped to be actuated by the user's fingers to transition clamp 518 from the locked state to the unlocked state. For example, handle 522 may be actuated to transition clamp 518 to the unlocked state for insertion of the surgical instrument into opening 516, and/or for removal of the surgical instrument from opening 516.

Moreover, coupler body 500 further may include switch 524 pivotally coupled to surgical instrument connection portion 502, and configured to facilitate securement of the surgical instrument within opening 516. For example, switch 524 may include one or more surgical instrument engagement portions 526, each having a geometry that corresponds with the outer diameter of the shaft of the surgical instrument to be inserted within opening 516. In addition, switch 524 may include handle portion 528 sized and shaped to be actuated by the user's fingers to transition switch 524 between an unlocked state and a locked state where surgical instrument engagement portion 526 engages with the surgical instrument shaft within opening 516 and applies a friction force to the surgical instrument shaft.

Moreover, in its locked state, surgical instrument engagement portion 526 further defines opening 516. Surgical instrument engagement portion 526 may have a coefficient of friction, such that when the surgical instrument is disposed within opening 516 and switch 524 is in its locked state, surgical instrument engagement portion 526 applies a friction force against the surgical instrument that prevents longitudinal movement of the surgical instrument relative to coupler body 500, while permitting rotational movement of the surgical instrument within opening 516. For example, the friction force applied to shaft 10a by surgical instrument engagement portion 526 facilitates securement of shaft 10a within coupler body 500, such that longitudinal movement of surgical instrument 10 is prevented unless the longitudinal force applied to surgical instrument 10 exceeds at least the friction force applied to shaft 10a by surgical instrument engagement portion 526, while the rotational force required to overcome the friction force and cause rotational of shaft 10a within opening 516 is minimized. Accordingly, when the surgical instrument is disposed within opening 516, switch 524 may be actuated to its unlocked state to permit the user to readjust/move the surgical instrument longitudinally relative to coupler body 500 within opening 516, and back to its locked state to prevent longitudinal movement of the surgical instrument relative to coupler body 500. Preferably, both switch 524 and clamp 518 must be in their unlocked states to permit removal of the surgical instrument from coupler body 500.

Figure 7G:
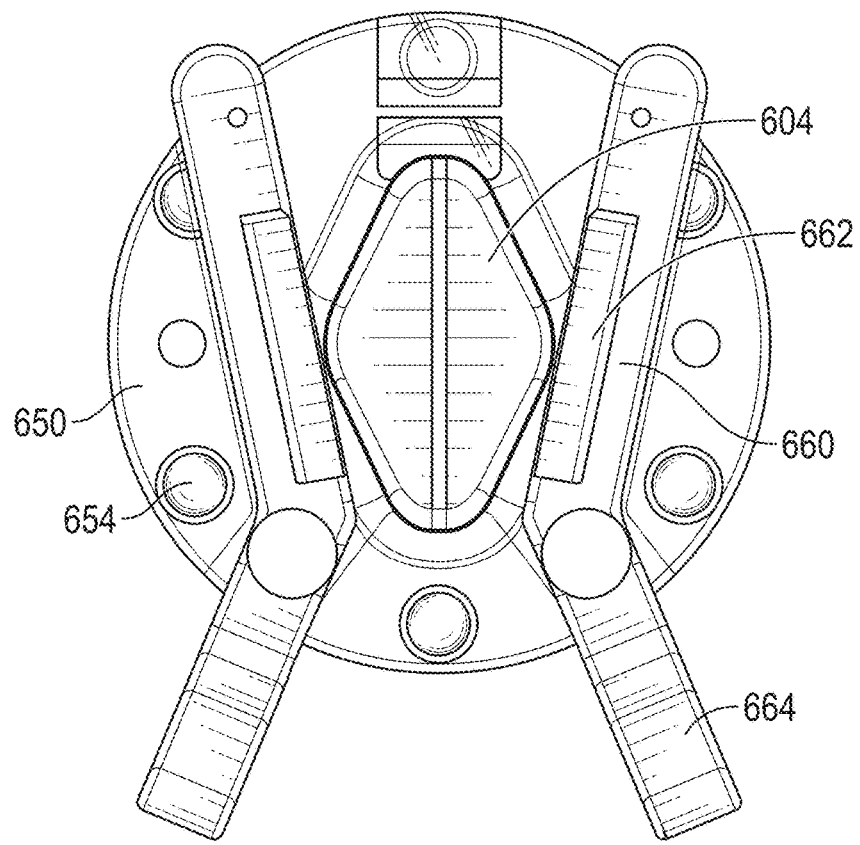

Alternatively, the coupler interface and the coupler body may be constructed as described in U.S. Patent Appl. Publ. No. 2023/0114137, as shown in FIGS. 7D to 7H. For example, coupler interface 600 may be coupled to or otherwise integrated with link 316, and connection portion 650 may be coupled to a coupler body, e.g., coupler body 500 or coupler body 900, for removably coupling the coupler body to coupler interface 600. As shown in FIG. 7D, coupler interface 600 may include protrusion 604 extending from flat portion 602. Flat portion 602 may have an outer diameter that coincides with the outer diameter of link 316. In addition, coupler interface 600 may include extended portion 608 extending from flat portion 602 and configured to be inserted within link 316. Like protrusion 404, protrusion 604 may have a non-circular profile, which corresponds to the geometry of groove 652 of connection portion 650 of the coupler body, as described in further detail below. For example, as shown in FIG. 7D, protrusion 604 may have a diamond-shaped profile. Accordingly, when protrusion 604 is disposed within groove 652 of connection portion 650, rotational movement between coupler interface 600 and connection portion 650 is prevented.

Moreover, protrusion 604 may include one or more locking portions 606 disposed on the outer surface of the sidewall of protrusion 604. For example, locking portions 606 may be indentations/grooves extending along the outer surface of protrusion 604, and sized and shaped to engage with locking arms 660 of connection portion 650, as described in further detail below, for securing the coupler body to coupler interface 600, and for securing the sterile drape between connection portion 650 and coupler interface 600. Preferably, protrusion 604 includes a pair of locking portions 606. For example, as shown in FIGS. 7D and 7F, the pair of locking portions 606 may be disposed on opposing apexes of the diamond-shaped profile of protrusion 604. Accordingly, connection portion 650 may be securely coupled to coupler interface 600 in two orientations.

As shown in FIG. 7D, coupler interface 600 may include one or more additional protrusions 610, e.g., "mating dots," disposed on flat portion 602. For example, coupler interface 600 may include a plurality of protrusions 610, preferably evenly spaced apart along flat portion 602, e.g., adjacent to the outer edge of flat portion 602. Protrusions 610 may have a geometry that corresponds with the geometry of one or more additional grooves 654 of connection portion 650, as shown in FIG. 7E. For example, protrusions 610 may have a semi-spherical shape, and grooves 654 may have a corresponding semi-spherical shape. As shown in FIG. 7E, grooves 654 may be disposed along connection portion 650, such that grooves 654 are aligned with protrusions 610 so that protrusions 610 may be disposed within grooves 654 when connection portion 650 is coupled to coupler interface 600, as shown in FIG. 7F. Accordingly, when protrusion 602 is disposed within groove 652 of connection portion 650, and protrusions 610 are disposed within grooves 654, rotational movement between coupler interface 600 and connection portion 650 is prevented. As will be understood by a person having ordinary skill in the art, coupler interface 600 and connection portion 650 may include more or less protrusions 610 and grooves 654, respectively, that are shown in FIGS. 7D and 7E. In addition, other coupler interfaces and coupler bodies described herein, e.g., coupler interface 400 and coupler body 500, 900, may include similar additional protrusions and grooves for providing additional stabilization when the coupler interface is coupled to the coupler body.

Figure 7H:
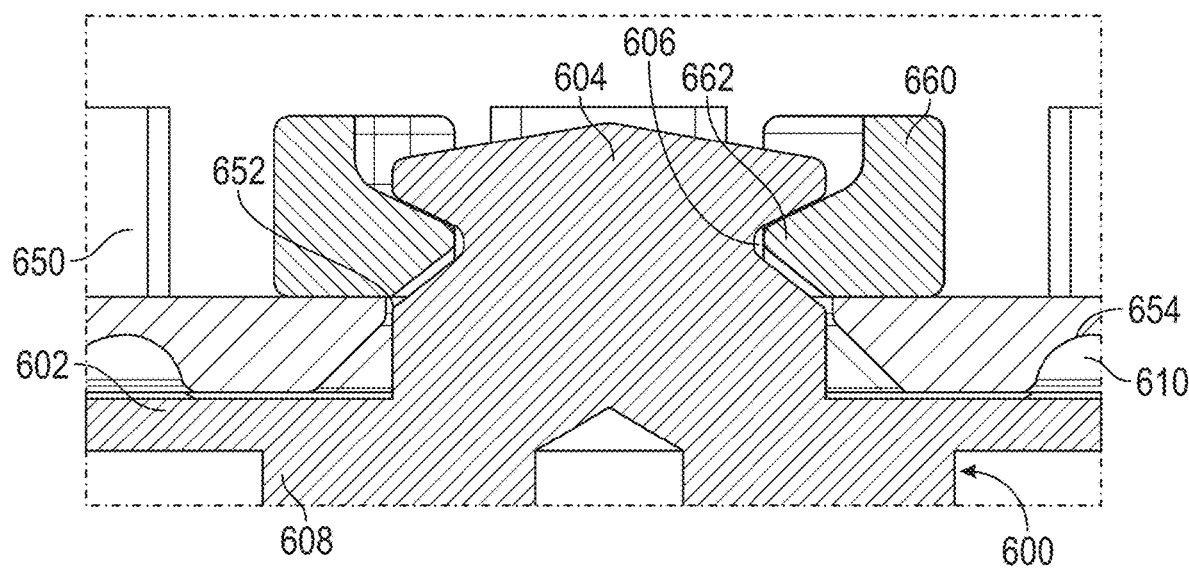

As shown in FIG. 7G, connection portion 650 may include a pair of locking arms 660, which may be constructed similar to locking arms 506 of connection portion 504, for releasably securing connection portion 650 to coupler interface 600. For example, locking arms 660 may include handle portion 664 sized and shaped to be actuated by the user's fingers, and connection portion 662 sized and shaped to engage with locking portions 606 of protrusion 604. Accordingly, locking arms 660 may transition between an unlocked state where locking arms 660 are disengaged from protrusion 604, as shown in FIG. 7G, and a locked state where connection portion 662 of locking arms 660 are engaged with locking portions 606 of protrusion 604, as shown in FIG. 7H, such that locking arms 660 are biased toward the locked state.

Figure 8C:
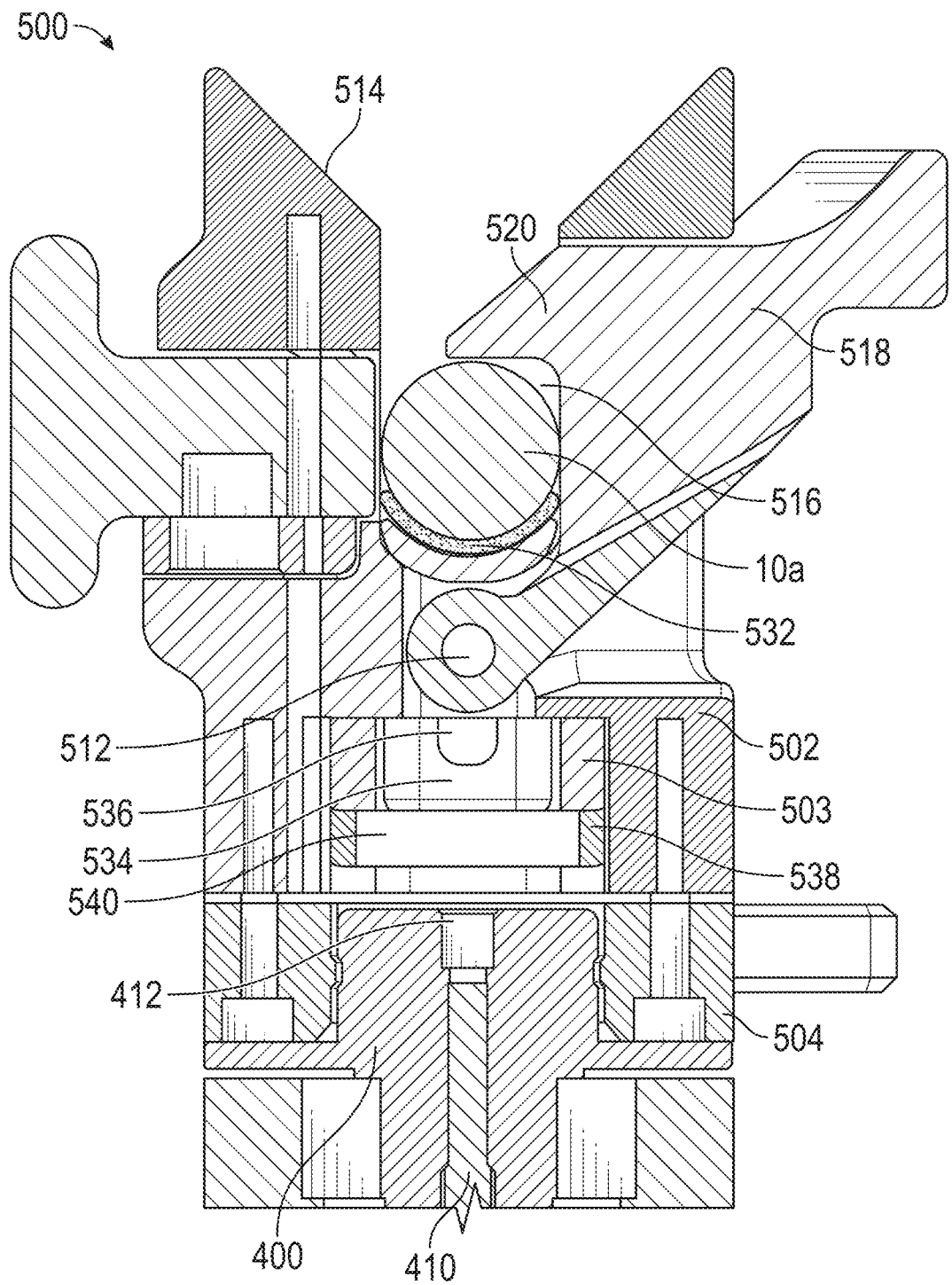
FIG. 8C is a cross-sectional view of the surgical instrument coupling mechanism of FIG. 5A when a surgical instrument is coupled to the coupler body.

FIG. 8A is a cross-sectional view of coupler body 500 when coupler body 500 is not coupled to coupler interface 400, FIG. 8B is a cross-sectional view of coupler body 500 when coupler body 500 is coupled to coupler interface 400, and FIG. 8C is a cross-sectional view of coupler body 500 when coupler body 500 is coupled to coupler interface 400, and a surgical instrument is coupled to coupler body 500. As shown in FIG. 8A, coupler body 500 further may include holder 530 disposed within surgical instrument connection portion 502. Holder 530 is configured to be slidably disposed within surgical instrument connection portion 502, e.g., toward or away from coupler interface connection portion 504. Moreover, holder 530 is configured to hold magnet 540. For example, holder 530 may include one or more cradles 534 extending between a contact surface, e.g., friction pad 532, and magnet harness 538 configured to hold magnet 540. Each cradle 534 of holder 530 may include channel 536 extending within cradle 534 in a direction from magnet harness 538 towards friction pad 532. Channels 536 may be sized and shaped to slidably receive a longitudinally extending rod therethrough, such that the longitudinally extending rod extends along axis 512 between channels 536. Clamp 518 may be pivotally coupled to the longitudinally extending rod, such that clamp 518 may rotate about axis 512, as described above. Axis 512 may be fixed relative to surgical instrument connection portion 502, such that holder 530 may move toward/away from coupler interface connection portion 504 via movement of channel 536 along the longitudinally extending rod.

As shown in FIG. 8A, the upper surface of friction pad 532 defines the lower surface of opening 516. The upper surface of friction pad 532 may have a curved profile, which may coincide with the curvature of the surgical instrument. Friction pad 532 may have a coefficient of friction, such that when the surgical instrument is disposed within opening 516 and switch 524 is in its locked state, friction pad 532 applies a friction force against the surgical instrument that prevents longitudinal movement of the surgical instrument relative to coupler body 500, while permitting rotational movement of the surgical instrument within opening 516. As will be understood by a person having ordinary skill in the art, friction pad 532 may be formed of a single or multiple pieces configured to contact the surgical instrument within opening 516, or alternatively, may be wrapped around the upper surface of holder 530 or otherwise integrated with holder 530. When switch 524 is moved to its unlocked state, the friction force of friction pad 532 may not be sufficient to prevent longitudinal movement of the surgical instrument relative to coupler body 500.

Magnet 540 may have a magnetic force such that when coupler body 500 is coupled to coupler interface 400, magnet 540 induces a magnetic field, which may be detected by one or more magnetic field sensors, e.g., disposed within link 316 and/or coupler interface 400. Accordingly, the strength of the induced magnetic field will be proportional to the distance between magnet 540 and coupler interface 400 such that the magnetic field detected by the magnetic field sensors may be indicative of the position of magnet 540, and accordingly holder 530, within coupler body 500. Similarly, when no magnetic field is induced via magnet 540, the magnetic field sensors may detect that coupler body 500 is not coupled to coupler interface 400. Moreover, the repulsion magnet of coupler interface 400 may have a magnetic force such that when coupler body 500 is coupled to coupler interface 400, the repulsion magnet applies a magnetic force to magnet 540 to thereby cause magnet 540, and accordingly holder 530, to move away from coupler interface connection portion 504. The position of holder 530 relative to coupler body 500 may be indicative of whether a surgical instrument is or is not coupled to coupler body 500 when coupler body 500 is coupled to coupler interface 400. For example, as shown in FIG. 8A, without the repulsion magnet of coupler interface 400 within the vicinity of magnet 540, no magnetic force will be applied to magnet 540 to cause displacement of holder 530, e.g., toward opening 516. Accordingly, holder 530 may be in a neutral position, e.g., towards coupler interface connection portion 504 due to gravity.

As shown in FIG. 8B, when coupler body 500 is coupled to coupler interface 400 and no surgical instrument is coupled to coupler body 500, the repulsion magnet may apply a magnetic force to magnet 540, thereby causing magnet 540, and accordingly holder 530, to move towards opening 516 and away from coupler interface 400 within channel 503, e.g., to a position within coupler body 500 with a maximum distance from coupler interface 400. Thus, when coupler body 500 is coupled to coupler interface 400, friction pad 532 may be closer to locking portion 520 of clamp 518, thereby reducing the size of opening 516. Moreover, the induced magnetic field by magnet 540 when magnet 540 is in the position within channel 503 farthest away from coupler interface 400 responsive to the magnetic force of the repulsion magnet when coupler body 500 is coupled to coupler interface 400 and no instrument is coupled to coupler body 500, may provide a clean signal that may be detected by the magnetic field sensors, indicative of coupler body 500 being coupled to coupler interface 400 without a surgical instrument attached thereto. Accordingly, the system may determine that coupler body 500 is coupled to coupler interface 400 with no surgical instrument coupled to coupler body 500, based on the strength of the magnetic field induced by magnet 540, e.g., when magnet 540 is a maximum distance from coupler interface 400 within coupler body 500.

As shown in FIG. 8C, when shaft 10a of surgical instrument 10 is inserted within opening 516, shaft 10a applies a downward force against friction pad 532, thereby causing holder 530 to move downward within channel 503 and increasing the size of opening 516 until shaft 10a is completely disposed within opening 516 and clamp 518 is permitted to transition back to its locked state, such that the shaft 10a is positioned between the lower surface of locking portion 520 and friction pad 532. Upon release of surgical instrument 10 by the user, friction pad 532 applies an upward force against shaft 10a due to the magnetic force of the repulsion magnet applied against magnet 540, such that shaft 10a is pinned between the lower surface of locking portion 520 and friction pad 532. Accordingly, the magnetic field induced by magnet 540 when magnet 540 is in the position within channel 503 responsive to the magnetic force of the repulsion magnet when coupler body 500 is coupled to coupler interface 400 as well as the force applied to holder 530, and accordingly magnet 540, by shaft 10a via friction pad 532, may be detected by the magnetic field sensors, and which may be indicative of coupler body 500 being coupled to coupler interface 400, and surgical instrument 10 being coupled to coupler body 500. Accordingly, the system may determine that coupler body 500 is coupled to coupler interface 400 and that surgical instrument 10 is coupled to coupler body 500, based on the strength of the magnetic field induced by magnet 540.

Moreover, the position of magnet 540 within channel 503 will depend on the diameter size of the surgical instrument disposed within opening 516 when coupler body 500 is coupled to coupler interface 400, such that the induced magnetic field will vary based on the surgical instrument shaft size disposed within opening 516. Accordingly, the system may identify the precise size of the surgical instrument shaft based on the strength of the magnetic field induced by magnet 540, as detected by the magnetic field sensors. Based on the identified type of surgical instrument coupled to coupler body 500, the system may load the calibration file associated with the identified surgical instrument as described above. Moreover, based on the identified make of the surgical instrument, provided that each specific make has a distinguishable shaft diameter size, the system may determine whether the attached surgical instrument is authorized for use with the system.

Figure 9:
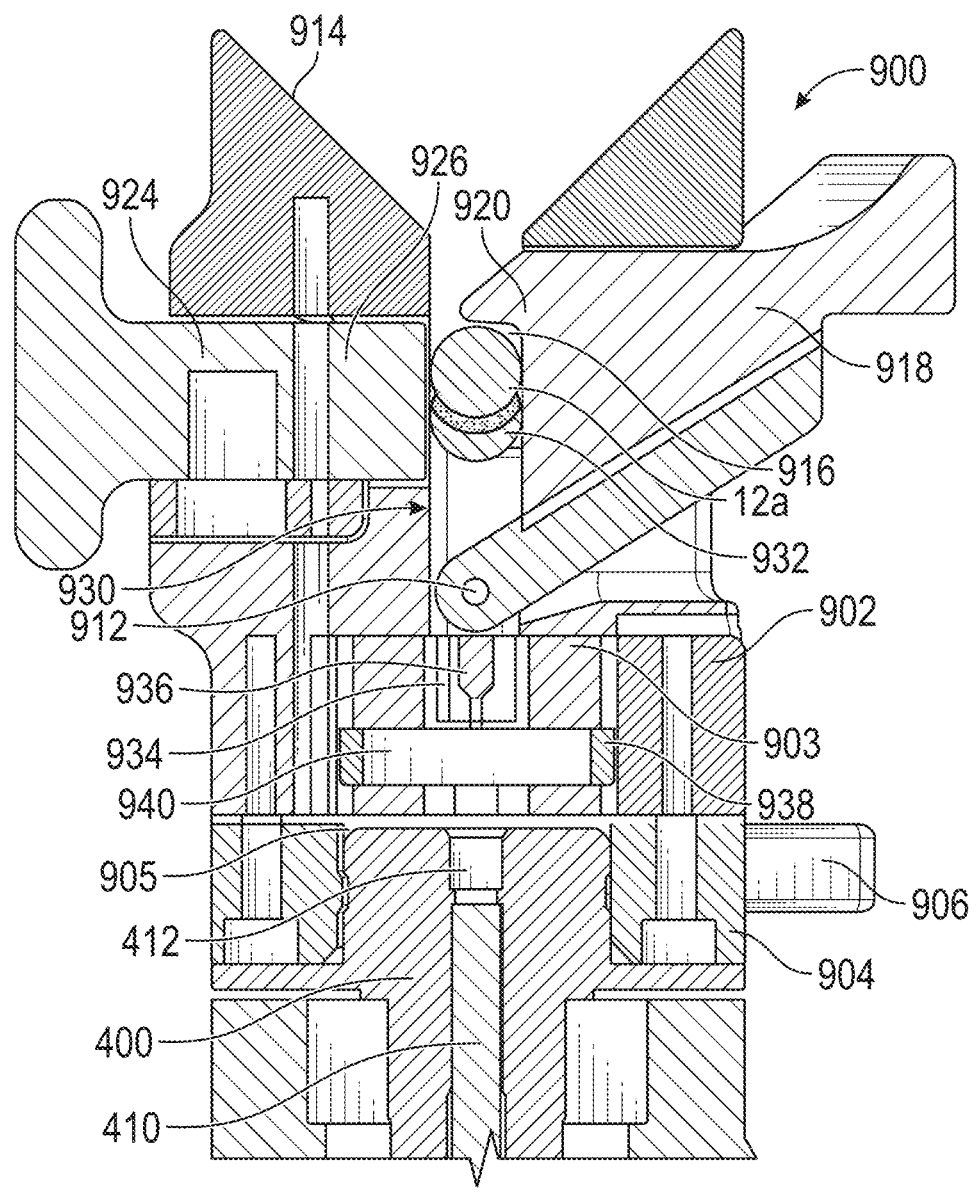
FIG. 9 is a cross-sectional view of another exemplary surgical instrument coupling mechanism when a surgical instrument is coupled to the coupler body, constructed in accordance with the principles of the present disclosure.

Referring now to FIG. 9, another coupler body configured to be removably coupled to a surgical instrument having a predefined shaft diameter is provided. Coupler body 900 may be constructed similar to coupler body 500. For example, surgical instrument connection portion 902, channel 903, coupler interface connection portion 904, groove 905, locking arms 906, axis 912, tapered portions 914, opening 916, clamp 918, switch 924, and holder 930 of coupler body 900 correspond with surgical instrument connection portion 502, channel 503, coupler interface connection portion 504, groove 505, locking arms 506, axis 512, tapered portions 514, opening 516, clamp 518, switch 524, and holder 530 of coupler body 500, respectively. Coupler body 900 differs from coupler body 500 in that coupler body 900 may be configured to be removably coupled to a smaller diameter surgical instrument, e.g., a 5 mm surgical instrument such as surgical instrument 12 described above. Coupler body 500 and coupler body 900 may include visual indicators, e.g., color and/or size markings, to readily inform a user of the respective coupler body size.

Figure 10A:
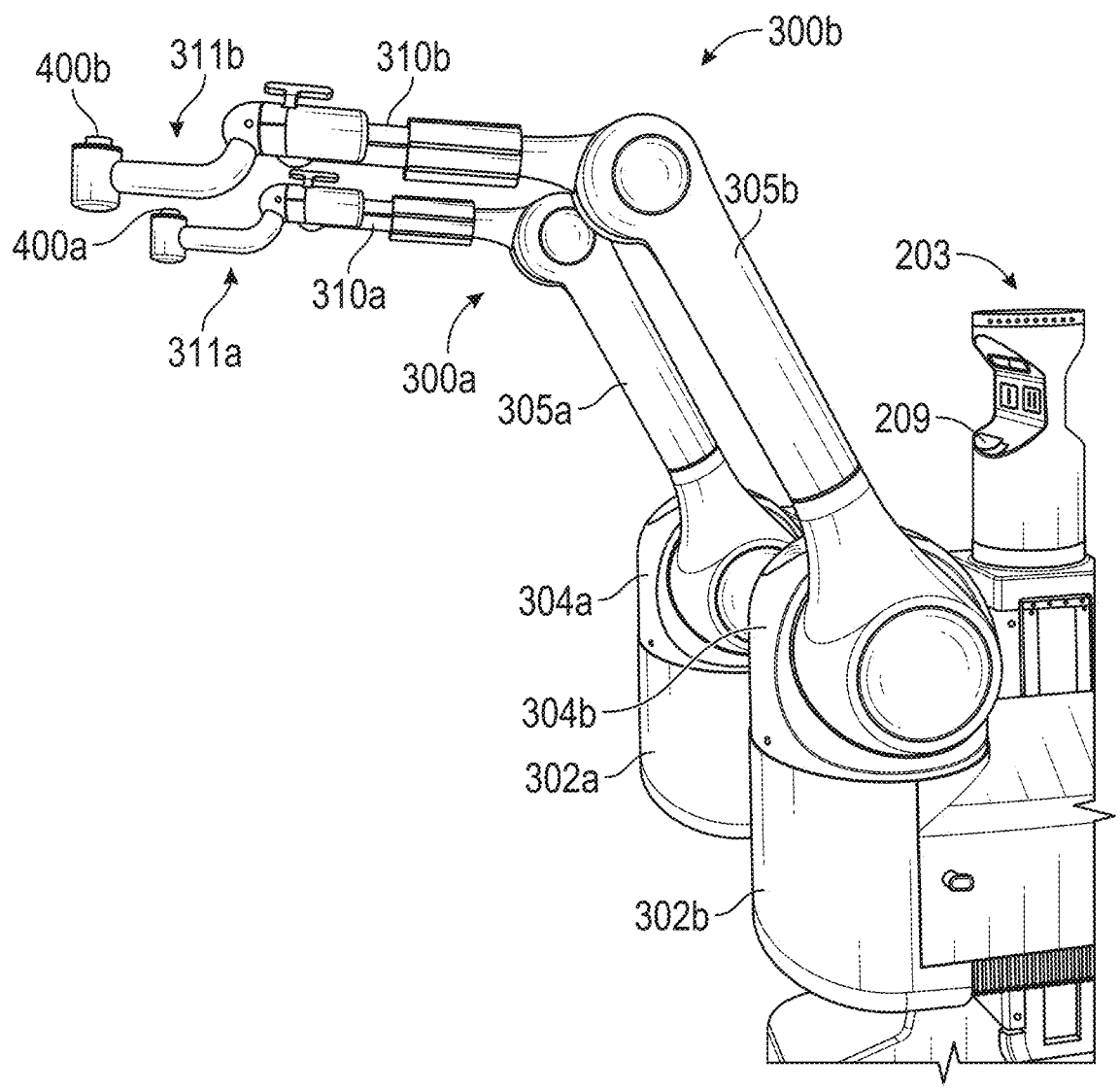
FIG. 10A illustrates the robot arms in a sterile-drape ready configuration.

Referring now to FIG. 10A, robot arms 300 may be positioned in a surgical drape-ready configuration (e.g., preset "drape mode"). For example, upon actuation of the drape mode, e.g., via GUI 210, the system may automatically cause robot arms 300a, 300a to be extended such that wrist portions 311a, 311b, elbow links 310a, 310b, and shoulder links 305a, 305b extend away from shoulder portions 304a, 304b of the respective base, as shown in FIG. 10A, to permit a surgical/sterile drape to be draped over each component of robot arms 300a, 300b, as shown in FIG. 10D. In addition, the system may automatically cause shoulder portion 304a to rotate relative to base portion 302a of robot arm 300a and/or shoulder portion 304b to rotate relative to base portion 302b of robot arm 300b, such that robot arms 300a, 300b extend away from platform 200. This configuration permits efficient and accessible draping of the respective robot arms with a single surgical/sterile drape, e.g., sterile drape 800 having first drape portion 801a sized and shaped for draping robot arm 300a and second drape portion 801b sized and shaped for draping robot arm 300b, as described in further detail below with regard to FIG. 10B. Preferably, robot arms 300a, 300b extend away from platform 200 such that shoulder links 305a, 305b extend at an angle away from shoulder portions 304a, 340b, and wrist portions 311a, 311b, and elbow links 310a, 310b are substantially parallel to each other and to the ground, as shown in FIG. 10A. Alternatively, robot arm 300a and robot arm 300b may be angled away from each other in the drape mode, e.g., by rotating shoulder portion 304a relative to base portion 302a of robot arm 300a and/or by rotating shoulder portion 304b relative to base portion 302b of robot arm 300b, such that wrist portion 311a, elbow link 310a, and shoulder link 305a extend away from wrist portion 311b, elbow link 310b, and shoulder link 305b. This configuration may be advantageous when robot arms 300a, 300b are individually draped.

In some embodiments, upon actuation of the drape mode, the system may automatically cause the stages of platform 200 to move base portions 302a, 302b, e.g., in the vertical direction relative to the ground, to thereby align wrist portions 311a, 311b and elbow links 310a, 310b with the height of the user to facilitate applying the sterile drape over robot arms 300a, 300b. The height of the user may be automatically determined by the system based on depth data collected by the one or more optical scanners. Additionally or alternatively, the height of the user and/or the preferred height of wrist portions 311a, 311b and elbow links 310a, 310b of the user for draping in drape mode may be stored in a memory of the system in a user-specific profile that may be uploaded for execution by the system responsive to user input at GUI 210. System 100 may store the predetermined drape-ready configuration, e.g., within the user-specific profile, such that upon actuation of the system in the "drape mode" during setup by the user, system 100 may cause robot arms 300 to automatically move to the predetermined drape-ready configuration.

Moreover, in the extended position in drape mode, the robot arms may be within the virtual haptic boundary, such that the robot arms are in the haptic mode and a high level of impedance is applied to the robot arms thereby making movement of the robot arms more viscous, which makes it easier for the operator to drape the robot arms, yet provide movement thereto if necessary. In addition, if the robot arms are not within the predefined virtual haptic boundary around the workspace in the drape-ready configuration, the system may apply a temporary localized virtual haptic boundary at least the distal end of the robot arms, as described in further detail below. The system may remove the temporary localized virtual haptic boundary upon detection that the coupler bodies are coupled to the distal ends of the respective robot arms. For example, the system may remove the temporary localized virtual haptic boundary from both robot arms upon determination that both coupler bodies have been coupled to both robot arms. Alternatively, the system may remove the temporary localized virtual haptic boundary from each robot arm upon determining that a coupler body has been coupled to the respective robot arm.

Figure 10B:
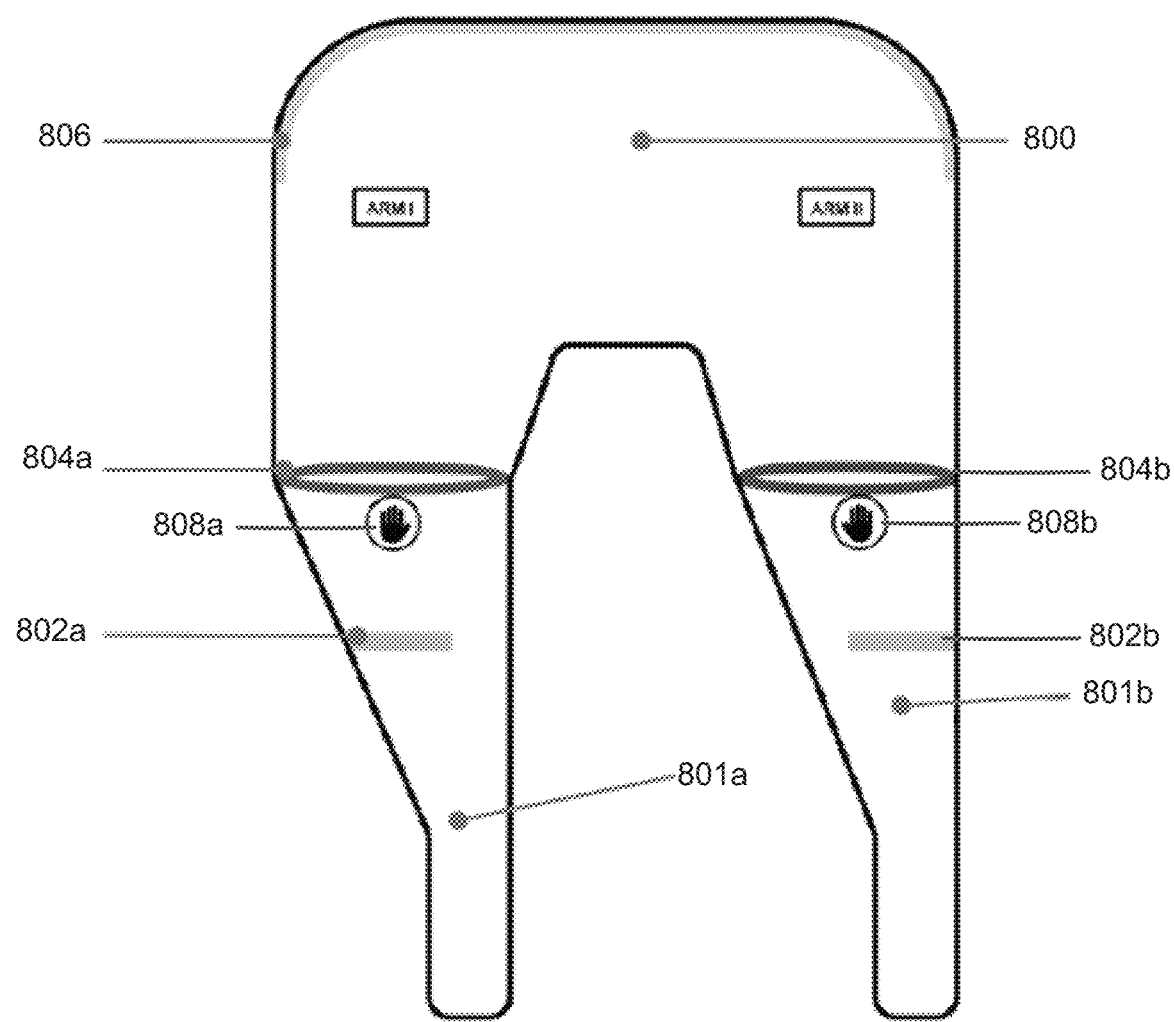
FIG. 10B illustrates an exemplary sterile drape having first and second drape portions constructed in accordance with the principles of the present disclosure.
Figure 10C:
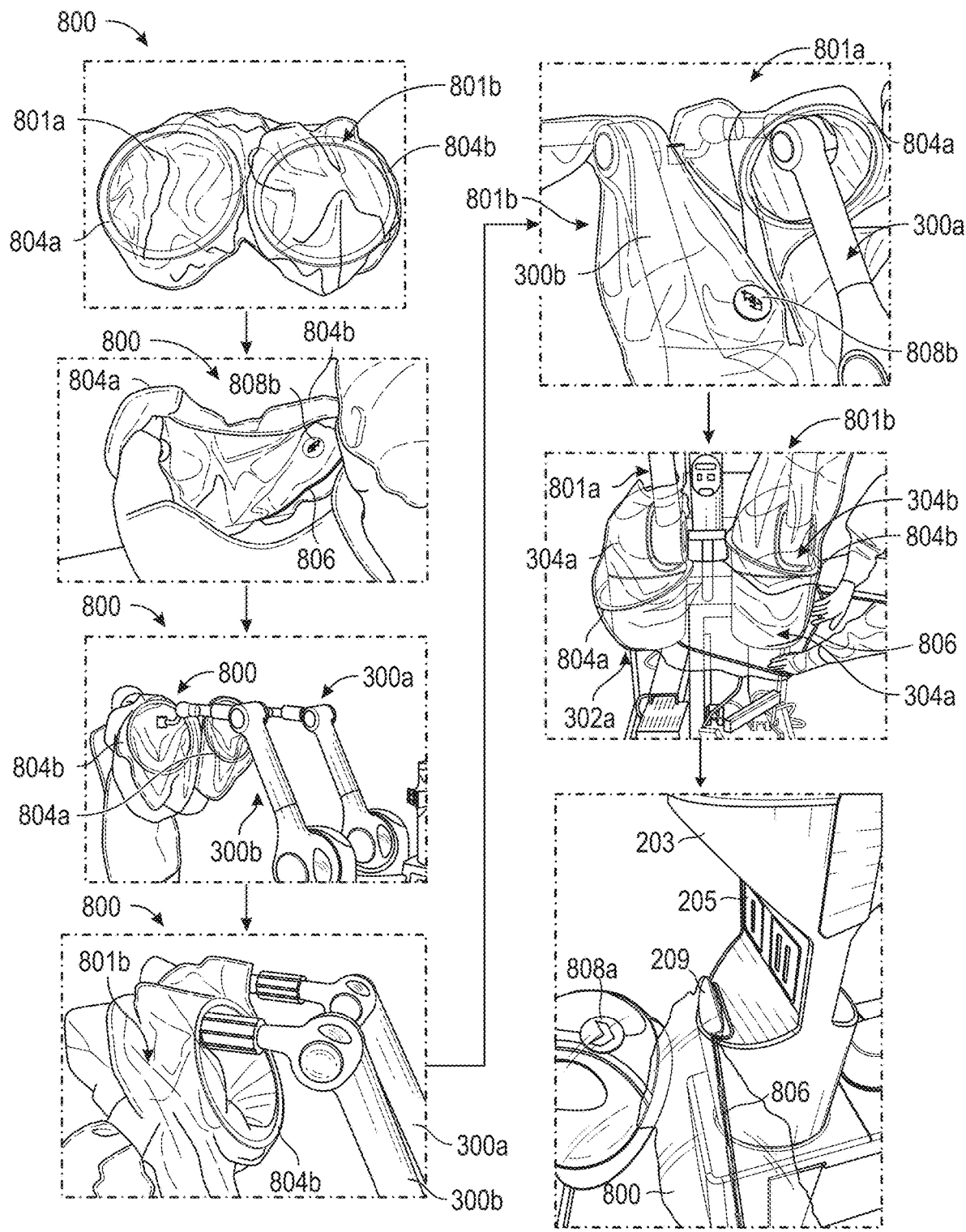
FIG. 10C illustrates exemplary method steps for draping the robot arms.

As shown in FIG. 10B, a single sterile drape 800 having first drape portion 801a sized and shaped for draping robot arm 300a and second drape portion 801b sized and shaped for draping robot arm 300b is provided. Sterile drape 800 may be used to drape both robot arms 300a, 300b and at least the front side of platform 200, as shown in FIG. 10D. As shown in FIG. 10B, sterile drape 800 may be completely closed at the end portions thereof, e.g., the distal portion of first and second drape portions 801a, 801b in contact with the respective coupler interface of the robot arm. Alternatively, in some embodiments, sterile drape 800 may have an opening (that can optionally have a sterile seal or interface) in a distal portion thereof that a portion of robot arm 300, coupler interface 400, coupler body 500, and/or the surgical instrument may pass through. Drapes having a sealed end portion without any openings, and being sealed along a length thereof may provide a better sterile barrier for system 100. Accordingly, all of robot arms 300a, 300b may be located inside sterile drape 800 and/or be fully enclosed within sterile drape 800, except at an opening at a proximal end of sterile drape 800, e.g., near the base of robot arms 300. In some embodiments, coupler body 500 and coupler interface 400 may have electrical connectors to produce an electronic connection between robot arm 300 and the surgical instrument. Accordingly, the electrical signals may be transmitted through sterile drape 800. The surgical instrument and the coupler body may instead be passive or non-electronic such that no electrical wires need pass through sterile drape 800.

Figure 10E:
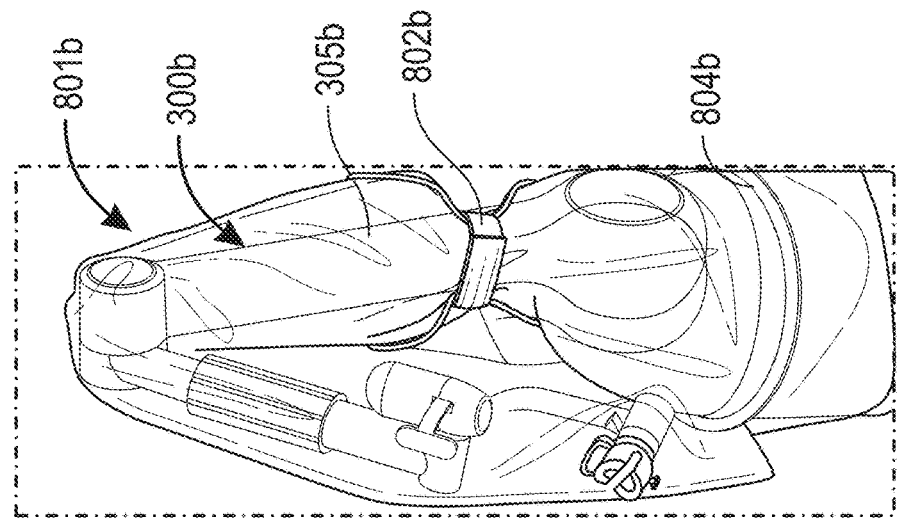
FIG. 10E illustrates a robot arm covered in a sterile drape with a strap.
Figure 10D:
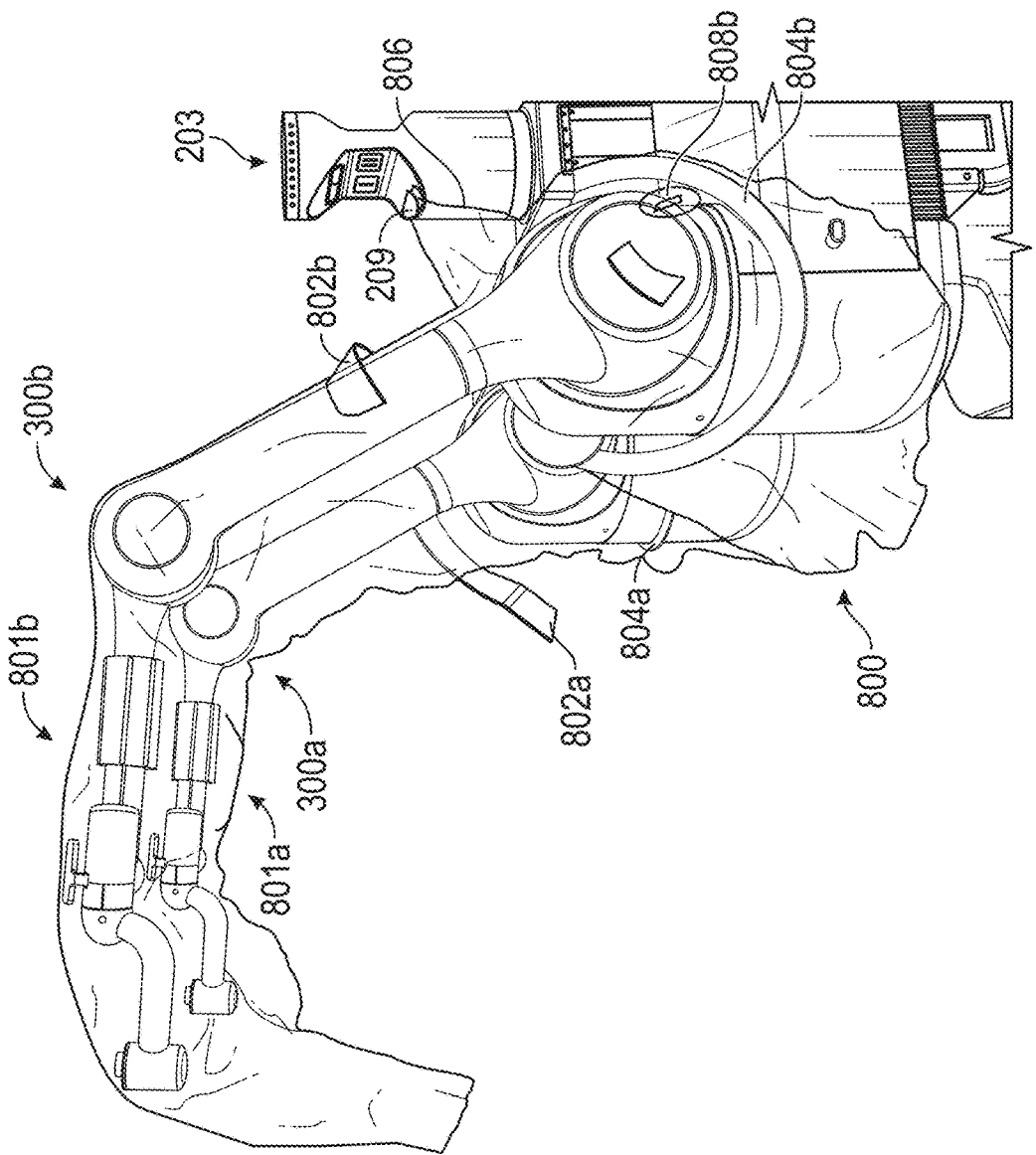
FIG. 10D illustrates the robot arms covered in a sterile drape.

As shown in FIG. 10B, sterile drape 800 may include one or more straps/bands, e.g., bands 802a, 802b, configured to secure drape portions 801a, 801b to robot arms 300a, 300b, respectively, as shown in FIG. 10E. Bands 802a, 802b may be integrated with sterile drape 800, and affixed to themselves when positioned at the target locations with respect to robot arms 300a, 300b, as shown in FIG. 10E. Alternatively, bands 802a, 802b may be made of an elastic material such that they may be easily stretched and passed over robot arms 300a, 300b until positioned at the target location. As will be understood by a person having ordinary skill in the art, less or more than two bands may be used to secure sterile drape 800 over each of the robot arms. For example, a first band may be used to secure drape portion 801a on elbow link 310a of robot arm 300a, a second band may be used to secure drape portion 801a on shoulder link 305a of robot arm 300a, a third band may be used to secure drape portion 801b on elbow link 310b of robot arm 300b, and/or a fourth band may be used to secure drape portion 801b on shoulder link 305b of robot arm 300b.

As shown in FIG. 10B, sterile drape 800 may include one or more rigid guides, e.g., guides 804a, 804b, integrated with sterile drape 800, which may be grabbed by the user to guide sterile drape 800 over each robot arm. For example, guides 804a, 804b may be formed of cardboard, plastic, metal, or another rigid material. As will be understood by a person having ordinary skill in the art, sterile drape 800 may include more than two guides and/or the two or more guides may be disposed on other locations of sterile drape 800 than as shown in FIG. 10B. Moreover, a proximal edge of sterile drape 800 may include elastic band 806 to facilitate wrapping sterile drape 800 over the stages of platform 200 and engagement with drape hook 209 of light house 203, as described in further detail below regarding FIG. 10C. In addition, as shown in FIG. 10B, sterile drape 800 further may be marked and/or secured with one or more peel-off labels, e.g., labels 808a, 808b, having directional markings to facilitate efficient application of the drape over the robot arms.

FIG. 10C illustrates exemplary method steps for draping robot arms 300a, 300b with sterile drape 800. First, sterile drape 800 may be laid flat such that drape portions 801a, 801b are side-by-side. The user may then tear perforated straps, if any, that may be provided to maintain sterile drape 800 in a compact state, to ensure that sterile drape 800 is released/not constrained. The user may then tent the opening of sterile drape 800, e.g., through elastic band 806, and grab the top portions of guides 804a, 804b, while elastic band 806 sits on the user's wrists. The user may refer to labels 808a, 808b to ensure that the right guide 804b is grabbed by the user's right hand and left guide 804a is grabbed by the user's left hand. While standing in front of robot arms 300a, 300b, the user may confirm that drape portion 801a is in front of robot arm 300a and drape portion 801b is in front of robot arm 300b, and if so, hang guide 804a on elbow link 310a of robot arm 300a and hang guide 804b on elbow link 310b of robot arm 300b. The user should ensure that drape portions 801a, 801b are securely positioned over wrist joint 324a, 324b, respectively, before releasing sterile drape 800.

Next, standing on the outer side of a robot arm, e.g., robot arm 300b, the user may pull drape portion 801b over elbow link 310b and shoulder link 305b via guide 804b until guide 804b is positioned at least partially over shoulder portion 304b. Preferably, the user pulls drape portion 801b over robot arm 300b while holding onto guide 804b from inside folded sterile drape 800 to maintain sterility. Then, standing on the outer side of the other robot arm, e.g., robot arm 300a, the user may pull drape portion 801a over elbow link 310a and shoulder link 305a via guide 804a until guide 804a is positioned at least partially over shoulder portion 304b, preferably while holding onto guide 804a from inside folded sterile drape 800 to maintain sterility. Guides 804a, 804b may rest on base portions 302a, 302b of robot arms 300a, 300b, when sterile drape 800 is completely draped over the robot arms. The user may then wrap the proximal portion of sterile drape 800 around base portions 302a, 302b and the stages of platform 200 via clastic band 806, and hook elastic band 806 to hook 209 of lighthouse 203. As shown in FIG. 10C, drape hook 209 may protrude outwardly from a surface of lighthouse 203, and further may include grooved portion to thereby form a hook shape for easily receiving the proximal edge of sterile drape 800. Accordingly, elastic band 806 may be hooked onto drape hook 209 of lighthouse 203 of platform 200, e.g., below markers 205 on the front side of lighthouse 203, as shown in FIG. 10D. As described above, bands 802a, 802b may be used to secure drape portions 801a, 801b to robot arms 300a, 300b in a manner such that there is enough slack of sterile drape 800 so that robot arms 300a, 300b may move without tearing sterile drape 800 or disengaging bands 802a, 802b, as shown in FIG. 10E.

Referring now to FIGS. 11A and 11B, rotation of distal shoulder link 308 relative to proximal shoulder link 306 of shoulder link 305 is provided. As described above, motorized axis Q3 axis, may be a "setup" axis, such that distal shoulder link 308 may be automatically rotated relative to proximal shoulder link 306 upon actuation of actuator 330, e.g., during a setup stage of robot arm 300, prior to operation of robot arm 300 in a surgical procedure. Prior to rotation of distal shoulder link 308 relative to proximal shoulder link 306, shoulder portion 304 optionally may be initially rotated relative to base portion 302 to a desired position, thereby causing rotation of all the link distal to proximal shoulder link 306, which is coupled to shoulder portion 304, to rotate relative to base portion 302 and provide ample space for rotation of robot arm 300 about joint 320. Moreover, wrist portion 311 may be at least partially extended away from base portion 302 so as to not collide with any components of robot arm 300 upon rotation of robot arm 300 about joint 320.

As described above, M4 must be actuated, e.g., via actuator 330, to automatically rotate distal shoulder link 308 relative to proximal shoulder link 306 at joint 320. As shown in FIG. 11A, motor M4 may be operatively coupled to a motion transmission mechanism coupled to distal shoulder link 308, e.g., worm gear 323, via gear 321, such that actuation of motor M4 causes rotation of distal shoulder link 308 relative to proximal shoulder link 306 via engagement between gear 321 and worm gear 323. FIG. 11B illustrates robot arm 300 in a desirable location for a specific laparoscopic procedure upon rotation of distal shoulder link 308 relative to proximal shoulder link 306.

As described in further detail below, system 100 may store one or more predetermined robot arm configurations including a predetermined degree of rotation of distal shoulder link 308 relative to proximal shoulder link 306 for one or more known surgical procedures, such that upon actuation of the system to an "operation-ready mode" during setup, system 100 may cause robot arms 300 to automatically move to the predetermined robot arm configuration. Moreover, as the robot arm is moved, either manually by the user or automatically during setup, based on depth data obtained from the one or more optical scanners, the system may detect when either the stages of platform 200 or the robot arm approaches a predetermined distance threshold relative to an object in the operating room, e.g., the surgical bed. Accordingly, the system may automatically reconfigure the robot arm to avoid a collision with the object, e.g., by automatically actuating motorized joint 320 to rotate distal shoulder link 308 relative to proximal shoulder link 306. Similarly, system 100 may automatically reconfigure the robot arm to avoid a collision with an object in the operating room by automatically actuating motorized joint 320 during a surgical procedure.

Figure 12A:
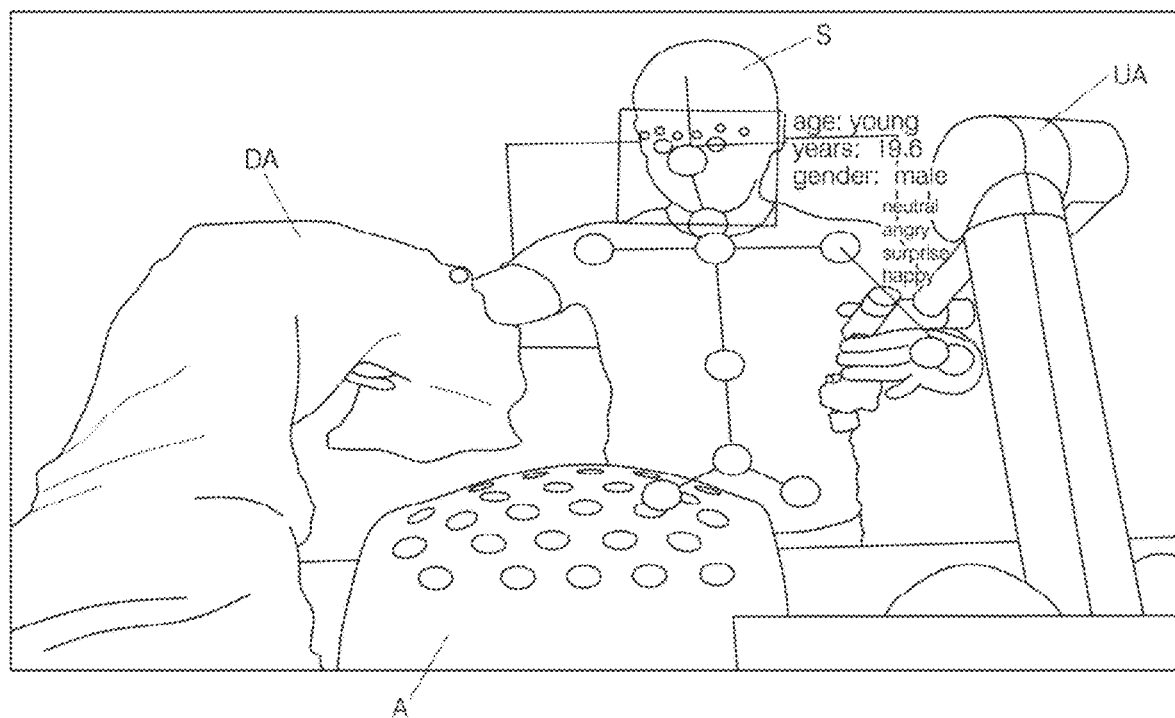
FIG. 12A illustrates a field of view of the optical scanner during a laparoscopic surgical procedure.
Figure 12B:
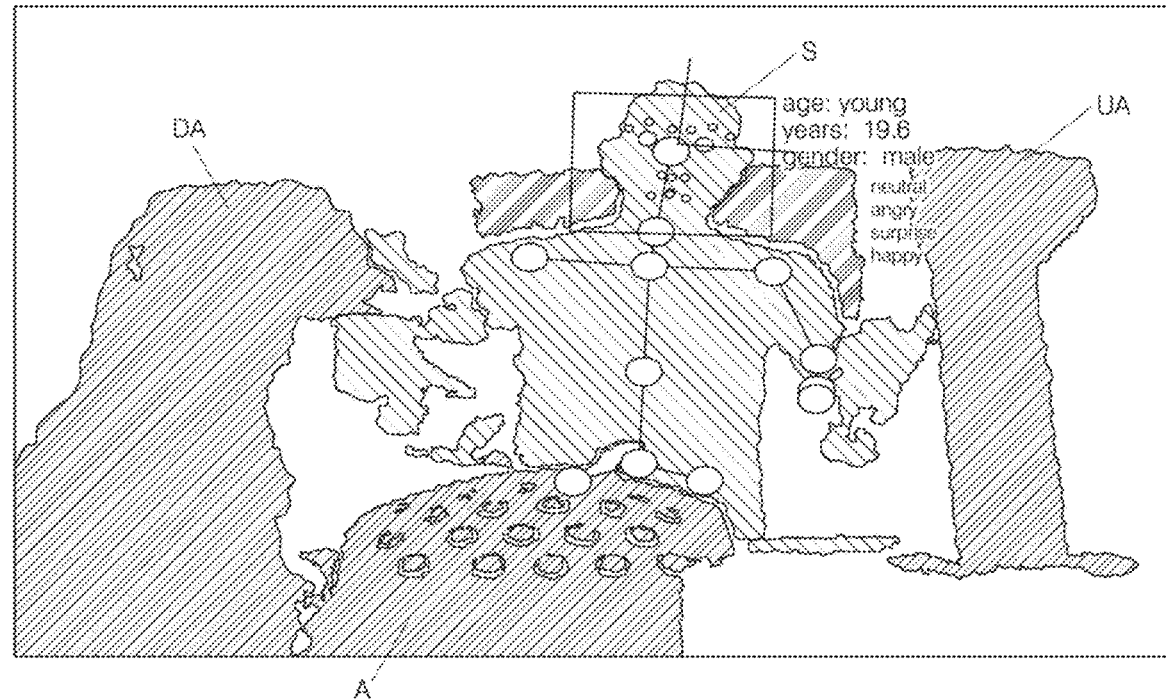
FIG. 12B illustrates a depth map of the field of view the optical scanner of FIG. 12A.

FIGS. 12A and 12B illustrate exemplary data produced by optical scanner 202. For example, FIG. 12A illustrates image data captured by optical scanner 202, and FIG. 12B illustrates a depth map of at least some objects within the surgical space generated from the data captured by optical scanner 202. Specifically, optical scanner 202 may create a depth map, e.g., point clouds, where each pixel's value is related to the distance from optical scanner 202. For example, the difference between pixels for a first object (such as a first surgical instrument) and a second object (for example, a trocar) will enable the system to calculate the distance between the surgical instrument and the trocar. Moreover, the difference between pixels for a first object (such as a first surgical instrument) at a first point in time and the first object at a second point in time will enable the system to calculate whether the first object has moved, the trajectory of movement, the speed of movement, and/or other parameters associated with the changing position of the first object.

For example, the system may measure and record any of the following within the coordinate space of the system: motion of the handheld surgical instruments manipulated by the surgeon (attached to or apart from a robot arm); the presence/absence of other surgical staff (e.g., scrub nurse, circulating nurse, anesthesiologist, etc.); the height and angular orientation of the surgical table; patient position and volume on the surgical table; presence/absence of the drape on the patient; presence/absence of trocar ports, and if present, their position and orientation; gestures made by the surgical staff; tasks being performed by the surgical staff; interaction of the surgical staff with the system; surgical instrument identification; attachment or detachment "action" of surgical instruments to the system; position and orientation tracking of specific features of the surgical instruments relative to the system (e.g., camera head, coupler, fiducial marker(s), etc.); measurement of motion profiles or specific features in the scene that allow for the phase of the surgery to be identified; position, orientation, identity, and/or movement of any other instruments, features, and/or components of the system or being used by the surgical team.

The system may combine measurements and/or other data described above with any other telemetry data from the system and/or video data from the laparoscope to provide a comprehensive dataset with which to improve the overall usability, functionality, and safety of the co-manipulation robot-assisted surgical systems described herein. For example, as the system is being setup to start a procedure, optical scanner 202 may detect the height and orientation of the surgical table. This information may allow the system to automatically configure the degrees of freedom of platform 200 supporting robot arms 300 to the desired or correct positions relative to the surgical table. Specifically, optical scanner 202 may be used to ensure that the height of platform 200 is optimally positioned to ensure that robot arms 300 overlap with the intended surgical workspace. In addition, as described above, the system may automatically reconfigure the degrees of freedom of platform 200 as well as the arrangement of robot arms 300 responsive to movement of the surgical table, and accordingly the trocar(s), to maintain relative position between the distal end of the robot arms and the trocar(s).

In addition, optical scanner 202 may identify the specific surgeon carrying out the procedure, such that the system may use the surgeon's identity to load a system profile associated with the particular surgeon into the system. The system profile may include information related to a surgeon's operating parameter and/or preferences, a surgeon's patient list having parameters for each patient, the desired or required algorithm sensitivity for the surgeon, the degree of freedom positioning of the support platform, etc. Examples of algorithm sensitivities that may be surgeon-specific include: adapting/adjusting the force required to transition from passive mode to co-manipulation mode (e.g., from low force to high force), adapting/adjusting the viscosity felt by the surgeon when co-manipulating the robot arm (e.g., from low viscosity to high viscosity), preferred surgical instrument trajectories when performing specific laparoscopic procedures, etc. Moreover, the surgeon's preferences may include preferred arrangements of robot arm 300, e.g., the positioning of the links and joints of robot arm 300 relative to the patient, with regard to specific surgical instruments, e.g., the preferred arrangement may be different between a laparoscope and a retractor.

Based on the data captured by optical scanner 202, the system may generate a virtual model of the pieces of capital equipment and/or other objects in an operating room that are within a range of movement of the robot arms in the same co-ordinate space as the robot arms and surgical instruments coupled thereto, such that the virtual model may be stored and monitor, e.g., to detect potential collisions. Additionally, the system may track the position and orientation of each virtual model, and the objects within the virtual models as the objects move relative to each other, such that the system may alert the user if the proximity of (i.e., spacing between) any of the virtual models or objects falls below a predefined threshold, e.g., within 50 mm, 75 mm, from 30 mm or less to 100 mm, or more. The system may use this information to recommend a repositioning of platform 200 and/or other components of the system, the surgical table, and/or patient, and/or prevent the robot arm from switching to the co-manipulation mode as a result of the force applied to the robot arm by the collision with the staff member, even if the force exceeds the predetermined force threshold of the robot arm. Moreover, the system may stop or inhibit (e.g., prevent) further movement of a robot arm, e.g., freeze the robot arm, if the proximity of any of the virtual models or objects, e.g., a robot arm reaches or falls below the predefined threshold relative to another objects within the surgical space.

Moreover, based on the data captured by optical scanner 202, the system may track the motion of the handheld surgical instruments that are directly and independently controlled by the surgeon, that are not coupled with the robot arm. For example, the optical scanner 202 may track a clearly defined feature of the instrument, a fiducial marker attached to the instrument or to the gloves (e.g., the sterile gloves) of the surgeon, the coupler between the robot arm and the instrument, a distal tip of the instrument, and/or any other defined location on the instrument. The following are examples of uses and purposes of the motion data: (i) closing a control loop between a handheld instrument and the robot arm holding the camera, thus allowing the surgeon to servo (i.e., move) the camera by "pointing" with a handheld instrument; (ii) tracking information that may be used independently or in combination with other data streams to identify the phase of the surgical procedure; (iii) to identify the dominant hand of the surgeon; (iv) to monitor metrics associated with the experience of the surgeon; (v) to identify which tools the surgeon is using and when to change them for other tools; and/or (vi) tracking of the skin surface of the patient, as well as the number, position and orientation of the trocar ports. This data and information also may be used and computed by the system as part of the co-manipulation control paradigm. As will be understood by a person having ordinary skill in the art, the location/movement of a surgical instrument coupled to a robot arm of the system will be known by the system based on the known robot telemetry and current kinematics of the robot arm, without the need of data captured by optical scanner 202.

Based on the data captured by optical scanner 202, the system further may track the which instrument is being used in a respective port, how often instruments are swapped between ports, which ports have manually held instruments versus instruments coupled to the robot arm, to monitor and determine if additional trocar ports are added, if the system is holding the instruments in place while the patient or surgical table is moving (in which case, the system may change the operational mode of the robot arms to a passive mode and accommodate the movement by repositioning robot arm 300 and/or platform 200), and/or other conditions or parameters of the operating room or the system. The knowledge of the position and orientation of the skin surface and trocar ports relative to the robot arms may facilitate the implementation of "virtual boundaries" as described in further detail below.

Figure 13B:
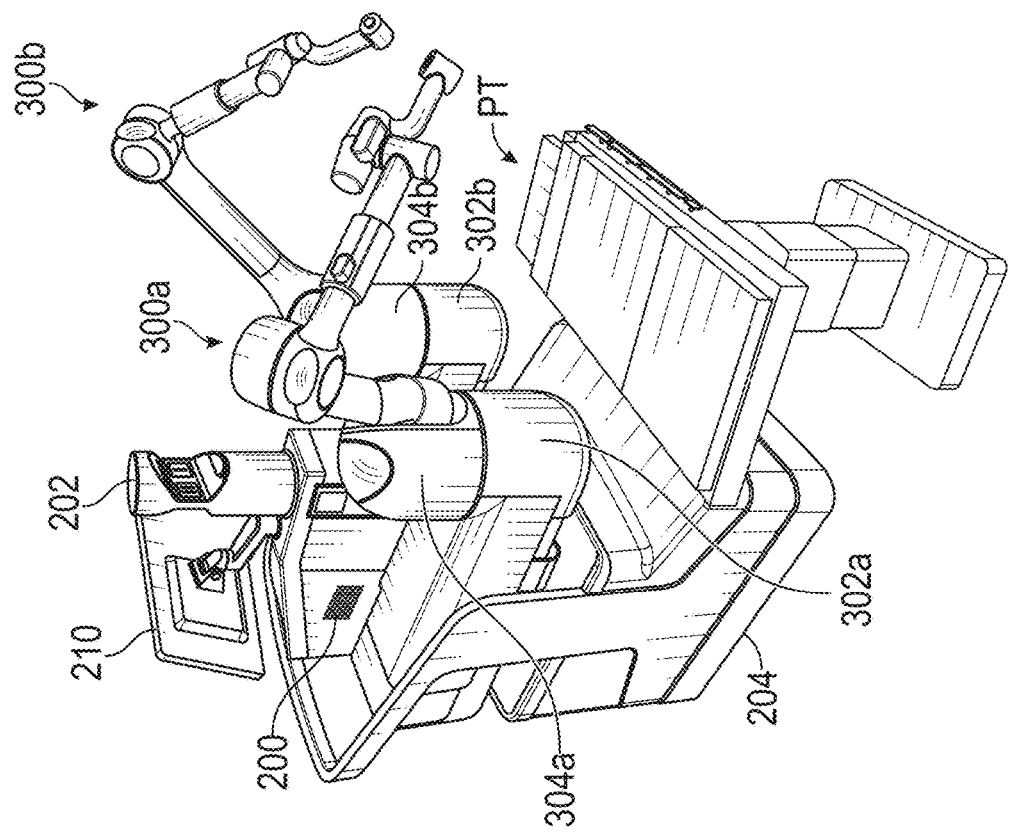
FIGS. 13A-13D illustrate setup of the co-manipulation surgical system in accordance with the principles of the present disclosure.
Figure 13A:
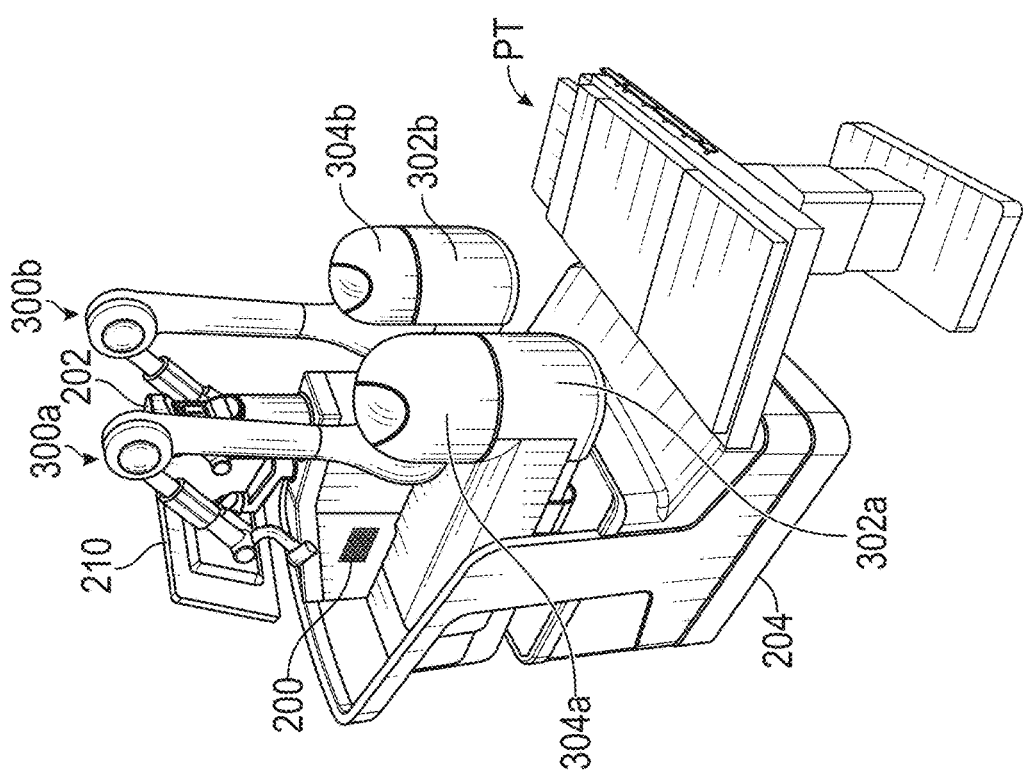

Referring now to FIGS. 13A to 13D, setup of the co-manipulation surgical system is provided. As shown in FIG. 13A, platform 200 may be moved to a desirable position relative to patient table PT by a user, e.g., via wheels 204, while robot arms 300*a*, 300*b* are in their respective stowed configurations. As platform 200 is being moved toward the patient, the scene may be directly observed by one or more optical scanners 202 and one or more proximity sensors 212. From the depth maps observed and generated by optical scanners 202 and the proximity data observed and generated by proximity sensors 212, key features may be identified such as, for example, the height and/or location of patient table PT, the surface of the patient's abdomen, the position and other characteristics of the surgeon, including the surgeon's height, the trocar port(s), and the base of robot arms 300*a*, 300*b*, e.g., base portions 302*a*, 302*b* and shoulder portions 304*a*, 304*b*, robot arms 300*a*, 300*b*, and/or one or more surgical instruments coupled with the robot arms, and the distance between platform 200 and robot arms 300*a*, 300*b* and other objects in the room such as the patient table PT. Identification of such key features may be carried out using standard computer vision techniques such as template matching, feature tracking, edge detection, etc.

As each feature is registered, its position and orientation may be assigned a local co-ordinate system and transformed into the global co-ordinate system the system using standard transformation matrices. Once all features are transformed into a single global co-ordinate system, an optimization algorithm, e.g., least squares and gradient descent, may be used to identify the most appropriate vertical and horizontal positions of robot arms 300*a*, 300*b*, which may be adjusted via platform 200, to maximize the workspace of the robot arms with respect to the insertion point on the patient. The optimal workspace may be dependent on the surgical operation to be performed and/or the surgeon's preferred position. Moreover, the system may generate and a display a virtual map, e.g., via GUI 210, graphically depicting the identified features within the operating room based on the depth and proximity data to guide the user when moving platform 200, as described in further detail below with regard to FIG. 33.

Figure 13D:
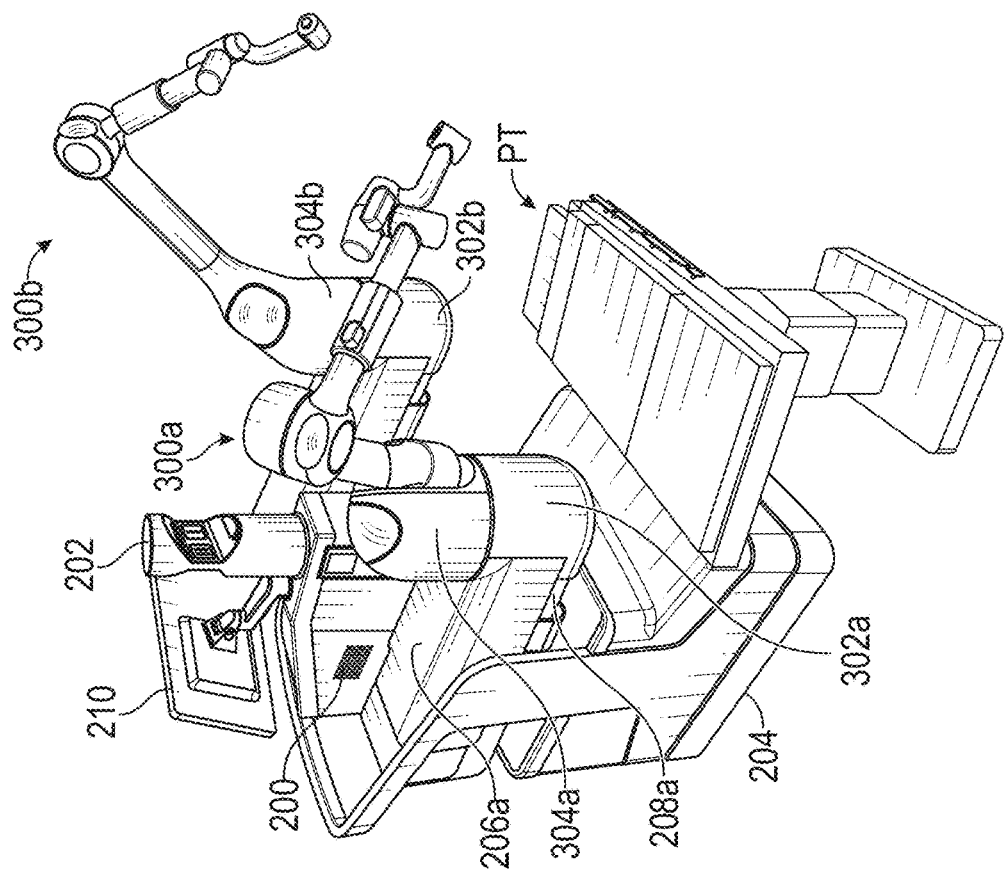
Figure 13C:
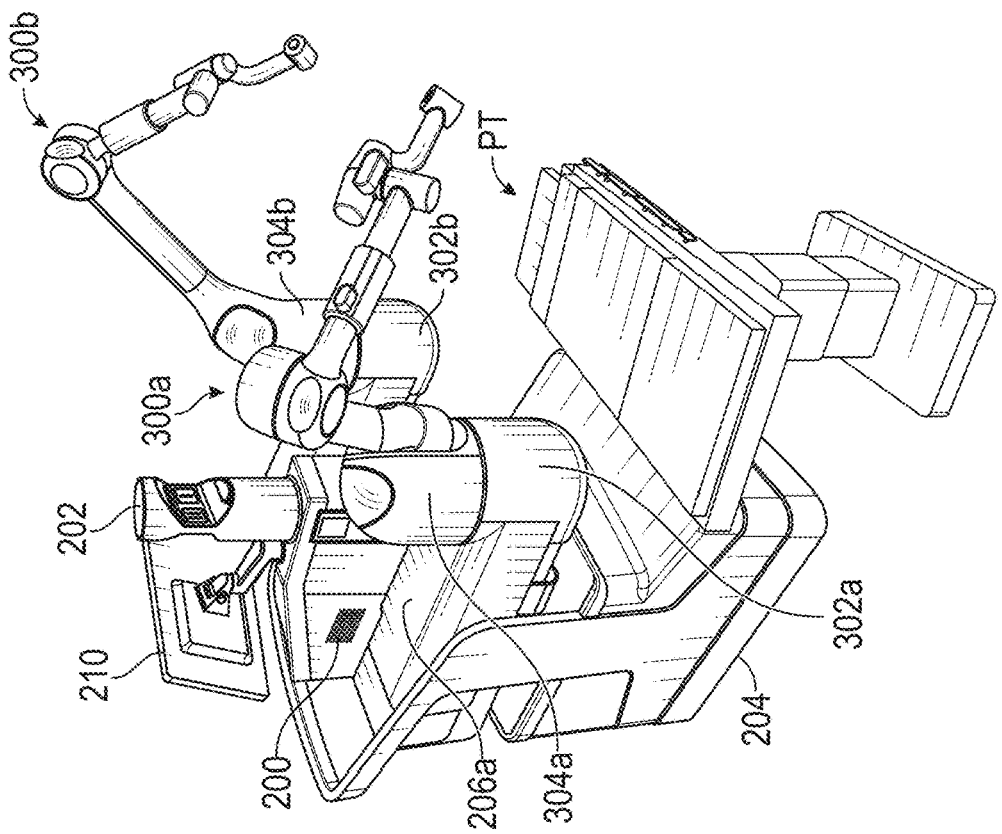

Referring again to FIG. 13B, when platform 200 is in its desired position relative to patient table PT, such that wheels 204 are locked, robot arms 300*a*, 300*b* may be extended away from their respective stowed configurations. As shown in FIG. 13C, the vertical position of the robot arms relative to platform 200 may be adjusted to the desired position, and as shown in FIG. 13D, the horizontal position of the robot arms relative to platform 200 may be adjusted to the desired position. The desired positions of the robot arms may be stored as an "operation-ready" configuration, which may be specific to the operation being performed, as well as the surgeon's preferences. Accordingly, when platform 200 is in the desired position relative to patient table PT, as shown in FIG. 13A, system may be actuated, e.g., via GUI 210 or voice control, etc., to automatically move platform 200 and robot arms 300*a*, 300*b* towards the "operation ready" configuration relative to patient table PT, while avoiding collisions between platform 200 and robot arms 300*a*, 300*b* and other objects in the room based on the depth and proximity data observed and generated by optical sensors 202 and proximity sensors 212.

Figure 14:
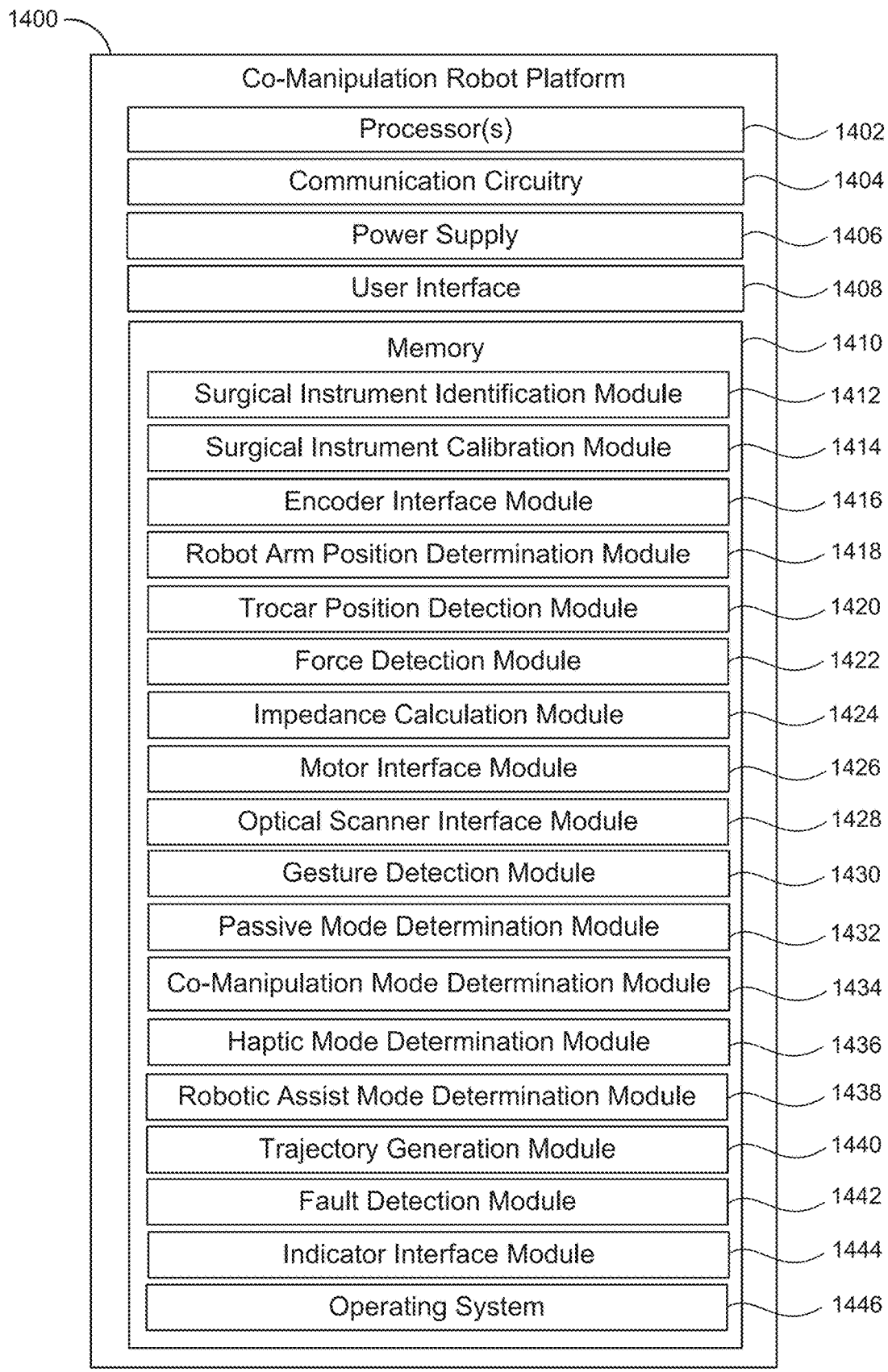
FIG. 14 shows some example components that may be included in a co-manipulation robot platform in accordance with the principles of the present disclosure.

Referring now to FIG. 14, components that may be included in co-manipulation robot platform 1400 are described. Platform 1400 may include one or more processors 1402, communication circuitry 1404, power supply 1406, user interface 1408, and/or memory 1410. One or more electrical components and/or circuits may perform some of or all the roles of the various components described herein. Although described separately, it is to be appreciated that electrical components need not be separate structural elements. For example, platform 1400 and communication circuitry 1404 may be embodied in a single chip. In addition, while platform 1400 is described as having memory 1410, a memory chip(s) may be separately provided.

Platform 1400 may contain memory and/or be coupled, via one or more buses, to read information from, or write information to, memory. Memory 1410 may include processor cache, including a multi-level hierarchical cache in which different levels have different capacities and access speeds. The memory also may include random access memory (RAM), other volatile storage devices, or non-volatile storage devices. Memory 1410 may be RAM, ROM, Flash, other volatile storage devices or non-volatile storage devices, or other known memory, or some combination thereof, and preferably includes storage in which data may be selectively saved. For example, the storage devices can include, for example, hard drives, optical discs, flash memory, and Zip drives. Programmable instructions may be stored on memory 1410 to execute algorithms for, e.g., calculating desired forces to be applied along robot arm 300 and/or the surgical instrument coupled thereto and applying impedances at respective joints of robot arm 300 to effect the desired forces.

Platform 1400 may incorporate processor 1402, which may consist of one or more processors and may be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. Platform 1400 also may be implemented as a combination of computing devices, e.g., a combination of a DSP and a microprocessor, a plurality of microprocessors, one or more microprocessors in conjunction with a DSP core, or any other such configuration. Platform 1400, in conjunction with firmware/software stored in the memory may execute an operating system (e.g., operating system 1446), such as, for example, Windows, Mac OS, QNX, Unix or Solaris 5.10. Platform 1400 also executes software applications stored in the memory. For example, the software may be programs in any suitable programming language known to those skilled in the art, including, for example, C++, PHP, or Java.

Communication circuitry 1404 may include circuitry that allows platform 1400 to communicate with an image capture devices such as optical scanner and/or endoscope. Communication circuitry 1404 may be configured for wired and/or wireless communication over a network such as the Internet, a telephone network, a Bluetooth network, and/or a WiFi network using techniques known in the art. Communication circuitry 1404 may be a communication chip known in the art such as a Bluetooth chip and/or a WiFi chip. Communication circuitry 1404 permits platform 1400 to transfer information, such as force measurements on the body wall at the trocar insertion point locally and/or to a remote location such as a server.

Power supply 1406 may supply alternating current or direct current. Power supply 1406 may be a port to allow platform 1400 to be plugged into a conventional wall socket, e.g., via a cord with an AC to DC power converter and/or a USB port, for powering components within platform 1400. Power supply 1406 may be operatively coupled to an emergency switch, such that upon actuation of the emergency switch, power stops being supplied to the components within platform 1400 including, for example, the braking mechanism disposed on at least some joints of the plurality of joints of robot arm 300. For example, the braking mechanisms may require power to disengage, such that without power supplied to the braking mechanisms, the braking mechanisms engage to prevent movement of robot arm 300 without power. In direct current embodiments, power supply may include a suitable battery such as a replaceable battery or rechargeable battery and apparatus may include circuitry for charging the rechargeable battery, and a detachable power cord. For example, the battery may be an uninterruptable power supply (UPS) that may be charged when the system is plugged in, and which is only operatively coupled to certain computing components of the system, e.g., processor 1402, such that the battery may automatically provide power to the computing components when the system is temporarily unplugged from the electrical power source, e.g., to move the system to another side of a patient table during a multi-quadrant procedure. In some embodiments, the braking mechanism of wheels 204 of platform 200 also may be operatively coupled to the battery, such that they may be engaged/disengaged while the system is unplugged and moved around the operating room.

User interface 1408 may be used to receive inputs from, and/or provide outputs to, a user. For example, user interface 1408 may include a touchscreen display (e.g., GUI 210), switches, dials, lights, etc. Accordingly, user interface 1408 may display information such as selected surgical instrument identity and force measurements observed during operation of robot arm 300. Moreover, user interface 1408 may receive user input including adjustments to the predetermined amount of movement at the handle of the surgical instrument or the predetermined dwell time period to cause the robot arm to automatically switch to the passive mode, the predetermined threshold of force applied at the handle of the surgical instrument to cause the robot arm to automatically switch to the co-manipulation mode, a position of the predefined haptic barrier, an identity of the surgical instrument coupled to the distal end of the robot arm, a vertical height of the robot arm, a horizontal position of the robot arm, etc., such that platform 1400 may adjust the information/parameters accordingly. In some embodiments, user interface 1408 is not present on platform 1400, but is instead provided on a remote, external computing device communicatively connected to platform 1400 via communication circuitry 1404.

Memory 1410, which is one example of a non-transitory computer-readable medium, may be used to store operating system (OS) 1446, surgical instrument identification module 1412, surgical instrument calibration module 1414, encoder interface module 1416, robot arm position determination module 1418, trocar position detection module 1420, force detection module 1422, impedance calculation module 1424, motor interface module 1426, optical scanner interface module 1428, gesture detection module 1430, passive mode determination module 1432, co-manipulation mode determination module 1434, haptic mode determination module 1436, robotic assist mode determination module 1438, trajectory generation module 1440, fault detection module 1442, and indicator interface module 1444. The modules are provided in the form of computer-executable instructions/algorithms that may be executed by processor 1402 for performing various operations in accordance with the disclosure.

For example, during a procedure, the system may continuously run the algorithms described herein based on the data collected by the system. That data may be collected and/or recorded using any of the components and methods disclosed herein, including, e.g., from sensors/encoders within the robots, from optical scanning devices in communication with the other components of the robotic system, and/or from manual inputs by an operator of the system. Accordingly, the algorithms, the data, and the configuration of the system may enable the user to co-manipulate the robot arms with minimal impact and influence from the weight of the robot arms and/or surgical instruments coupled thereto, force of gravity, and other forces that traditional robot arms fail to compensate for. Some of the parameters of the algorithms described herein may control an aspect of the behavior of the system including, e.g., robustness of detected features, sensitivity to false positives, robot control gains, number of features to track, dead zone radius, etc.

Surgical instrument identification module 1412 may be executed by processor 1402 for identifying the surgical instrument coupled to each of the robot arms, and loading the appropriate calibration file into the controller system. For example, the calibration file for each surgical instrument may be stored in a database accessible by surgical instrument identification module 1412, and may include information associated with the surgical instrument such as, e.g., instrument type, make, weight, center of mass, length, instrument shaft diameter, etc. Accordingly, when the appropriate calibration file is loaded, and the associated surgical instrument is coupled to robot arm 300, the system will automatically account for the mass of the surgical instrument, e.g., compensate for gravity on the surgical instrument, when the surgical instrument is attached to robot arm 300 based on the data in the calibration file, such that robot arm 300 may hold the surgical instrument in position after the surgical instrument is coupled to the robot arm and the operator lets go of the surgical instrument. For example, surgical instrument identification module 1412 may identify the surgical instrument based on user input via user interface 1408, e.g., the operator may select the surgical instrument from a database of surgical instruments stored in memory 1410.

Moreover, in some embodiments, the system may be configured such that only pre-approved, verified surgical instruments, e.g., of a certain make, are authorized to be used with the system. A list of authorized instruments may be stored within a database in memory 1410 and/or uploaded from a remote database, e.g., a cloud database. Surgical instrument identification module 1412 may determine that a surgical instrument is authorized for use with the system via, e.g., user input by the user via user interface 1408 indicating that the surgical instrument is among a list of pre-approved instruments, the calibration file loaded for the surgical instrument either automatically when the surgical instrument is attached to the robot arm or manually loaded by a user, and/or real-time surgical instrument identification by the system. For example, surgical instrument identification module 1412 may identify the make of the surgical instrument based on image data observed and generated via optical scanners 202 and/or a laparoscope, before or during a procedure. Specifically, surgical instrument identification module 1412 may identify distinctive features of the surgical instrument, e.g., manufacture logo, handle design, instrument packaging, etc., from the image data to determine the type/make of the instrument. For example, many surgical instruments include an identification marker, e.g., brand logo, etched into or otherwise labeled at or near the distal tip of the instrument, and thus, the make of a surgical instrument may be identified via the video feed of a laparoscope received by optical scanner interface module 1428 having the distal tip of the surgical instrument within the field of view of the laparoscope. Additionally or alternatively, the image data obtain by optical scanner 202 may include measurement data associated with the specific instrument, such that surgical instrument identification module 1412 may compare such data with information contained within the database to identify the instrument and load the appropriate calibration file into the controller system.

Moreover, provided that each specific make of a laparoscope may have distinguishable output video feed quality, e.g., x-y pixel count, frame rate, noise signature, codec, etc., surgical instrument identification module 1412 may identify the make of the instrument by comparing the metadata acquired via the output video feed quality with those expected from an authorized laparoscope. Further, provided that each specific make of a surgical instrument may have a distinguishable and precise mass, surgical instrument identification module 1412 may identify the make of the instrument based on the mass of the surgical instrument, e.g., during surgical instrument calibration as described in further detail below. Additionally, provided that each specific make of a surgical instrument may have a distinguishable and precise shaft diameter, surgical instrument identification module 1412 may identify the surgical instrument based on the specific magnetic field strength measured by sensor 414 induced by the displaced magnet within the coupler body due to the diameter of the surgical instrument when the surgical instrument is coupled to the coupler body and the coupler body is coupled to coupler interface 400, as described above. Provided that each specific make of a surgical instrument may have distinguishable and precise impedance properties, the system may send a vibration pulse down the surgical instrument when the surgical instrument is coupled to the robot arm, such that surgical instrument identification module 1412 may identify the make of the surgical instrument based on the response data. Moreover, surgical instrument identification module 1412 may identify the make of the surgical instrument based on other measurable properties such as electrical resistance of the surgical instrument and/or magnetism of the surgical instrument, provided that such properties are distinguishable for each make of the surgical instrument.

In some embodiments, surgical instrument identification module 1412 may automatically identify the surgical instrument coupled with the robotic arm via the coupler body and the coupler interface using, e.g., an RFID transmitter chip and reader or receiver (e.g., placing an RFID sticker or transmitter on the surgical instrument that may transmit information about the surgical instrument to a receiver of the system), an near field communication ("NFC") device such as a near field magnetic induction communication device, a barcode and scanner or other optical device, a magnet based communication system, reed switches, a Bluetooth transmitter, the weight of the instrument and/or data gathered from the optical scanner and a lookup table, an activation code associated with an authorized surgical instrument, and/or any other features or mechanisms described herein or suitable for identification of the surgical instrument. Surgical instrument identification module 1412 further may confirm that a surgical instrument is authorized by checking for a license and/or a hospital inventory.

In some embodiments, authorized surgical instruments may include indicators such as invisible ink on the tool shaft or handle that may be illuminated and detected via optical sensor 202, e.g., infra-red illumination that may be illuminated/detected via an IR-sensitive sensor of optical scanner 202, a unique reflective marking that may be illuminated and detected at a specific wavelength of light, a unique feature on the tool and/or coupling mechanism, e.g., shape, profile, indent, latching feature, etc., that facilitates a unique kinematic engagement between the tool and the coupling mechanism, a unique feature built into the sterile drape coupled between the coupler body and the coupler interface. In some embodiments, the system may be operatively coupled to a docking station configured to receive the surgical instrument therein, and to record measurements and detect identity indicators of the surgical instrument, to thereby update the calibration file and determine whether the surgical instrument is authorized.

Accordingly, upon coupling of an unauthorized surgical instrument to the robot arm, the system may generate an audible, visual, and/or haptic alert to inform the user of such unauthorized use, such that corrective action may be taken, e.g., replacing the unauthorized tool with an authorized tool. In some embodiments, the system may apply an increased level of viscosity to the robot arms when an unauthorized tool is coupled to the robot arm to inform the user via haptic feedback, and/or prevent motion of the system by engaging the braking mechanisms of the robot arm and applying impedance via the motors of the system. Moreover, some advanced features of the system such as instrument centering may be disabled until an authorized tool is used. In some embodiments, prior to the start of a procedure, upon attachment of an unauthorized tool, the system may lock the robot arm via the braking mechanisms and motors until the unauthorized tool is replaced with an authorized tool.

Moreover, based on the data obtained by optical scanner 202, e.g., tracked movements of the distal end of a laparoscope coupled to robot arm 300, and/or robot telemetry data obtained by system 100, e.g., known positions/movements of robot arm 300 based on the current kinematics of robot arm 300 calculated by system 100, in addition to image data captured by the laparoscope, the system may identify the type of laparoscope coupled to robot arm 300. For example, laparoscopes commonly used during laparoscopic procedures include flat-tipped laparoscopes and angled-tipped laparoscopes, e.g., a laparoscope having a 30 degree angled tip. The system may determine which laparoscope type is currently coupled to robot arm 300 by comparing the image data obtained by optical scanner 202 of a predefined pattern of movement of the laparoscope and/or known kinematic data of robot arm 300 during the predefined pattern of movement of the laparoscope, e.g., moving the distal end of the laparoscope in a circular pattern in a plane perpendicular to the longitudinal axis of the laparoscope, with the image data obtained by the laparoscope as the laparoscope is being moved in the predefined pattern of movement. For example, for a flat-tipped laparoscope, the image data captured by the laparoscope as the distal end of the laparoscope is moved in a circular pattern in the plane perpendicular to the longitudinal axis of the laparoscope should move along a circular planar path, e.g., there will be no change in depth of the field of view of the laparoscope; whereas, for an angled-tipped laparoscope, the image data captured by the laparoscope as the distal end of the laparoscope is moved in a circular pattern in the plane perpendicular to the longitudinal axis of the laparoscope will observe a change of depth of the field of view of the laparoscope.

Surgical instrument calibration module 1414 may be executed by processor 1402 for calibrating a surgical instrument, e.g., a surgical instrument that does not currently have an associated calibration file in the database stored in memory 1410. Accordingly, surgical instrument calibration module 1414 may calculate measurements and specifications of a surgical instrument when it is coupled to robot arm 300 and the system is in calibration mode, as described in further detail below with regard to FIG. 19, based on force measurements of robot arm 300 applied by the surgical instrument via force detection module 1422. For example, surgical instrument calibration module 1414 may generate a calibration file for the surgical instrument including information such as instrument type, make, weight, center of mass, length, instrument shaft diameter, a viscosity parameter of the surgical instrument, etc. At least some of the surgical instrument information in the calibration file may be provided by user input via user interface 1408, e.g., the instrument type/make, or may be detected by optical scanner interface module 1428, e.g., the instrument type, the center of mass of the instrument, the instrument length, and the instrument diameter.

Similarly, memory 1410 may include an additional module, e.g., a system calibration module, which may be executed by processor 1402 for calibrating a new robot arm when a current robot arm is replaced, e.g., during a surgical procedure, based on the data obtained by optical scanner 202, with or without utilizing a tracker at the distal end of the new robot arm, to ensure the system is accurately aware of the kinematics of the new robot arm. Specifically, the system may calibrate optical scanner 202 to platform 200, calibrate the new robot arm with respect to the base portion of the new robot arm, and calibrate the new robot arm with respect to platform 200 when the new robot arm is coupled to platform 200. For example, based on the telemetry data obtained by optical scanner 202, the system calibration module may compare the actual real-time movements of the new robot arm as captured by optical scanner 202 to the movements expected based on commands sent to the new robot arm by the system, e.g., to execute a preprogrammed routine intended to move the new robot arm in specific positions, and generate a degree of error indicative of a deviation between the actual real-time movements of the new robot arm and the expected movements of the robot arm based on the preprogrammed routine. Surgical the system calibration module further may execute an optimization algorithm to reduce or eliminate the degree of error between the actual real-time movements and the expected movements, e.g., until the degree of error falls below a predetermined threshold. This calibration process may occur when the system is in a predefined calibration mode, or alternatively, in real-time during a surgical procedure after the new robot arm is coupled to platform 200.

Encoder interface module 1416 may be executed by processor 1402 for receiving and processing angulation measurement data from the plurality of encoders of robot arm 300, e.g., encoders E1-E7, in real time. For example, encoder interface module 1416 may calculate the change in angulation over time of the links of robot arm 300 rotatably coupled to a given joint associated with the encoder. As described above, the system may include redundant encoders at each joint of robot arm 300, to thereby ensure safe operation of robot arm 300. Moreover, additional encoders may be disposed on platform 100 to measure angulation/position of each robot arm relative to platform 200, e.g., the vertical and horizontal position of the robot arms relative to platform 200. Accordingly, an encoder may be disposed on platform 200 to measure movement of the robot arms along the vertical axis of platform 200 and another encoder may be disposed on platform 200 to measure movement of the robot arms along the horizontal axis of platform 200.

Robot arm position determination module 1418 may be executed by processor 1402 for determining the position of robot arm 300 and the surgical instrument attached thereto, if any, in 3D space in real time based on the angulation measurement data generated by encoder interface module 1416. For example, robot arm position determination module 1418 may determine the position of various links and joints of robot arm 300 as well as positions along the surgical instrument coupled to robot arm 300. Based on the position data of robot arm 300 and/or the surgical instrument, robot arm position determination module 1418 may calculate the velocity and/or acceleration of movement of robot arm 300 and the surgical instrument attached thereto in real time. For example, by determining the individual velocities of various joints of robot arm 300, e.g., via the encoder associated with each joint of the various joints, robot arm position determination module 1418 may determine the resultant velocity of the distal end of robot arm 300, which may be used by passive mode determination module 1432 to determine whether movement of the distal end of robot arm 300 is within a predetermined threshold for purposes of transitioning system 100 to passive mode, as described in further detail below.

Trocar position detection module 1420 may be executed by processor 1402 for determining the position and/or orientation of one or more trocar port inserted within the patient. The position and/or orientation of a trocar port may be derived based on data obtained from, e.g., inertial measurement units and/or accelerometers, optical scanners, electromechanical tracking instruments, linear encoders, the sensors and data as described above. For example, the position of the trocar ports on the patient may be determined using a laser pointing system that may be mounted on one or more of the components of the system, e.g., wrist portion 311 of the robot arm, and may be controlled by the system to point to the optimal or determined position on the patient's body to insert the trocar. Moreover, upon insertion of the surgical instrument that is attached to robot arm 300 through a trocar, virtual lines may continuously be established along the longitudinal axis of the surgical instrument, the alignment/orientation of which may be automatically determined upon attachment of the surgical instrument to coupler interface 400 via the coupler body via the magnetic connection as described above, in real time as the surgical instrument moves about the trocar point. Moreover, when the surgical instrument is inserted within the trocar port, it will be pointing toward the trocar point, and accordingly, distal wrist link 316 will also point toward the trocar point, the angle of which may be measured by an encoder associated therewith. Accordingly, the trocar point may be calculated as the intersection of the plurality of virtual lines continuously established along the longitudinal axis of the surgical instrument. In this manner, the calculated trocar point will remained fixed relative to the patient as the surgical instrument is maneuvered about the trocar point, e.g., rotated or moved in or out of the patient. In addition, the orientation of the trocar port and its position relative to robot arm 300 may be determined based on image data received from one or more optical scanners, e.g., a LiDAR camera and/or an RGBD camera. By measuring the true position and orientation of the trocar ports, the system may be provided an additional safety check to ensure that the system level computations are correct, e.g., to ensure that the actual motion of the robot arms or instrument matches a commanded motion of the robot arms or instrument in robotic assist mode.

Based on the known position and/or orientation of a trocar port in addition to the known position of the distal end of robot arm 300 from robot arm position determination module 1418, the system may maintain the position of the distal end of robot arm 300 relative to the trocar point as robot arm 300 moves, e.g., via vertical or horizontal adjustment thereof by platform 200, or as the patient table height is adjusted, thereby causing the height of the patient's abdomen to move, thereby keeping the surgical instrument within the patient's body and coupled to robot arm 300 steady during these external movements. To achieve this, the known position of the distal end of robot arm 300 from robot arm position determination module 1418 is calculated in the global frame of the system by adding position of platform 200 to the kinematics calculations (e.g., the "forward kinematics" of robot arm 300 in the context of serial chain robotic manipulators).

With the position of the distal end of robot arm 300 known globally, the system may hold that position steady by applying appropriate forces to robot arm 300 during the external movements that minimize the error between its current and desired positions. Accordingly, for example, when a surgical instrument coupled to the distal end of robot arm 300 is inserted through a trocar port such that the tip of the instrument is inside of the patient, and a user adjusts the height of the patient table, the system may apply forces/torques to robot arm 300 to reconfigure robot arm 300 and/or cause movement of the stages of platform 200 to maintain the relative position between the distal end of robot arm 300, and accordingly the surgical instrument, and the trocar port. In some embodiments, the system may cause the distal end of robot arm 300 to retract slightly such that the tip of the surgical instrument is positioned within the trocar port and out of contact with anatomical structures within the patient's body prior to reconfiguring robot arm 300 to maintain the relative position between the surgical instrument and the trocar port.

Force detection module 1422 may be executed by processor 1402 for detecting forces applied on robot arm 300, e.g., at the joints or links of robot arm 300 or along the surgical instrument, as well as applied on the trocar, e.g., body wall forces. For example, force detection module 1422 may receive motor current measurements in real time at each motor, e.g., M1, M2, M3, disposed within the base of robot arm 300, which are each operatively coupled to a joint of robot arm 300, e.g., base joint 303, shoulder joint 318, elbow joint 322, wrist joint 332. The motor current measurements are indicative of the amount of force applied to the associated joint. Accordingly, the force applied to each joint of robot arm 300 as well as to the surgical instrument attached thereto may be calculated based on the motor current measurements and the position data generated by robot arm position determination module 1418 and/or trocar position detection module 1420.

Due to the passive axes at the distal end of robot arm 300, the force applied by the instrument coupled with the robot arm on the trocar may remain generally consistent throughout the workspace of the robot arm. The force on the trocar may be affected by the interaction of the distal tip of the instrument with tissue within the body. For example, if a tissue retractor advanced through the trocar is engaged with (e.g., grasping) bodily tissue or another object inside the body, the force exerted on the end of the instrument from the bodily tissue or other object may cause a change in the force applied to the trocar. In some aspects, the force on the trocar may be a function of how much weight is being lifted by the instrument being used.

Impedance calculation module 1424 may be executed by processor 1402 for determining the amount of impedance/torque needed to be applied to respective joints of robot arm 300 to achieve the desired effect, e.g., holding robot arm 300 in a static position in the passive mode, permitting robot arm 300 to move freely while compensating for gravity of robot arm 300 and the surgical instrument attached thereto in the co-manipulation mode, applying increased impedance to robot arm 300 when robot arm 300 and/or the surgical instrument attached thereto is within a predefined virtual haptic barrier in the haptic mode, etc.

For example, impedance calculation module 1424 may determine the amount of force required by robot arm 300 to achieve the desired effect based on position data of robot arm 300 generated by robot arm position determination module 1418 and the position data of the trocar generated by trocar position detection module 1420. For example, by determining the position of the distal end of robot arm 300, as well as the point of entry of the surgical instrument into the patient, e.g., the trocar position, and with knowledge of one or more instrument parameters, e.g., mass and center of mass of the surgical instrument stored by surgical instrument calibration module 1414, impedance calculation module 1424 may calculate the amount of force required to compensate for gravity of the surgical instrument (compensation force), as described in further detail below with regard to FIG. 23A. Accordingly, the amount of compensation force required to compensate for the gravity of the surgical instrument may be converted to torque to be applied at the joints of robot arm 300, e.g., by the motors operatively coupled to the joints of robot arm 300, as indicated by the motor current measurements.

Figure 23A:
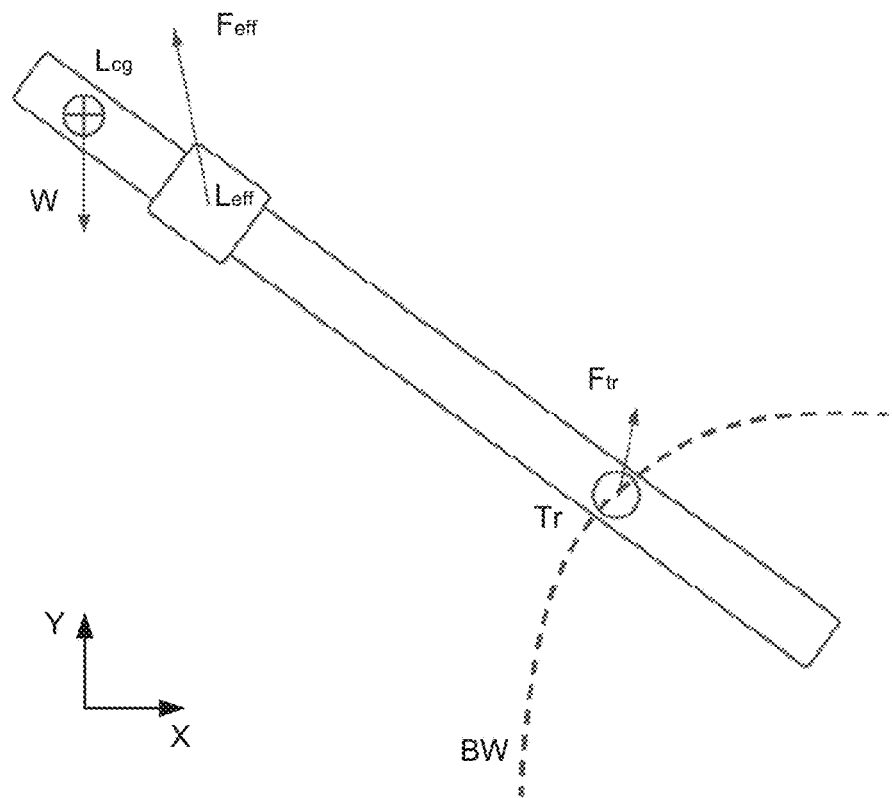
FIGS. 23A and 23B are free-body diagrams illustrating forces applied to the surgical instrument coupled to the robot arm during a laparoscopic surgical procedure.
Figure 23B:
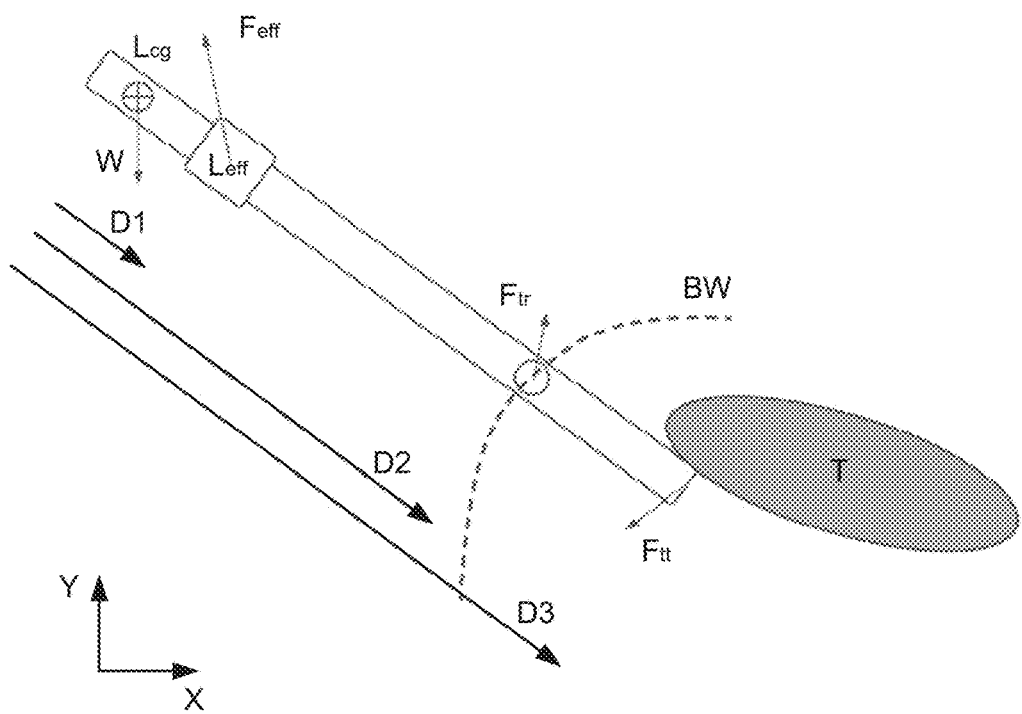

Moreover, by determining the position of the distal end of robot arm 300, and accordingly, a change in position of the distal end of robot arm 300 over time, for example, due to an external force applied to the distal end of robot arm 300, e.g., by tissue held by the operating end of the surgical instrument, and with knowledge of one or more instrument parameters, e.g., mass, center of mass, and length of the surgical instrument stored by surgical instrument calibration module 1414, impedance calculation module 1424 may calculate the amount of force required to maintain the surgical instrument in a static position (hold force), as described in further detail below with regard to FIG. 23B. Accordingly, the amount of hold force required to resist the change in position of the distal end of robot arm 300, in addition to the amount of compensation force required to compensate for the gravity of the surgical instrument, may be converted to torque to be applied at the joints of robot arm 300 to maintain robot arm 300 in a static position, e.g., by the motors operatively coupled to the joints of robot arm 300, as indicated by the motor current measurements. In addition, impedance calculation module 1424 and/or force detection module 1422 may calculate the amount of force applied by the surgical instrument to the patient at the point of entry, e.g., at the trocar, as well as the amount of force applied to the operating end of the surgical instrument, e.g., the grasper end of a surgical instrument, based on the compensation force, the hold force, one or more parameters of the surgical instrument such as the mass, center of mass, and length of the surgical instrument, and the distance from the center of mass to the point of entry.

Additionally or alternatively, by determining the forces applied on robot arm 300 via force detection module 1422, as well as the position/velocity/acceleration of the distal end of robot arm 300 in 3D space via robot arm position determination module 1418, the desired force/impedance to be applied to robot arm 300 to compensate for the applied forces may be calculated, e.g., for gravity compensation or to hold robot arm 300 in a static position in the passive mode. Accordingly, the desired force may be converted to torque to be applied at the joints of robot arm 300, e.g., by the motors operatively coupled to the joints of robot arm 300. For example, the robot Jacobian may be used for this purpose.

Motor interface module 1426 may be executed by processor 1402 for receiving motor current readings at each motor, e.g., M1, M2, M3, M4, disposed within the base of robot arm 300, and for actuating the respective motors, e.g., by applying a predetermined impedance to achieved the desired outcome as described herein and/or to cause the joints operatively coupled to the respective motors to move, such as in the robotic assist mode. For example, motor interface module 1426 may actuate M4 to cause rotation of distal shoulder link 308 relative to proximal shoulder link 306.

As described above, the data streams from the robot arms, the camera feed from the laparoscope, the data acquired from optical scanner 202 and/or proximity sensors 212, as well as data optionally captured from one or more imaging devices disposed on a structure adjacent to the robot arms, the walls, ceiling, or other structures within the operating room, may be recorded, stored, and used individually or in combination to understand and control the surgical system and procedures of the surgical system. The foregoing components, devices, and combinations thereof are collectively referred to herein as optical scanners or optical scanning devices.

Optical scanner interface module 1428 may be executed by processor 1402 for receiving depth data obtained by an optical scanning device, e.g., optical scanner 202, and processing the depth data to detect, e.g., predefined conditions therein. Moreover, optical scanner interface module 1428 may generate depth maps indicative of the received depth data, which may be displayed to the operator, e.g., via a monitor. Based on the depth map generated by the optical scanning devices, optical scanner interface module 1428 may cluster different groups of (depth) pixels into unique objects, a process which is referred to as object segmentation. Examples of such algorithms for segmentation may include: matching acquired depth map data to a known template of an object to segment; using a combination of depth and RGB color image to identify and isolate relevant pixels for the object; and/or machine learning algorithms trained on a real or synthetic dataset to objects to identify and segment. Examples of such segmentation on a depth map may include: locating the robot arms or determining the position of the robot arms; identifying patient ports (e.g., trocar ports) in 3D space and determining a distance from the instruments to the trocar ports; determining the relative distances between, e.g., the stages of platform 200, robot arm 300, any surgical instruments attached thereto, and objects/persons in the operating room such as the surgical table, drapes, etc.; identifying the surgeon and distinguishing the surgeon from other operators in the room; and/or identifying the surgeon in the sensor's field of view. Moreover, the system may use object segmentation algorithms to uniquely identify the surgeon and track the surgeon with respect to, for example, a surgical table, a patient, one or more robot arms, etc. In addition, the system may use object segmentation algorithms to determine if a surgeon is touching or handling either of the robot arms and, if so, identify which robot arm is being touched or handled by the surgeon.

Figure 17A:
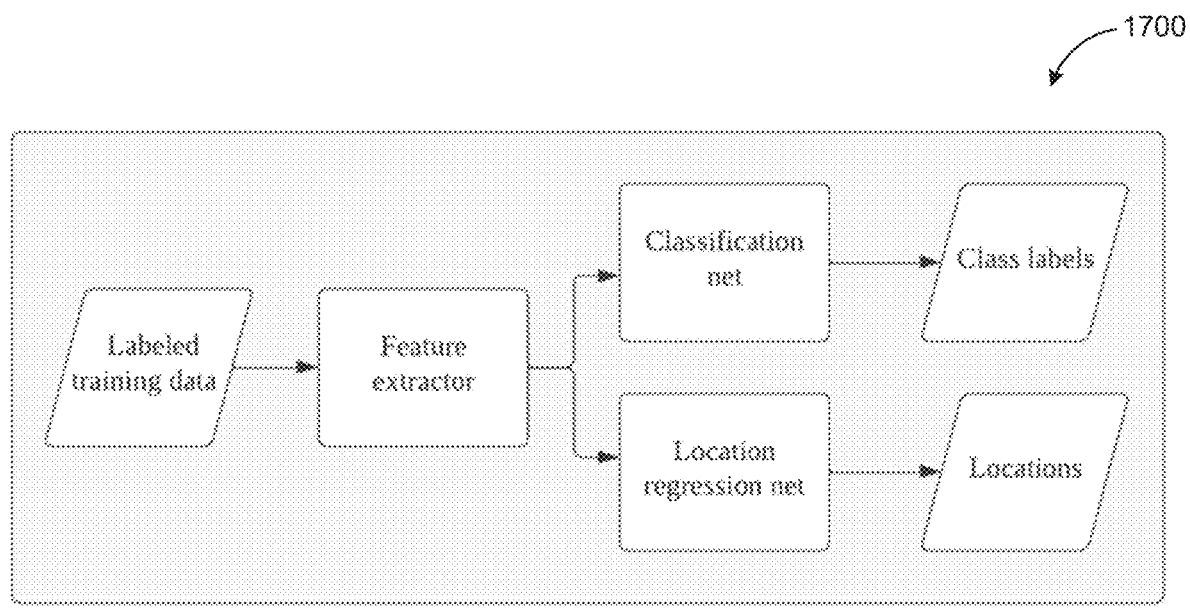
FIG. 17A is a flow chart illustrating training of the co-manipulation surgical system to identify and track a surgical instrument for instrument centering in accordance with the principles of the present disclosure.

Optical scanner interface module 1428 further may use object segmentation algorithms to analyze image data obtained from a laparoscope to locate and track one or more surgical instruments and/or anatomical structures and distinguish the tracked surgical instrument(s) and/or anatomical structure(s) from other objects and structures within the field of view of the laparoscope. For example, the object segmentation algorithms may include deep learning approaches. Specifically, a neural network may be trained for instrument/anatomical structure detection via a manually annotated video dataset sampled from multiple laparoscopic surgeries includes various surgical instruments and anatomical environments. For example, as shown in FIG. 17A, labeled training data including manual annotations indicative of surgical instrument/anatomical structure locations as well as class labels indicative of surgical instrument/anatomical structure type may be fed through a feature extractor to train the neural network to generate class labels and identify surgical instrument/anatomical structure location within an image dataset. The trained neural network may then be implemented by the system to detect the target surgical instrument/anatomical structure in image data obtained by the laparoscope via optical scanner interface module 1428 in real time to provide instrument centering as described in further detail below.

Optical scanner interface module 1428 further may receive image data from additional optical scanning devices as defined herein, including for example, an endoscope operatively coupled to the system. Moreover, optical scanner interface module 1428 may receive depth data obtained by proximity sensors 212 coupled to platform 200 and process the depth data to generate a virtual map of the area surrounding platform 200, as described below with regarding to FIG. 33, which may be displayed to the operator via a monitor, e.g., display 210. For example, optical scanner interface module 1428 may generate graphical representations of system 100 including platform 200 and robot arms 300a, 300b, and any objects and/or persons within the area surrounding platform 200 for display in the virtual map to guide movement of platform 200 and robot arms 300a, 300b through the operating room.

Gesture detection module 1430 may be executed by processor 1402 for detecting predefined gestural patterns as user input, and executing an action associated with the user input. The predefined gestural patterns may include, for example, movement of a surgical instrument (whether or not attached to robot arm 300), movement of robot arm 300 or other components of the system, e.g., foot pedal, buttons, etc., and/or movement of the operator in a predefined pattern. For example, movement of the surgical instrument back and forth in a first direction (e.g., left/right, up/down, forward/backward, in a circle) may be associated with a first user input requiring a first action by the system and/or back and forth in a second direction (e.g., left/right, up/down, forward/backward, in a circle) that is different than the first direction may be associated with a second user input requiring a second action by the system. Similarly, pressing the foot pedal or a button operatively coupled with the system in a predefined manner may be associated with a third user input requiring a third action by the system, and movement of the operator's head back and forth or up and down repeatedly may be associated with a fourth user input requiring a fourth action by the system. Various predefined gestural patterns associated with different components or operators of the system may be redundant such that the associated user input may be the same for different gestural patterns. The predefined gestural patterns may be detected by, e.g., an optical scanning device such as a laparoscope or optical scanner 202 via optical scanner interface module 1428 or directly by force applied to robot arm 300 via force detection module 1422 or other components of the system.

Actions responsive to user input associated with predefined gestural patterns may include, for example, enabling tool tracking to servo (i.e., move) the laparoscope based on the motion of a handheld tool and/or automatically to maintain the handheld tool within a field of view of the laparoscope; engaging the brakes on (e.g., preventing further movement of) the robot arm; engaging a software lock on the robot arm; dynamically changing the length of time that the robot arm takes to transition between states from a default setting; loading a virtual menu overlay on the video feed whereby a surgical instrument in the field of view of the laparoscope functions as a pointer to trigger further actions available from the virtual menu; start/stop a recording of image data; and/or identifying which member of the surgical staff is touching the robot arm, if any. This information may be used to ensure that the system does not move if the surgeon is not touching the robot arm, e.g., to avoid the scenario where an external force is acting on the robot arm (e.g., a light cable or other wire being pulled across the robot arm) and the system perceives the force to be intentional from the surgeon. The same information may be used to detect the gaze direction of the surgeon, e.g., whether the surgeon is looking at the video feed or somewhere else in the room, such that the system may freeze the robot arm if the surgeon's gaze is not in the direction it should be. Additionally, the system may reposition a field of view of a camera based on, for example, the direction a surgeon is facing or based on the objects that the surgeon appears to be looking at, based on the data from the optical scanner 1100. Moreover, moving the distal tip of a surgical instrument to a center portion of the laparoscopic field of view, e.g., defined by a predetermined boundary region, and holding the position for more than a predetermined time threshold may be associated with a user input detected by gesture detection module 1430 to enable took tracking, as described in further detail below.

Moreover, a predefined gestural pattern such as double-tapping a distal portion of the robot arm and/or a predetermined sinusoidal movement of the camera head of the laparoscope about the trocar may be associated with a user input detected by gesture detection module 1430 to start and/or stop a recording of image/audio data by the optical scanning devices. Specifically, there may be key moments during a procedure that the user may want recorded, and which the user may want to be able to locate in a quick manner without having to go through an entire recording of the entire procedure to find the key moments. By providing an easy way for the user to initiate and stop a recording via simple predefined gestural patterns, such that the recording is saved to a folder with a timestamp associated with that particular procedure, the user may easily locate the recording for review and/or teaching purposes. This feature may be particularly useful for diagnostic procedures. In some embodiments, in response to detection of the predefined gestural pattern by gesture detection module 1430, the system may record and save a predetermined portion of the image data, e.g., ten seconds before and ten seconds after the predefined gestural pattern is detected. Moreover, the select recordings of key moments by the user may be used by the system to indicate key phase segmentation for a given procedure. The user further may generate case notes via the recordings, e.g., by indicating progression through different phases of a procedure when performing a procedure based on a template of the procedure accessible via the system.

Figure 15:
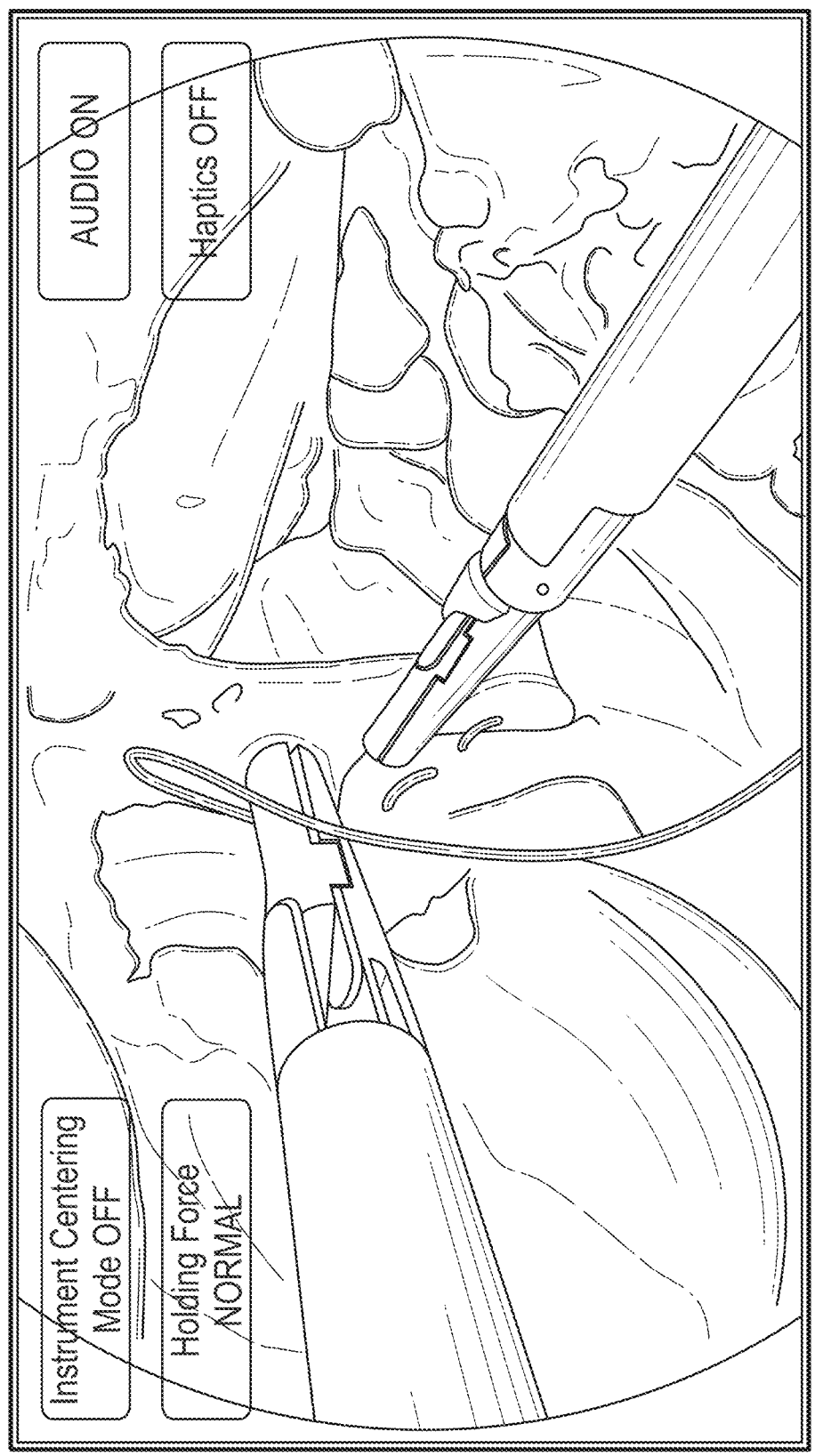
FIG. 15 illustrates an exemplary virtual overlay of a graphical user interface of the co-manipulation surgical system.

As described above, responsive to detection of a predefined gestural pattern by the user, e.g., a predefined pattern of movement of the distal tip of the surgical instrument within the field of view of the laparoscope, gesture detection module 1430 may cause a virtual menu to overlay on the video feed, such that the surgical instrument within the field of view of the laparoscope functions as a pointer, as shown in FIG. 15. Moreover, gesture detection module 1430 may detect further predefined patterns of movement of the distal end of the surgical instrument, e.g., two quick movements in the same direction or a circular movement over a select area of the virtual menu, which may be interpreted as a selection actuation, e.g., a click on the virtual menu. For example, as shown in FIG. 15, the virtual menu overlay on the video feed may include menu options in the corners of the video feed, e.g., "hot corners", such as: turning on/off instrument centering mode where the system automatically moves the robot arm coupled to a laparoscope to follow the surgical instrument and/or zoom in or out to change the field of view of the laparoscope and maintain the target instrument within a predetermined reference distance from the tip of the laparoscope; adjusting the holding force of robot arm coupled to a retractor, e.g., the amount of force that may be applied to the distal tip of the surgical instrument before the system transitions from passive mode to co-manipulation mode; turning on/off audio; and turning on/off haptic feedback. As will be understood by a person having ordinary skill in the art, more or less menu options may be provided via the virtual menu.

In some embodiments, initiation of the display of the virtual menu overlay on the video feed may be triggered by, e.g., actuation of an external actuator such as a foot pedal, a predefined pattern of force applied to the robot arm such double tapping wrist portion 311 and/or the surgical instrument coupled to the robot arm as detected by encoders at the distal end of the robot arm, voice activation, wireless buttons, hot buttons, etc. In some embodiments, the operator may actively switch the system to a command mode, e.g., via user interface 1408, where particular movements or gestures of the robot arm, surgical instrument, operator, or otherwise as described herein are monitored by gesture detection module 1430 to determine if they are consistent with a predefined gestural pattern associated with a predefined user input.

Passive mode determination module 1432 may be executed by processor 1402 for analyzing the operating characteristics of robot arm 300 to determine whether to switch the operational mode of robot arm 300 to the passive mode where the system applies impedance to the joints of robot arm 300 via motor interface module 1426 in an amount sufficient to maintain robot arm 300, and accordingly a surgical instrument attached thereto, if any, in a static position, thereby compensating for mass of robot arm 300 and the surgical instrument, and any other external forces acting of robot arm 300 and/or the surgical instrument. If robot arm 300 is moved slightly while in the passive mode, but not with enough force to switch out of the passive mode, the system may adjust the amount of impedance applied the robot arm 300 to maintain the static position, and continue this process until robot arm 300 is held in a static position. For example, passive mode determination module 1432 may determine to switch the operational mode of robot arm 300 to the passive mode if movement of the robot arm due to movement at the handle of the surgical instrument as determined by force detection module 1422 is less than a predetermined amount, e.g., no more than 1 to 5 mm, for at least a predetermined dwell time period associated with robot arm 300. The predetermined dwell time period refers to the length of time that robot arm 300 and/or the surgical instrument attached thereto, if any, are held in a static position. For example, the predetermined dwell time may range between, e.g., 0.1 to 3 seconds or more, and may be adjusted by the operator. FIG. 16 illustrates a table or exemplary values of the threshold dwell times for a range of sample instrument types.

In some embodiments, passive mode determination module 1432 may determine to switch the operational mode of robot arm 300 to the passive mode if movement of the distal end of the robot arm due to movement at the handle of the surgical instrument as determined by force detection module 1422 has a velocity that is less than a predetermined dwell velocity/speed. For example, if passive mode determination module 1432 determines that the distal end of the robot arm 300 and/or the surgical instrument attached thereto, if any, moves at a speed that is lower than the predetermined dwell speed during an entire predetermined dwell period, then passive mode determination module 1432 may switch the operational mode of robot arm 300 to the passive mode. FIG. 16 illustrates a table or exemplary values of the threshold dwell speeds for a range of sample instrument types. For example, for surgical instruments such as scopes and tissue manipulation devices, the threshold dwell speeds may be, e.g., 3-5 mm/second, and for surgical instruments such as suturing instruments, needle drivers, high force instruments, staplers, and clip appliers, the threshold dwell speeds may be, e.g., 1-2 mm/second. In some embodiments, passive mode determination module 1432 may determine to switch the operational mode of robot arm 300 to the passive mode based on the identity of the surgical instrument upon attachment of the surgical instrument to robot arm 300 and/or responsive detachment of the surgical instrument from robot arm 300.

Co-manipulation mode determination module 1434 may be executed by processor 1402 for analyzing the operating characteristics of robot arm 300 to determine whether to switch the operational mode of robot arm 300 to the co-manipulation mode where robot arm 300 is permitted to be freely moveable responsive to movement at the handle of the surgical instrument for performing laparoscopic surgery using the surgical instrument, while the system applies an impedance to robot arm 300 via motor interface module 1426 in an amount sufficient to account for mass of the surgical instrument and robot arm 300. Moreover, the impedance applied to robot arm 300 may provide a predetermined level of viscosity perceivable by the operator. FIG. 16 illustrates a table or exemplary values of viscosity levels for a range of sample instrument types. In some embodiments, the viscosity level may be a function of the speed that the surgical instrument is being moved and the distance of the tip of the instrument from the trocar point. For example, co-manipulation mode determination module 1434 may determine to switch the operational mode of robot arm 300 to the co-manipulation mode if force applied at robot arm 300 due to force applied at the handle of the surgical instrument exceeds a predetermined threshold associated with robot arm 300 (e.g., a "breakaway force"). The predefined force threshold may be, e.g., at least 7 Newtons, approximately 7 Newtons, at least 7 Newtons, 4-15 Newtons, 4-10 Newtons. The predefined force threshold may be dependent on the type of surgical instrument that is being used and/or whether there is an external force being applied to the surgical instrument.

FIG. 16 illustrates a table or exemplary values of the predefined force thresholds for a range of sample instrument types. As shown in FIG. 16, the predefined force thresholds may reflect the typical external tissue forces that may be exerted on the surgical instrument. In some embodiments, the predefined force threshold may be increased if a force is exerted on the surgical instrument by tissue or an organ or otherwise, depending on the direction of the breakaway force. For example, if the breakaway force is in the same direction as the force exerted on the surgical instrument from the tissue or organ, the predefined force threshold may be increased by an amount equal to or commensurate with the force exerted on the surgical instrument from the tissue or organ, as described in further detail below with regard to FIGS. 27A and 27B. In some embodiments, the predefined force threshold for a respective robot arm be adjusted based on a patient's body mass index ("BMI"). For example, a patient with a higher BMI may have a heavier liver that would likely exert a greater force on the instrument. Accordingly, the predefined force threshold may selected to be higher for the patients with a higher BMI. Accordingly, the operation may actuate a "high force mode," e.g., via user interface 1408, where predefined force threshold is increased to accommodate for engaging with heavier tissue or organs. For example, the predefined force threshold may be selectively increased by 20-100% or more.

Moreover, the force exerted by the user on the surgical instrument and any external tissue forces applied to the surgical instrument may be directionally dependent. For example, if the force exerted by the user on the surgical instrument is in the same direction as an external tissue force applied to the surgical instrument, the two forces may be additive such that the amount of force exerted by the user on the surgical instrument needed to overcome the predefined force threshold may be reduced by the magnitude of the external tissue force such that a lower force than the predefined force threshold would be required to exit the passive mode and enter the co-manipulation mode. On the other hand, if the force exerted by the user on the surgical instrument is in a direction opposite to an external tissue force applied to the surgical instrument, than the necessary amount of force exerted by the user on the surgical instrument needed to overcome the predefined force threshold may be increased by the magnitude of the external tissue force such that a higher force than the predefined force threshold would be required to exit the passive mode and enter the co-manipulation mode.

In addition, if the force exerted by the user on the surgical instrument is in a direction that is perpendicular to an external tissue force applied to the surgical instrument, than the necessary amount of force exerted by the user on the surgical instrument needed to overcome the predefined force threshold may not be affected by the magnitude of the external tissue force such that the necessary force exerted by the user on the surgical instrument needed to exit the passive mode and enter the co-manipulation mode will equal the predefined force threshold. For other directions, the force vectors of the applied forces may be added to or offset by the force vectors of the external tissue forces to overcome predefined force threshold values for the system or the particular surgical instrument that is coupled with the robot arm, depending on the direction of the external tissue force, if any, and the force applied by the user. In some embodiments, co-manipulation mode determination module 1434 may determine to switch the operational mode of robot arm 300 to the co-manipulation mode based on the identity of the surgical instrument.

Haptic mode determination module 1436 may be executed by processor 1402 for analyzing the operating characteristics of robot arm 300 to determine whether to switch the operational mode of robot arm 300 to the haptic mode where the system applies an impedance to robot arm 300 via motor interface module 1426 in an amount higher than applied in the co-manipulation mode, thereby making movement of robot arm 300 responsive to movement at the handle of the surgical instrument more viscous in the co-manipulation mode. For example, haptic mode determination module 1436 may determine to switch the operational mode of robot arm 300 to the haptic mode if at least a portion of robot arm 300 and/or the surgical instrument attached thereto is within a predefined virtual haptic boundary. Specifically, a virtual haptic boundary may be established by the system, such that the robot arm or the surgical instrument coupled thereto should not breach the boundary. For example, a virtual boundary may be established at the surface of the patient to prevent any portion of the robot arms or the instruments supported by the robot arms from contacting the patient, except through the one or more trocars. Similarly, the virtual haptic boundary may include a haptic funnel to help guide the instrument into the patient as the operator inserts the instrument into a trocar port.

Moreover, a virtual haptic boundary, e.g., haptic shell, may be established at a predetermined distance surrounding the workspace to prevent over-extension of the robot arm away from the operation site, as well as to minimize "runaway" of the robot arm. For example, after an instrument is decoupled from the coupler body coupled to the robot arm, the magnet within the coupler body described above should return its maximum position away from the repulsion magnet within coupler interface 400 to thereby indicate that the surgical instrument has been removed; however, if the magnet does not return to that position, the system may think that the surgical instrument is still attached to the robot arm and continue to compensate for the mass of the surgical instrument, thereby causing the distal end of the robot arm to "runaway," e.g., drift upward. Accordingly, the virtual haptic boundary may slow down the drifting robot arm to avoid potential collision with other objects or people. For example, the virtual haptic boundary may set at chest-level of a user to prevent the robot arm from colliding with the user's head.

Accordingly, based on position data of robot arm 300 and/or the surgical instrument coupled thereto, e.g., received by robot arm position determination module 1418 and/or trocar position detection module 1420, haptic mode determination module 1436 may determine if robot arm 300 and/or the surgical instrument is within the predefined virtual haptic boundary, and accordingly transition robot arm 300 to the haptic mode where processor 1402 may instruct associated motors to apply an effective amount of impedance to the joints of robot arm 300 perceivable by the operator to communicate to the operator the virtual haptic boundary. Accordingly, the viscosity of robot arm 300 observed by the operator will be much higher than in co-manipulation mode. In some embodiments, haptic mode determination module 1436 may determine to switch the operational mode of robot arm 300 to the haptic mode based on the identity of the surgical instrument.

Moreover, haptic mode determination module 1436 may generate temporary localized virtual haptic boundaries at the distal ends of the robot arms during predetermined phases of a procedure/clinical workflow to prevent "runaway" and further enhance safety of the system. The predetermined phases may include, e.g., during draping/tear-down of the drape, immediately after tool removal is detected, and/or immediately after coupler body removal is detected. For example, increasing viscosity of the robot arms during draping/tear-down may help stabilize the robot arms and prevent excessive movement/runaway thereof, and increasing viscosity during tool/coupler body removal may prevent "runaway" due to a force applied to the robot arm by the user during the removal process. The localized virtual haptic boundary may be temporary in that it may only be applied for a predetermined time period, e.g., a few seconds after the predetermined phase is identified. The predetermined phases of a procedure may be determined/estimated via, e.g., user input via GUI 210 and/or voice command, uploaded from a database stored within the system, and/or via telemetry of the robot arms and identification and/or positions of the surgical instruments. For example, the system may gather and analyze telemetry data regarding forces being applied to the robot arm to assess or estimate whether a user is attempting to remove a tool from the robot arm, and accordingly, haptic mode determination module 1436 may generate a temporary localized virtual haptic boundary at the distal end of the robot arm to facilitate tool removal.

In addition, haptic mode determination module 1436 may adjust the amount of viscosity, e.g., impedance, applied at the distal ends of the robot arms during predetermined phases of a surgical procedure to guide specific movements during the predetermined phase based on the type of surgical instrument coupled to the robot arm, e.g., wristed instruments such as a needle driver or grasper, stapling devices, dissection devices, suturing devices, retraction devices such as a fan retractor, tissue removal devices such as a gallbladder bag, clip applier devices, etc. For example, during a suturing phase of a procedure, viscosity at the distal end of the robot arm may be increased to provide more viscous control to the user during operation of the suture device. Additionally, during a stapling phase of a procedure, viscosity at the distal end of the robot arm may be increased to provide very stiff grounding for force application of the stapling device operated by the user. Accordingly, the increased viscosity may facilitate performance of a specific movement by the user without actively moving the robot arm to perform the specific movement.

Robotic assist mode determination module 1438 may be executed by processor 1402 for analyzing the operating characteristics of robot arm 300 to determine whether to switch the operational mode of robot arm 300 to the robotic assist mode where processor 1402 may instruct associated motors via motor interface module 1426 to cause movement of corresponding link and joints of robot arm 300 to achieve a desired outcome. For example, robotic assist mode determination module 1438 may determine to switch the operational mode of robot arm 300 to the robotic assist mode if a predefined condition exists based on data obtained from, e.g., optical scanner interface module 1428.

For example, robotic assist mode determination module 1438 may determine that a condition exists, e.g., that one or more trocars are not in an optimal position, for example, due to movement of the patient, such that robot arm 300 should be repositioned to maintain the trocar in the optimal position, e.g., in an approximate center of the movement range of robot arm 300, thereby minimizing the risk of reaching a joint limit of the robot arm during a procedure. Thus, in robotic assist mode, processor 1402 may instruct system to reposition robot arm 300, e.g., via vertical/horizontal adjustment by platform 100 or via the joints and links of robot arm 300, to better align the surgical instrument workspace.

Robotic assist mode determination module 1438 may determine that a condition exists, e.g., the distance between an object, e.g., capital equipment or a member of the surgical staff other than the surgeon, and robot arm 300 reaches or falls below a predetermined threshold, based on image data obtained from the laparoscope or optical scanner 202 via optical scanner interface module 1428, such that the robot arm should be frozen to avoid collision with the object. Thus, in robotic assist mode, processor 1402 may instruct robot arm 300 apply the brakes to slow down the robot arm or inhibit or prevent movement within a predetermined distance from the other object to thereby prevent the inadvertent movement of the robot arm that may otherwise result from such a collision or inadvertent force.

Robotic assist mode determination module 1438 further may determine that a condition exists, e.g., robot arm 300 is in an extended position for a period of time exceeding a predetermined threshold during a surgical procedure, such that the robot arm should be repositioned to provide the user more available workspace in the vicinity of the surgical instrument coupled to the extended robot arm. Thus, in robotic assist mode, processor 1402 may instruct the system to reposition robot arm 300, e.g., via vertical/horizontal adjustment by platform 100 and/or via the joints and links of robot arm 300, to move robot arm 300 closer to the surgical instrument.

In addition, robotic assist mode determination module 1438 may determine that a condition exists, e.g., the field of view of a laparoscope coupled to robot arm 300 or optical scanner 202 is not optimal for a given surgical procedure, e.g., due to blocking by the surgeon or assistant or another component of the system, based on image data obtained from the laparoscope or optical scanner 202 via optical scanner interface module 1428, such that the robot arm coupled to the laparoscope or optical scanner 202 should be repositioned or zoom in/out to optimize the field of view of the surgical site for the operator. Thus, in robotic assist mode, processor 1402 may instruct robot arm 300, either automatically/quasi-automatically or responsive to user input by the operator, to move to reposition the laparoscope and/or cause the laparoscope to zoom in or zoom out, or to increase a resolution of an image, or otherwise. For example, the user input by the operator may be determined by gesture detection module 1430, as described above, such that movement of the robot arm or a surgical instrument in a predefined gestural pattern in a first direction causes the endoscope to increase resolution or magnification and in a second direction causes the endoscope to decrease resolution or magnification, and movement in another predefined gestural pattern causes the robot arm holding the laparoscope to retract away from the patient's body.

In some embodiments, robotic assist mode determination module 1438 may determine that a condition exists, e.g., initiation of an "instrument centering" mode by the user and identification of a target surgical instrument such as a handheld tool within the field of view of the laparoscope attached to the robot arm, such that the robot arm should switch to robotic assist mode to provide assisted scope control to center the instrument within the field of view of the laparoscope. For example, as described above, positioning and maintaining the distal tip of a surgical instrument at a center portion of the laparoscopic field of view, e.g., defined by a predetermined boundary region, for more than a predetermined time threshold may be associated with a user input detected by gesture detection module 1430 to enable tool tracking of the surgical instrument, such that robotic assist mode determination module 1438 switches the robot arm attached to the laparoscope to the robotic assist mode to provide automated instrument centering. For example, robotic assist mode determination module 1438 may execute one or more machine learning algorithms on the image data received from the laparoscope to identify the target surgical instrument within the field of view of the laparoscope, e.g., by evaluating pixels of the image data received by the laparoscope and indicating if the pixels correspond to the target surgical instrument, to thereby identify the target surgical instrument. The machine learning algorithms may be trained with a database of annotated image data of associated surgical instruments using trained modules, such as convolution kernels. For example, the machine learning algorithms may pass convolution kernels across the images and attribute a score indicative of the likelihood that a given pixel, or group of pixels, is correctly identified/classified. The score may be derived from a feature map generated by the kernels. By training the machine learning algorithms on more data, the algorithms may be improved by updating the weights in the kernels. As will be understood by a person having ordinary skill in the art, other machine learning algorithms may be used, e.g., pattern matching.

In the robotic assist mode, robotic assist mode determination module 1438 may determine one or more conditions exist, e.g., the target surgical instrument within the field of view of the laparoscope moves out of a predefined boundary region, e.g., a predefined rectangular or circular region about a center point of the field of view, within the field of view indicating that the robot arm should reposition the laparoscope to maintain the target surgical instrument within the predefined boundary region within the field of view of the laparoscope, and/or the resolution of the target surgical instrument in the laparoscope feed falls below a predetermined resolution threshold indicating that the robot arm should move the laparoscope to zoom out, and/or the detected size of the surgical instrument falls below a predetermined size threshold indicating that the robot arm should move the laparoscope to zoom in. In some embodiments, the predefined boundary region may be a selected fraction of the field of view, e.g., the inner two-thirds of the field of view of the laparoscope. Thus, movement of the target surgical instrument within the predefined boundary region may not cause movement of the robot arm, and accordingly movement of the laparoscope; whereas, movement of the target surgical instrument outside of the predetermined boundary region causes the robot arm to move the laparoscope to maintain the target surgical instrument within the predefined boundary region within the field of view of the laparoscope. Further, upon initiation of the instrument centering mode by the system to track a handheld surgical instrument within the field of view of the laparoscope, using object segmentation to distinguish surgical instruments when more than one surgical instrument is within the field of view of the laparoscope, the system may disregard non-target surgical instruments, e.g., surgical instrument(s) coupled to a robot arm within the field of view of the laparoscope, and track only the target surgical instrument, e.g., the handheld surgical instrument within the field of view of the laparoscope.

Moreover, robotic assist mode determination module 1438 may determine one or more conditions exist, e.g., the surgical procedure being performed by the operator enters a known phase of the surgical procedure indicating that the laparoscope should focus on a specific surgical instrument and/or a specific anatomical structure. As described above, the system may use object segmentation to identify anatomical structures within the field of view of the laparoscope during a procedure, such that upon detection of a specific surgical instrument/anatomical structure, the system may determine that the surgical procedure has entered a known phase. For example, during a cholecystectomy procedure, upon detection and identification of the cystic duct and target artery, e.g., via object segmentation and an stored/online database, robotic assist mode determination module 1438 may determine that the laparoscope should track the cystic duct and the artery, e.g., such that surgical clips may be applied, and therefore maintain the cystic duct and the artery within the field of view of the laparoscope during this known phase of the cholecystectomy procedure. Accordingly, the system may cause the robot arm to cause movement of the laparoscope to center its field of view on the cystic duct and the artery. As will be understood by a person having ordinary skill in the art, robotic assist mode determination module 1438 may be trained to identify various phases of various surgical procedures, such that the system may provide instrument centering to focus the field of view of the laparoscope on key surgical instruments and/or anatomical structures based on the phase of the surgical procedure. Moreover, the system may provide automated centering to focus the field of view of the laparoscope on key anatomical structures rather than a surgical instrument based on the type of surgical instrument identified within the field of view of the laparoscope using any of the surgical instrument identification methods described herein. For example, if the surgical instrument is identified as a suture device, the system may provide assisted scope control to focus the field of view of the laparoscope on the anatomical structure(s) being sutured rather than the suture device.

Figure 17B:
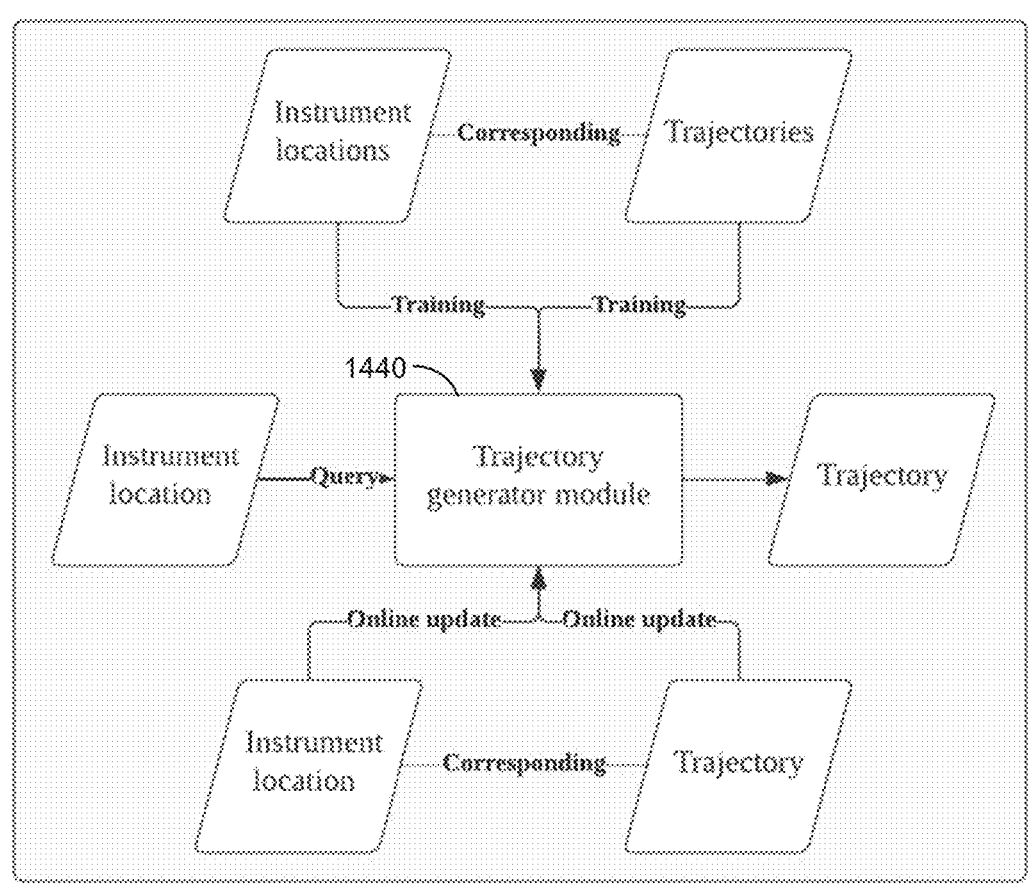
FIG. 17B is a flow chart illustrating robot arm trajectory generation for instrument centering in accordance with the principles of the present disclosure.

Trajectory generation module 1440 may be executed by processor 1402 for generating a trajectory from the current position of the distal end of the robot arm to a desired position of the robot arm, which will result in moving the distal end of the laparoscope from its current position to a desired position to maintain the target surgical instrument within the field of view of the laparoscope to thereby provide instrument centering in the robotic assist mode. The generated trajectory is configured to provide the robot arm precise control over the speed and smoothness of the motion of the laparoscope as it is moved along the trajectory. Specifically, as shown in FIG. 17B, the trajectory generation module 1440 may query an online trajectory generation module trained with data obtained from previous surgical procedures including of preferred trajectories of various surgeons and associated surgical instrument locations to therein, to thereby generate the trajectory based on a determined surgical instrument location within the field of view of the laparoscope.

In some embodiments, the surgeon's preferences may be learned based on data from past procedures and/or sensors collecting information about current procedure including a surgeon's current pose, a surgeon's height, a surgeon's hand preference, and other similar factors. For example, the system may record when a user interacts with the system and also record what the user does with the system, such that the dataset may allow for surgeon preferences to be "learned" and updated over time, as described below with regard to FIG. 37. This learning may be done either via traditional algorithmic methods (i.e., trends over time, averaging, optical flow, etc.) or via machine learning approaches (classification, discrimination, neural networks, reinforcement learning, etc.). For example, when the system provides instrument centering by tracking a surgical instrument within the field of view of the laparoscope, the operator at any time may "override" executed motion of the robot arm along the trajectory generated by trajectory generation module 1440 in the robotic assist mode, e.g., by applying a force to the handle of the laparoscope that exceeds a predetermined force threshold to cause the system to automatically switch the robot arm to the co-manipulation mode.

For example, the system may provide a predetermined override time period where the user may manually move the laparoscope, e.g., to change the field of view, clean the laparoscope, adjust the zoom, etc., and return the laparoscope to a stationary position before the system exits instrument centering mode. For example, the predetermined override time period may be, e.g., 6 to 12 seconds, or preferably 8 seconds. During the override time period, the user may adjust the reference distance, e.g., the distance between the tip of the laparoscope and the tip of the target instrument, by bringing the instrument tip to the desired distance from the laparoscope for the laparoscope to follow once the target instrument is detected in the instrument centering mode. Upon exiting of the instrument centering mode, instrument centering mode may be reentered via, e.g., actuation at GUI 210. Moreover, the overriding motion of the robot arm may be recorded as the operator's preferred trajectory given the current position of the target surgical instrument, such that the trajectory generation module associated with the given operator's surgeon profile may be updated to include the operator's preferred trajectory. Moreover, as shown in FIG. 17B, the online trajectory generation module may be updated/trained with data indicative of the operator's preferred trajectory and associated surgical instrument location.

In addition, trajectory generation module 1440 may account for an angular offset between a camera sensor module, e.g., the camera head of the laparoscope, and the laparoscope coupled to the robot arm, e.g., distal end of the robot arm, when generating the trajectory. For example, the camera head of the laparoscope may be attached to the laparoscope at an arbitrary location relative to the robot coordinate system, with an unknown rotational position relative to the laparoscope. Thus, for an angled-tip laparoscope, movement of the robot arm along the generated trajectory will not result in the desired movement of the field of view of the laparoscope when the laparoscope is not in the appropriate orientation relative to the laparoscope. For example, if the camera head is upside-down relative to the laparoscope, movement of the robot arm that moves the laparoscope in the up direction will result in a shift of the field of view of the laparoscope in the down direction. Trajectory generation module 1440 may detect the angular offset between the camera head and the distal end of the robot arm, as described in further detail below with regard to FIG. 29.

For example, trajectory generation module 1440 may detect the angular offset by causing the robot arm to execute a predefined movement pattern, e.g., moving forward/backward and/or side-to-side, and comparing the expected movement of a static object within the field of view of the laparoscope, e.g., an anatomical structure or a surgical instrument, with the actual movement of the static object within the field of view of the laparoscope. As will be understood by a person having ordinary skill in the art, a "static object" may be any object within the field of view of the laparoscope which is generally considered "static" with respect to the movement of the robot arm, and thus, may include objects in the background scene that move slightly due to, e.g., respiratory motion, cardiac motion, etc. Based on the detected offset, trajectory generation module 1440 may calibrate the trajectory generation module to account for the offset and generate a calibrated trajectory, such that movement of the laparoscope along the calibrated trajectory will result in the expected shift of the field of view of the laparoscope to maintain the target surgical instrument within the field of view of the laparoscope. In some embodiments, the system may include one or more rotation sensors configured to detect the angular position of the camera head relative to the laparoscope, and accordingly an angular offset, and thus would not need to execute the predefined movement pattern. Moreover, in some embodiments, additional image data, e.g., from optical scanner 202, indicative of movement of the proximal end of the laparoscope external to the patient may be used to facilitation determination of the offset.

Similarly, trajectory generation module 1440 may account for positional offset of the attachment point of the coupler body along the shaft of the surgical instrument. For example, as described above, the coupler body is preferably coupled to the instrument shaft at the proximal-most point along the shaft, such that the distance between the distal end of the robot arm and the instrument tip may be known for the force measurements described in further detail below. However, in the event that the coupler body is not attached at the proximal-most point along the instrument shaft, movement of the distal end of the robot arm may not result in the desired movement of the instrument tip. Accordingly, the system may detect the positional offset of the coupler body attachment point, if any, and calibrate its force measurement algorithms to account for the offset, such that movement of the distal end of the robot arm will result in the expected movement of the instrument tip.

Fault detection module 1442 may be executed by processor 1402 for analyzing the data indicative of the operating characteristics of the system, e.g. position data generated by robot arm position determination module 1418 and/or trocar position detection module 1420 and/or force measurement calculated by force detection module 1422, to detect whether a fault condition is present. For example, fault detection module 1442 may a fault condition of the system and determine whether the fault condition is a "minor fault," a "major fault," or a "critical fault," wherein each category of fault condition may be cleared in a different predefined manner.

For example, fault detection module 1442 may detect a minor fault condition such as robot arm 300 being moved with a velocity exceeding a predetermined velocity threshold, which may be cleared, e.g., by slowing down the movement of robot arm 300. In some embodiments, the system may automatically apply additional impedance to robot arm 300 when robot arm 300 is moving too fast, e.g., a temporary localized virtual boundary, to thereby force the operator to slow down movement of robot arm 300. The temporary localized virtual boundary may be applied whether or not an instrument is attached to the robot arm, but that the velocity of the distal end of the robot arm exceeds a predetermined velocity threshold. Moreover, fault detection module 1442 may detect a major fault condition such as an inadvertent bump of robot arm 300 as indicated by a large force applied to robot arm 300 by a person other than the operator. In response to detection of a major fault condition, fault detection module 1442 may actuate the braking mechanism associate with each motorized joint of robot arm 300

(or at least the joints associated with the major fault condition), to thereby freeze robot arm 300 and inhibit further movement of robot arm 300. Such a major fault condition may be cleared by the operator actuating a "clear" option displayed on user interface 1408. Fault detection module 1442 may detect a critical fault condition such as redundant encoders associated with a given joint of robot arm 300 generating different angulation measurements with a delta exceeding a predetermined threshold. In response to detection of a critical fault condition, fault detection module 1442 may actuate the braking mechanism associate with each motorized joint of robot arm 300 to thereby freeze robot arm 300 and inhibit further movement of robot arm 300. Such a critical fault condition may be cleared by the operator restarting the system. Upon restart of the system, if the critical fault condition is still detected by fault detection module 1442, robot arm 300 will remain frozen until the critical fault condition is cleared.

Indicator interface module 1444 may be executed by processor 1402 for causing indicators 334 to communicate the state of the system, e.g., the operational mode of robot arm 300, to the operator or other users, based on, for example, determinations made by passive mode determination module 1432, co-manipulation mode determination module 1434, haptic mode determination module 1436, and/or robotic assist mode determination module 1438. For example, indicator interface module 1444 may cause indicators 334 to illuminate in specific color light associated with a specific state of the system. For example, indicator interface module 1444 may cause indicators 334 to illuminate in a first color (e.g., yellow) to indicate that no surgical instrument is attached to the robot arm, and that the robot arm may be moved freely such that the system compensates for the mass of the robot arm; in a second color (e.g., purple) to indicate that a surgical tool is attached to the robot arm, and that the robot arm may be moved freely such that the system compensates for the mass of the robot arm and the mass of the surgical instrument coupled to the robot arm; in a third color (e.g., blue) to indicate that a surgical instrument is attached to the robot arm, and that the robot arm is in the passive mode as determined by passive mode determination module 1432; in a fourth color (e.g., pulsing orange) to indicate that at least a portion of the robot arm and/or the surgical instrument attached thereto is within the virtual haptic boundary, e.g., 1.4 m or more above the ground; in a fifth color (e.g., pulsing red) to indicate that a fault has been detected by the system by fault detection module 1442. As will be understood by a person having ordinary skill in the art, different colors and patterns may be communicated by indicators 334 to indicate the states of the system described above.

Additionally, indicators 334 may be illuminated in other distinct colors and/or patterns to communicate additional maneuvers by robot arm 300, e.g., when robot arm 300 retracts the surgical arm in the robotic assist mode, or performs another robotically-assisted maneuver in the robotic assist mode. As described above, indicators 334 further may include devices for emitting other alerts such as an audible alert or text alert. Accordingly, indicator interface module 1444 may cause indicators 334 to communicate the state of the system to the operator using audio or text, as well as or instead of light. For example, indicator interface module 1444 may cause one or more speakers to emit an audible alert that changes in, e.g., amplitude and/or frequency, as robot arm 300 approaches a potential collision with one or more objects/persons within the operating room.

Additionally or alternatively, indicator interface module 1444 may communicate the state of the system, e.g., transition from co-manipulation mode to passive mode, via haptic feedback at the distal end of robot arm 300, and accordingly on the surgical instrument coupled thereto. For example, when the surgical instrument is held in a position for the predetermined dwell time such that the system switches to passive mode, the user may feel a vibration at the surgical instrument indicating that the system has transitioned to passive mode and that the user may let go of the surgical instrument. As another example, the user may feel a vibration after the surgical instrument is coupled to the coupler body to indicate that the surgical instrument is successfully coupled to the robot arm. The vibration may be strong enough to be felt by the user, but weak enough such that any movement at the distal tip of the surgical instrument resulting therefrom is negligible.

The co-manipulation surgical robot systems described herein may include additional modules within memory 1410 of platform 1400 for executing additional tasks based on the data obtained. For example, the system may determine if the surgical instrument has been detached from robot arm 300 based on data indicative of the position of the distal end of robot arm 300 relative to the trocar point generated by trocar position detection module 1420, as well as the direction of an instrument shaft and/or an orientation of the distal-most link of robot arm 300, e.g., distal wrist link 316. For example, if the instrument is pointing directly at the trocar, then there is a higher probability that a tool is attached to the robot arm. Moreover, axis Q7 of robot arm 300 may indicate the pointing direction of the instrument and, if the instrument is passing through the trocar port, the distal wrist link 316 will point in a direction of the trocar port. Therefore, if distal wrist link 316 is not pointing toward the trocar port, then the system may determine that the robot arm is not supporting an instrument or the instrument is not advanced through the trocar port. For example, when an instrument is detached from robot arm 300 and robot arm 300 is moved, the computed direction of the instrument shaft (e.g., the direction that the instrument would point if attached to robot arm 300) may no longer point to the trocar entry point and likely will not point to the trocar entry point. Accordingly, the may alert a user if the system determines that no tool is coupled with robot arm 300, e.g., via indicators 334, and/or apply a localized virtual haptic boundary to slow down the robot arm if the robot arm is moving in a single direction and there is no movement at Q7.

Figure 18:
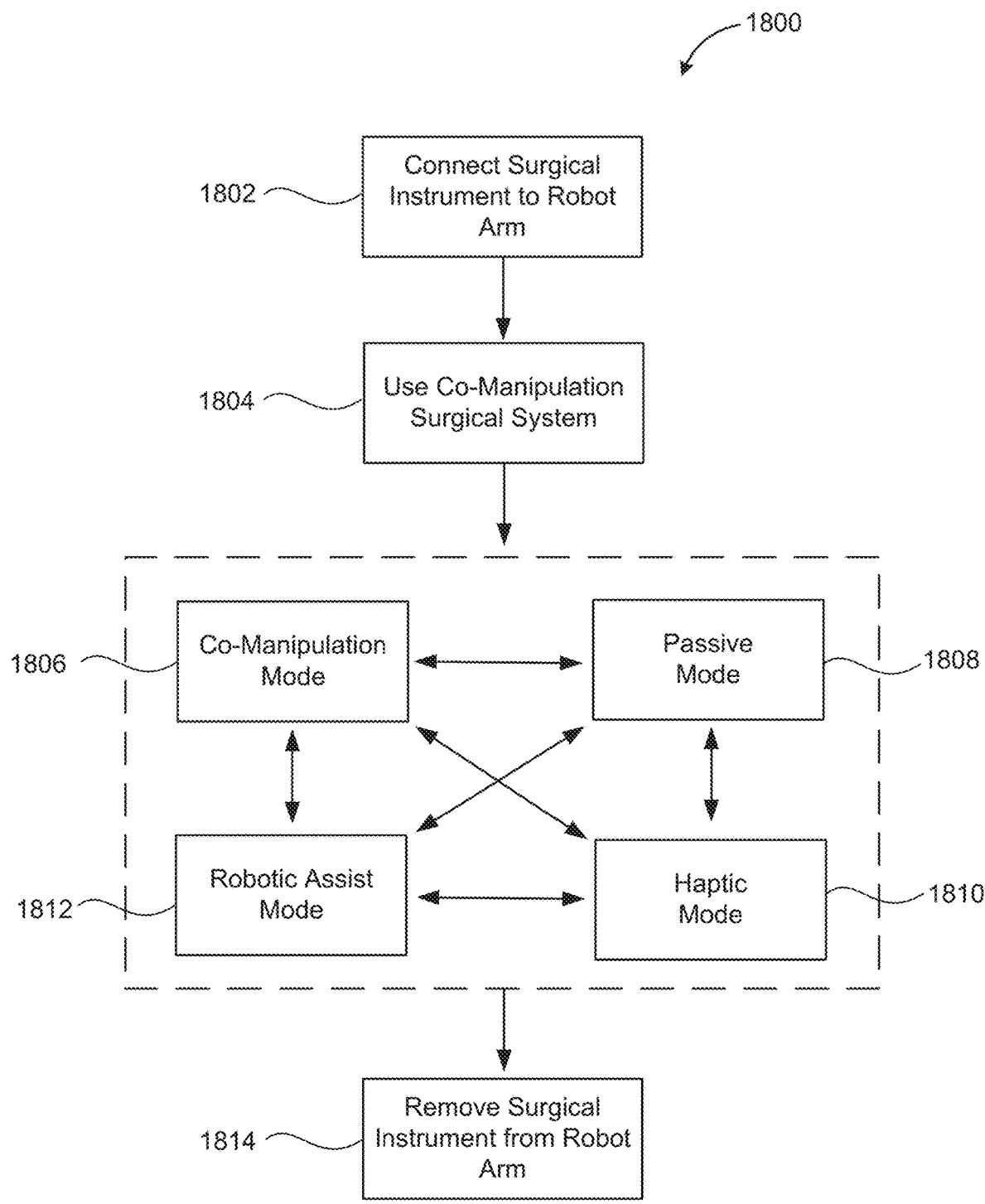
FIG. 18 is a flow chart illustrating operation of the co-manipulation surgical system in accordance with the principles of the present disclosure.

Referring now to FIG. 18, operation 1800 of the co-manipulation surgical robot systems described herein is provided. As shown in FIG. 18, at step 1802, the operator may couple a selected surgical instrument to coupler interface 400 of robot arm 300 via a coupler body, e.g., coupler body 500, 900. As described above, the operator may select a coupler body sized and shaped to couple with the selected surgical instrument, e.g., based on the elongated shaft diameter of the surgical instrument. When the surgical instrument and coupler body are ready to be coupled to robot arm 300, the operator may load the calibration file of the selected surgical instrument, e.g., via user interface 1408, such that information associated with the selected surgical instrument, e.g., a laparoscope or retractor, is loaded into the system. For example, the operator may select the calibration file from a database of calibration files for a variety of surgical instruments. The calibration files may be stored from previous procedures, and may be pre-loaded to include calibration files of commonly used laparoscopic instruments.

Alternatively, as described above, the system may automatically identify the surgical instrument upon attachment to the robot arm, and accordingly, may automatically load the corresponding calibration file. For example, as described above, the system may identify at least the shaft diameter of the surgical instrument coupled to the coupler body (or that will be coupled to the coupler body) when the coupler body is coupled to the coupler interface based on the specific magnetic field strength measured by sensor 414 induced by the displaced magnet within the coupler body, which may be indicative of whether a 5 mm or 10 mm coupler body is coupled to the coupler interface, with or without the surgical instrument attached. Accordingly, the system may automatically load a calibration file associated with a surgical instrument having the identified shaft diameter, which may be used to automatically calibrate a surgical instrument in real-time via adaptive gravity compensation, as described in further detail below with regard to FIG. 24.

Figure 19:
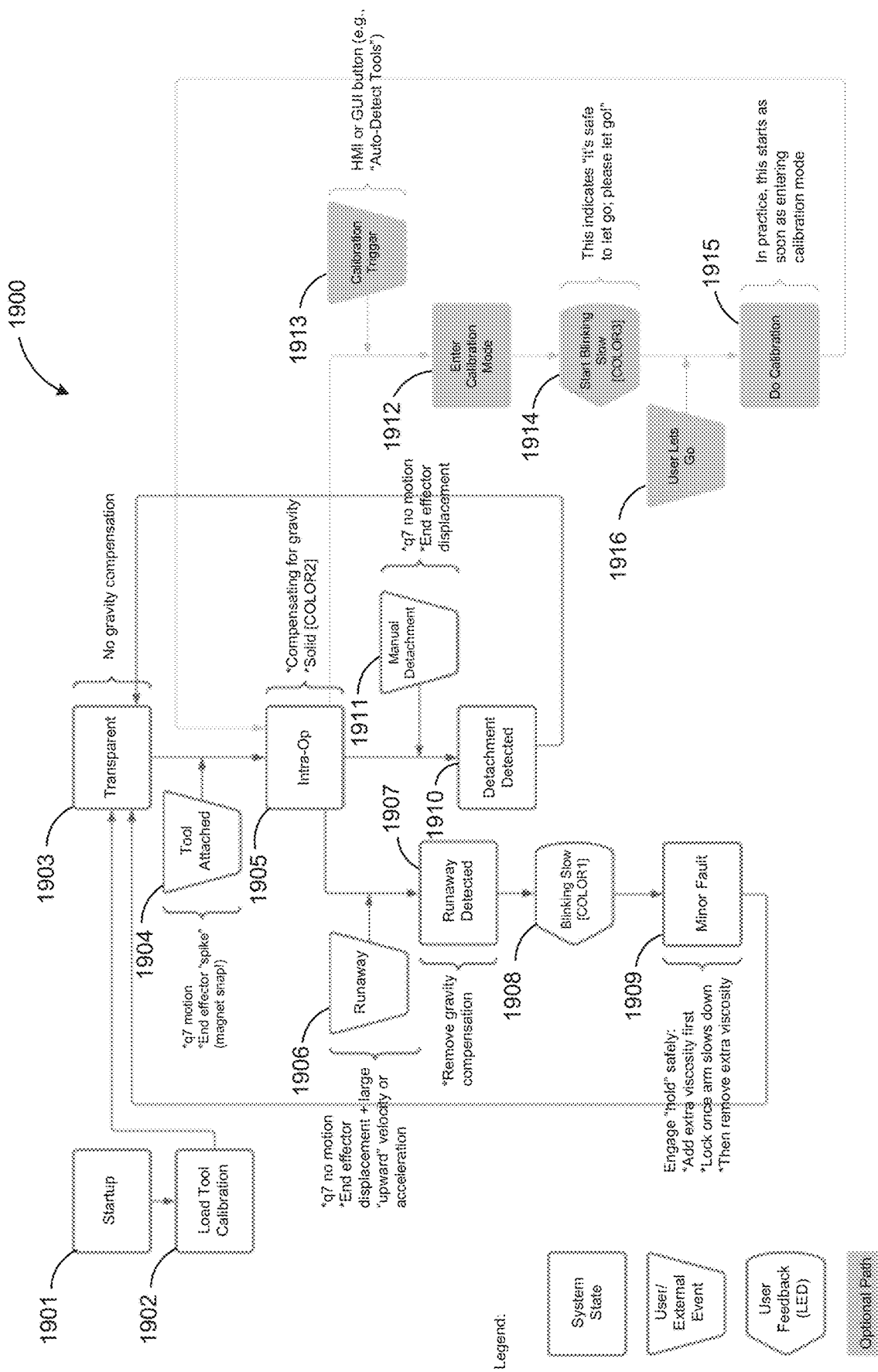
FIG. 19 is a flow chart illustrating surgical instrument calibration of the co-manipulation surgical system in accordance with the principles of the present disclosure.

If the calibration file for the selected surgical instrument is not available in the database, the operator may self-calibrate the surgical instrument using the system. For example, FIG. 19 illustrates surgical instrument calibration process 1900 for calibrating a surgical instrument, e.g., to determine the center of mass of the surgical instrument, which may be used in calculating accurate force measurements on the surgical instrument and robot arm 300 during operation. At step 1901, the operator may actuate the "startup" option on user interface 1408. At step, 1902, the operator may select the "load tool calibration" to begin the calibration process. At step 1903, the system does not apply any impedance to robot arm 300 for gravity compensation of a surgical instrument. The system may apply impedance to robot arm 300 to account for the weight of robot arm 300, e.g., to prevent robot arm 300 from dropping to the ground. At step 1904, the surgical instrument is coupled to coupler interface 400 of robot arm 300 via the appropriate sized coupler body, which may cause wrist portion 411 of robot arm 300 to rotate about axis Q7 to engage with the coupler body.

At step 1905, the system compensates for the gravity of the surgical instrument and the force applied by the hand of the operator, e.g., by measuring the force applied to the distal end of robot arm 300 due to the mass of the surgical instrument. As described above, the force applied to the distal end of robot arm 300 may be measured by measuring the motor current across the motors disposed in the base of robot arm 300. If the system overcompensates for the gravity of the surgical instrument, at step 1906, robot arm 300 may "runaway", e.g., drift upward. The runaway effect may be detected at step 1907, and at step 1908, indicators 334 may blink to indicate to the operator of the runaway. At step 1909, the system may identify the runaway as a minor fault, and accordingly apply additional impedance to robot arm 300 and freeze robot arm 300 when robot arm 300 slows down before removing the additional impedance. Once the minor fault is addressed, calibration process 1900 may return to step 1903.

After step 1905, when the system compensates for the gravity of the surgical instrument, if the surgical instrument is detached, either accidentally or manually by the operator at step 1911, at step 1910, the system detected the detachment of the surgical instrument from robot arm 300. As a result, the system will stop compensating for the gravity of the surgical instrument, and calibration process 1900 may return to step 1903. Moreover, as described above, the system may apply a temporary localized virtual haptic boundary at the distal end of the robot arm upon detection of the detachment of the surgical instrument from robot arm 300. After step 1905, when the system compensates for the gravity of the surgical instrument, calibration process 1900 is ready to enter calibration mode at step 1912. For example, the operator may initiate calibration mode via user interface 1408 at step 1913. At step 1914, the system may indicate to the operator, e.g., via user interface 1408 and/or blinking of indicators 334, that it is safe to let go of surgical instrument, such that the operator may let go of the surgical instrument at step 1916. At step 1915, the system calibrates the surgical instrument. As described above, provided that each specific make of a surgical instrument may have a distinguishable, precise mass, the make of the surgical instrument may be determined by comparing the calibrated mass with a stored or online database of surgical instruments. Accordingly, a surgical instrument may be labeled as an unauthorized surgical instrument during calibration.

Referring again to FIG. 18, when the surgical instrument and coupler body are coupled to robot arm 300, and the appropriate calibration file is loaded, the system will now accurately compensate for the gravity of the selected surgical instrument. At step 1804, the user may use the co-manipulation surgical system by freely manipulating the surgical instrument coupled to robot arm 300 in the ordinary manner that the operator would without robot arm 300 coupled thereto. As shown in FIG. 18, as the operator manipulates the surgical instrument, and accordingly robot arm 300 coupled thereto, the system may continuously monitor the robot arm and forces applied thereto to detect predefined conditions and automatically switch between, e.g., co-manipulation mode 1806, passive mode 1808, haptic mode 1810, and robotic assist mode 1812 (collectively referred to as "operational modes"), upon detection of the predefined conditions.

Figure 20:
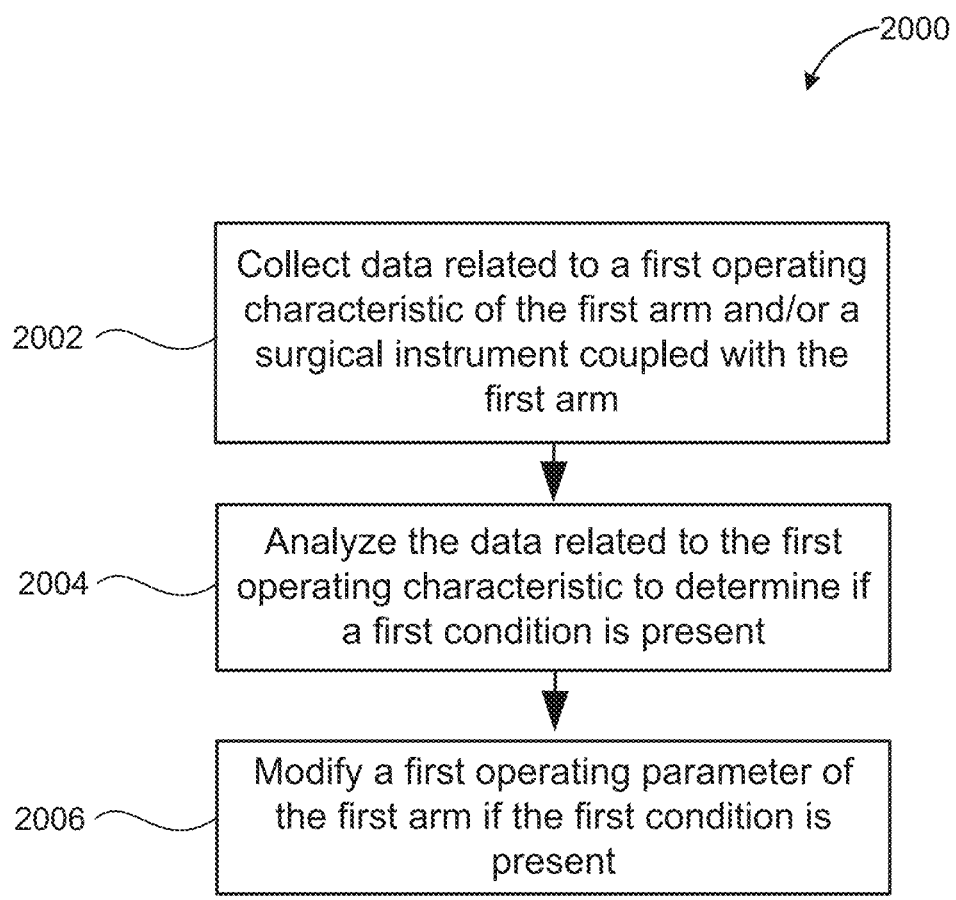
FIG. 20 is a flow chart illustrating operation of the robot arm in accordance with the principles of the present disclosure.

For example, as shown in FIG. 20, at step 2002, the system continuously collects data related to a first operating characteristic of the robot arm and/or of the surgical instrument coupled with the robot arm. For example, as described above, the system may measure motor current of the motors operatively coupled to the joints of the robot arm as well as angulations of the links of the robot arm based on measurements by the encoders of the robot arm to calculate the positon of the robot arm and the surgical instrument as well as the forces acting on any portion of the robot arm as well as on the surgical instrument, if any, in real time. At step 2004, the system may analyze the data related to the first operating characteristic to determine if a first condition is present. For example, based on the position and force data of the robot arm and/or surgical instrument, the system may determine if the movement of the robot arm due to movement of the surgical instrument coupled thereto is within a predetermined movement threshold of the robot arm for a period of time longer than the predetermined dwell time of the robot arm. Upon detection of this first condition, at step 2006, the system may modify a first operating parameter of the robot arm. For example, the system may switch the operational mode of the robot arm to the passive mode, where the robot arm maintains the surgical instrument in a static position.

Referring again to FIG. 18, the operational mode of any one of the robot arms may be changed independent of the operational mode of the other robot arms of the system. The sensors, motors, etc. of the system may be active in all modes, but may act very differently in each mode, e.g., including acting as if inactive. As will be understood by a person having ordinary skill in the art, the system may include more than two robot arms, such that the operator may couple a third surgical instrument, e.g., a grasper device, to a third robot arm and a fourth surgical instrument, e.g., a surgical scissor device, to a fourth robot arm for operation during the laparoscopic procedure. In addition, when no surgical instrument is coupled to the distal end of a robot arm of the system, the system is still capable of automatically switching the operational modes of the robot arm responsive to movement of the robot arm by an operator upon detection of the predefined conditions described above. Accordingly, the system will apply an impedance to the joints of the robot arm to compensate for the mass of the robot arm such that the robot arm may remain in a static position when in the passive mode, and will permit the robot arm to be freely moveably by the operator in the co-manipulation mode if the system detects that the force applied to the robot arm by the operator exceeds the predetermined force threshold of the robot arm.

Moreover, as the operator freely moves the retractor in the co-manipulation mode, e.g., prior to inserting the tip of the retractor through the trocar within the patient, if the operator moves the tip of the retractor too close to the patient's skin away from the trocar port, and a virtual haptic boundary has been established by the system on the skin of the patient outside the trocar ports, the system may automatically switch to the haptic mode. Accordingly, the system may apply an impedance to the second robot arm that is much higher than the impedance applied to the second robot arm in co-manipulation mode to indicate to the operator that they are approaching or within the virtual haptic boundary. For example, movement of the retractor by the operator may feel much more viscous in the haptic mode. The system may remain in the haptic mode until the operator moves the retractor out of the virtual haptic boundary. In some embodiments, in the haptic mode, the second robot arm may reduce the effects of gravity, eliminate tremor of the instrument tip, and apply force feedback to avoid critical structures as defined by the virtual haptic boundary. Accordingly, the system does not replace the operator, but rather augments the operator's capabilities through features such as gravity compensation, tremor removal, haptic barriers, force feedback, etc.

In some embodiments, the system may switch the second robot arm to the robotic assist mode. For example, as the operator attempts to retract the tissue, if more force is required to retract the tissue than the operator is able or willing to apply to the retractor, the operator may provide user input to the system indicating that the operator wants the second robot arm to assist in the retraction of the tissue. For example, as described above, the operator may perform a predefined gestural pattern that may be detected by, e.g., optical scanner 202, such that the system switches the second robot arm to the robotic assist mode and causes the motors of the second robot arm to move the second robot arm, and accordingly the retractor, to provide the additional force required to retract the tissue.

In addition, instead of manually manipulating the laparoscope coupled to the first robot arm as described, the operator may provide another user input to the system indicating that the operator wants the system to reposition the laparoscope. For example, if the operator is actively manipulating a surgical scissor, which may or may not be coupled to a robot arm of the system, such that the tip of the surgical scissor is within the field of view of the laparoscope coupled to the first robot arm, the operator may perform a predefined gestural pattern with the tip of the surgical scissor, e.g., moving the surgical scissor quickly back in forth in a particular direction. The predefined gestural pattern of the surgical scissor may be captured as image data by the laparoscope, and based on the data, the system may detect and associate the predefined gestural pattern with a predefined user input requiring that the system switch the first robot arm from the passive mode to the robotic assist mode, and cause the first robot arm to reposition itself, and accordingly the laparoscope, to adjust the field of view in the direction of the pattern motion of the surgical scissor, or alternatively, reposition itself to adjust the field of view to ensure that the tip of the surgical scissors remain within an optimum position within the field of view of the laparoscope during the procedure. As described above, additional gestural patterns may be performed via the surgical scissor within the field of view of the laparoscope to cause the first robot arm to retract the laparoscope and/or to cause the laparoscope itself to zoom in or zoom out or improve resolution.

In some embodiments, as described above, based on the image data captured by the laparoscope, using object tracking of the additional tools in the field of view of the laparoscope, e.g., the surgical scissors actively operated by the operator, the system may cause the first robot arm coupled to the laparoscope to switch to the robotic assist mode and cause the first robot arm to automatically reposition itself to adjust the field of view to ensure that the tip of the surgical scissors remains within an predefined optimum position, e.g., a boundary region, within the field of view of the laparoscope during the procedure.

Figure 21:
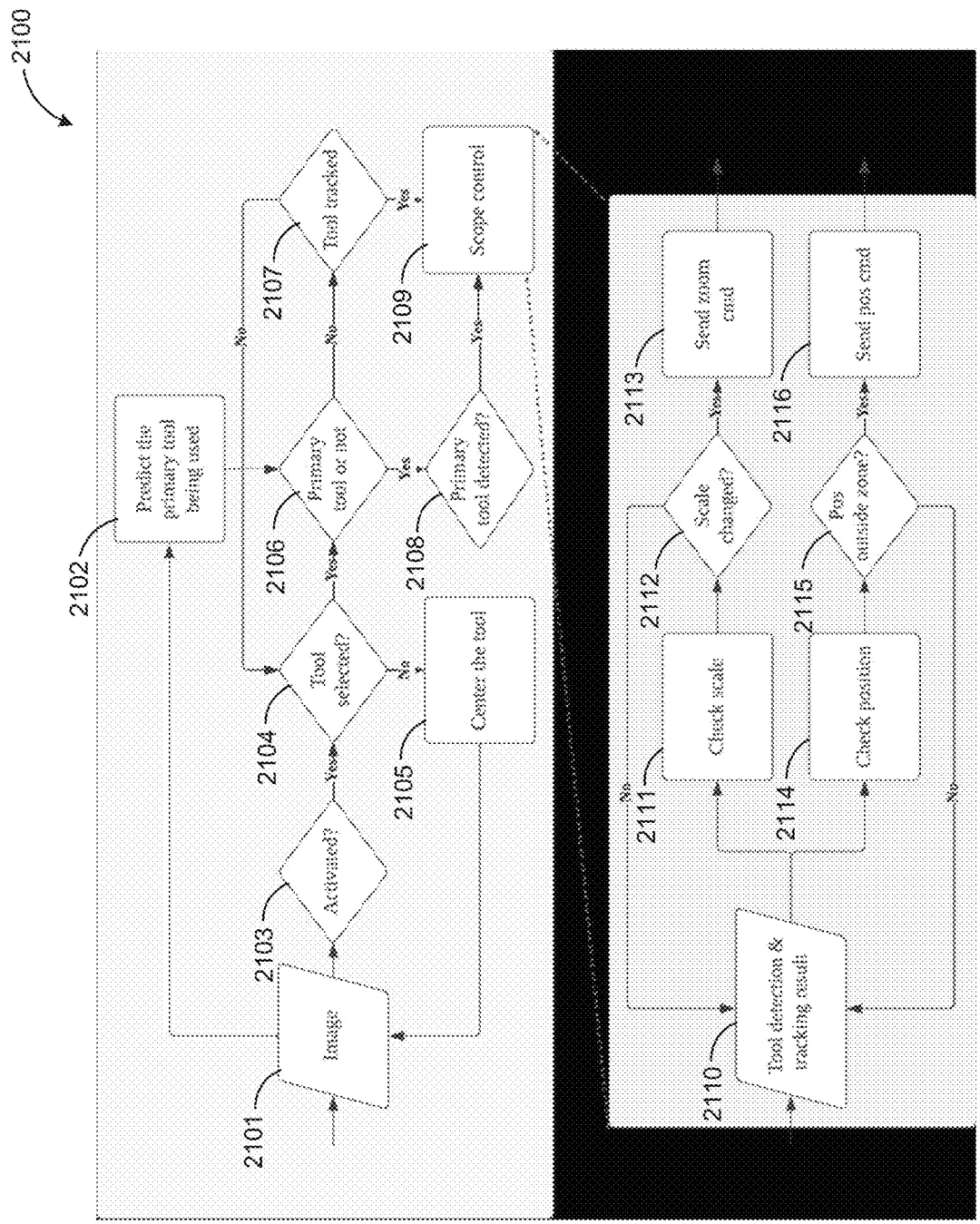
FIG. 21 is a flow chart illustrating instrument centering in accordance with the principles of the present disclosure.

For example, FIG. 21 illustrates exemplary instrument centering process 2100 for tracking a surgical tool, e.g., the surgical scissors, within the field of view of the laparoscope. At step 2101, image data obtained by the laparoscope is obtained by the system. For example, the laparoscope may be any off-the-shelf laparoscope, and the camera control unit of the laparoscope may be electrically connected to the system via a video cable, e.g., HDMI, SDI, etc., such that the controller of the system may receive the image data from the laparoscope. At step 2103 actuation of the instrument centering mode is detected by the system, e.g., via user input or automated actuated based on the detected phase of the procedure. Step 2103 also may occur before or simultaneously with step 2101. Upon actuation of the instrument centering mode, the system determines whether a surgical instrument to be followed has been selected at step 2104, e.g., manually via user input via GUI 210 or automatically via detection of a predefined gestural pattern associated with user input of tool selection. For example, if a surgical instrument has not been selected, at step 2105, the user may perform a predefined gestural pattern, e.g., move a surgical instrument to the center portion of the field of view of the laparoscope and hold the surgical instrument in position for longer than a predetermined hold period, which is interpreted by the system as user input of selecting to follow a surgical instrument. In addition, the distance between the tip of the surgical instrument and the tip of the laparoscope may be established as the reference distance, such that the robot arm may move the laparoscope to maintain the surgical instrument within the field of view of the laparoscope while also maintaining the reference distance between the instrument and the laparoscope. Alternatively, in some embodiments, at step 2104, the system may automatically select the surgical instrument to be followed, e.g., via object segmentation and knowledge of the current phase of the surgical procedure, as described above. Simultaneously, at step 2102, the system optionally may identify/predict if there is a primary tool for a given phase of the surgical procedure, which may be determined, e.g., based on one or more identified surgical instruments and/or anatomical features within the field of view of the laparoscope, as described above.

If the system determines that a surgical instrument has been selected to be followed at step 2104 and/or if the system identifies that there is a primary tool for the given phase of the surgical procedure, at step 2106, the system may determine whether the selected surgical instrument is the primary tool for the given phase of the surgical procedure. If the surgical instrument to be followed is not the primary tool, at step 2107, the system determines whether it can successfully track the selected surgical instrument across consecutive images of the laparoscope video feed. If the system determines that it can track the selected surgical instrument, the system proceeds to provide instrument centering at step 2108. If the system determines that the surgical instrument to be followed is the primary tool at step 2106, then at step 2108, the system detects the selected surgical instrument within the image data, e.g., a single image of the laparoscope video feed, and proceeds to provide instrument centering at step 2109.

At step 2110, the system continuously detects/follows/tracks the surgical instrument within the field of view of the image data. For example, at step 2111, the system checks the scale, e.g., resolution/size, of the surgical instrument within the image data, and determines at step 2112 whether or not the scale of the surgical instrument within the image data has changed. If the scale has not changed, the system continues to detect/follow/track the surgical instrument within the image data. If the scale has changed, at 2113, the system may send a command to the robot arm to move the laparoscope, e.g., along the longitudinal axis of the laparoscope, to zoom in/out based on the change of scale of the surgical instrument within the image data. For example, if the scale changes such that the size of the surgical instrument increase, and thus, the resolution decreases, the command may be to zoom out, e.g., retract the laparoscope.

Simultaneously, at step 2114, the system checks the position of the surgical instrument within the image data, and determines at step 2115 whether or not the position of the surgical instrument within the image data has changed, e.g., moved outside of a predefined virtual boundary region within the field of view of the laparoscope. If the position has not changed, such that the surgical instrument, though moving, has not been detected to have moved outside of the predefined boundary region, the system continues to detect/follow/track the surgical instrument within the image data. If the position has changed such that the surgical instrument is detected to have moved outside of the predefined boundary region, at 2116, the system may generate a trajectory, as described above, and send a command to the robot arm to move the laparoscope along the trajectory to a desired position to maintain the surgical instrument within the predefined boundary region. For example, the command may cause the robot arm to move the laparoscope to a position where the surgical instrument is at the center of the predefined boundary region. Moreover, as described above, the system may correct for a detected angular offset between the camera head of the laparoscope and the laparoscope in robotic assist mode to provide accurate instrument centering.

Figure 22:
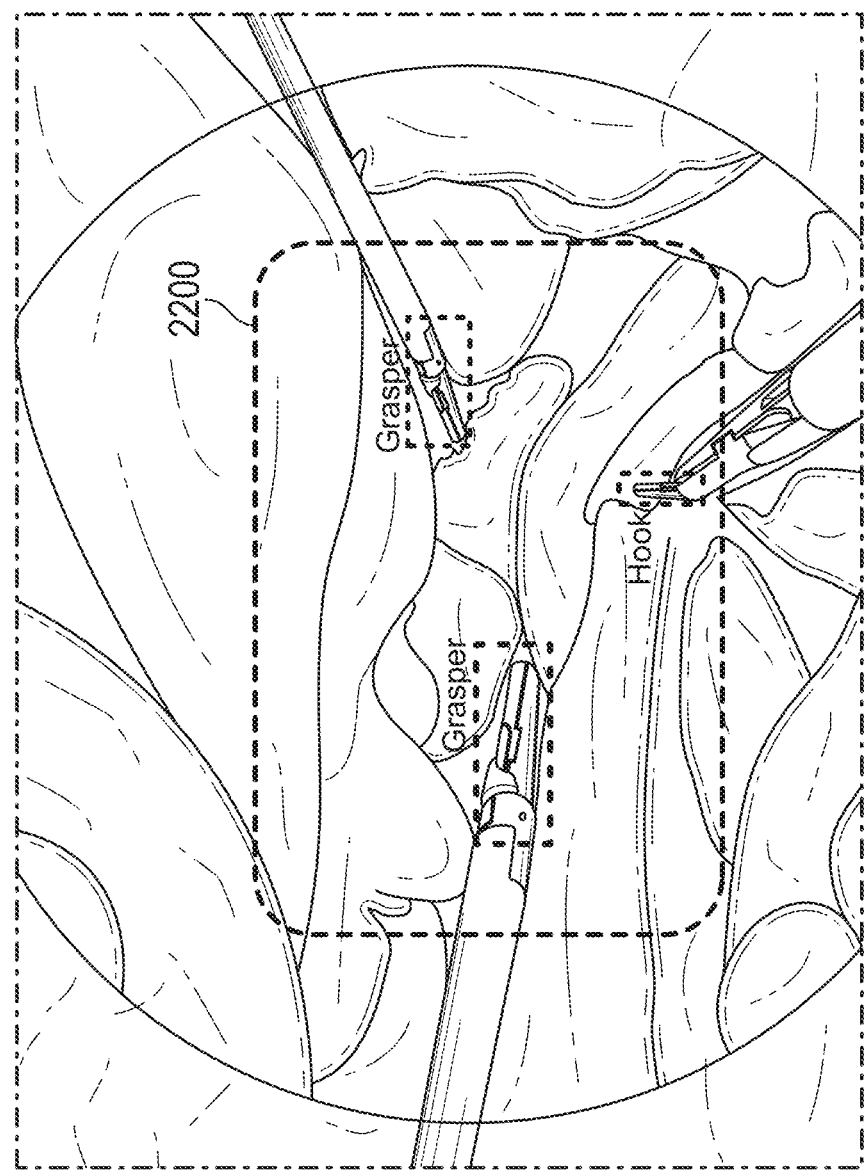
FIG. 22 illustrates an exemplary tracking overlay of a graphical user interface of the co-manipulation surgical system.

As shown in FIG. 22, an overlay of the tracked surgical instrument as well as other tools within the field of view of the laparoscope may be displayed, e.g., via GUI 210, to indicate which tools are being tracked and which tools are not. Moreover, FIG. 22 illustrates boundary region 2200, which may or may not be displayed as part of the overlay.

As described above, once the trajectory is determined, the system calculates the force required to apply at the joints of the robot arm to move the robot arm, and accordingly the laparoscope, along the trajectory. FIGS. 23A to 23B illustrates exemplary force measurements of the system during operation of robot arm 300. As described above, the calibration file of the surgical instrument coupled to robot arm 300 loaded on the system may include information of the surgical instrument including, e.g., the mass of the surgical instrument, the center of mass of the surgical instrument, and the length of the surgical instrument, such that distance D3 between the center of mass and the instrument tip may be derived. In addition, as described above, the position of the surgical instrument at the trocar, e.g., where the surgical instrument enters the patient's body, may be calculated in real-time, such that distance D2 between the center of mass of the surgical instrument and the trocar may be derived in real time. Additionally, as described above, the coupler body is preferably coupled to the surgical instrument at a fixed, known position along the elongated shaft of the surgical instrument (which may be included in the calibration file), e.g., adjacent to the proximal portion of the surgical instrument, and thus distance D1 between the center of mass of the surgical instrument and the coupler body, e.g., the point of attachment to the distal end of robot arm 300, may be derived. Alternatively or additionally, as described above, optical scanning devices may be used to determine any one of D1, D2, or D3.

As shown in FIG. 23A, when the surgical instrument is positioned through trocar Tr, without any additional external forces acting on the surgical instrument other than at trocar Tr, e.g., the surgical instrument is not lifting or retracting tissue within the patient, the force applied to the surgical instrument at trocar Tr by the body wall (e.g., the "body wall force" or the "trocar force") may be calculated with the following equation:

$$F_{eff}+W+F_{tr}=0 => F_{tr}=-W-F_{eff}$$

Where $F_{eff}$ is the force at the distal end of robot arm 300 (e.g., the "end-effector force" of robot arm 300), W is the weight vector of the surgical instrument (=−mgz), and $F_{tr}$ is the trocar force. Accordingly, $F_{eff}$ is the desired force sent to the system, which is the sum of all the forces generated in the algorithm pipeline including, e.g., gravity compensation, hold, etc.

As shown in FIG. 23B, when the surgical instrument is positioned through trocar Tr and holding/retracting tissue, such that an external force is applied to the tip of the surgical instrument, there are two forces to resolve: $F_{tr}$ and $F_{tt}$. Accordingly, two equations are needed to solve for the two unknown vectors, which may be the balances of forces and also the balance of moments around the center of mass of the surgical instrument, e.g., $L_{cg}$.

$$W+F_{eff}+F_{tr}+F_{tt}=0$$

$$F_{eff} \times D1 + F_{tr} \times D2 + F_{tt} \times D3 = 0$$

Here, distances D1 and D3 are known as described above, and D2 may be derived based on the known position of the distal end of robot arm 300 and the calculated position of trocar Tr. As shown in FIG. 23B, the center of mass Lcg of the surgical instrument is behind the point of attachment of the coupler body to the distal end of robot arm 300.

As described above, the system may alert the operator if the forces, e.g., force $F_{tt}$ applied to the tip of the instrument and/or force $F_{tr}$ applied by the instrument at trocar Tr, are greater than the respective threshold forces, and accordingly freeze the system if the calculated force is greater than the threshold force, and/or reduce the force exerted at the trocar point at the body wall or at the tip of the instrument by automatically applying brakes or stopping forces to robot arm 300, by slowing or impeding further movement of the instrument in the direction that would increase forces applied at the tip of the instrument or the trocar, and/or automatically moving the robotic arm in a direction that reduces the force being exerted at the instrument tip and/or at the trocar point at the body wall.

Accordingly, with knowledge of, e.g., the position of the trocar, the distance from the coupler body to the instrument tip, the current position of the distal end of the robot arm, the current position of the instrument tip, the desired position of the distal end of the robot arm that provides the desired position of the instrument tip, the system may calculate the force required to apply to the distal end of the robot arm to move it from its current position to its desired position to thereby move the instrument tip from its current position to its desired position. For example, when a robot arm is in passive mode, the desired position of the distal end of the robot arm/instrument tip will be the static position of the distal end of the robot arm/instrument tip when passive mode was initiated, and any forces below the breakaway force applied to the distal end of the robot arm, e.g., due to perturbations, may cause a change in the current position of the distal end of the robot arm/instrument tip. Accordingly, the system may calculate the force required to apply to the distal end of the robot arm to move it from its current position to the desired static position (i.e., the "hold force"), and apply the requisite torque to the robot arm to effectively maintain the robot arm in the desired static position in passive mode.

Figure 23C:
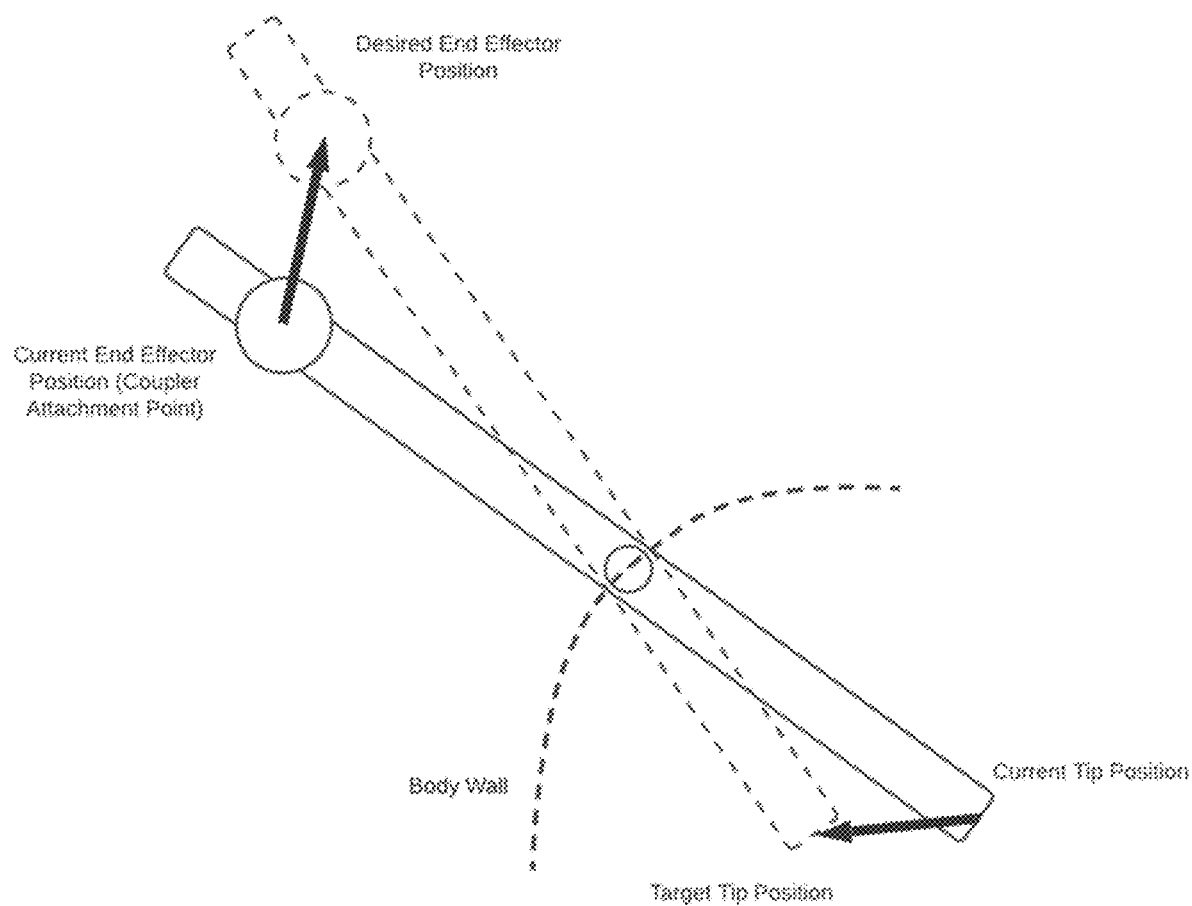
FIGS. 23C-23E are free-body diagrams illustrating movement of the surgical instrument coupled to the robot arm along a trajectory for instrument centering.
Figure 23D:
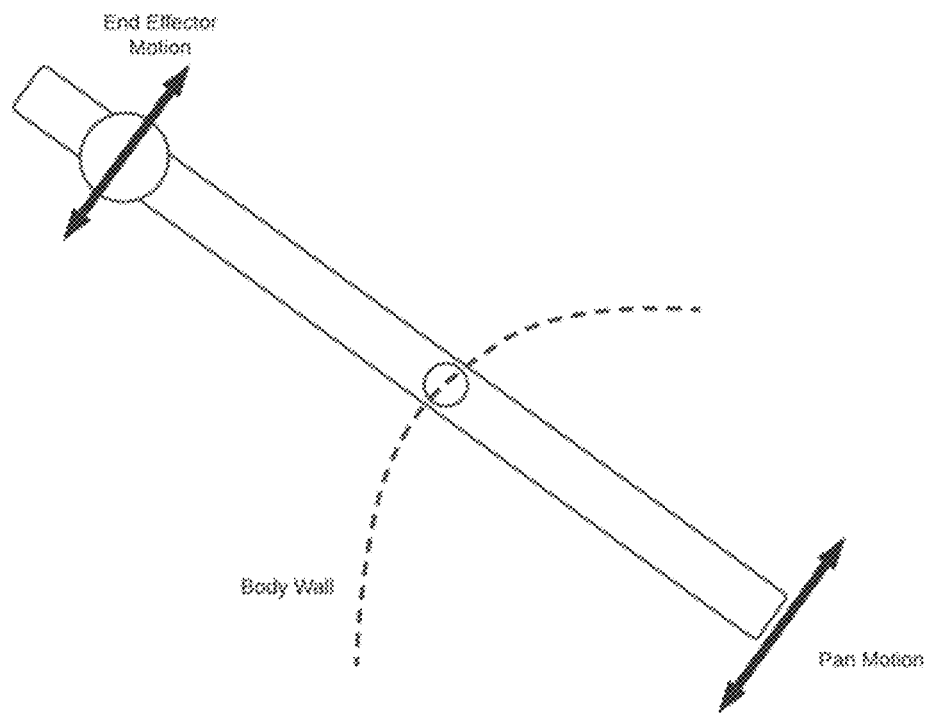
Figure 23E:
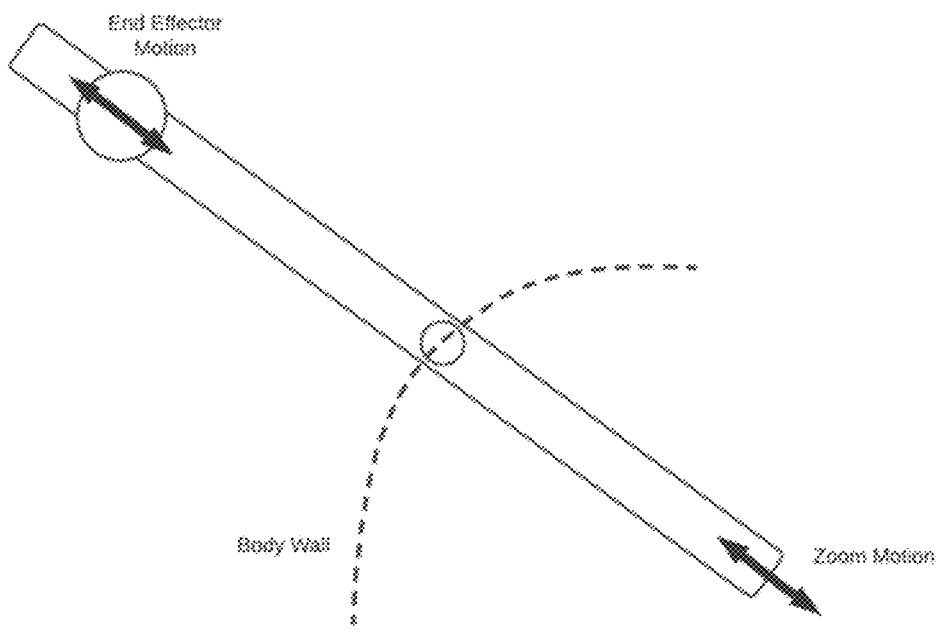

Similarly, as shown in FIG. 23C, when the robot arm is in robotic assist mode where the system provides instrument centering, upon determination of the trajectory for moving the distal end of the robot arm, and accordingly, the laparoscope coupled thereto, between the current position and the desired position to maintain the tracked instrument within the predefined boundary region within the field of view of the laparoscope, the system may calculate the hold force required to apply to the distal end of the robot arm to move it from its current position along the trajectory to the desired position, and apply the requisite torque to the robot arm to move the laparoscope and maintain the tracked instrument within the predefined boundary region. As shown in FIG. 23D, when the trajectory required to move the laparoscope to maintain the surgical instrument within the predefined boundary region only requires a lateral movement, e.g., along an axis perpendicular to the longitudinal axis of the laparoscope, the trocar position is not required, and the system may command the robot arm to move along the lateral trajectory to pan the field of view of the laparoscope. Similarly, as shown in FIG. 23E, when the trajectory required to move the laparoscope to maintain the surgical instrument within the predefined boundary region only requires a movement along the longitudinal axis of the laparoscope, e.g., to zoom in/out, the trocar position is not required, and the system may command the robot arm to move along the longitudinal trajectory.

Figure 24:
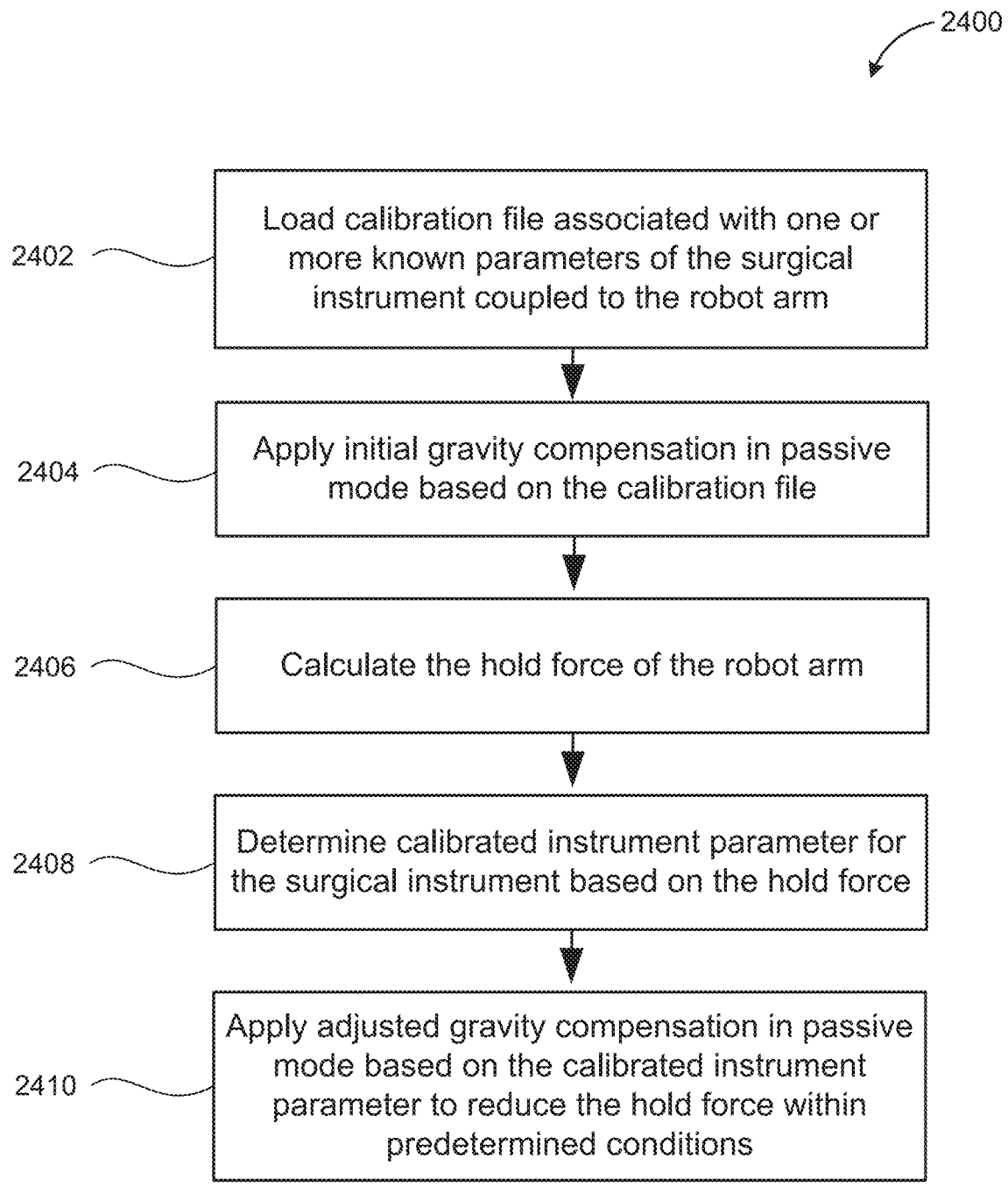
FIG. 24 illustrates an exemplary adaptive gravity compensation process for dynamically adjusting gravity compensation in accordance with the principles of the present disclosure.

Moreover, as described above, the system may automatically calibrate a surgical instrument in real-time via adaptive gravity compensation, e.g., based on the hold forces required to maintain the robot arm in a static position in passive mode. For example, an instrument's gravity characteristics may change dynamically at different locations and/or with different attachments, e.g., scope cables, forces from the patient's body wall, during operation of the robot arm. Accordingly, the system may update a calibration file of the surgical instrument in real-time, e.g., in passive mode, to thereby dynamically adjust the gravity compensation applied by the system. FIG. 24 illustrates exemplary adaptive gravity compensation process 2400 for dynamically adjusting the gravity compensation applied by the system based on whether the hold force is helping or opposing the applied gravity compensation.

At step 2402, the system may automatically load a calibration file associated one or more known parameters of a surgical instrument coupled to the robot arm. For example, as described above, at least the shaft diameter of the surgical instrument may be determined upon coupling of the coupler body to the coupler interface (with or without the surgical instrument attached), e.g., based on the specific magnetic field strength induced by the displaced magnet within the coupler body. Additionally, or alternatively, image data captured by the optical scanner(s) may be used to identify one or more known parameters of the surgical instrument, e.g., the length and/or instrument type, and/or measured motor currents may be used to estimate the mass of the instrument and/or a gravity category of the instrument such as "light," "medium," or "heavy." Accordingly, the system may load a calibration file associated with the known parameter(s), e.g., a calibration file associated with a 5 mm or 10 mm surgical instrument. As will be understood by a person having ordinary skill in the art, various surgical instruments having the same shaft diameter also may have other similar parameters, such as mass, center of gravity, etc. Accordingly, the loaded calibration file may include one or more instrument parameters that deviate from the actual parameters of the attached surgical instrument within an acceptable range. Moreover, the loaded calibration file may be used to inform acceptable gravity compensation adjustments, as described in further detail below.

At step 2404, the system may apply gravity compensation to the robot arm coupled to the surgical instrument based on the instrument parameters within the loaded calibration file. For example, based on the mass of the surgical instrument stored in the calibration file (whether or not it is accurate), the system may calculate the amount of force to apply to the robot arm to compensate for the presumed weight of the surgical instrument and maintain the robot arm in a static position in passive mode, and apply the requisite torque to the robot arm to provide the gravity compensation.

At step 2406, the system may calculate the hold force required to maintain the robot arm in a static position in passive mode. Preferably, the system continuously calculates the hold force while in passive mode; however, in some embodiments, the system may begin calculating the hold force after a predetermined time period to ensure that the robot arm is steady in a static position, as described in further detail below with regard to FIGS. 26A to 26C. For example, when the surgical instrument coupled to the robot arm is not subjected to any external forces other than gravity in passive mode, e.g., by a trocar, tissue, and/or organ, if the instrument mass stored in the calibration file is equal to the actual mass of the surgical instrument coupled to the robot arm, the gravity compensation force applied by the system will completely compensate for the weight of the instrument such that no extra force, i.e., hold force, is required to be applied to the robot arm to maintain the robot arm in the desired static position. If the instrument mass stored in the calibration file is less than the actual mass of the surgical instrument coupled to the robot arm, the gravity compensation force applied by the system will be less than needed to completely compensate for the weight of the instrument such that the robot arm may drift downward due to the actual weight of the instrument, requiring an upward hold force to be applied to the robot arm to maintain the robot arm in the desired static position. Similarly, if the instrument mass stored in the calibration file is more than the actual mass of the surgical instrument coupled to the robot arm, the gravity compensation force applied by the system will be more than needed to completely compensate for the weight of the instrument such that the robot arm may drift upward due to the actual weight of the instrument, requiring a downward hold force to be applied to the robot arm to maintain the robot arm in the desired static position.

At step 2408, the system may determine one or more calibrated instrument parameters for the surgical instrument, e.g., the mass and/or center of mass of the surgical instrument, based on the calculated hold force, and update the calibration file accordingly. For example, the system may determine and update the mass of the surgical instrument within the calibration file to a mass that corresponds with a gravity compensation force that would result in no hold force being required to be applied to the distal end of the robot arm to maintain the surgical instrument in the desired static position, e.g., the updated mass is equal to the actual mass of the surgical instrument. As will be understood by a person having ordinary skill in the art, the system may update and save the loaded calibration file as a new calibration file associated with the specific surgical instrument coupled to the robot arm and/or create a new calibration file for the specific surgical instrument.

At step 2410, the system may calculate and apply a subsequent, adjusted gravity compensation force to the distal end of the robot arm based on the calibrated instrument parameter, e.g., the updated mass of the surgical instrument, which will minimize the hold force required to maintain the surgical instrument in the desired static position within a predetermined condition, e.g., by reducing the hold force to or near zero. Moreover, the system may be programmed to only permit gravity compensation adjustments within a predetermined range for a particularly sized instrument, e.g., based on the known shaft diameter upon coupling of the coupler body to the coupler interface. For example, if the system knows that the instrument coupled to the robot arm is a 5 mm diameter instrument, which is generally associated with a known range of masses, the mass of the instrument within the calibration file may be updated to a mass only within a predetermined range of the presumed mass within the loaded calibration file, such that gravity compensation also may only be adjusted within a predetermined range. Moreover, additional known parameters, e.g., gravity category, instrument type, instrument length, etc., may also be associated with a respective known range of mass for that particular parameter, to thereby limit the range of gravity compensation adjustment for the particular surgical instrument. In addition, adjustments to the gravity compensation applied to the robot arm by the system may be applied gradually so as to avoid jumpy motion of the robot arm.

Figure 25A:
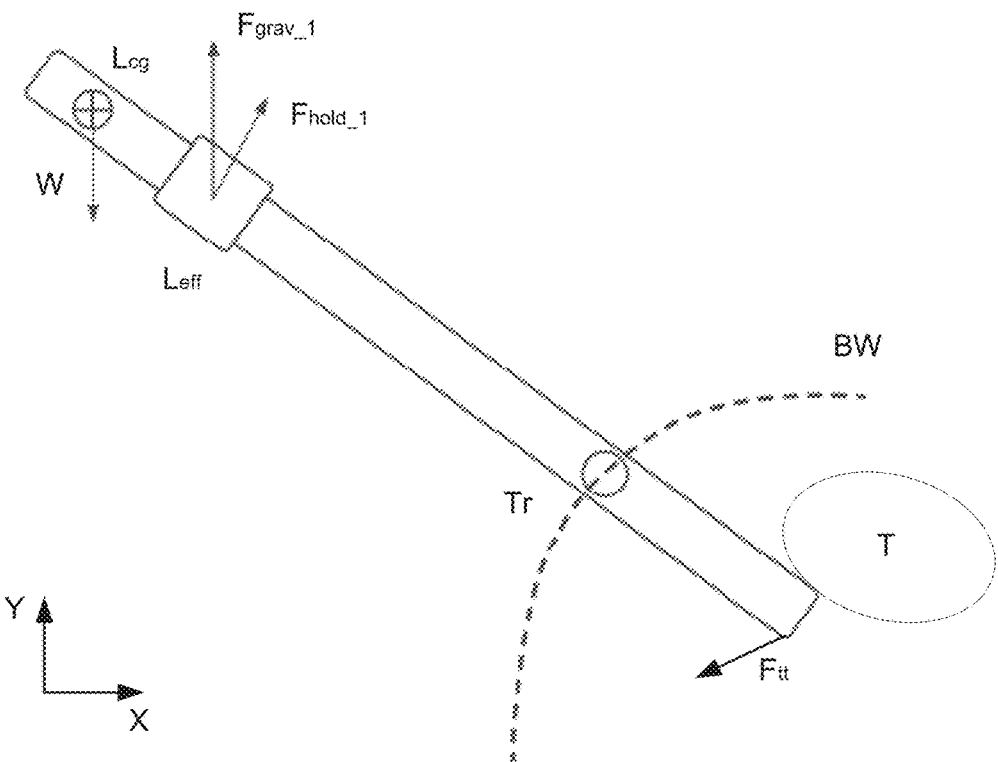
FIGS. 25A and 25B illustrate adaptive gravity compensation as applied to a robot arm coupled to a surgical instrument subjected to external forces in addition to gravity.
Figure 25B:
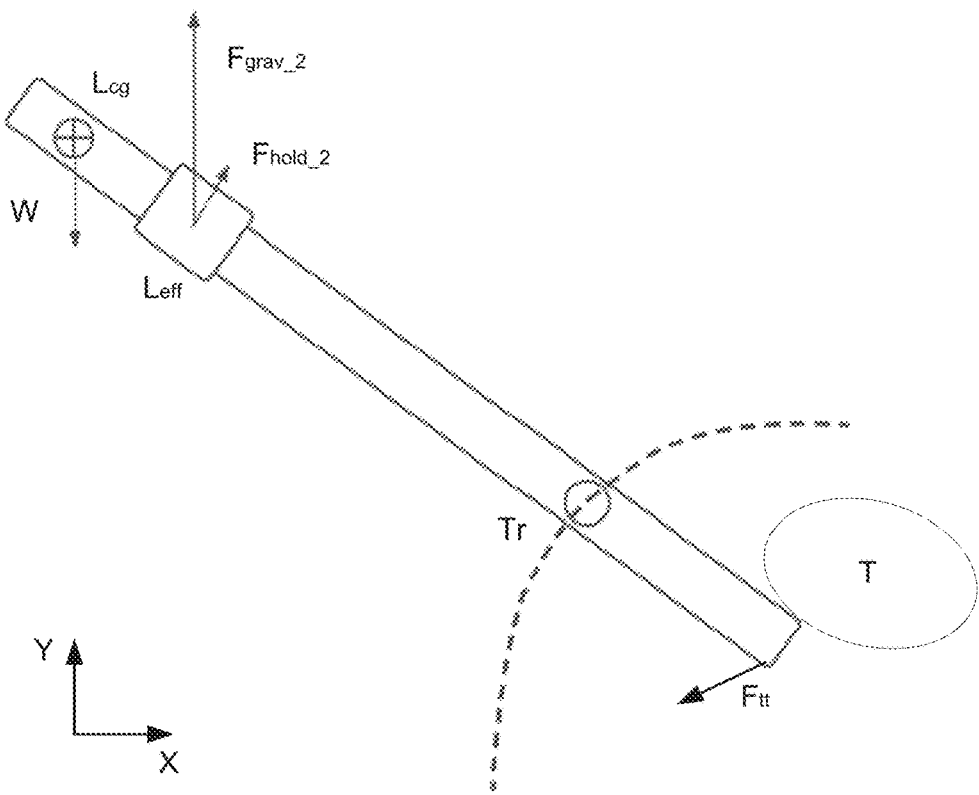

FIGS. 25A and 25B illustrate adaptive gravity compensation process 2400 as applied to a robot arm coupled to a surgical instrument subjected to external forces in addition to gravity in passive mode. For example, as shown in FIG. 25A, at step 2404, the system may apply initial gravity compensation force $F_{grav\_1}$ to the distal end of the robot arm coupled to the instrument, e.g., at location $L_{eff}$, based on the mass of the surgical instrument stored in the calibration file. Moreover, as shown in FIG. 25A, the tip of the instrument may be passed through trocar Tr, and engaged with tissue T, such that force $F_{tt}$ is applied to the tip of the instrument by tissue T. At step 2406, the system may calculate hold force $F_{hold\_1}$ required to be applied to the distal end of the robot arm to maintain the tip of the instrument in the desired static position responsive to force $F_{tt}$. For example, the system may only need to calculate the vertical vector component of hold force $F_{hold\_1}$ along a vertical axis parallel to the direction of gravity based on the vertical vector component of force $F_{tt}$.

At step 2408, the system may determine and update, e.g., the mass and/or center of mass $L_{cg}$ of the instrument within the loaded calibration file to a mass and/or center of mass that corresponds with an increased gravity compensation force that would result in a reduction of the hold force required to be applied to the distal end of the robot arm to maintain the surgical instrument in the desired static position. Accordingly, as shown in FIG. 25B, at step 2410, the system may apply a subsequent gravity compensation force $F_{grav\_2}$ to the distal end of the robot arm coupled to the instrument, e.g., at location $L_{eff}$, based on the updated mass of the surgical instrument stored in the calibration file to thereby reduce/minimize the hold force, e.g., hold force $F_{hold\_2}$, required to maintain the surgical instrument in the desired static position within a predetermined condition, e.g., based on known acceptable ranges associated with a given instrument type. For example, the acceptable range within which the instrument parameters, and accordingly, gravity compensation, may be adjusted to reduce the hold force for a given instrument may be predetermined based on, e.g., the known shaft diameter of the instrument, as described above.

Figure 26A:
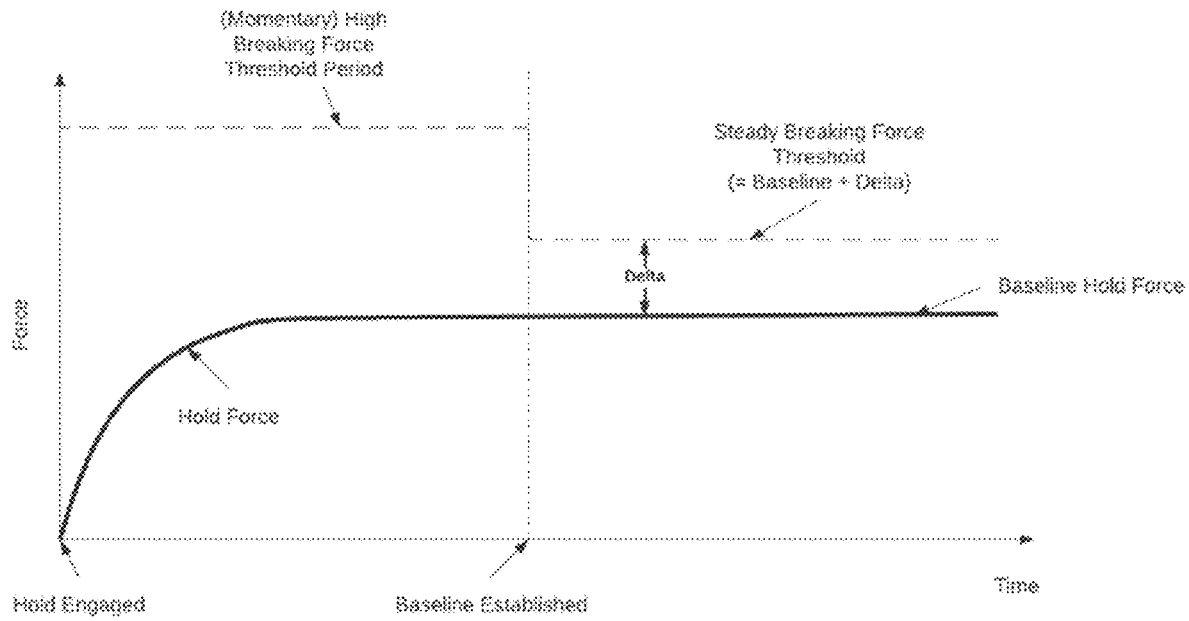
FIGS. 26A-26C illustrate hold force over time to establish a breakaway force threshold based on the hold force in accordance with the principles of the present disclosure.
Figure 26B:
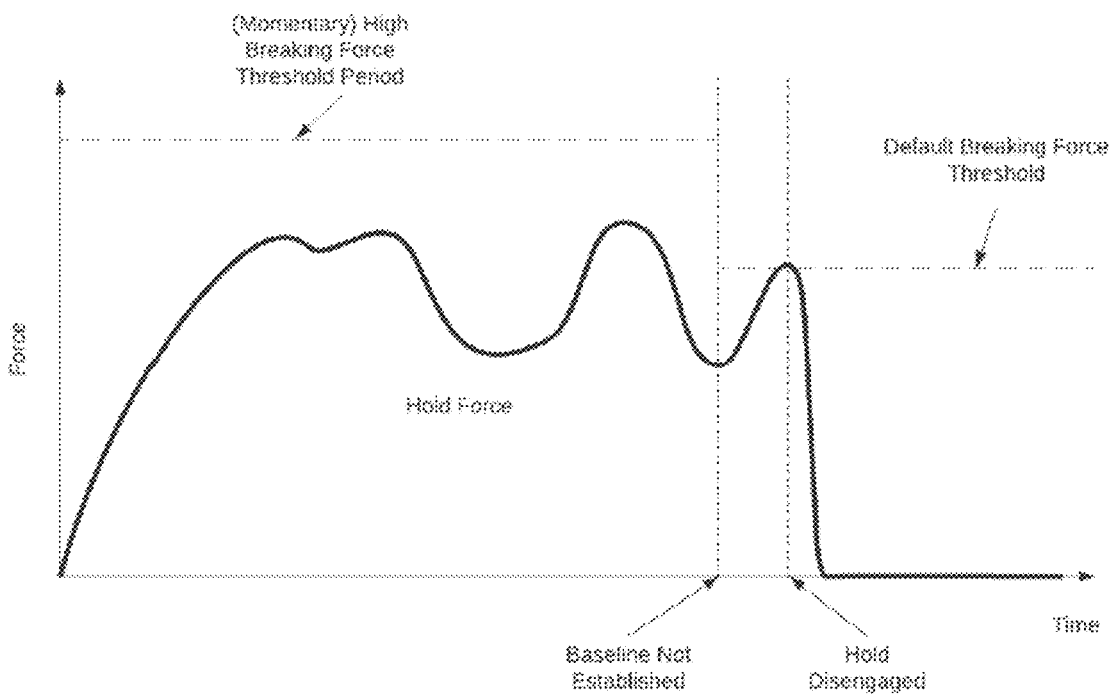
Figure 26C:
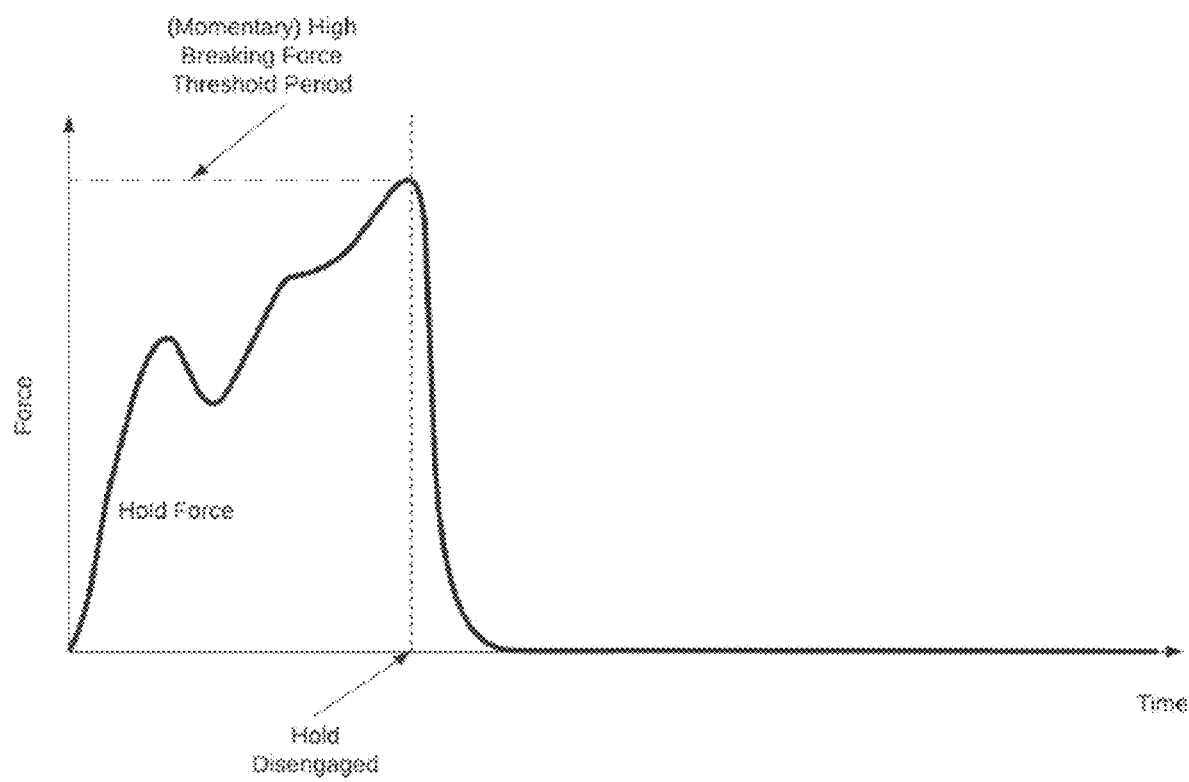

Referring now to FIGS. 26A to 26C, as described above, the system preferably continuously calculates the hold force while in passive mode; however, the system may establish a baseline hold force after a predetermined time period upon initiation of passive mode to ensure that the robot arm is steady in a static position, e.g., when one or more external forces are applied to the instrument coupled to the distal end of the robot arm by one or more anatomical structures, e.g., tissue, bone, an organ, a body wall, etc. For example, under some circumstances, the hold force required to maintain the robot arm in the desired static position may require time to become steady upon initiation of passive mode and release of the surgical instrument by the user. For example, when the user operates the surgical instrument to engage a tissue, e.g., to retract an organ, upon release of the instrument by the user, the hold force may gradually increase over time due to forces applied to the tip of the instrument by the tissue before becoming steady. Accordingly, the system may wait until the hold force has become steady, up to a predetermined time period upon initiation of passive mode.

Moreover, the rate/pattern of the change in the hold force over time upon initiation of passive mode may further be indicative of whether the perturbations are due to, e.g., the instrument holding tissue or the user repositioning the instrument. For example, a slow gradual increase of hold force may indicate that the instrument is holding tissue in passive mode; whereas, a change in hold force having a fluctuating profile may indicate that the user is still interacting with the instrument and has not released the instrument, e.g., with forces less than the breakaway force. In addition, the system may temporarily change the breakaway force of the robot arm to a predetermined, high value that would require a large amount of force to transition the robot arm from passive mode to co-manipulation mode for at least the duration of the predetermined time period before which the hold force is expected to become steady. Moreover, the system may set the hold force calculated after the predetermined time period as a baseline hold force, and adjust the breakaway force based on the baseline hold force to compensate for otherwise large hold forces required to maintain a surgical instrument in a desired static position in passive mode, as described in further detail with regard to FIGS. 27A and 27B.

As shown in FIG. 26A, the hold force may gradually increase over time, e.g., due to one or more external forces applied to the instrument by one or more anatomical structures, upon initiation of passive mode, e.g., when hold is initially engaged, and eventually become steady. As described above, the system may apply a temporary high breakaway force to the robot arm coupled to the instrument for a predetermined time period upon initiation of passive mode until the baseline hold force is established, to thereby prevent inadvertent disengagement of the robot arm from passive mode. For example, the temporary breakaway force should be high enough such that inadvertent bumps or other perturbations of the robot arm do not exceed the temporary breakaway force, but not so high that a user could not manually disengage the robot arm from passive mode via the application of force.

As described above, the system may continuously calculate the hold force required to maintain the distal end of the robot arm, and accordingly the surgical instrument coupled thereto, in the desired static position while in passive mode, and may calculate the average hold force after the predetermined time period upon initiation of passive mode, and establish this value as the baseline hold force. As further described above, gravity compensation may be dynamically adjusted to thereby adjust the gravity compensation force to the robot arm and reduce the baseline hold force within acceptable limits associated the surgical instrument. Accordingly, the baseline hold force may be the hold force calculated after the predetermined time period minus any reductions due to increased gravity compensation. Moreover, the system may then establish the breakaway force based on the baseline hold force, e.g., as a value having a predetermined delta from the baseline hold force, as shown in FIG. 26A. Accordingly, the amount of additional force required to be applied to the surgical instrument to transition the robot arm from passive mode to co-manipulation mode may be the same, e.g., delta, in all directions regardless of the amount of force being applied to the instrument by a tissue/organ, as described in further detail with regard to FIGS. 27A and 27B. In addition, the system may continue to apply the adjusted gravity compensation while the robot arm is operated in the co-manipulation mode.

As shown in FIG. 26B, the hold force may having a fluctuating profile over time, e.g., due to perturbations and/or small user hand movements before letting go of the instrument, following initiation of passive mode, e.g., when hold is initially engaged. As described above, the system may apply a temporary high breakaway force to the robot arm coupled to the instrument for a predetermined time period upon initiation of passive mode, to thereby prevent inadvertent disengagement of the robot arm from passive mode. As shown in FIG. 26B, if the hold force of the robot arm detected by the system continues to fluctuate at the end of the predetermined time period while less than temporary high breakaway force, the system may determine that a baseline hold force cannot be established, and set a default breakaway force, e.g., not based on a baseline hold force. Accordingly, when the force applied to the surgical instrument reaches the default breakaway force, the system will disengage the hold and switch the robot arm from passive mode to co-manipulation mode.

As shown in FIG. 26C, if the hold force reaches/achieves the temporary high breakaway force applied by the system within the predetermined time period upon initiation of passive mode, the system will disengage the hold and switch the robot arm from passive mode to co-manipulation mode, as this movement is likely intended by the user. As described above, the system may be manually set to a "high force mode" by a user, e.g., via the graphical user interface, where a predetermined higher breakaway force is established for a given phase of a procedure. However, by automatically adjusting the breakaway force based on the established baseline hold force, the system may account for higher forces being applied to the instrument, e.g., via a heavy organ, in real-time in passive mode, without requiring manual actuation of the "high force mode."

Figure 27A:
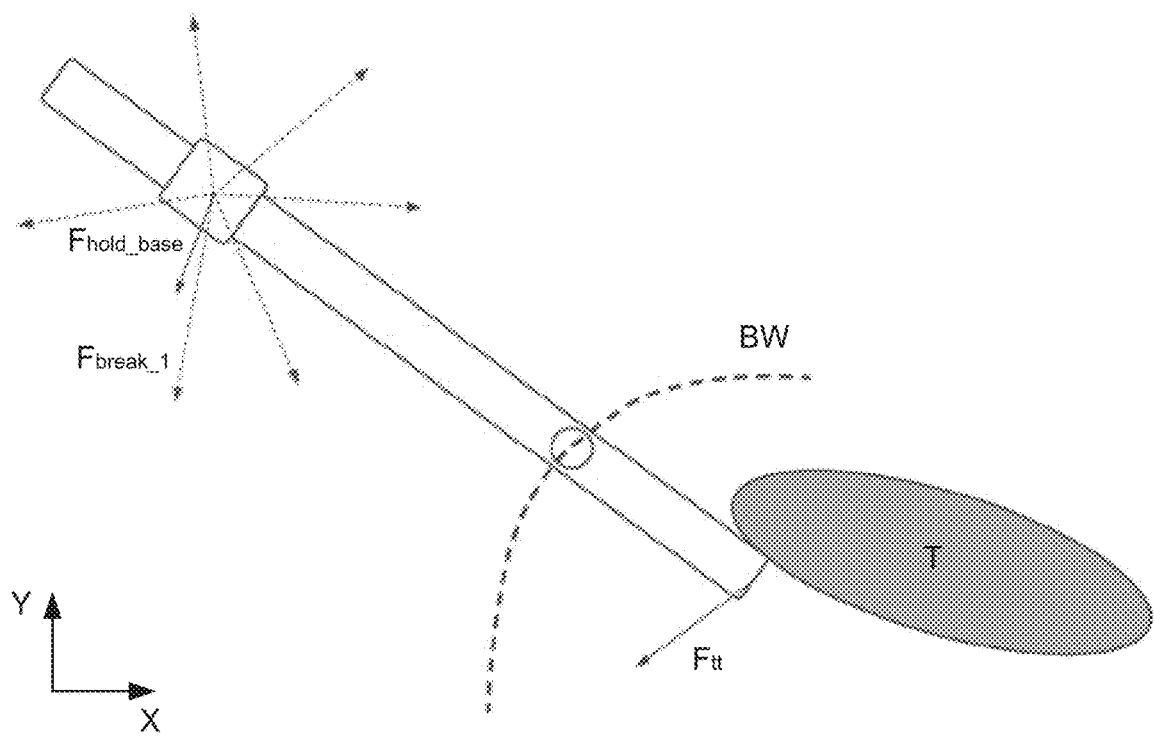
FIG. 27A illustrates the breakaway force threshold independent of the hold force.

For example, FIG. 27A illustrates force $F_{tt}$ applied to the tip of the instrument by tissue T, the baseline hold force $F_{hold\_base}$ required to maintain the surgical instrument in the desired static position responsive to force $F_{tt}$, and breakaway force $F_{break\_1}$ required to be applied to the robot arm to exit the passive mode and enter the co-manipulation mode when the breakaway force is not established based on the baseline force. Accordingly, as shown in FIG. 27A, although the breakaway force $F_{break\_1}$ is equal in magnitude in every direction, the amount of additional force required in addition to baseline hold force $F_{hold\_base}$ in the direction of baseline hold force $F_{hold\_base}$ to achieve breakaway force $F_{break\_1}$ is reduced by the magnitude of baseline hold force $F_{hold\_base}$ along the direction of baseline hold force $F_{hold\_base}$.

Figure 27B:
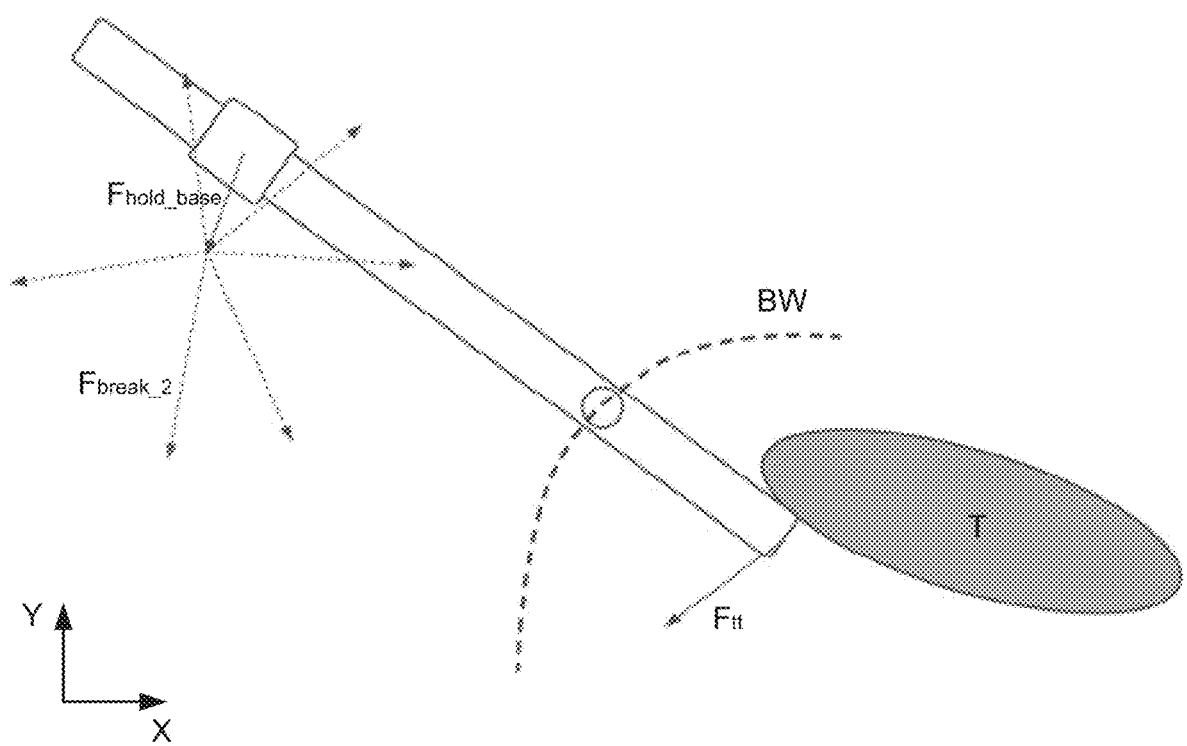
FIG. 27B illustrates the breakaway force threshold based on the hold force.

As shown in FIG. 27B, by establishing breakaway force $F_{break\_2}$ based on baseline hold force $F_{hold\_base}$, the same amount of force will be required to be applied to the distal end of the robot arm to achieve breakaway force $F_{break\_2}$ in every direction when the instrument is in the desired static position. For example, although the total amount of force applied to the distal end of the robot arm in the direction of baseline hold force $F_{hold\_base}$ to achieve breakaway force $F_{break\_2}$ in that direction is the sum of baseline hold force $F_{hold\_base}$ and breakaway force $F_{break\_2}$, the amount of additional force required by, e.g., a user, to be applied to the robot arm is only breakaway force $F_{break\_2}$, as the system is already applying baseline hold force $F_{hold\_base}$ to the robot arm.

Figure 28A:
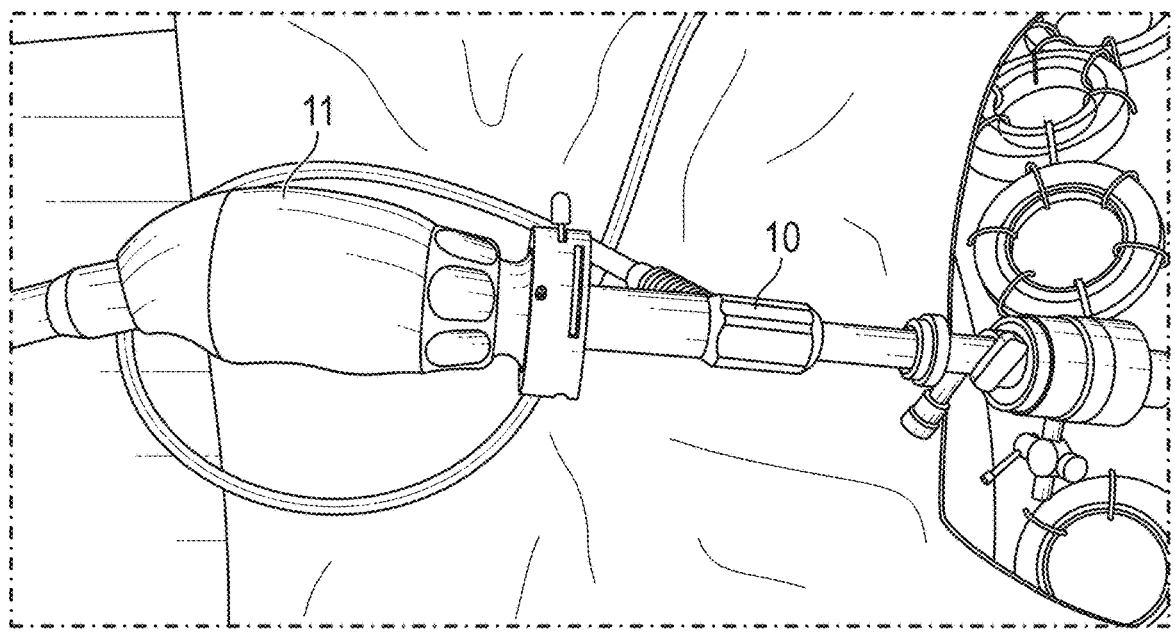
FIG. 28A illustrates a conventional laparoscope device.
Figure 28B:
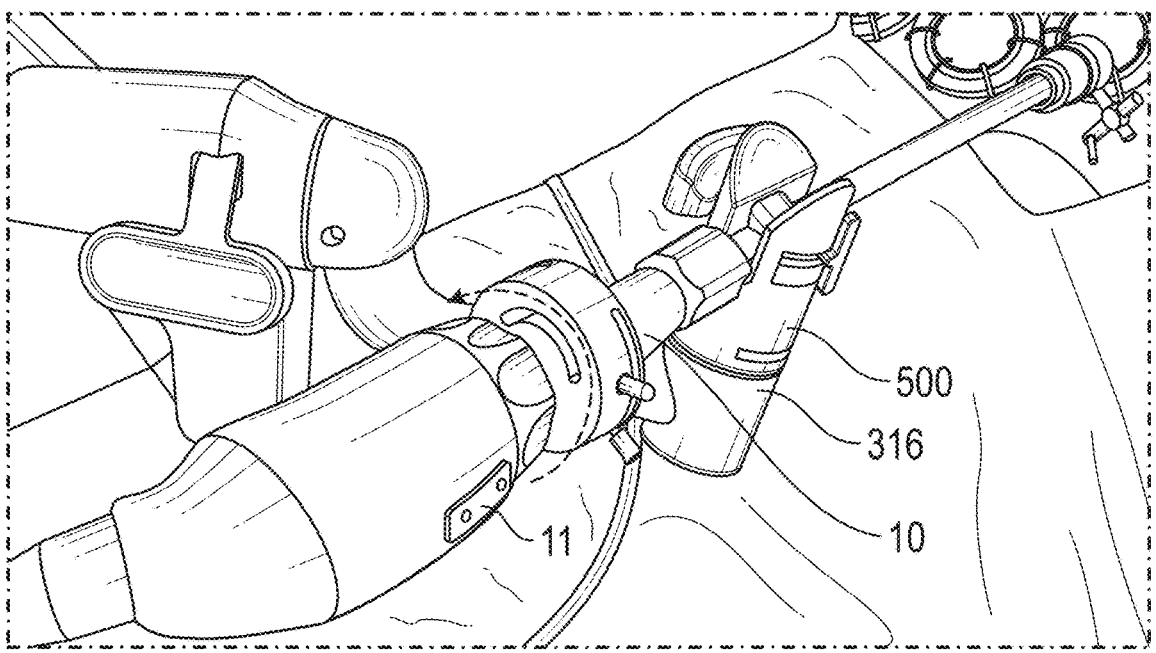
FIG. 28B illustrates the laparoscope device coupled to the distal end of the robot arm.

As described above, the systems described herein may detect the angular offset between a camera head of a laparoscope and the distal end of the robot arm coupled to the laparoscope. For example, FIG. 28A illustrates conventional laparoscopic device 10 having camera sensor module 11, which may be removeably coupled to and rotatable relative to laparoscope device 10, e.g., at the proximal end of laparoscope device 10. During a surgical laparoscopic procedure, camera sensor module 11 may be attached to laparoscope device 10 to allow the user to modify the orientation of camera sensor module 11 intraoperatively. As shown in FIG. 28B, during operation when laparoscope device 10 is removeably coupled to distal link 316 of the robot arm via coupler body 500, camera sensor module 11 may be rotated relative to laparoscope device 10, and accordingly, the distal end of the robot arm, either intentionally or inadvertently, such that the orientation of camera sensor module 11 would change relative to the distal end of the robot arm, e.g., where laparoscope device 10 is coupled to the robot arm, resulting in an angular offset between camera sensor module 11 and the distal end of the robot arm.

Figure 29:
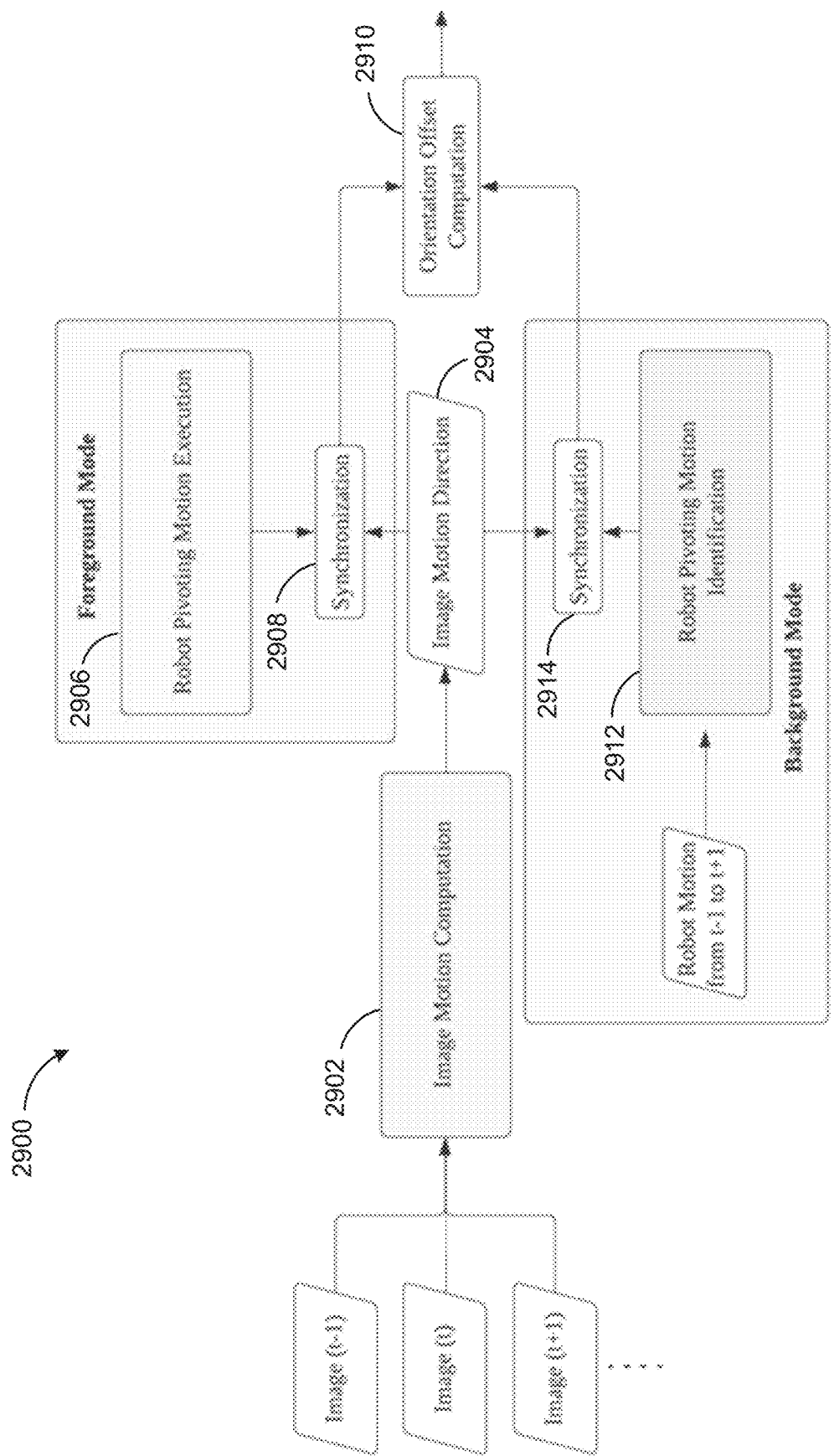
FIG. 29 is a flow chart illustrating an exemplary framework for detecting and determining an angular offset between a laparoscopic camera sensor module and the distal end of the robot arm in accordance with the principles of the present disclosure.

Referring now to FIG. 29, an exemplary framework for detecting and determining an angular/rotation offset between camera sensor module 11 and the distal end of the robot arm is provided. As shown in FIG. 29, computational framework 2900 may comprise two main steps: image motion calculation, e.g., image motion computation 2902 and image motion direction computation 2904, and image-to-robot synchronization, e.g., robot pivoting motion execution 2906 and synchronization 2908 in a foreground mode and/or robot pivoting motion identification 2912 and synchronization 2914 in a background mode, such that the angular offset may be determined by orientation offset computation 2910.

Image motion calculation may be used to quantify image motion, e.g., the changes across consecutive images acquired from the laparoscopic camera resulting from movement of the laparoscope during operation, e.g., during the robotic instrument centering mode. For example, to quantify image motion for image registration, the motion of individual pixels of the laparoscopic images between consecutive images may be computed at image motion computation 2902, and the motion results may then be combined to obtain the image motion direction on the image space at image motion direction 2904.

At image motion computation 2902, a plurality of 2D images may be received from the laparoscope device, and a computer vision technique such as, for example, optical flow, may be used to compute the motion of individual pixels of the laparoscopic images between consecutive images, which provides displacements of each individual pixel between consecutive images in the x and y directions within the 2D plane of the images. With the x and y displacements of the individual pixels between consecutive images, at image motion direction 2904, the averages, e.g., means/median, of both the x and y displacements may be calculated to obtain the motion vector in the 2D image space, to thereby calculate the image motion direction. For example, the image motion direction (in angle) may be calculated as:

$$\tan^{-1} \frac{y_{mean}}{x_{mean}}$$

Figure 30A:
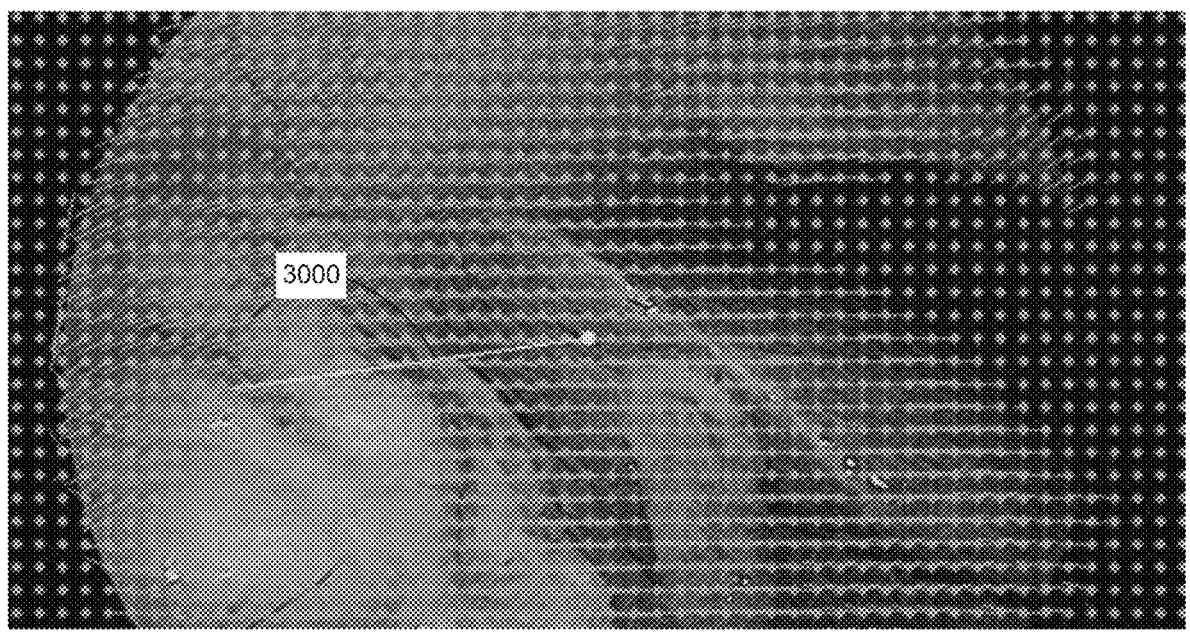
FIG. 30A illustrates determination of image motion direction via a computer vision technique.
Figure 30B:
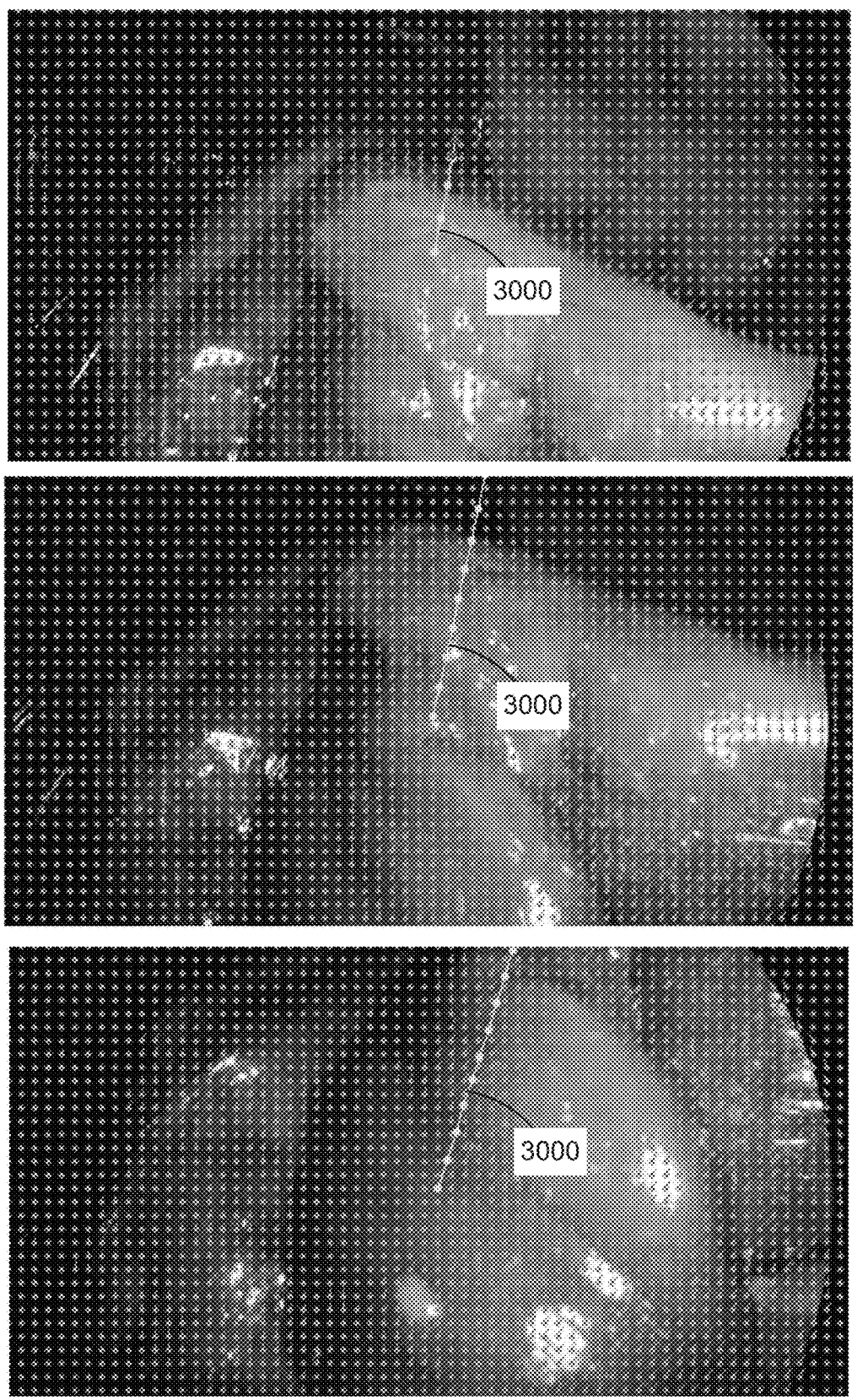
FIG. 30B illustrates motion of a laparoscopic video feed along an image motion direction.

FIG. 30A illustrates the motion vector of each individual pixel between the current image and the previous image, and image motion direction vector 3000, calculated based on the averages of the x and y displacements of the individual pixels between consecutive images. FIG. 30B illustrates image motion direction vector 3000 across consecutive images over time, calculated in real-time as the laparoscope moves during operation, e.g., by averaging the image motion directions computed over time. Moreover, the image motion direction (in angle) further may be validated to confirm that the computed angle may be trusted, e.g., by analyzing metrics such as motion magnitude, percentage, and consensus. For example, the norm of the motion vector may be calculated to determine the motion magnitude, which may be indicative of whether the computed image motion is significant or not. Accordingly, in some embodiments, the motion magnitude may be compared against a predetermined motion magnitude threshold, such that the motion magnitude is determined to be significant if it is greater than the predetermined motion magnitude threshold. The norm of the motion vector may be calculated as:

$$\sqrt{x_{mean}^2 + y_{mean}^2}$$

Moreover, motion percentage may be calculated as the percentage of image pixels that moved between consecutive images, which may be indicative of whether the motion is global motion introduced by movement of the laparoscope device, or local motions caused by, e.g., tissue-tool interaction. In addition, the percentage of moved pixels that agree on the computed image motion direction may be counted to calculate motion consensus. The agreement may be checked by calculating the relative angle between the motion vector of each individual pixel between consecutive images and the image motion direction vector. For example, the relative angle may be calculated as:

$$\cos^{-1}\left( \frac{x_{ind} * x_{mean} + y_{ind} * y_{mean}}{\sqrt{\sqrt{x_{ind}^2 + y_{ind}^2}} * \sqrt{x_{mean}^2 + y_{mean}^2}} \right)$$

The relative angle may be compared against a predetermined relative angle threshold, such that the individual pixel motion vector is determined to agree with the computed image motion vector is the relative angle is greater than the predetermined relative angle threshold. Accordingly, based on the validation metrics above, the pixels in the black boarders and the pixels indicating local tissue motion may be filtered from the optical flow displayed in FIG. 30A.

Image-to-robot synchronization may be used to differentiate the image motion caused by the movement of the laparoscope device from the image motion caused by local tissue/instrument movement. For example, the motion of the laparoscope device, e.g., the motion of the distal end of the robot arm, may be retrieved from the robot arm sensors, e.g., encoders, during operation. Moreover, the corresponding motions of the image and the laparoscope device may be synchronized based on the available timestamps of robot arm motion and the laparoscopic images. As shown in FIG. 29, image-to-robot synchronization may be implemented in a foreground mode where the system causes the robot arm coupled to the laparoscope device to move in a predefined pattern of motion to provide the image motion, and/or a background mode where the image motion is generated as the laparoscope device is moved by the user during an operation, e.g., for surveying and/or view angle adjustment.

Figure 31:
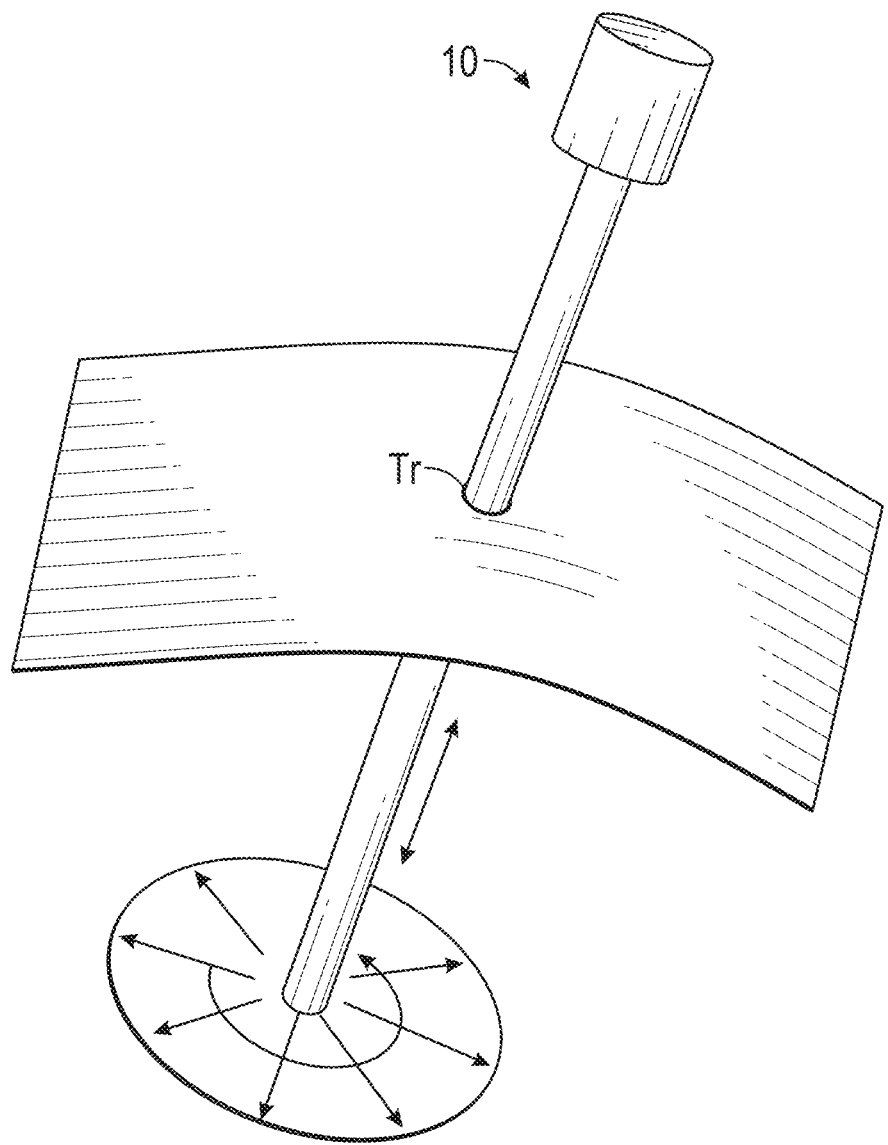
FIG. 31 illustrates exemplary pivoting motion for computing an angular offset between a laparoscopic camera sensor module and the distal end of the robot arm.

As shown in FIG. 29, in foreground mode, at robot pivoting motion execution 2906, the system may cause the robot arm to move the laparoscope along a predetermined pivoting trajectory, as shown in FIG. 31. As shown in FIG. 31, laparoscope device 10 may be moved in/out, and/or pivoted about trocar Tr. Referring again to FIG. 29, at synchronization 2908, based on the timestamps of when the predetermined pivoting trajectory is executed, corresponding timestamps of the computed image motion may be extracted. Accordingly, at orientation offset comparison 2910, a comparison between the robot arm motion and the computed image motion may be performed to calculate the angular offset between the orientation of the camera sensor module and the distal end of the robot arm, e.g., by calculate the angle between the computed image motion direction vector and the retrieved robot arm motion vector.

In background mode, at robot pivoting motion identification 2912, movement of the distal end of the robot arm, e.g., passive robot arm motion, responsive to movement of the laparoscope device by the user may be retrieved from the robot arm sensors. At synchronization 2914, based on the timestamps of the retrieved robot arm movements, corresponding timestamps of the computed image motion may be extracted. Accordingly, at orientation offset comparison 2910, a comparison between the robot arm motion and the computed image motion may be performed to calculate the angular offset between the orientation of the camera sensor module and the distal end of the robot arm, e.g., by calculate the angle between the computed image motion direction vector and the retrieved robot arm motion vector.

Moreover, manual rotation of the camera sensor module relative to the laparoscope device by the user during operation may be detected in real-time. For example, when the robot arm is stationary while the camera sensor module is being rotated by the user, the motion of each individual pixel of the images may be computed between consecutive images responsive to the rotation, and aggregated in the angle space to obtain the rotation change. The computer vision techniques described herein further may be used to identify the laparoscope device type, e.g., whether the laparoscope device is has a flat tip or an angled tip. For example, the system may cause the robot arm to move the laparoscope device back/forth along the longitudinal axis of the laparoscope device. Accordingly, based on the validation metrics described above, if the computed image motion direction is greater than a predetermined threshold indicating a major direction on the image space, the system may determine that the laparoscope device is not a flat tip laparoscope device. In contrast, if the computed image motion direction is less than the predetermined threshold indicating a minor direction on the image space, e.g., zoom in/out, the system may determine that the laparoscope device is a flat tip laparoscope device.

Referring again to FIG. 18, at step 1814, when the laparoscopic procedure is complete, the operator may remove the surgical instruments from the respective robot arms.

Figure 32:
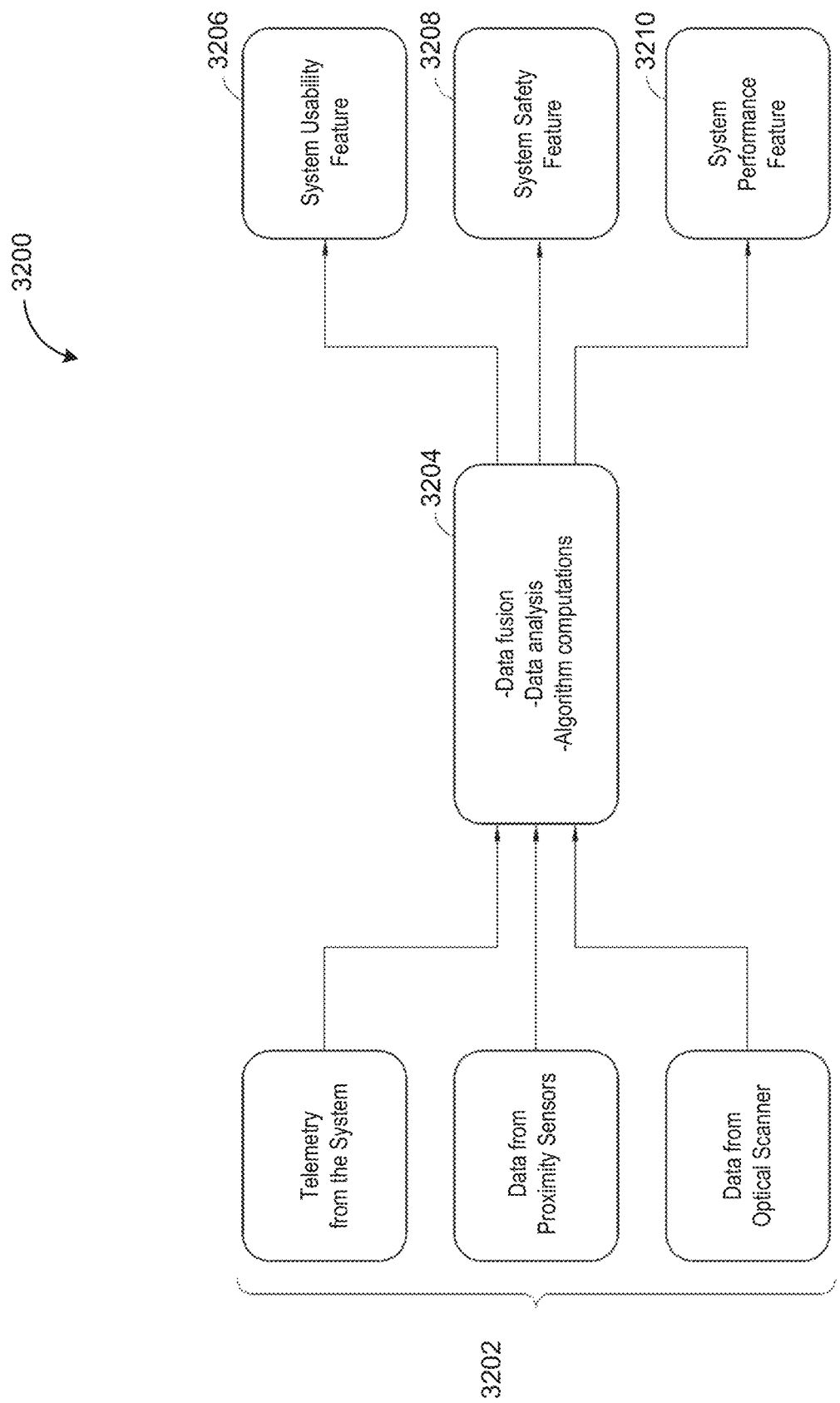
FIG. 32 illustrates an example overview of some features and capabilities of the co-manipulation surgical system in accordance with the principles of the present disclosure.

Referring now to FIG. 32, a high level example 2400 of the different combinations of data inputs for the various sensors and devices of the systems disclosed herein, e.g., system 100, and the multiple features and capabilities that any implementations of the systems disclosed herein may have and can produce based at least in part on the multiple possible data inputs is provided. As shown in FIG. 32, some implementations of the system may be configured to gather data from at least three monitoring sources 2402, including telemetry from the system (which may include force data from the robot arms, position data from the robot arms, etc.), data from proximity sensors 212, and/or depth data from optical scanner 202. The data gathered from the monitoring sources 2402 may undergo data processing steps 2404 using one or more processors in the system. The data processing steps may include, e.g., data fusion (e.g., fusion of the data gathered from the monitoring sources 2402) and data analysis, which may include algorithm computations. In addition, the data from the monitoring sources 2402 may undergo processing 2404 for the development of system usability features 2406, system safety features 2408, and system performance features 2410. The system may provide the features in real-time. For example, the system usability features may include identifying the surgeon and adjusting the platform height based on the surgeon's profile, detecting the skin surface of the patient and creating a virtual boundary around the skin surface to prevent inadvertent contact with the skin surface of the patient, detecting an instrument type and automatically loading the calibration file appropriate for the particular instrument, etc. In addition, the system safety features may include displaying a virtual map of the area surrounding platform 200, as shown in FIG. 33, e.g., as an operator moves platform 200 throughout the operating room, to provide the operator with a view of the area surrounding platform 200, such that the operator may avoid collisions between platform 200 and any objects and/or persons within the area surrounding platform 200.

Figure 33:
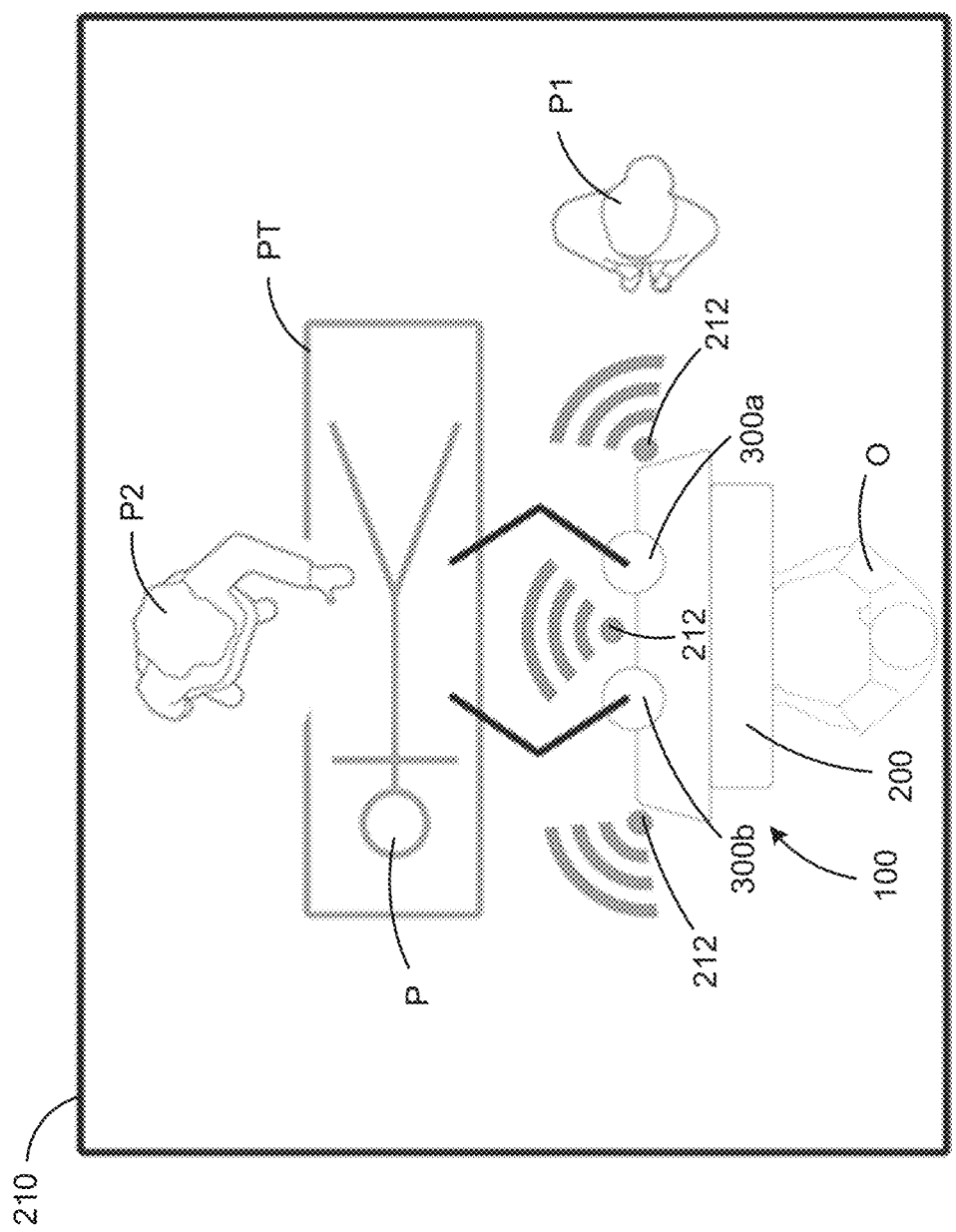
FIG. 33 illustrates a virtual map of the co-manipulation surgical system within an operating room.

As shown in FIG. 33, the depth data generated by the plurality of optical sensors may be used by the controller of system 100 to generate a virtual map, e.g., a "bird's eye view", of the area surrounding platform 200, e.g., within the operating room, in real-time. For example, the virtual map may illustrate the operating room from a top perspective. Moreover, as shown in FIG. 33, the virtual map may include graphical representations of platform 200 (including robot arms 300a, 300b), as well as one or more objects, e.g., patient table PT, and/or one or more persons, e.g., operator O, person P1, and person P2, within the area surrounding platform 200 in the same co-ordinate space as the platform and robot arms. Specifically, the virtual map may graphically illustrate the proximity between platform 200 and the one or more objects/persons, e.g., as platform 200 is being moved through the operating room by operator O. The controller may cause display 210 to display the virtual map, such that operator O can view the virtual map on display 210 in real-time as operator O moves platform 200 through the operating room. Accordingly, operator O may see objects and/or persons in the area surrounding platform 200 that operator O could not otherwise see with their own eyes, e.g., due to platform 200 and/or robot arms 300a, 300b obstructing the view of operator O, and avoid collisions between platform 200 and/or robot arms 300a, 300b with the objects/persons in the operating room. Moreover, the controller may cause display 210 to display an alert, e.g., a visual or audible alert, when the virtual map indicates that platform 200 and/or robot arms 300a, 300b are approaching or within a predetermined distance from the one or more objects/persons within the operating room.

In some embodiments, the controller may only cause display 210 to display the virtual map while platform 200 is being moved within the operating room. For example, platform 200 may include one or more actuators, e.g., a button, lever, or handlebar, that may be operatively coupled to the braking mechanism of the wheels of platform 200, such that upon actuation of the actuator, the braking mechanism is disengaged such that mobility of platform 200 is permitted. Accordingly, when the actuator is not actuated, the braking mechanism is engaged such that mobility of platform 200 is prevented. Thus, upon actuation of the actuator, the controller may automatically cause display 210 to display the virtual map, such that operator O can view the area surrounding platform 200 before, during, or after movement of platform 200 while the braking mechanism is disengaged. Once the actuator is released, such that the braking mechanism is reengaged, display 210 may stop displaying the virtual map. In some embodiments, when the virtual map indicates that platform 200 and/or robot arms 300a, 300b are approaching or within the predetermined distance from the one or more objects/persons within the operating room, the controller may override actuation of the actuator by the operator and reengage the braking mechanism to thereby prevent further movement of platform 200. Accordingly, the actuator may need to be released and re-actuated by the operator to disengage the braking mechanism and permit further movement of platform 200.

Moreover, the system may process color and/or depth data obtained from optical scanners 202 and proximity sensors 212 to identify objects within the operating room, e.g., the patient bed or the trocar, as well as the planes associated with the identified objects. With knowledge of the location platform 200 and robot arms 300a, 300b relative to the identified objects, the system may cause the stages coupled to the base portions of robot arms 300a, 300b to automatically move (or stop movement of) robot arms 300a, 300b to avoid collision with the identified objects during setup, e.g., when robot arms 300a, 300b approaches a predetermined distance threshold relative to the identified objects. In addition, the system may generate and emit, e.g., an audible alert indicative of the proximity of the stages of platform 200 and/or robot arms 300a, 300b relative to the identified objects. For example, the audible alert may change in amplitude and/or frequency as the distance between the stages of platform 200 and/or robot arms 300a, 300b and the identified objects decreases, as perceived by the system based on the depth data.

In addition, with knowledge of the location platform 200 and robot arms 300a, 300b relative to the trocar, if the system detects that the position of the patient bed, and accordingly the trocar, is changing, e.g., via adjustment by a user, the system may automatically adjust the arrangement of the robot arm to accommodate the movement of the patient bed and maintain relative position between the distal end of the robot arm and the trocar. In some embodiments, upon detection of movement of the patient bed, the system may automatically move the robot arm to retract the surgical instrument coupled thereto within the trocar, prior to automatically adjusting the arrangement of the robot arm to maintain relative position between the distal end of the robot arm and the trocar, such that the distal end of the surgical instrument is positioned within the trocar and away from anatomical structures within the patient.

Figure 34:
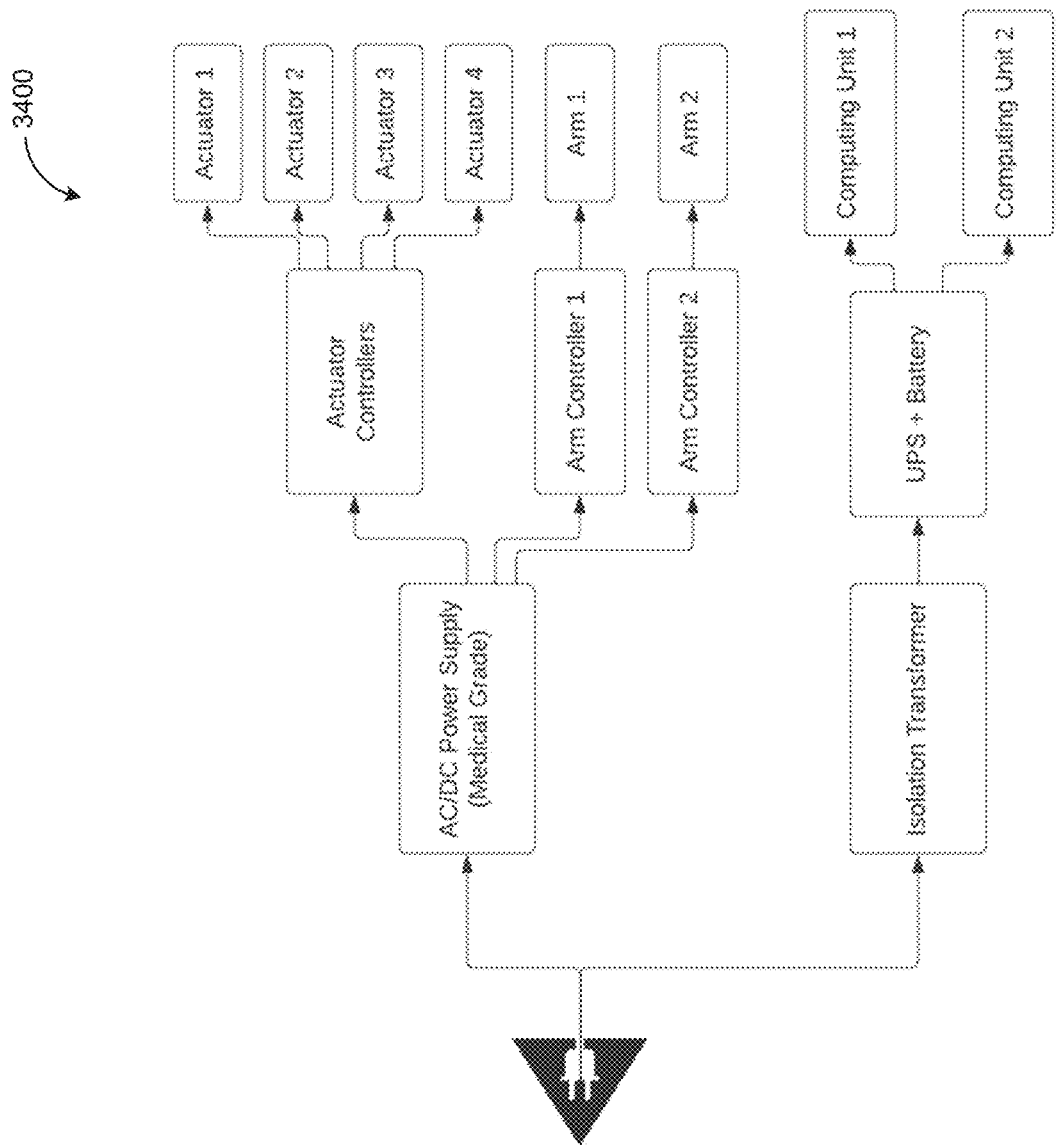
FIG. 34 is a schematic overview of some electrical components and connectivity of the co-manipulation surgical system in accordance with the principles of the present disclosure.

Referring to FIG. 34, a schematic overview of the electrical components of the electrical system and connectivity 2600 of the system is provided. This includes the flow of energy throughout the illustrated portion of the system. As shown in FIG. 34, all of the electrical components may be powered via an electrical connection with a conventional electrical power source, e.g., plugging the system into a conventional power outlet. For example, each of the stages of platform 200, e.g., vertical extenders 206a, 206b and horizontal extenders 208a, 208b, for adjusting the horizontal and vertical position of robot arms 300a, 300b relative to platform 200 (actuators 1-4), and each of the motors, e.g., M1-M4, of each robot arm for applying impedance and/or actuating the respective robot arms (arms 1-2), may be controlled via respective actuator controllers and arm controllers 1-2, which are powered by the electrical connection via an AC/DC power supply. Moreover, the computing components of each robot arm (computing units 1-2) also may be powered by the electrical connection when the system is plugged in. As shown in FIG. 34, the system may include an uninterruptable power supply (UPS) that may be charged while the system is plugged in via an isolation transformer, and which is operatively coupled to computing units 1-2, such that the UPS battery may automatically provide power to computing units 1-2 when the system is temporarily unplugged from the electrical power source, e.g., to move the system to another side of a patient table during a multi-quadrant procedure. Accordingly, computing units 1-2 may remain online, and will not need to be restarted, when the system is re-plugged, such that computing units 1-2 are ready to operate once power is restored to the rest of the system, thereby saving valuable time in the operating room. In some embodiments, the braking mechanism of wheels 204 of platform 200 also may be operatively coupled to the UPS battery, such that they may be engaged/ disengaged while the system is unplugged and moved around the operating room.

Figure 35:
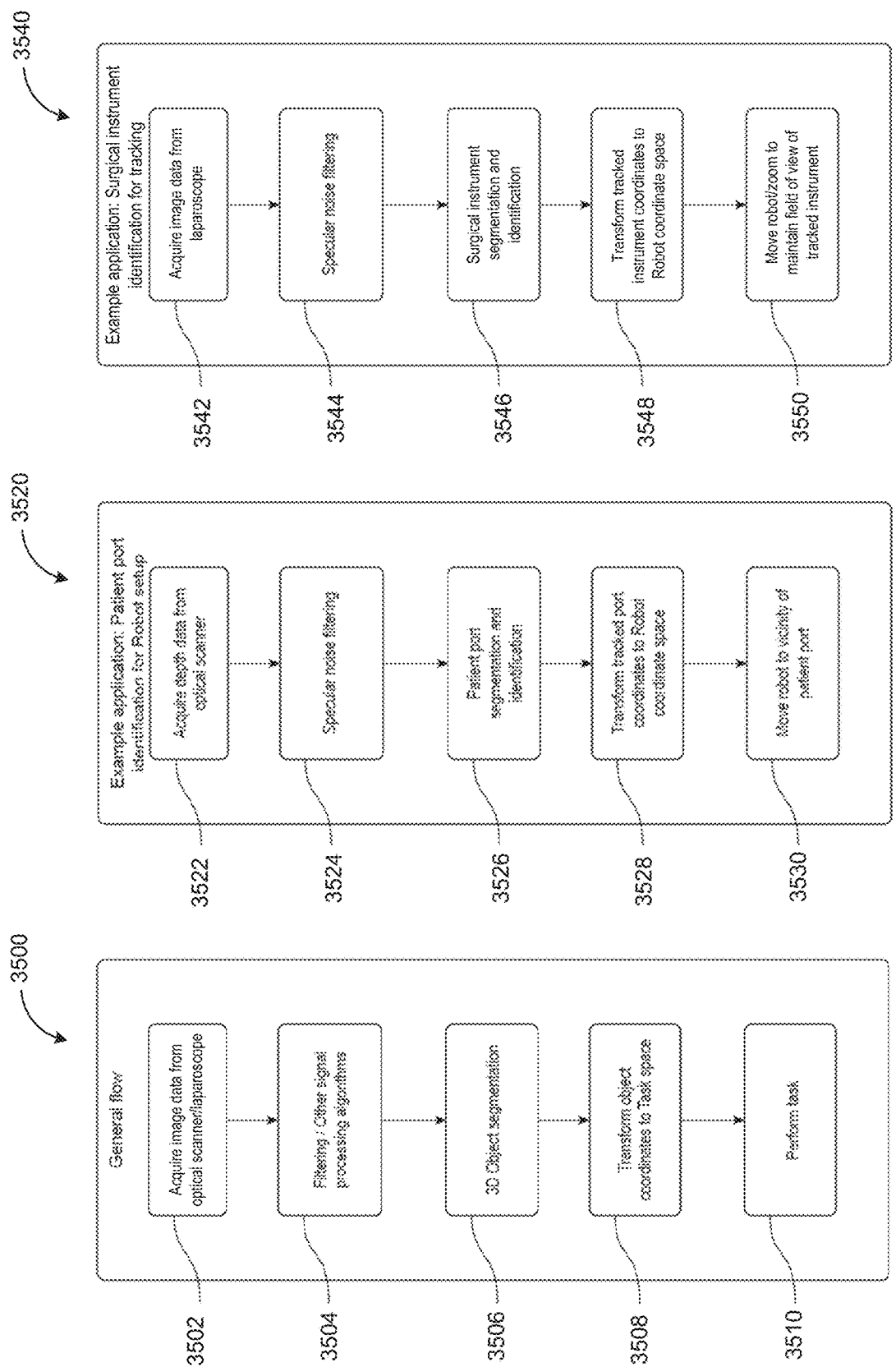
FIG. 35 is a flow chart illustrating an example process of acquisition and processing of data from an imaging device and example applications of the data in accordance with the principles of the present disclosure.

Referring now to FIG. 35 a flow chart of process 3500 for the acquisition and processing of data from an optical scanning device is provided. As shown in FIG. 35, at step 3502, depth data may be acquired from one or more optical scanning devices, e.g., optical scanner 202 and/or proximity sensors 212. At step 3504, filtering/other signal processing algorithms may be performed, e.g., median filter, Gaussian noise removal, anti-aliasing algorithms, morphological operations, ambient light adjustments, etc. At step 3506, 3D object segmentation may be performed using, e.g., template matching, machine learning, Brute force matching, color plus depth segmentation, object segmentation, 2D-3D registration, pixel value thresholding, etc. At step 3508, object coordinates may be transformed to task space. For example, transforming object coordinates to task space may include converting a position and an orientation of an object from the optical scanning device's coordinate frame to the coordinate frame of the task needed (e.g., a robot frame for robot control, a cart frame for system setup, etc.). Additionally or alternatively, transforming object coordinates to task space may include using known optical scanning device to the support platform (e.g., a cart) transformations, the surgical robot transformations, and/or the user interface screen transformations, and generating new transformations for specific tasks such as tracking the surgeon's body (e.g., face, hands, etc.) with respect to different elements of the system (e.g., support platform, robot arms, screen, etc.), tracking the surgical table with respect to the cart platform, tracking patient orientation for system setup, tracking trocar port location and orientation for setup, and tracking the position of operating room staff for safety. At step 3510, the desired task may be performed, e.g., moving the robot arms into the vicinity of the patient/trocar port for easy setup, tracking operating room staff to ensure the system only responds to surgeon commands, recording the surgeon's hand movements during different phases of surgery, tracking a surgical instrument within a field of view of the laparoscope, etc.

In addition, FIG. 35 illustrates a flow chart of process 3520 for the acquisition and processing of data from an optical scanning device to identify a trocar port for setting up the robot arm for a procedure. At step 3522, depth data may be acquired from one or more optical scanning devices, e.g., optical scanner 202. At step 3524, specular noise filtering may be performed. At step 3526, patient/trocar port segmentation and identification may be performed. At step 3528, tracked port coordinates may be transformed to robot coordinate space. At step 3530, the robot arms may be moved to a desired vicinity of the patient/trocar port. Moreover, FIG. 35 illustrates a flow chart of process 3540 for the acquisition and processing of data from an optical scanning device for identifying a surgical instrument for tracking to provide instrument centering. At step 3542, depth data may be acquired from one or more optical scanning devices, e.g., a laparoscope coupled to the robot arm. At step 3544, specular noise filtering may be performed. At step 3546, surgical instrument segmentation and identification may be performed to distinguish the surgical instrument to be tracked from other objects within the field of view of the laparoscope. At step 3548, tracked surgical instrument coordinates may be transformed to robot coordinate space. At step 3550, the robot arm holding the laparoscope may be moved to thereby move the laparoscope to maintain the tracked surgical instrument within the field of view of the laparoscope.

Figure 36:
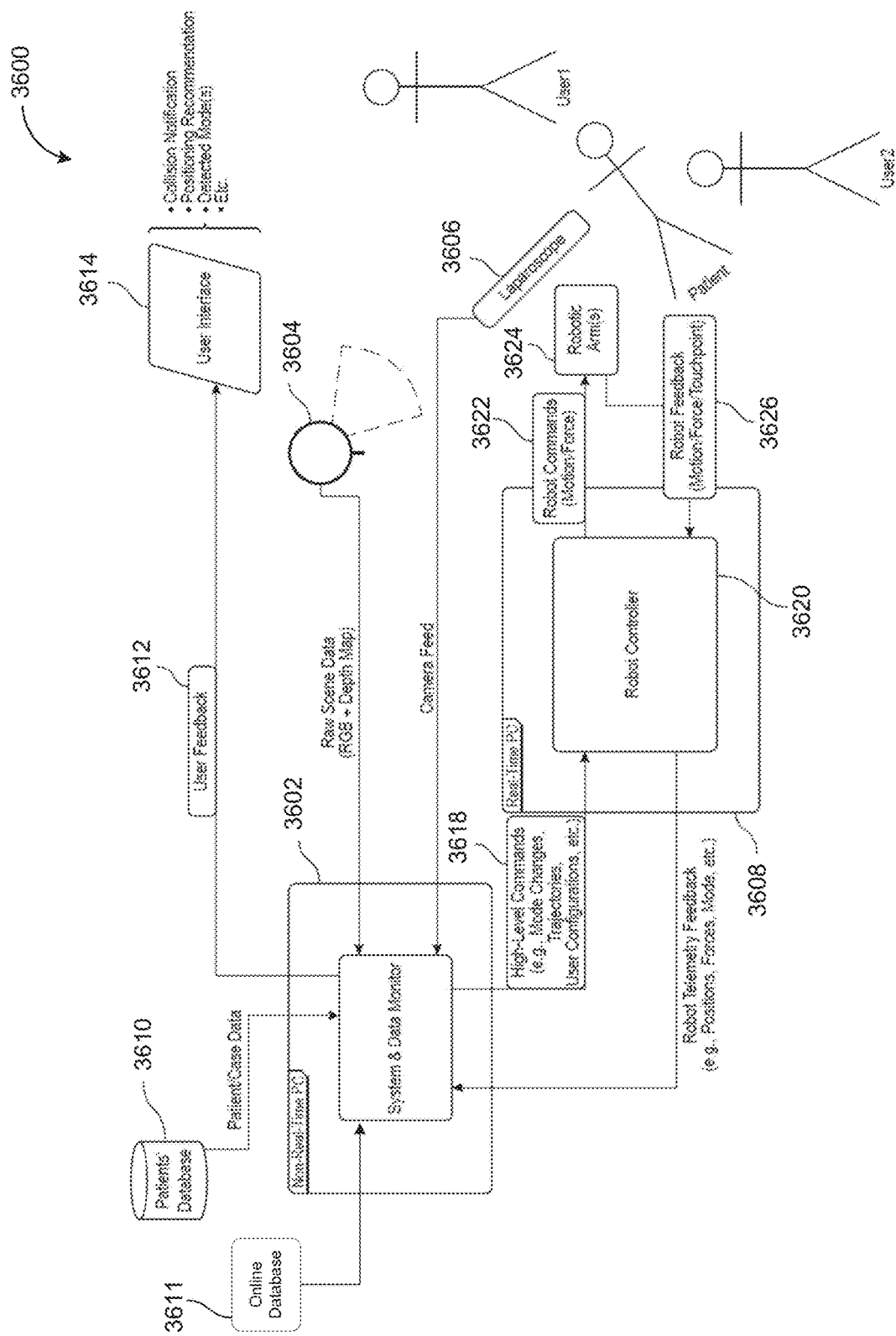
FIG. 36 is a schematic overview of data flow of the co-manipulation surgical system in accordance with the principles of the present disclosure.

Referring now to FIG. 36 an example data flow 3600 of the system is provided. As shown in FIG. 36, non-real-time computer 3602 may gather data from an optical scanning device, e.g., optical scanner 202 and/or from a camera feed from a laparoscope. Non-real-time computer 3602 also may receive data from real-time computer 3608 having a robot controller, including telemetry information such as positions of the robot arms, forces applied to the various motors/sensors of the robot arms, operational mode information, etc. Non-real-time computer 3602 also may receive data from patient database 3610 having information specific to the patient in the procedure including, e.g., CT scan data, relevant health conditions, and other information that may be desired by the surgeon, and further may receive data from online database 3611 for training/updating a trajectory generation model. For example, the online database further may include a hospital medical record database, such that the system may access the procedure type and any other medical data available (e.g., CT scan images, x-ray images, MRI images, and/or other patient specific information), which may be used to inform positioning of the trocar ports, and the position and orientation of platform 200 relative to the patient.

Non-real-time computer 3602 further may provide user feedback 3612 to the user via user interface 3614. User feedback may include, e.g., collision notifications, positioning information and/or recommendations regarding the various components of the system, the operational mode that has been detected by the system, etc. Non-real-time computer 3602 further may provide commands 3618, e.g., high level commands, to real-time computer 3608. High-level commands may include, e.g., mode changes, trajectories, haptic barriers, user configurations, etc. Real-time computer 3608 may include robot controller 3620 programmed to provide robot commands 3622, e.g., motion or force commands, to the one or more robot arms 3624, e.g., robot arms 300. Robot controller 3620 may receive robot feedback data 3626, e.g., motion, force, and/or touchpoint data, etc., from the one or more robotic arms 3624.

Figure 37:
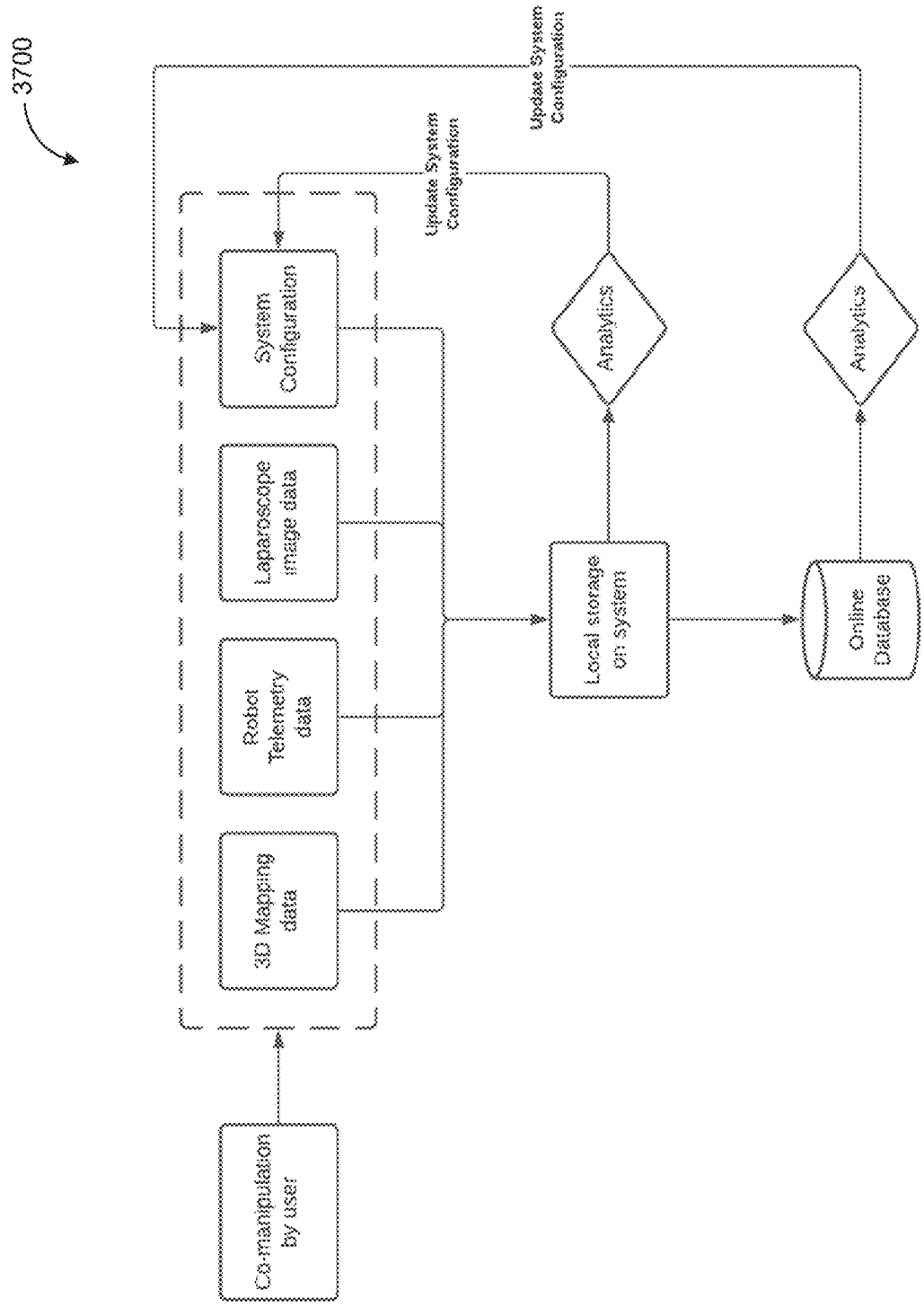
FIG. 37 is another schematic overview of data flow the co-manipulation surgical system in accordance with the principles of the present disclosure.

FIG. 37 illustrates data flow 3700 for updating the system configurations based on learned behaviors of the user. As shown in FIG. 37, the system may be connected to an online database that may store a surgeon profile and each of a plurality of possible data sources, which may include optical sensors, encoders, and/or other sensors, and/or a database of manually entered user input. The data sources may be associated with a given surgeon, their preferred robot arm arrangement and operating parameters, and each procedure performed with the system, which may allow the recording and analysis of the system configuration and how it changes from procedure to procedure, and within the procedure. In the case of machine learning, the co-manipulation capability of the system may be leveraged such that the user's actions may be used to annotate the data to create a training dataset. For example, the trajectory generation module may be trained with the recorded trajectories of a given surgeon using the instrument centering mode in a previous procedure and updated to enhance that surgeon's experience in a subsequent procedure, as well as other surgeons using the instrument centering mode.

Figure 38:
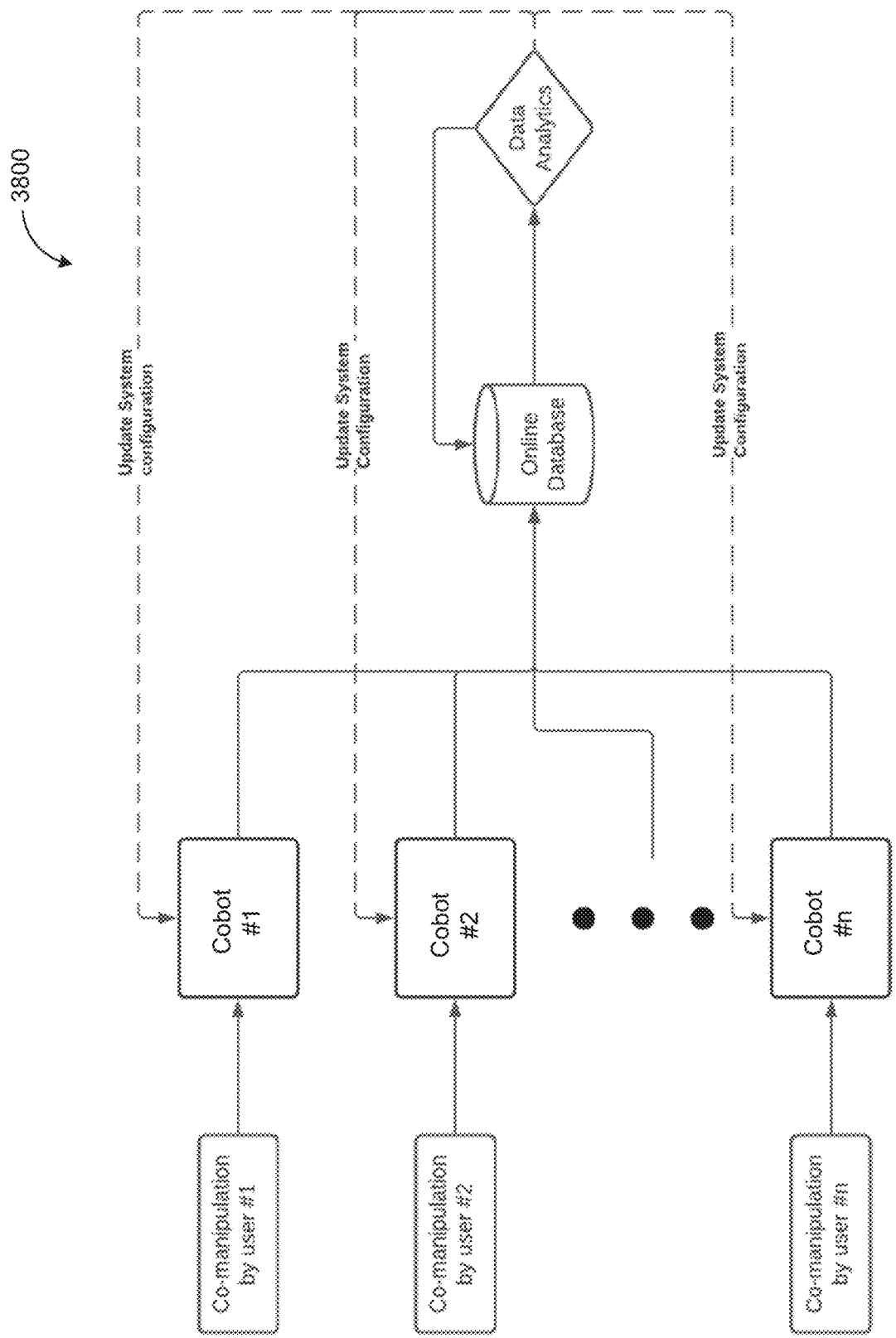
FIG. 38 is a schematic overview of data flow in a network of co-manipulation surgical systems in accordance with the principles of the present disclosure.

Referring now to FIG. 38, dataflow 3800 of a distributed network of co-manipulation surgical robot systems is provided. For example, a distributed network of co-manipulation robotic ("cobot") surgical systems may be used in multiple hospitals, each of which may be connected to an online database. This arrangement may provide considerably more data and user information that may be used by any of the cobot systems in operation. The systems may aggregate the data from the distributed network of systems to identify the optimum configuration/trajectories based on factors such as procedure type, surgeon experience, patient attributes etc. Through analytics or clinician input, the cobot systems may identify a routine procedure versus a procedure that may be more complicated. This information may be used to provide advice or guidance to novice surgeons.

Moreover, centralizing procedure data may enable the running of large data analytics on a wide range of clinical procedures coming from different users. Analysis of data may result in optimized settings for a specific procedure, including, e.g., optimized system positioning, optimal ports placement, optimal algorithms settings for each robot arm and/or detection of procedure abnormalities (e.g., excessive force, time, bleeding, etc.). These optimal settings or parameters may depend on patient and tool characteristics. As described above, a surgeon may load and use optimal settings from another surgeon or group of surgeons. This way, an optimal setup may be achieved depending on, e.g., the surgeon's level of expertise. To keep track of the various users in the distributed network of cobot systems, it may be beneficial to identify each user. As such, the user may log into the cobot system and access their profile online as necessary. This way the user may have access to their profile anywhere and will be able to perform a clinical procedure with their settings at a different hospital location.

An example user profile may contain the user's specific settings and information, including, e.g., username; level of expertise; different procedures performed, and/or region of clinical practice. In addition, the clinical procedure may require a user to store specific settings such as clinical procedure (e.g., cholecystectomy, hernia, etc.), table orientation and height, preferred port placement, settings per assistant arm for each algorithm, patient characteristics (e.g., BMI, age, sex), and/or surgical tools characteristics and specifications (e.g., weights, length, center of gravity, etc.). The user may be able to enable his own profile, and optionally may enable another user's profile, such as the profile of a peer, the most representative profile of a surgeon of the user's area of practice, the most representative profile of a surgeon with a specific level of expertise, and/or the recommended profile according to patient characteristics.

The identification of a user may be performed via password, RFID key, facial recognition, etc. Learning from a large number of procedures may result in a greater level of optimization of the cobot system setup for a given procedure. This may include, e.g., cart position, individual robot arm position, surgical table height and orientation, port placement, setup joints position, laparoscope trajectories during instrument centering. These settings may be based on patient height, weight, and sex, and further may be interdependent. For example, the optimal port placement may depend on patient table orientation.

Additionally, a clinical procedure may be described as a sequence of clinical procedures steps. Learning these different steps may allow the cobot system to infer in real time the actual step for a given procedure. For example, learning clinical steps from procedures may allow or enable: adjustment of algorithm settings, adjustment of robot arm configuration to facilitate user action in a given phase, adjustment of a laparoscope position based on the phase of the procedure, the system to give the practical custom reminders, the system to notify staff of an estimate procedure end time, the system to alert staff if necessary equipment is not available in the room, and/or the system to alert staff of the occurrence of an emergency situation.

During a clinical procedure, the surgeon will often realize simple and routine surgical tasks such as grasping, retracting, cutting etc. Learning these different tasks may allow the cobot system to infer in real time preferences and habits of the surgeon regarding a sequence of a procedure in real time. Some algorithms of the cobot system may be tuned (i.e., adjusted and optimized) during the procedure based on this sequence recognition and help the user to be better at this simple surgical task. An example of such a task is the automated retraction of a liver during a gall bladder procedure. By aggregating the information over many cases, the optimized force vectors may be developed.

Further, some complications may occur during a clinical procedure that may result in unexpected steps or surgical acts. Learning how to discriminate these unexpected events would help the cobot system to enable some specific safety features. In case of emergency, the robot arms may be stopped or motion restricted depending on the level of emergency detected by the system.

Figure 39A:
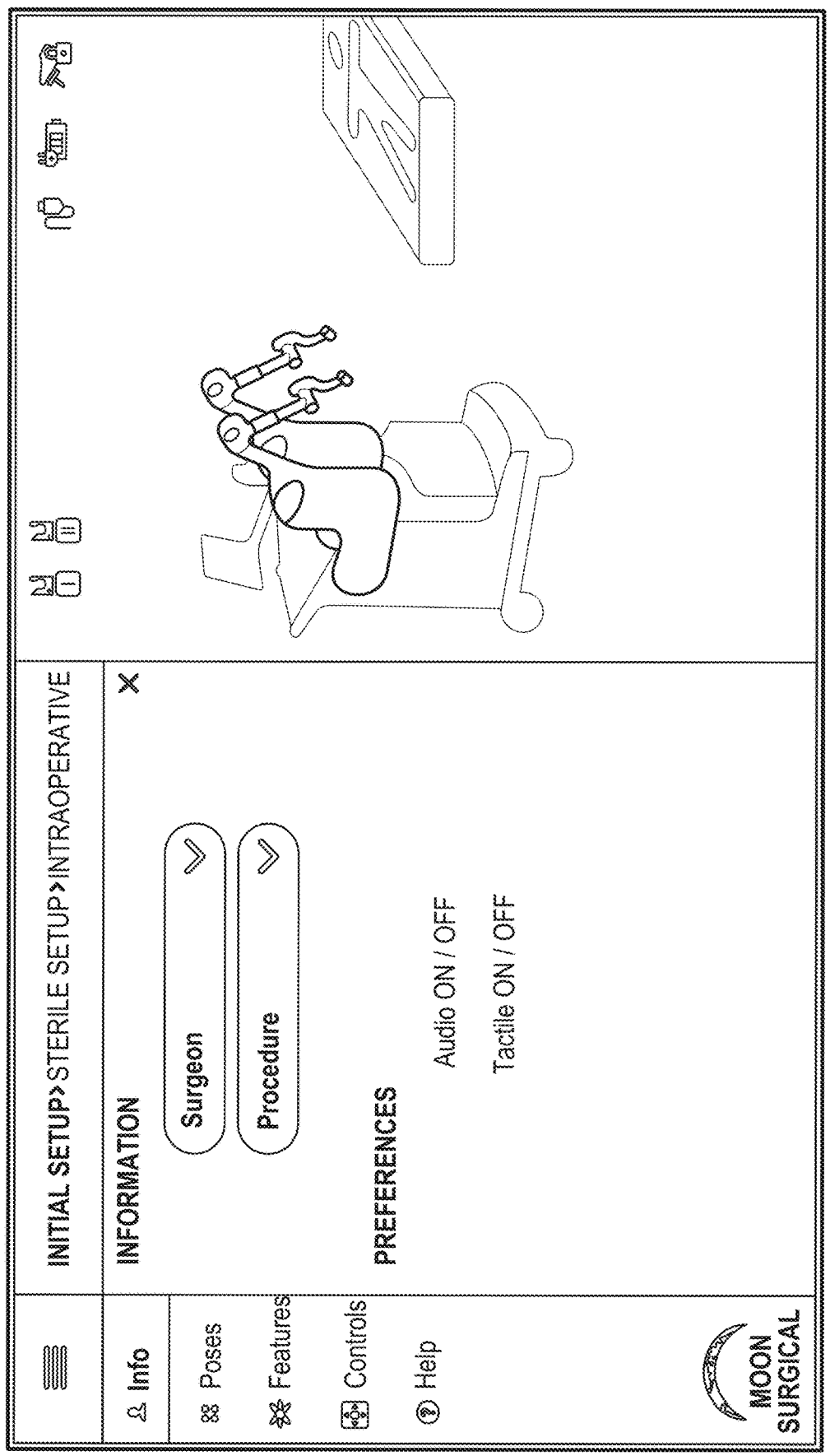
FIGS. 39A-39R illustrate an exemplary graphical user interface of the co-manipulation surgical system.
Figure 39B:
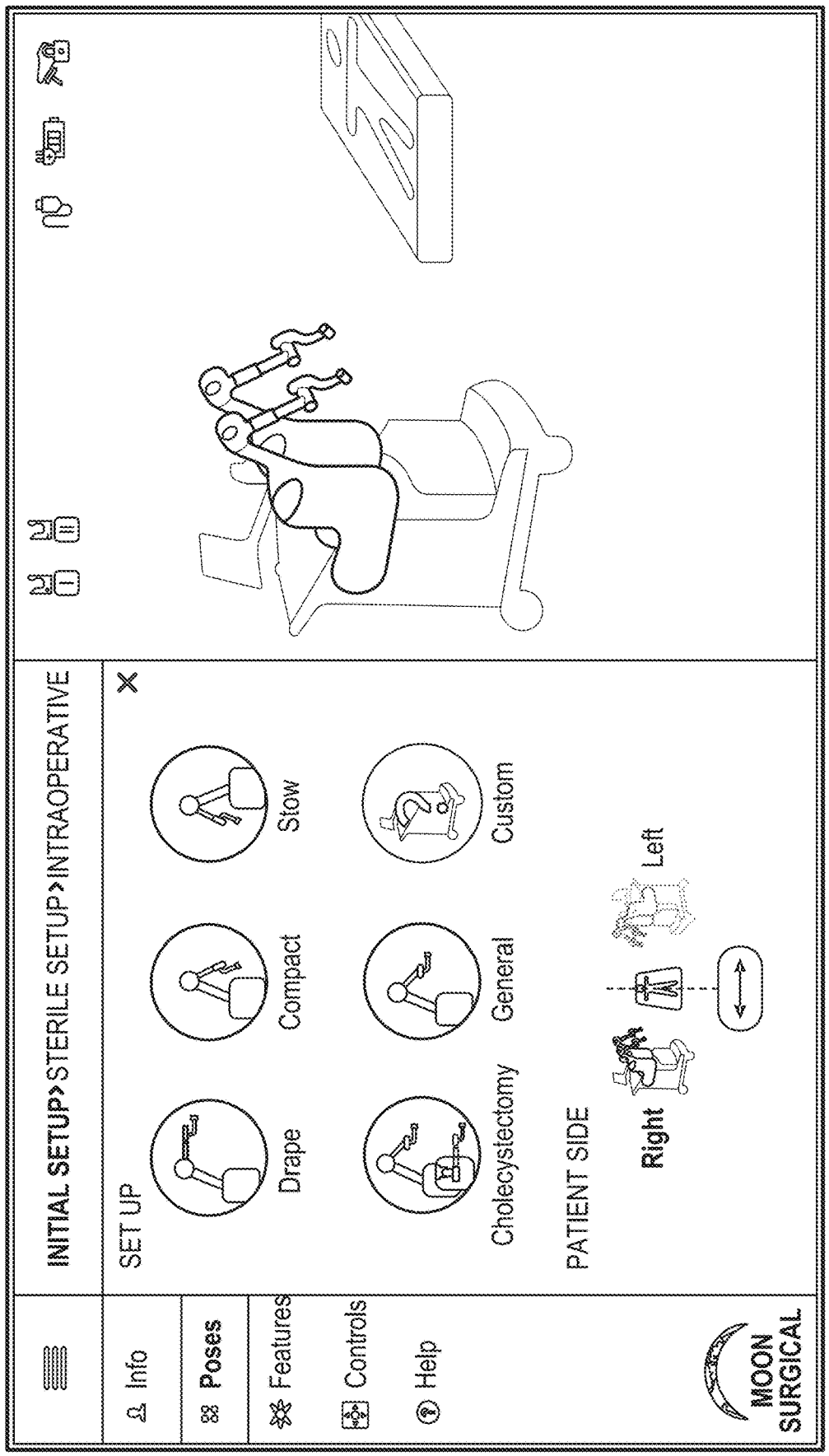
Figure 39C:
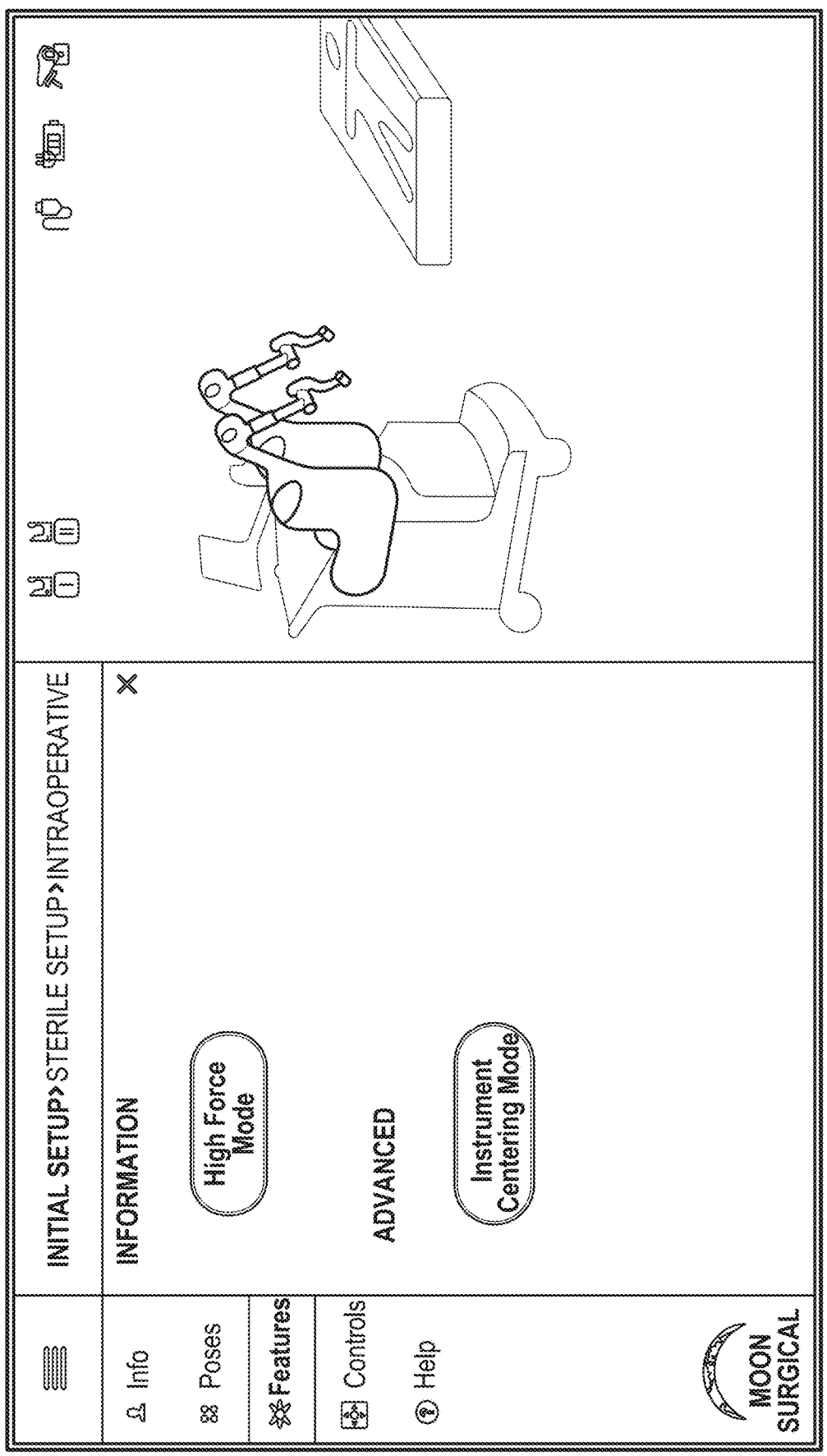
Figure 39D:
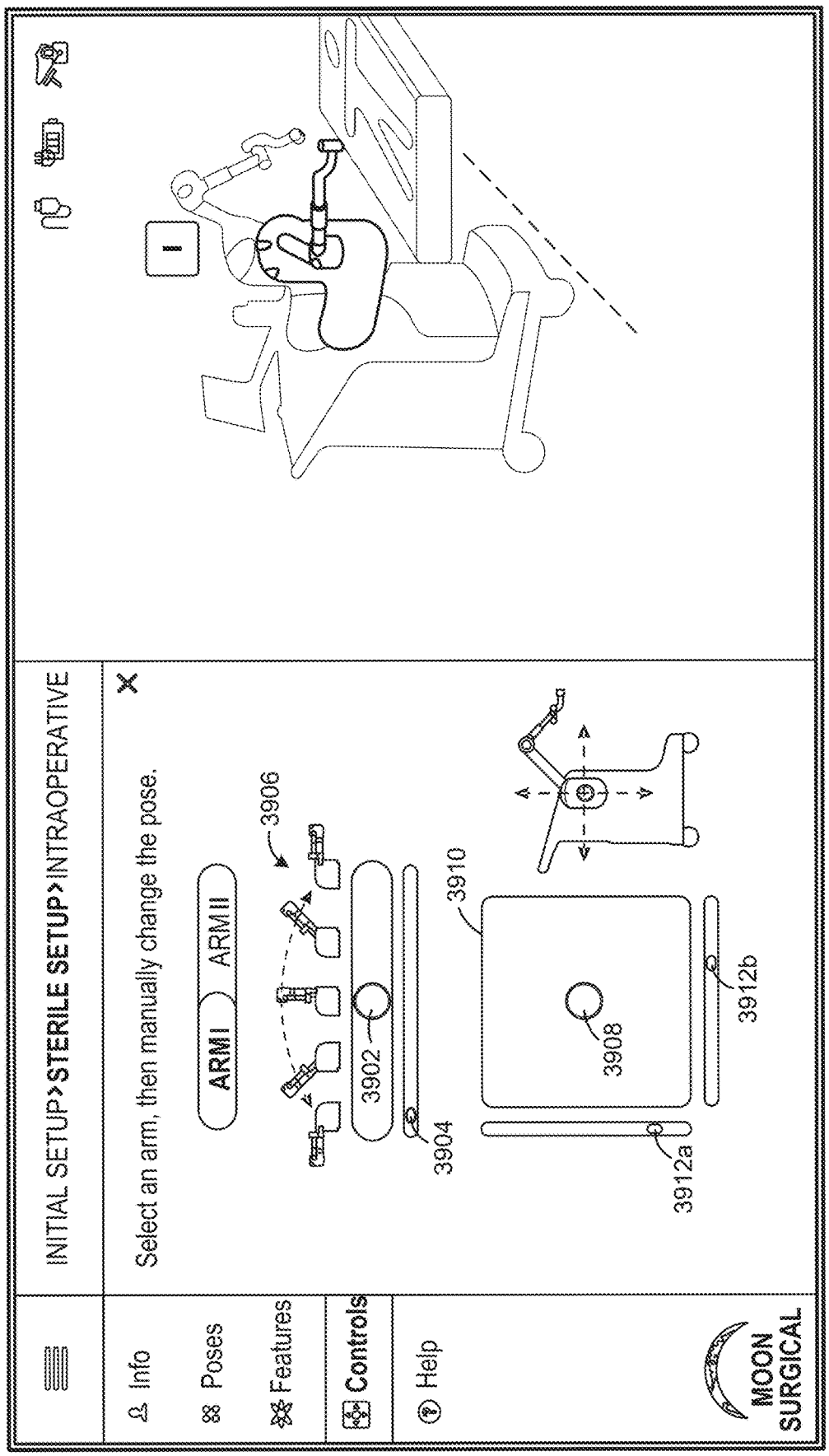
Figure 39E:
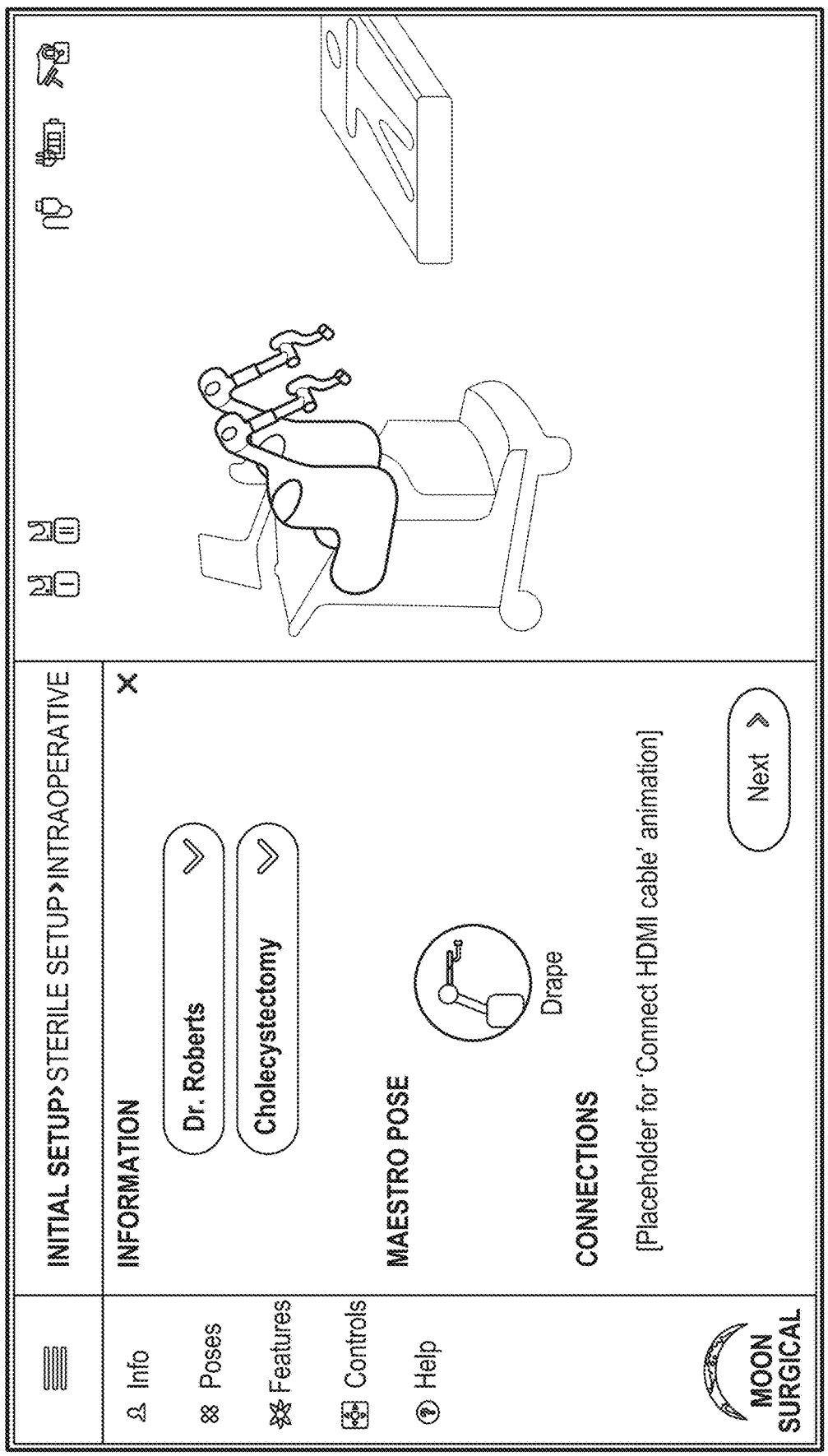
Figure 39F:
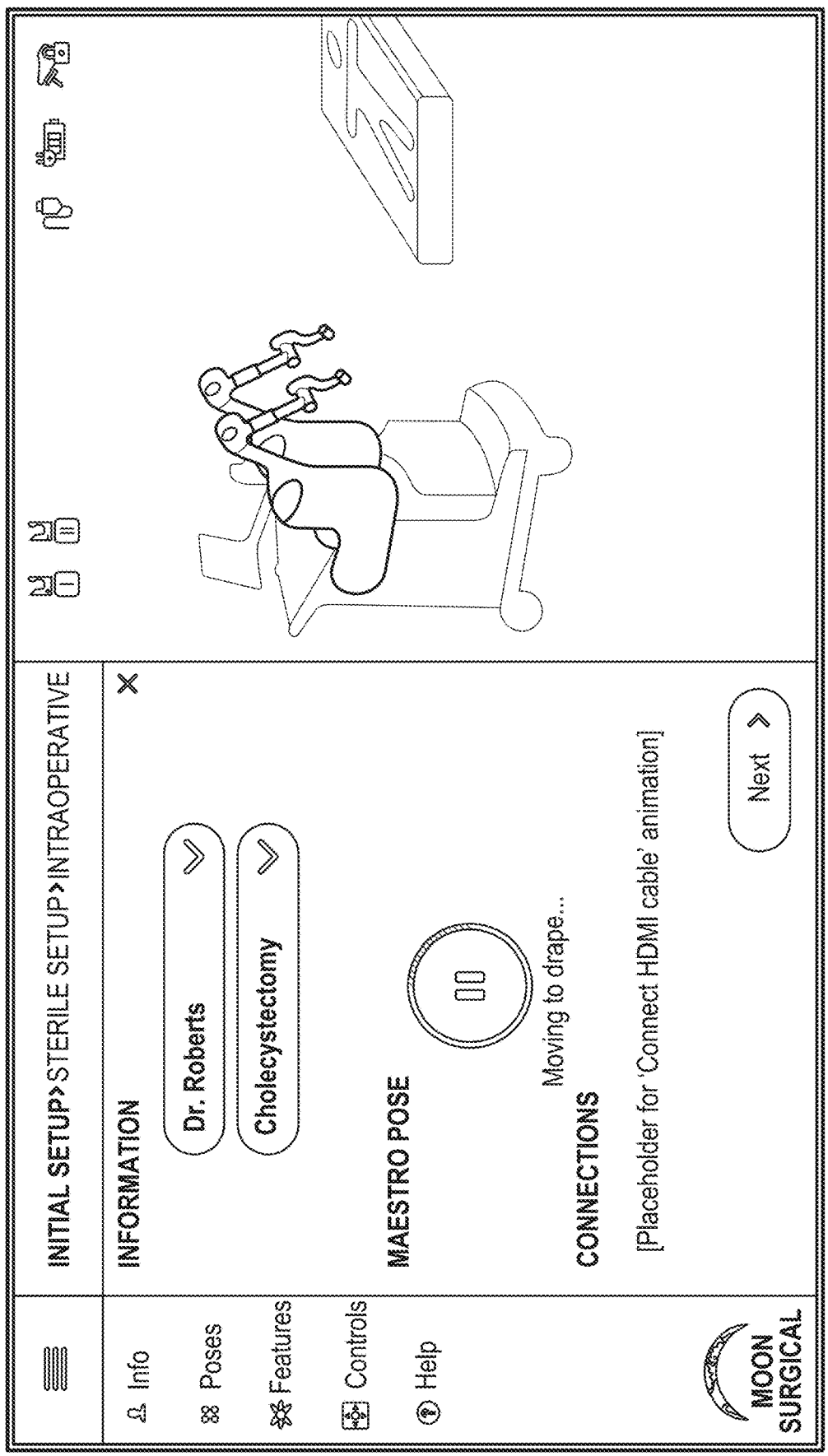
Figure 39G:
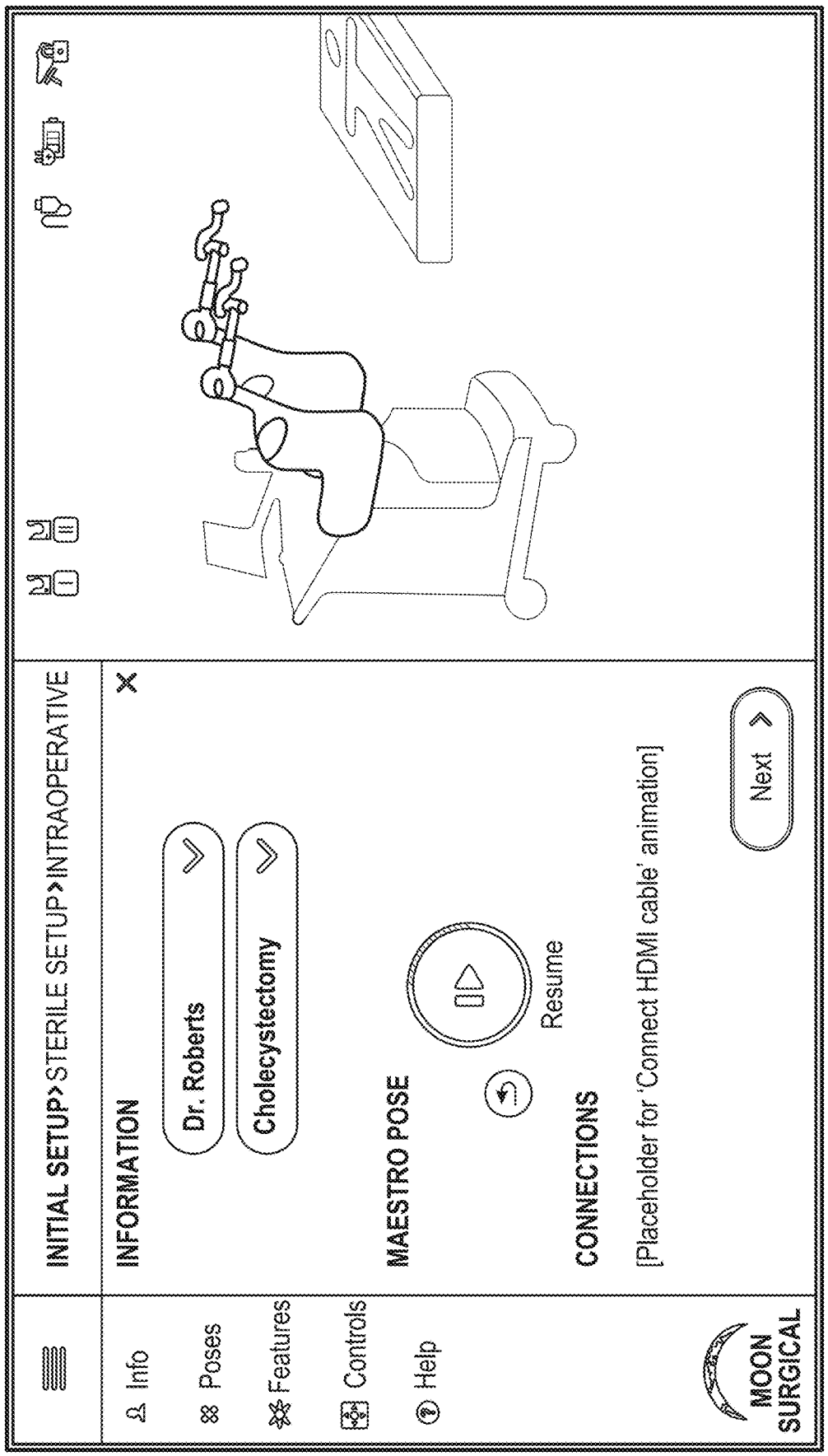
Figure 39H:
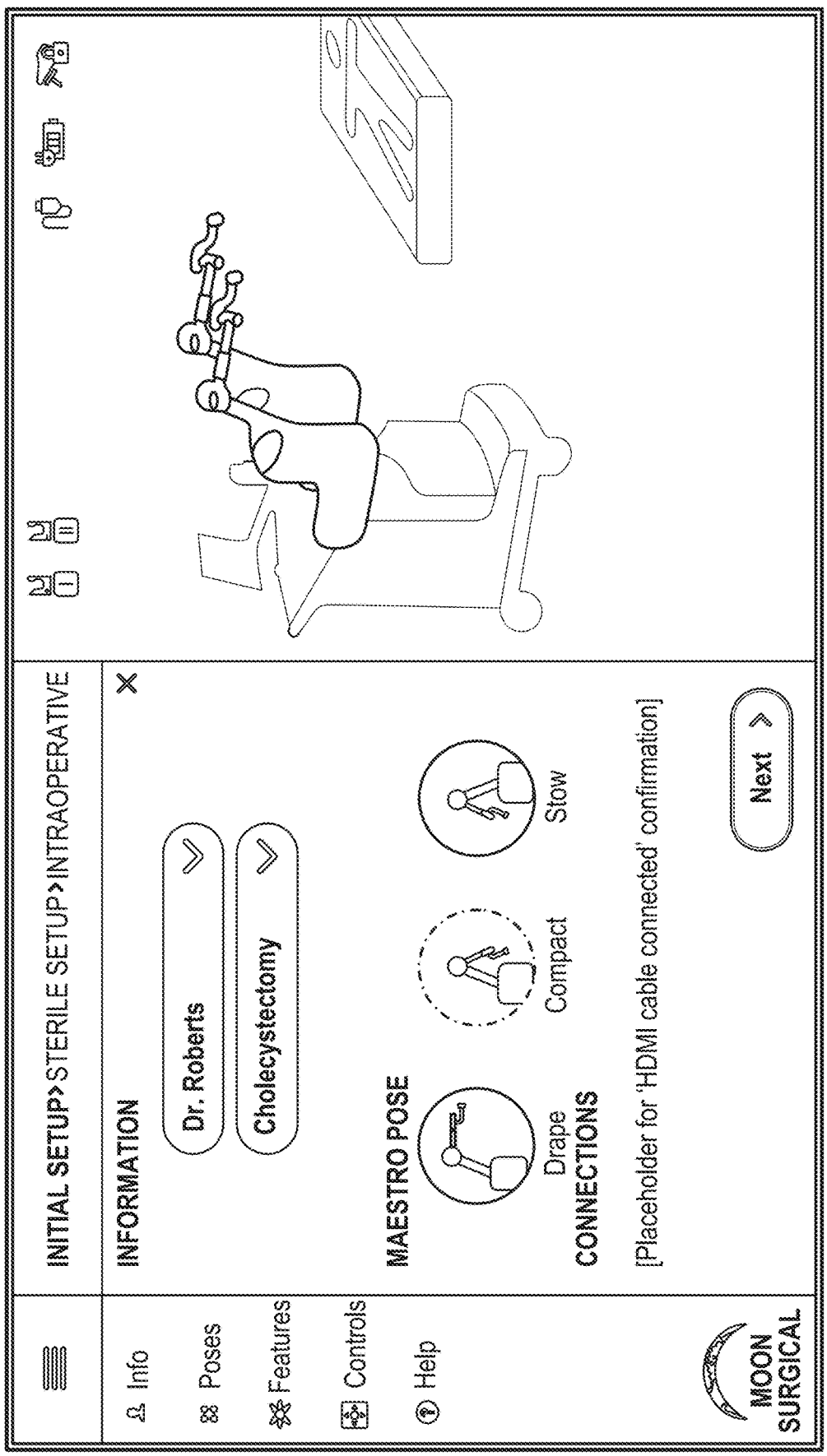
Figure 39I:
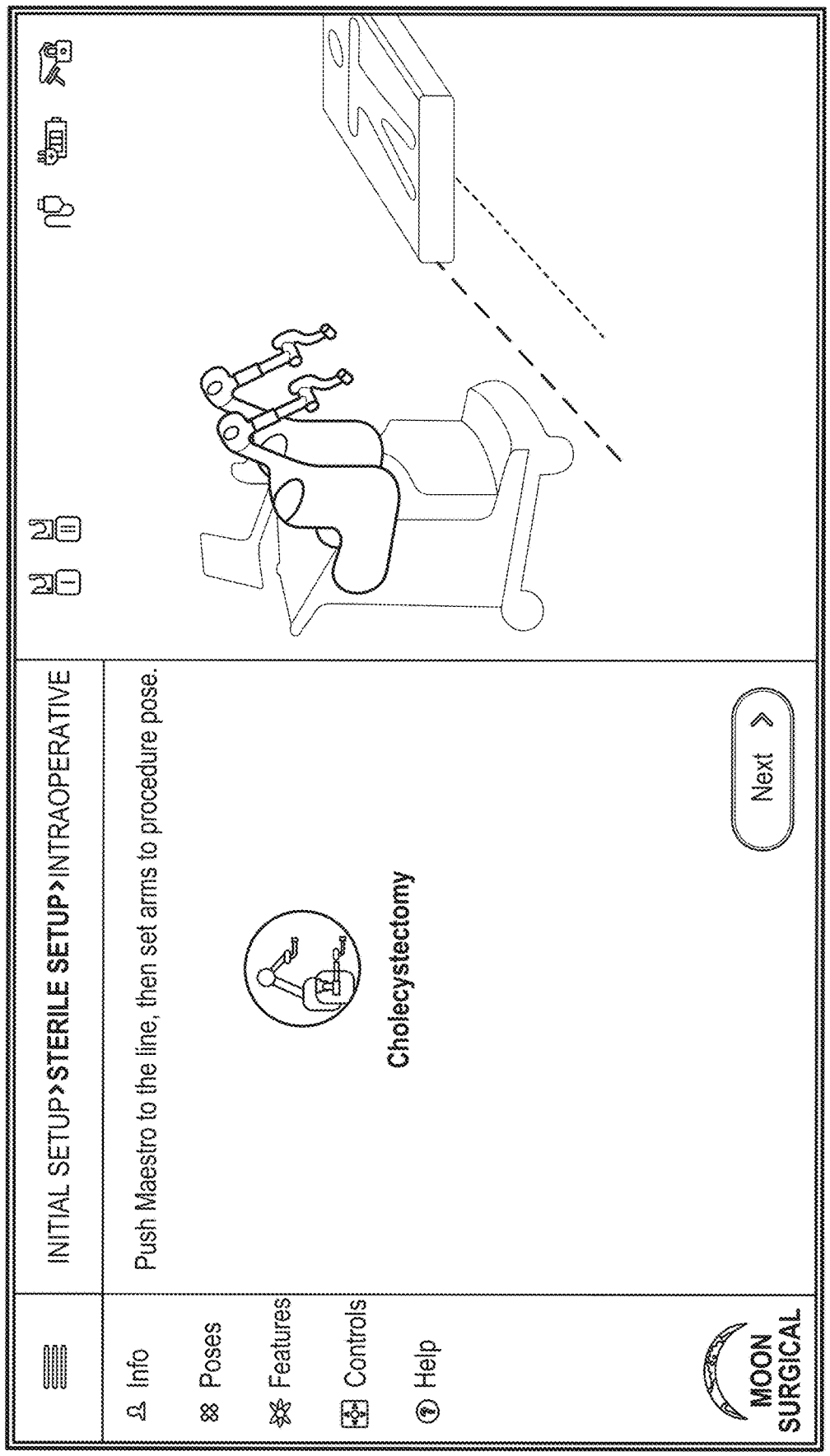
Figure 39J:
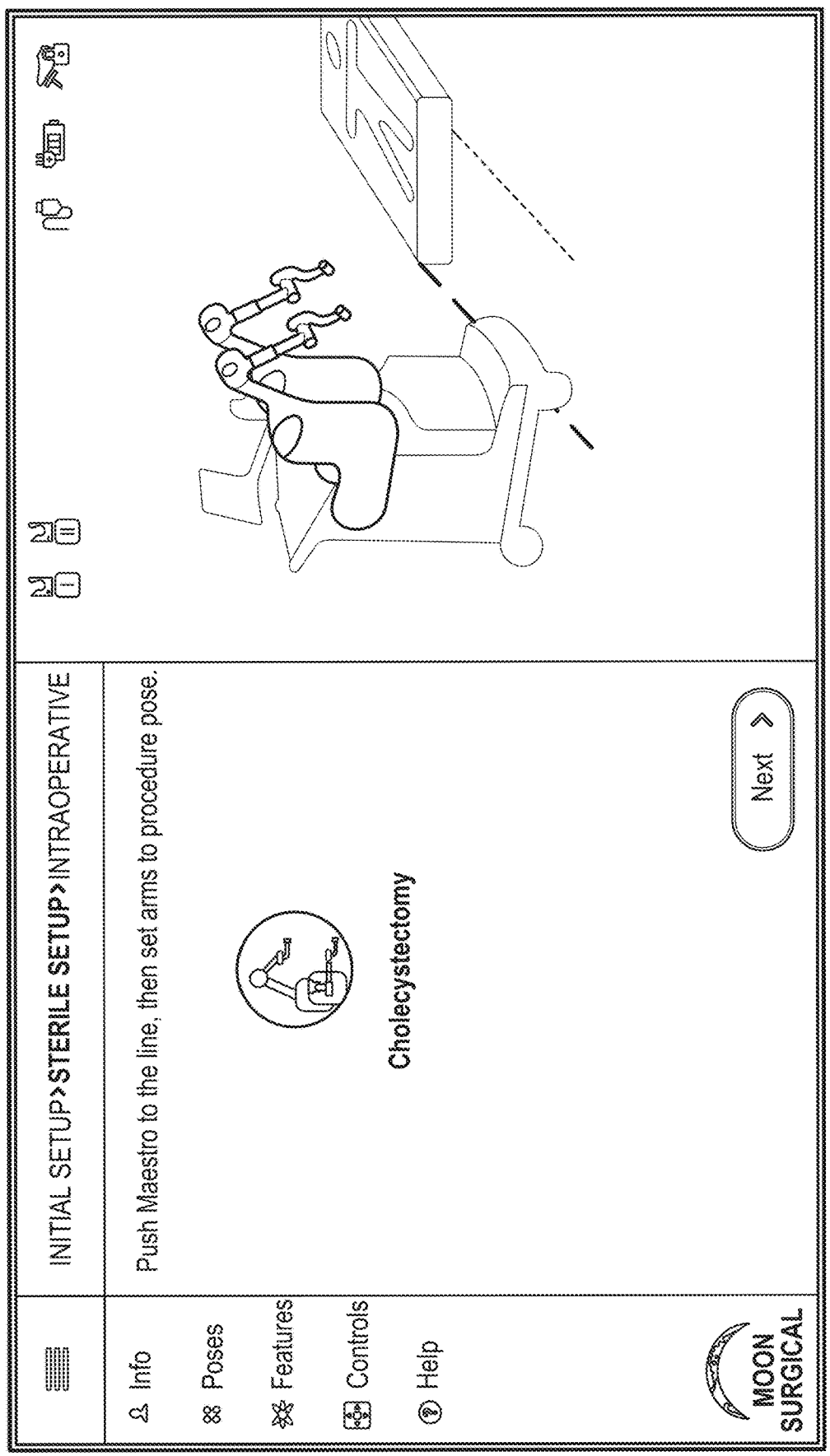
Figure 39K:
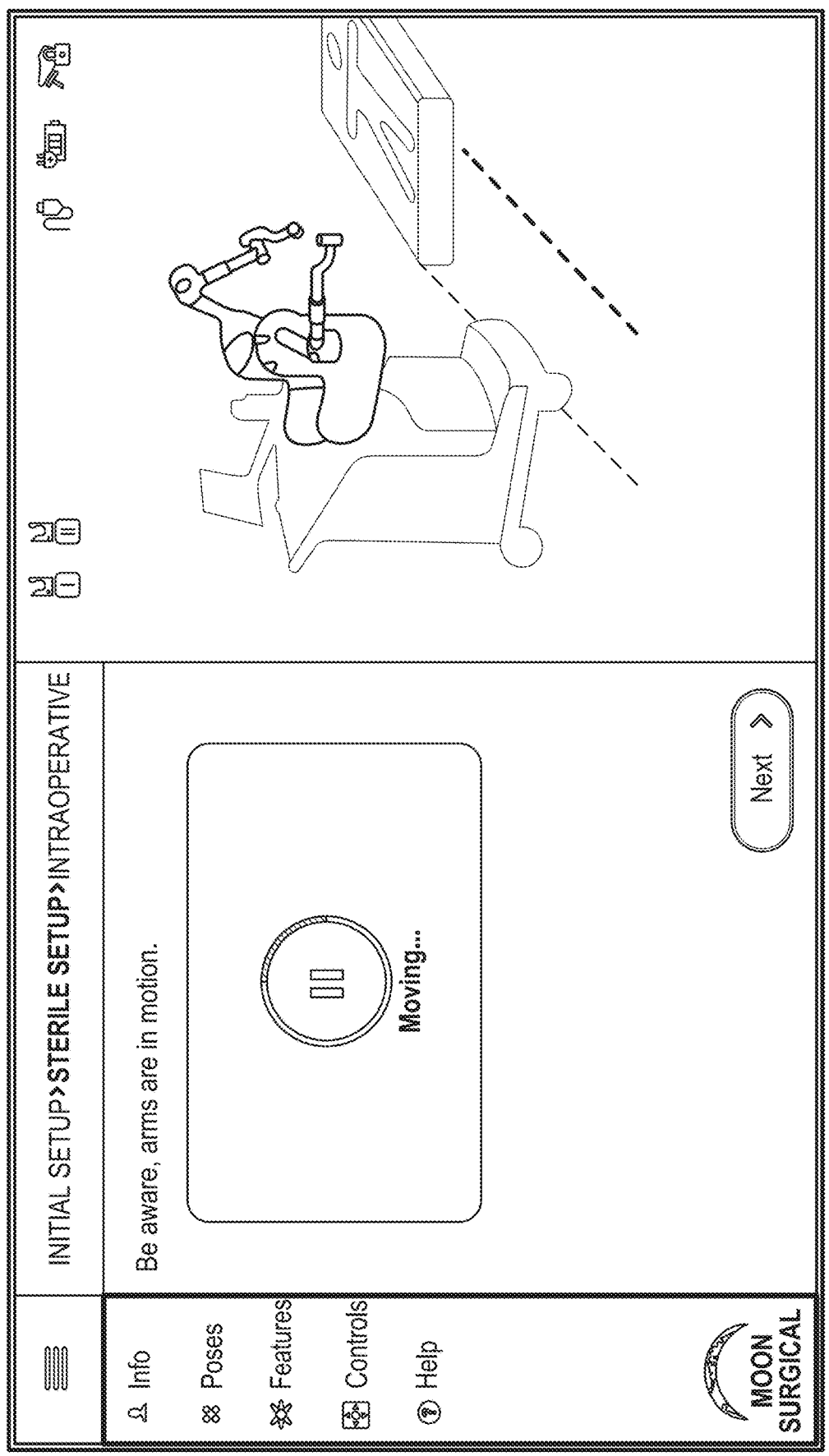
Figure 39L:
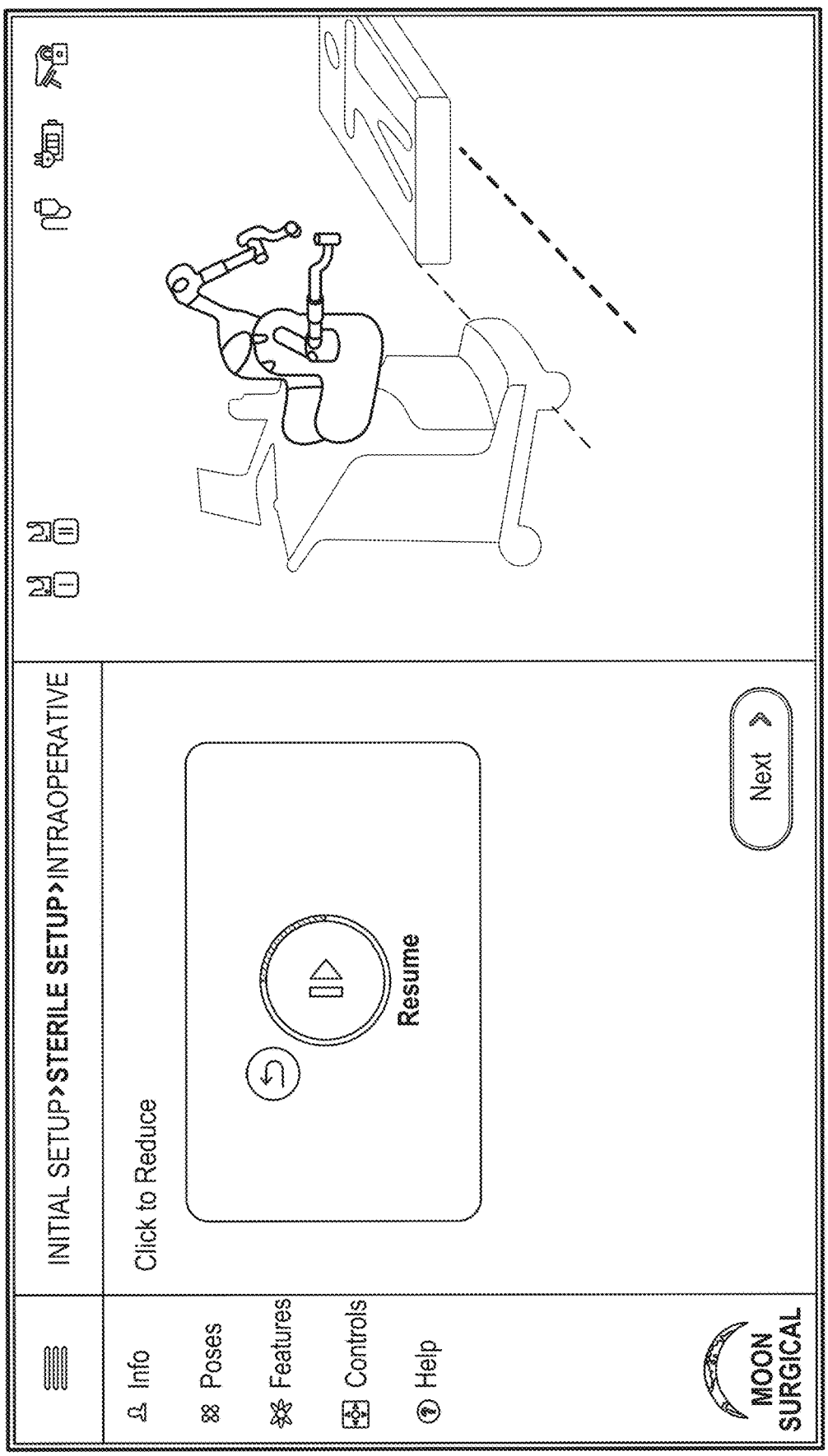
Figure 39M:
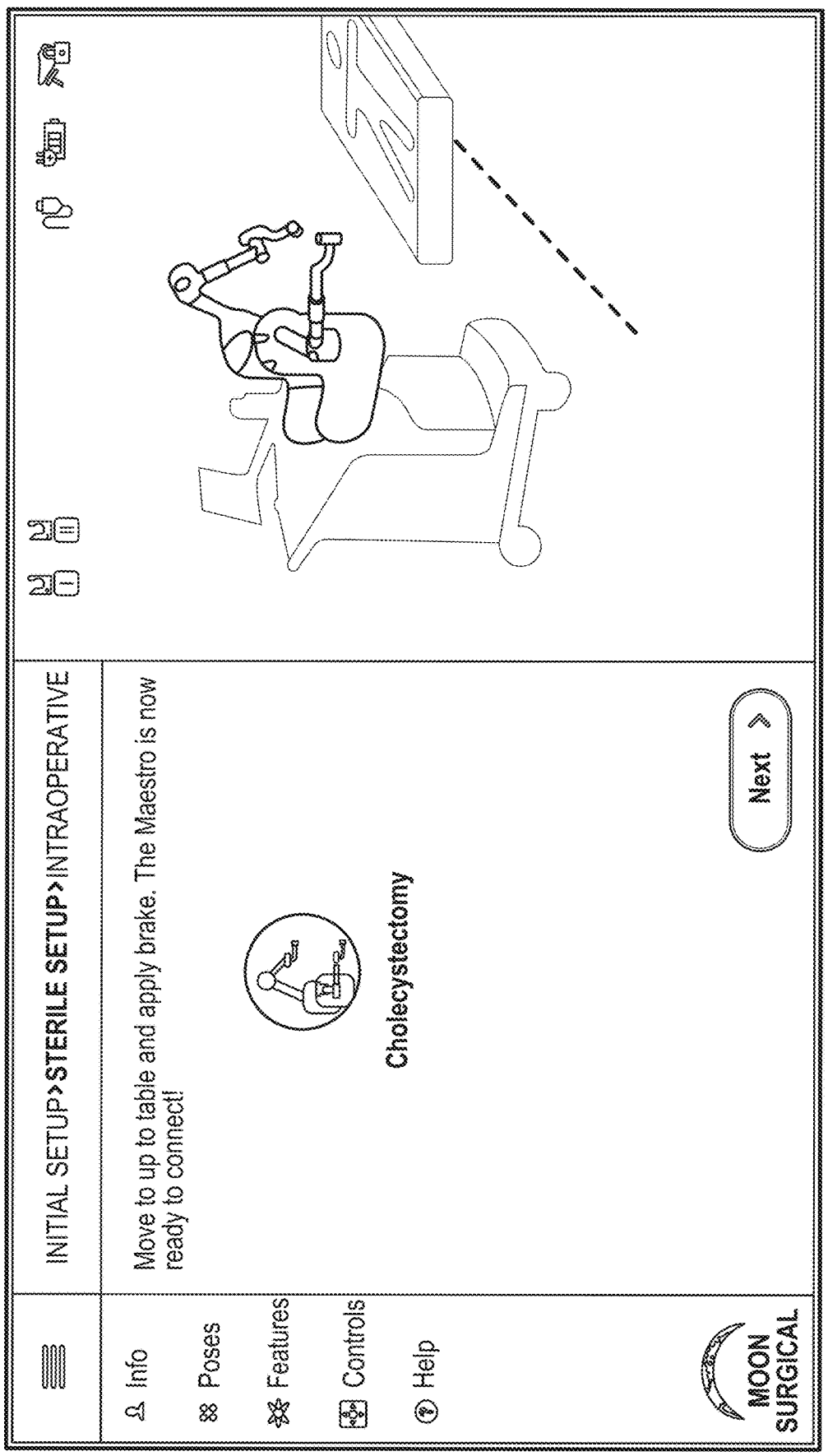
Figure 39N:
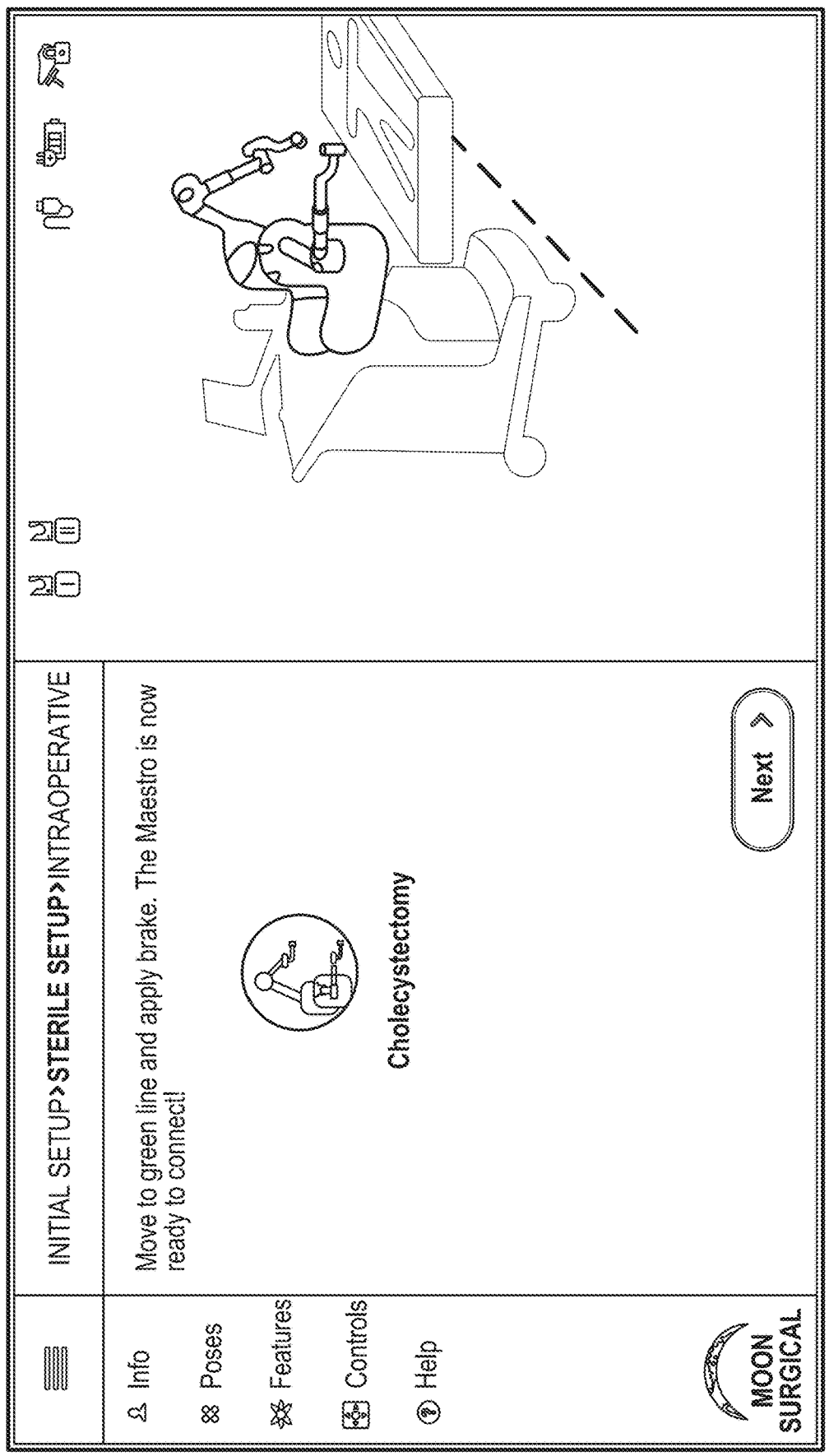
Figure 39O:
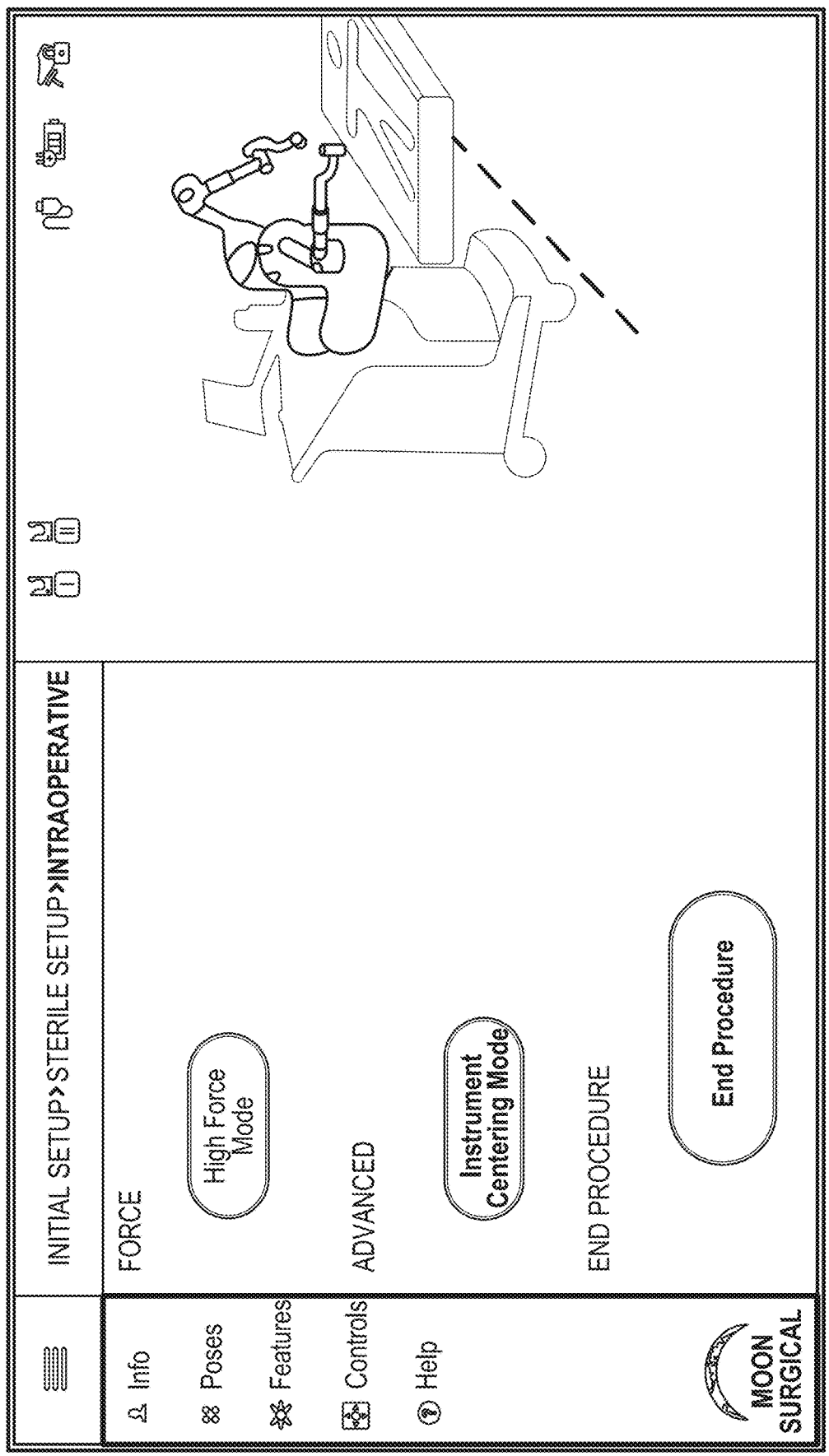
Figure 39P:
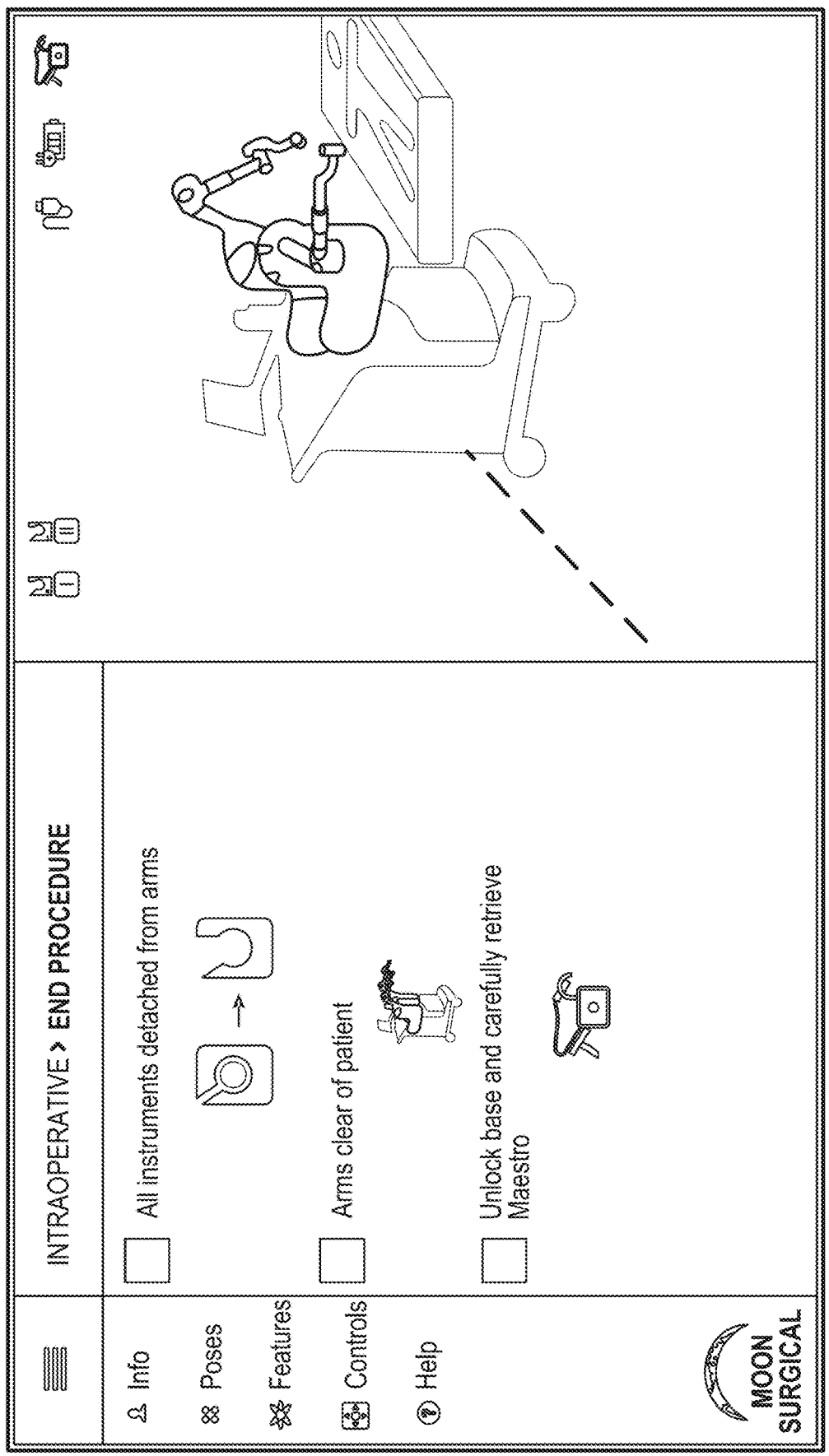
Figure 39Q:
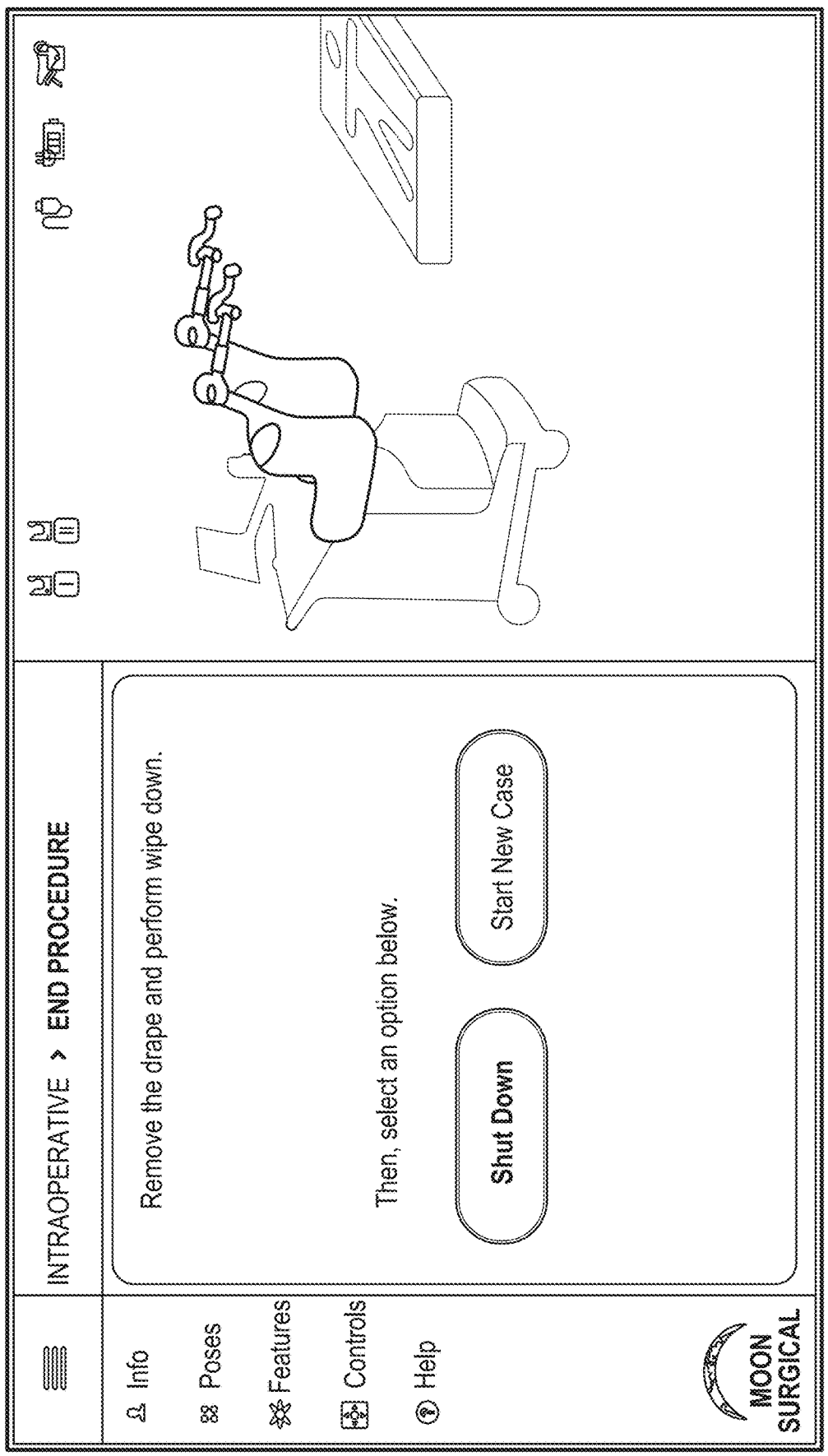
Figure 39R:
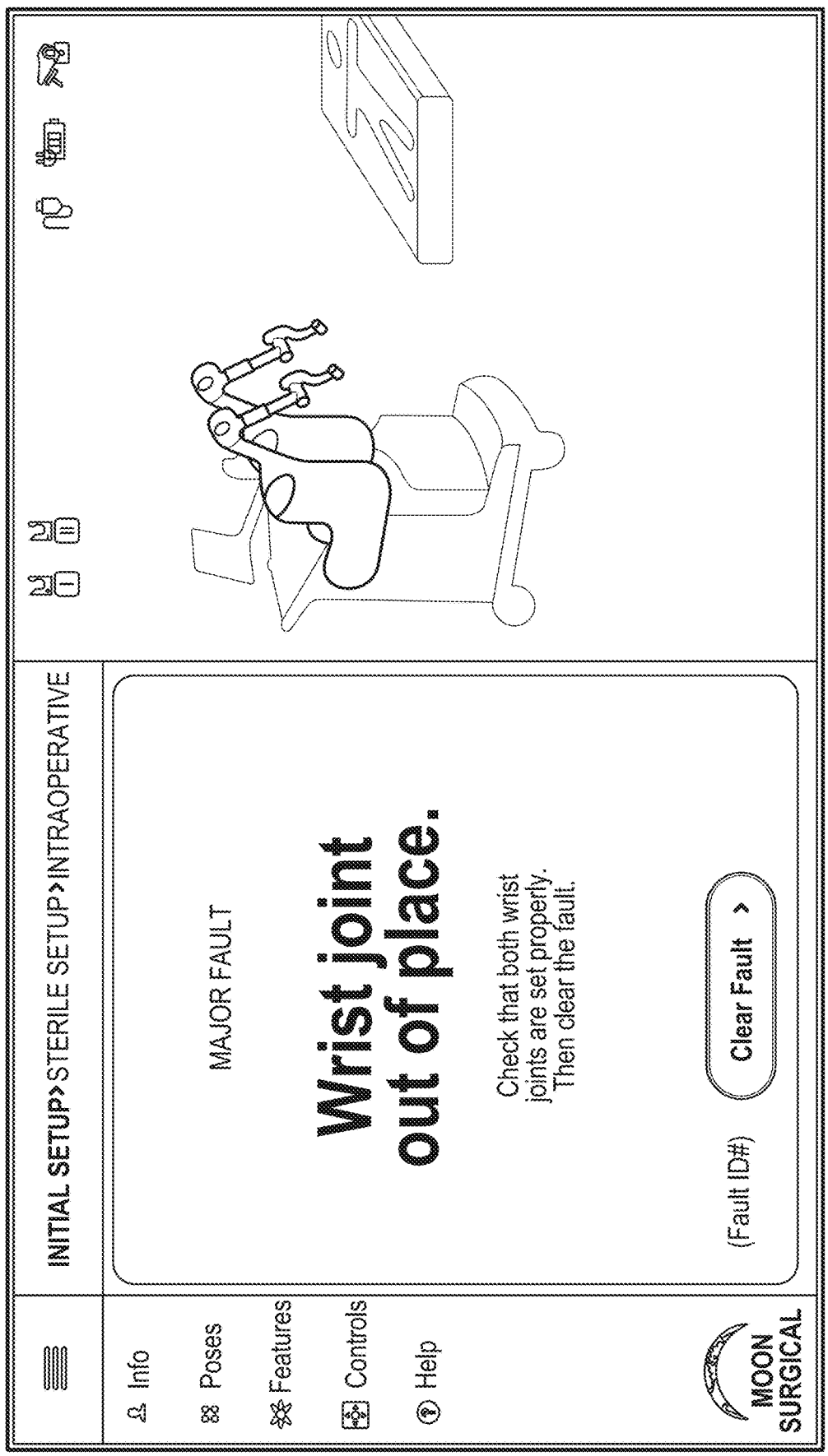

Referring now to FIGS. 39A to 39R, screenshots of an exemplary graphical user interface are provided. The graphical user interface may be configurable by a user and may be integrated with display 210. As shown in FIG. 39A, during an initial setup, the user may select a specific surgeon and/or specific surgical procedure, e.g., from a pre-loaded drop down list of surgeons and/or procedures. In this manner, the user may select from a plurality of predetermined, selectable surgical procedures, which will permit the system to automatically position the robot arms in the optimal configuration to start that specific surgical procedure. For example, as shown in FIGS. 39A and 39B, a cholecystectomy procedure is a selectable option, although other selectable procedures are available as described below. Moreover, the user may select whether to turn on/off the audio and/or tactile feedback features of the system. As shown in FIG. 39B, the user may select between and configure various preset configurations of the system, e.g., platform 200 and robot arms 300a, 300b, which may be specific to which side of the patient table the system is positioned as well as the location of the trocar port(s), and further may depend on which quadrant of the patient body the surgical procedure will take place on and/or the anticipated configuration of the surgical bed. As shown in FIG. 39C, the user may select to turn on/off features such as high force mode, and/or advanced features such as instrument centering mode.

As shown in FIG. 39D, the user may reconfigure the position of the robot arms by rotating the shoulder link of the robot arms about Q3 as described above, as well as by adjusting the stages of the platform to adjust the vertical/horizontal position of the robot arms relative to the platform via GUI 210. For example, the user may toggle, e.g., slide, first digital actuator 3902 on display 210, e.g., left and right, relative to a neutral position (e.g., a center position on display 210) to cause rotation of the distal shoulder link of the robot arm relative to the proximal shoulder link of the robot arm. In addition, display 210 may display indicator 3904 alongside graphical representations 3906 of the robot arm in different angular configurations to inform the user of the current configuration of the robot arm in real-time. For example, the position of indicator 3904 relative to graphical representations 3906 may be moved responsive to actual rotation of the shoulder link of the robot arm via actuation of first digital actuator 3902. First digital actuator 3902 may automatically return to the neutral position upon release of first digital actuator 3902 by the user; whereas, indicator 3904 may remain in position relative to graphical representations 3906 to accurately indicate the degree of rotation and configuration of the shoulder link of the robot arm. In some embodiments, the distance of first digital actuator 3902 from the neutral position, as actuated by the user, may determine the velocity of rotation of the shoulder link. For example, by moving first digital actuator 3902 only a short distance from the neutral position, the distal shoulder link of the robot arm may be rotated relative to the proximal shoulder link of the robot arm in a corresponding direction at a first velocity, and by moving first digital actuator 3902 a larger distance from the neutral position, the distal shoulder link of the robot arm may be rotated relative to the proximal shoulder link of the robot arm in a corresponding direction at a second velocity greater than the first velocity. Rotation of the distal shoulder link relative to the proximal shoulder link in the corresponding direction may slow down as the distal shoulder link approaches its maximum range of rotation relative to the proximal shoulder link until reaching a complete stop.

Similarly, as shown in FIG. 39D, the user may toggle, slide, second digital actuator 3908 on display 210, e.g., left, right, up, down, and/or diagonally, within cursor pad 3910 to cause corresponding horizontal and/or vertical movement of the stages of the robot arm relative to the platform. In addition, display 210 may display one or more indicators, e.g., vertical indicator 3912a and horizontal indicator 3912b, to inform the user of the current vertical and horizontal configuration of stages of the robot arm in real-time. For example, the position of indicator 3912a, e.g., relative to cursor pad 3910, may be moved responsive to actual vertical movement of the robot arm via actuation of second digital actuator 3908, and the position of indicator 3912b, e.g., relative to cursor pad 3910, may be moved responsive to actual horizontal movement of the robot arm via actuation of second digital actuator 3908. Second digital actuator 3908 may automatically return to a neutral position (e.g., a center position on cursor pad 3910) upon release of second digital actuator 3908 by the user; whereas, indicators 3912a, 3912b may remain in respective positions relative to cursor pad 3910 to accurately indicate the vertical and horizontal configuration of the robot arm relative to the platform. In some embodiments, the distance of second digital actuator 3908 from the center point of cursor pad 3910, as actuated by the user, may determine the velocity of movement of the stages relative to the platform. For example, by moving second digital actuator 3908 only a short distance from the center point of cursor pad 3910, the stage will move in the base of the robot arm in a corresponding direction at a first velocity, and by moving second digital actuator 3908 a larger distance from the center point of cursor pad 3910, the stage will move in the base of the robot arm in the corresponding direction at a second velocity greater than the first velocity. Movement of the base of the robot arm via the stage assembly in the corresponding direction may slow down as the stage assembly approaches its maximum range of extension relative to the platform until reaching a complete stop. As described herein, if the distal end of the robot arm is coupled to a surgical instrument, e.g., positioned through a trocar, movement of the base of the robot arm via the stage assembly via user input at the graphical user interface may further automatically cause movement of the robot arm via one or more of the motorized joints of the robot arm so as to maintain a static position of the surgical instrument during movement of the stages. Moreover, the system may generate an alert when the stage assembly and/or robot arm reaches or nears its respective maximum extension limit.

As shown in FIG. 39E, when the surgeon and/or surgical procedure has been selected, the user may actuate a "drape" mode, such that the system moves the robot arms and optionally the stages of the platform to a preset drape configuration, as shown in FIGS. 39F and 39G, to provide ample space for the user to drape the robot arms and the platform, as described above with regard to FIG. 10A. As shown in FIG. 39H, once the system has been properly draped, the user may actuate a "compact" mode, such that the system moves the stages of the platform and the robot arms to a preset configuration that will allow the user to easily move the platform, e.g., toward the patient/surgical bed, with minimal potential of collision with other objects in the operating room. As shown in FIG. 39I, the user may actuate the system to configure the platform and the robot arms for the selected surgical procedure, e.g., a cholecystectomy procedure. As shown in FIGS. 39H-39N, the graphical user interface may display step-by-step instructions with accompanying graphical illustrations to guide the user in configuring the system to begin the surgical procedure. For example, the graphical user interface may guide the movement of the platform relative to the surgical bed, as shown in FIGS. 39I and 39J and FIGS. 39M and 39N. Moreover, the graphical user interface may display visual markers to guide positioning of the platform and/or robot arms relative to the surgical bed, e.g., boundary lines, which may illuminate in different colors upon proper placement of the platform and/or robot arms relative to the boundary lines, and accordingly, the surgical bed. As described in further detail below with regard to FIGS. 40A-40C, while the platform is moving relative to the surgical bed, the graphical user interface may display a virtual map depicting graphical representations of the platform and robot arms and the surgical bed relative to one another.

Additionally, as shown in FIGS. 39J, the graphical user interface may permit the user to select a surgical procedure, e.g., a cholecystectomy, such that, upon selection by the user, the system causes the platform and/or robot arms to automatically move, e.g., relative to the surgical bed, to a preset configuration optimized for performing the surgical procedure, as shown in FIGS. 39K and 39L. Although only the cholecystectomy surgical procedure selection is shown in FIG. 39J, as will be understood by a person having ordinary skill in the art, the graphical user interface may display a plurality of surgical procedure selections for the user to choose from. For example, the surgical procedures further may include, e.g., gastric sleeve, hiatal hernia repair, Nissen fundoplication, inguinal hernia repair (TEP), right, left, and/or complete colectomy, gastric bypass, sigmoid colectomy, umbilical hernia repair, incisional hernia repair, etc. Accordingly, the preset configuration for each surgical procedure, and in some embodiments depending on the surgical procedure, the preset configuration for a phase of a given surgical procedure, may be selected and stored prior to operation. The preset configuration for a given surgical procedure may be specific to which side of the patient table the system is positioned, the location of the trocar port(s), which quadrant of the patient body the surgical procedure will take place on, and/or the anticipated configuration of the surgical bed. For example, the quadrant of the patient body and the anticipated surgical bed configuration may drive the preset configurations as they both dictate in which direction, e.g., up or down relative to the horizontal plane, a laparoscope may need to be pointed for a given surgical procedure. Moreover, one or more preset configurations may be user specific based on user preference for a given surgical procedure, and may be stored in the user's profile.

Figure 41:
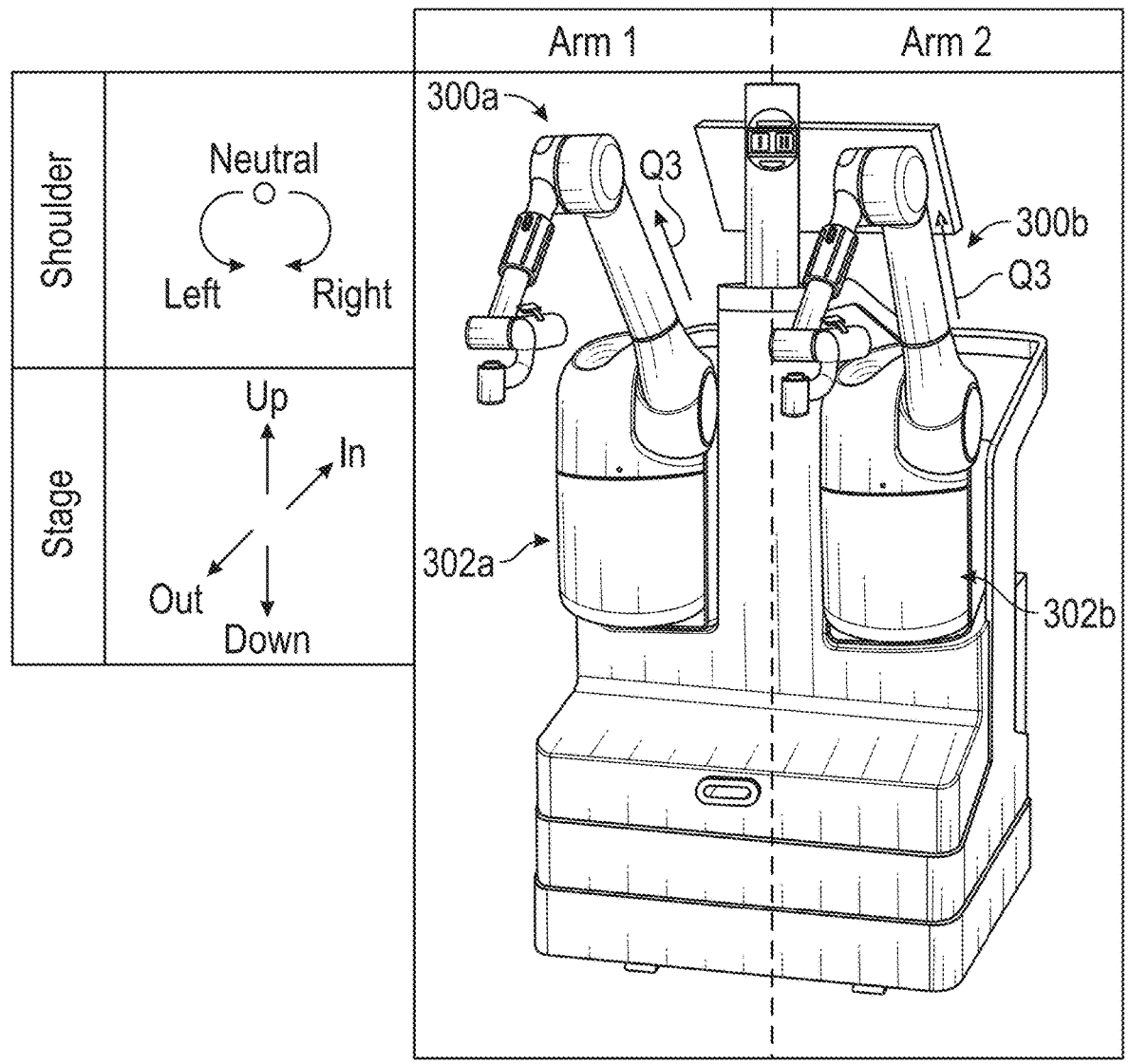
FIG. 41 illustrates the degrees of freedom of movement of the shoulder portion and the stages of the co-manipulation surgical system for preset configurations of the platform and robot arms in accordance with the principles of the present disclosure.

The system may cause the platform and/or robot arms to move to each preset configuration by causing movement of the platform and/or robot arms in a limited number of degrees of freedom. For example, as shown in FIG. 41, the shoulder portion of each robot arm, 300a, 300b may be rotated about the respective Q3 axis, e.g., in a left or right direction from a neutral configuration, and each of base 302a, 302b may be moved via the stages of the platform, e.g., in/out along the horizontal plane and up/down along the vertical plane. Accordingly, based on the limited degrees of freedom of movement of the shoulder portions of the robot arm and stages of the platform, the system may cause the platform and/or robot arms to move to any one of a plurality of preset configurations based on the selected surgical procedure. For example, Table 1 below illustrates exemplary movements/configurations of the stage and/or the shoulder portion for each of the robot arms, e.g., ARM 1 and ARM 2 of FIG. 41, to achieve the respective preset configuration.

TABLE 1

| Surgical Procedure | ARM 1 | | ARM 2 | |
|---|---|---|---|---|
| | Stage | Shoulder | Stage | Shoulder |
| Cholecystectomy (upper right quadrant) | Down, Out | Left | Up, In | Neutral |
| Gastric Sleeve (midline to upper left quadrant) | Down, In | Neutral | Up, In | Right |
| Left Colectomy (lower left quadrant) | Up, Out | Right | Up, Out | Left |

Figure 42:
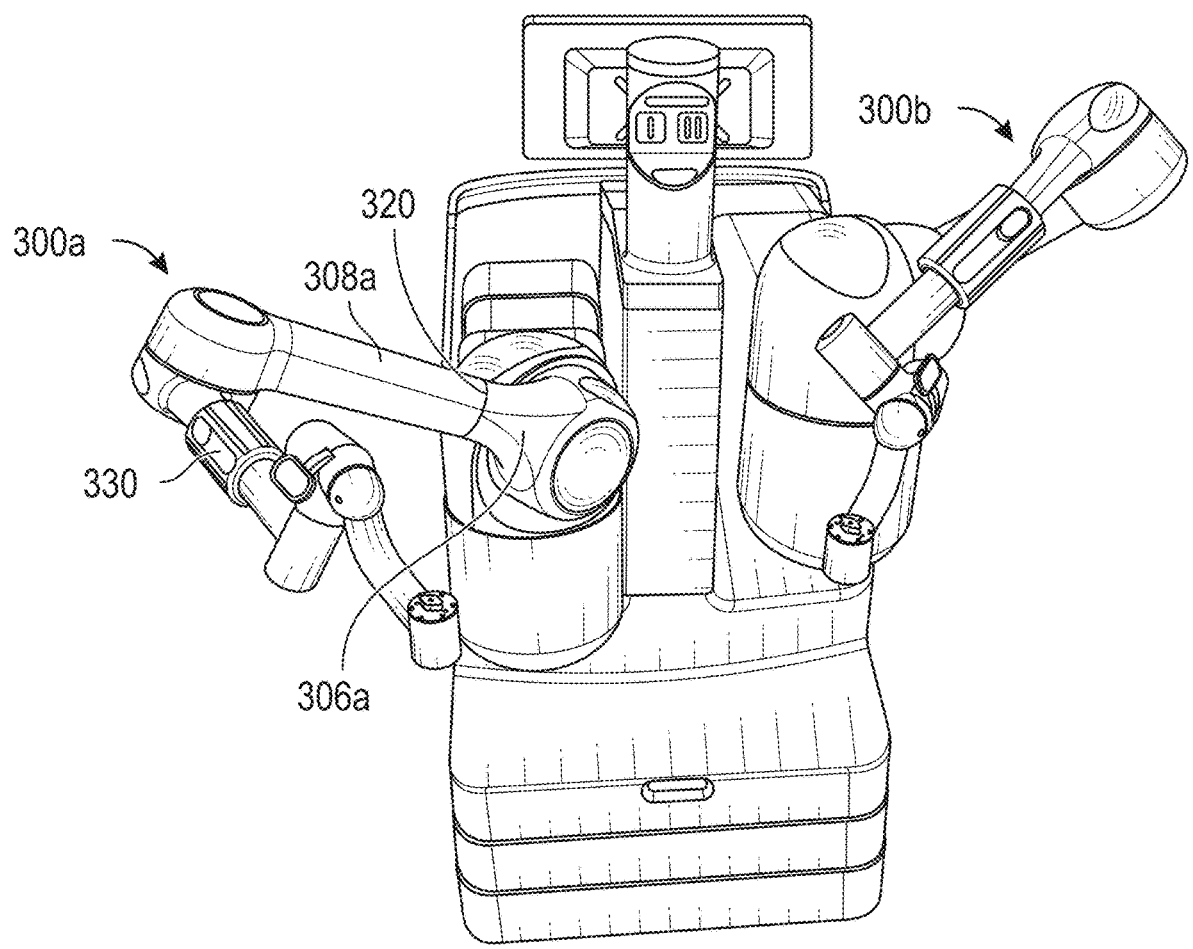
FIG. 42 illustrates the co-manipulation surgical system in an exemplary preset cholecystectomy configuration.

For example, in the case of the laparoscopic cholecystectomy in the upper right quadrant of the patient's body, Arm 1 may hold a laparoscope and Arm 2 may hold a grasper, the surgical bed angle may be steep reverse Trendelenberg (head up), and the system may be positioned on the right side of the patient. Moreover, the grasper held by Arm 2 will be used to push tissue superiorly (in the direction of the patient's right shoulder), and the laparoscope would be best positioned at the umbilicus, also pointing superiorly in the direction of the patient's right shoulder. Thus, to optimize the surgeon's workspace for a cholecystectomy surgical procedure, as shown in Table 1, the preset configuration is such that the Arm 1 stages are down and out, and the Arm 1 shoulder is rotated to the left about the Q3 axis; whereas, the Arm 2 stages are up and in, and the Arm 2 shoulder is in the neutral configuration, as shown in FIG. 42. Accordingly, the surgeon may hold active instruments between the arms, with Arm 1 reaching underneath the surgeon's arms.

Moreover, in the case of a laparoscopic gastric sleeve from the midline to the upper left quadrant of the patient's body, Arm 1 may hold a laparoscope and Arm 2 may hold a grasper, the surgical bed angle may be steep reverse Trendelenberg (head up), and the system may be positioned on the right side of the patient. However, because the area of the operation is larger, e.g., from the midline to upper left quadrant, and the procedure involves retracting tissue inferiorly (towards the patient's feet), to optimize the surgeon's workspace for a gastric sleeve surgical procedure, as shown in Table 1, the preset configuration is such that the Arm 1 stages are down and in, and the Arm 1 shoulder is in the neutral configuration; whereas, the Arm 2 stages are up and in, and the Arm 2 shoulder is rotated to the right about the Q3 axis. Accordingly, the surgeon may hold active instruments and reach underneath Arm 2, with more space to retract towards the feet. In addition, in the case of a laparoscopic left colectomy in the upper and lower left quadrants of the patient's body, the surgical bed angle may be Trendelenberg tilt right, and the system may be positioned on the left side of the patient. Thus, to optimize the surgeon's workspace for a left colectomy surgical procedure, as shown in Table 1, the preset configuration is such that the Arm 1 stages are up and out, and the Arm 1 shoulder is rotated to the right about the Q3 axis; whereas, the Arm 2 stages are up and out, and the Arm 2 shoulder is rotated to the left about the Q3 axis. In this manner, the robot arm(s) may be automatically positioned in a configuration specific to the selected surgical procedure to assist with arm setup for that specific procedure.

Referring now to FIG. 39O, during operation of the system to perform the surgical procedure, the user may select which features to turn on/off at any given phase of the surgical procedure, and/or select to end the procedure. Upon selecting to end the procedure, as shown in FIG. 39P, the graphical user interface may display, e.g., a checklist of actions required to end the procedure, such as detaching all the instruments from the robot arm, making sure the arms are in a configuration away from the patient, and moving the platform away from the workspace. As shown in FIG. 39Q, the user may select to shut down the system and/or start another procedure. FIG. 39R illustrates an exemplary fault alert, such that the user may clear the fault and proceed with the operation once the fault condition has been removed.

Figure 40A:
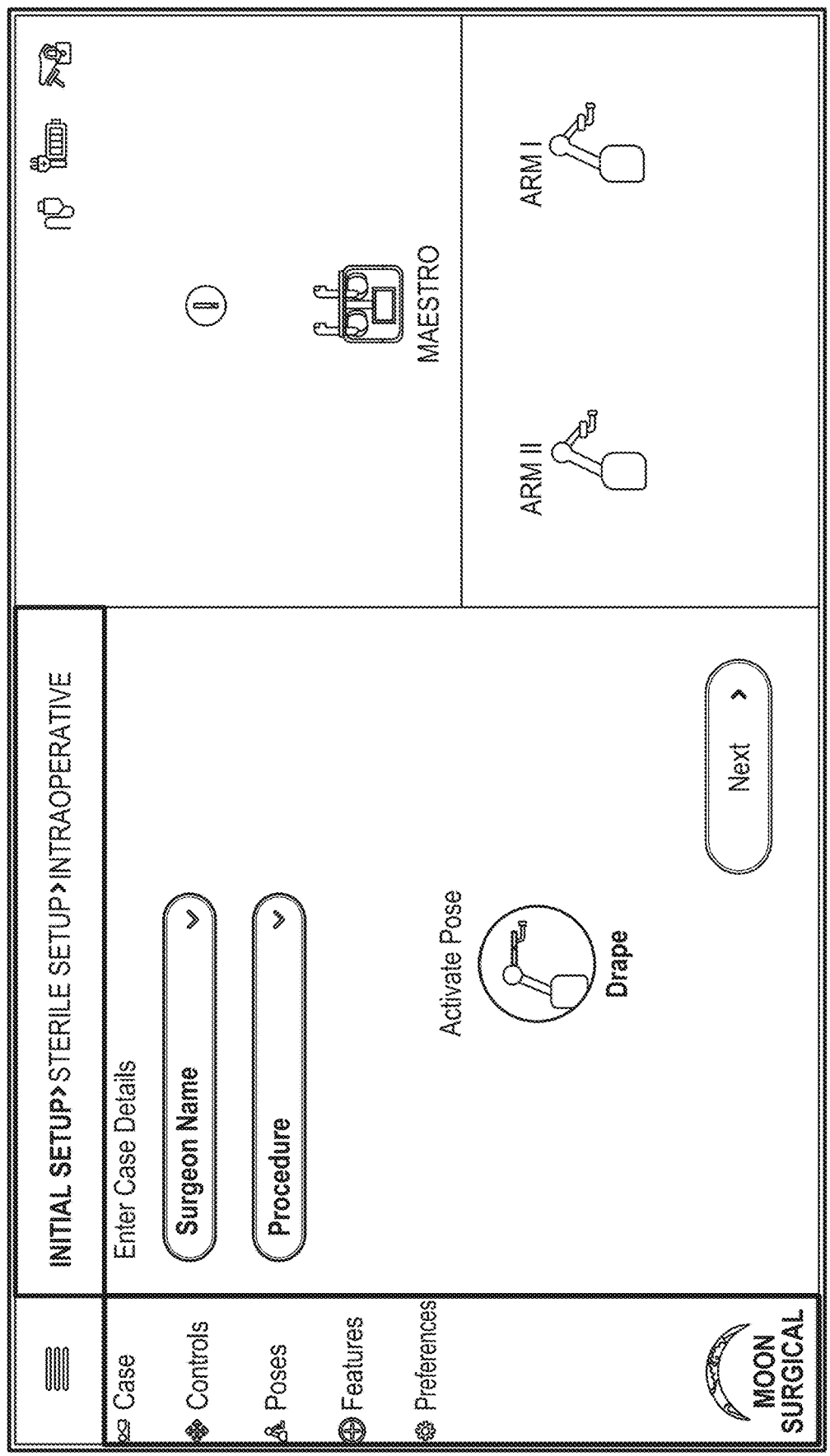
Figure 40B:
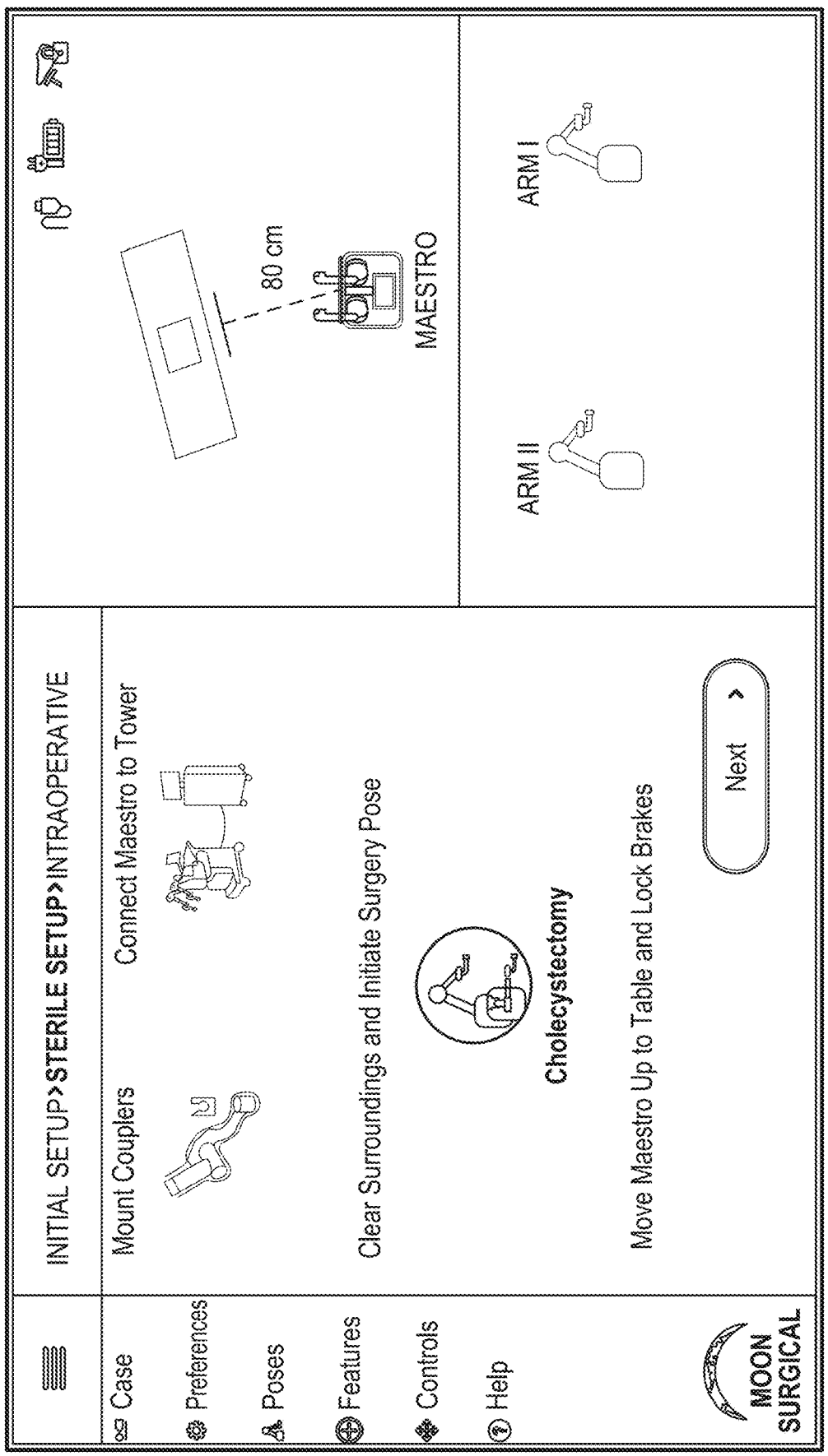
Figure 40C:
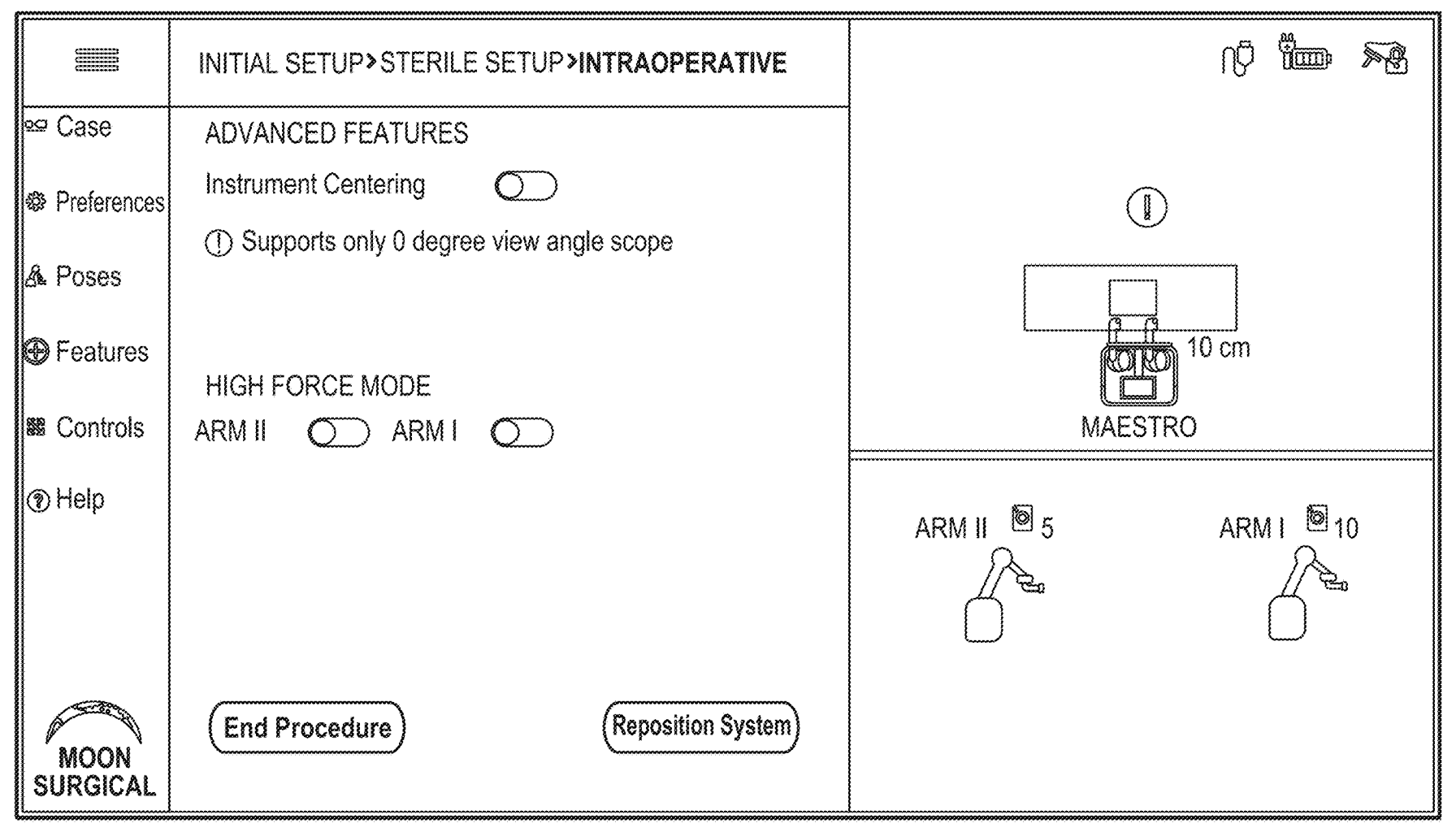

Referring now to FIGS. 40A-40C, screenshots of exemplary graphical user interface displaying a virtual map to guide movement of the platform relative to a surgical bed are provided. The graphical user interface may be configurable by a user and may be integrated with display 210. As shown in FIG. 40A, when the surgical bed is not within an acceptable proximity of the platform sensors, e.g., optical sensors 202 and/or proximity sensors 212, the graphical user interface may not display the virtual map depicting graphical representations of the platform and robot arms and the surgical bed, and may display an alert that the distance to the surgical bed/operation table is undetectable. As shown in FIG. 40B, upon detection of the surgical bed by the platform sensors, e.g., during movement of the platform, the graphical user interface may automatically display the virtual map, e.g., a "bird's eye view" of the area surrounding the platform, depicting the platform and robot arms relative to the surgical bed. Moreover, the graphical user interface may display information indicative of, e.g., the distance between the platform (and/or the most extended stage/robot arm) and the surgical bed and the angle of the platform relative to the surgical bed, in real-time as the platform is moved relative to the surgical bed. When motion of the platform has stopped, e.g., when the platform has reached the target location relative to the surgical bed, the graphical user interface may stop displaying the virtual map, as shown in FIG. 40C. Accordingly, the graphical user interface may display the virtual map only during movement of the platform by the user, such that when the platform stops moving, the virtual map is no longer displayed. Alternatively, the graphical user interface may display the virtual map once the surgical bed is within an acceptable proximity to the platform sensors until the platform stops moving at the target location relative to the surgical bed. The graphical user interface further may indicate when the platform is in a locked state where mobility of the platform is prohibited, e.g., when the user actuates a locking pedal to engage the braking mechanism of the platform.

Figure 43B:
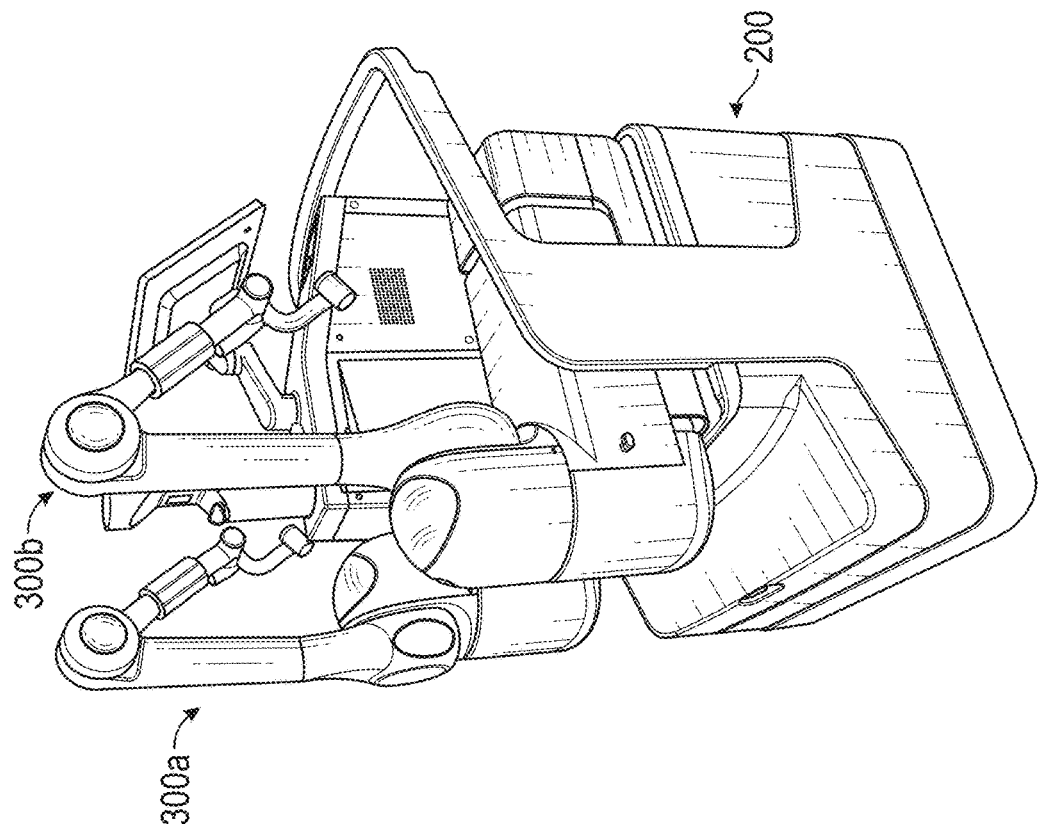
FIGS. 43A-43D illustrate the co-manipulation surgical system in an exemplary preset stow configuration.
Figure 43A:
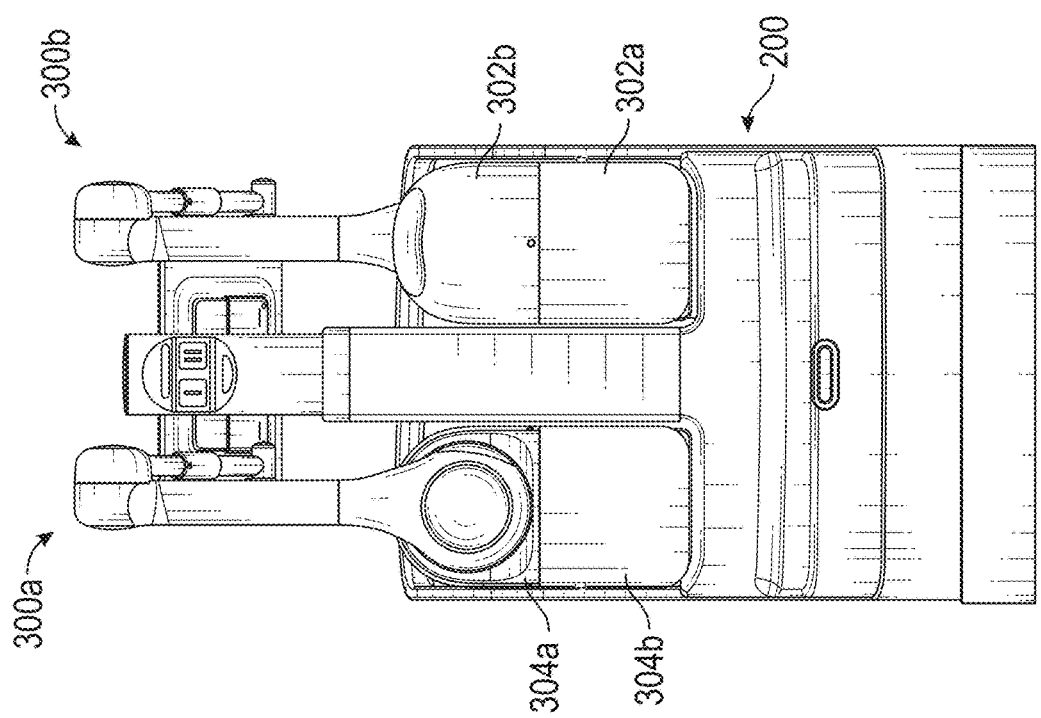
Figure 43D:
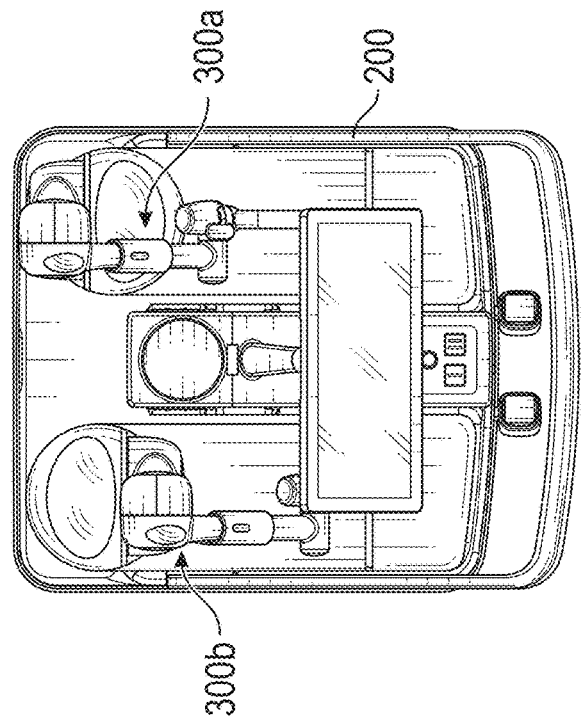
Figure 43C:
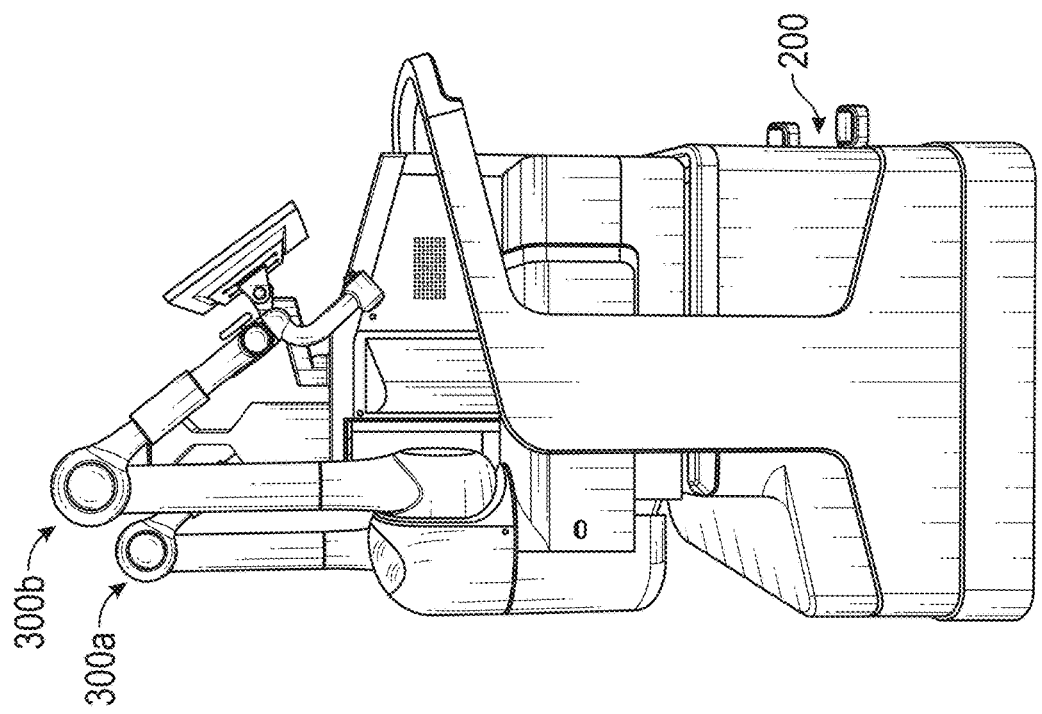

Referring again to FIG. 39G, the user may choose to actuate a "stow" mode, such that the system moves the robot arms and the stages of the platform to a preset stow configuration where the robot arms are within the footprint of the platform, e.g., the outermost perimeter of platform 200, to facilitate transport and/or storage of the system. For example, FIGS. 43A to 43D illustrate robot arms 300a, 300b in an exemplary stow configuration where the stages are automatically actuated to move and position robot arms 300a, 300b downward and inward relative to platform 200, such that shoulder portions 304a, 304b and base portions 302a, 302b are within the footprint of platform 200. Moreover, upon actuation of stow mode, robot arms 300a, 300b automatically move such that they are also positioned within the footprint of platform 200. Preferably, in the stow configuration, the entirety of robot arms 300a, 300b including base portions 302a, 302b and shoulder portions 304a, 304b are fully and completely within the footprint of platform 200, as shown in FIG. 43D. In addition, in the stow configuration, the robot arms may have a minimal height relative to platform 200 to facilitate transportation and/or storage of the co-manipulation surgical system while in the stow configuration.

FIG. 44 illustrates the automated movements of the robot arms and stages relative to platform 200 upon actuation of stow mode from an arbitrary configuration, e.g., drape-ready configuration, toward the stow configuration illustrated in FIGS. 43A to 43D. For example, as shown in FIG. 44, shoulder portion 304a may automatically rotate relative to base portion 302a in a clockwise direction about axis Q1 at joint 303a, proximal shoulder link 306a may automatically rotate relative to shoulder portion 304a in a clockwise direction about axis Q2 at joint 318a, distal shoulder link 308a may automatically rotate relative to proximal shoulder link 306a in a clockwise direction about axis Q3 at joint 320a, and elbow link 310a may automatically rotate relative to distal shoulder link 308a in a counter-clockwise direction about axis Q4 at joint 322a, while the stages of platform 200 automatically move base portion 302a in a downward direction along the Z axis relative to platform 200 via vertical extenders 206a and in an inward direction along the X axis relative to platform 200 via horizontal extenders 208a. Similarly, shoulder portion 304b may automatically rotate relative to base portion 302b in a counter-clockwise direction about axis Q1 at joint 303b, proximal shoulder link 306b may automatically rotate relative to shoulder portion 304b in a clockwise direction about axis Q2 at joint 318b, distal shoulder link 308b may automatically rotate relative to proximal shoulder link 306b in a counter-clockwise direction about axis Q3 at joint 320b, and elbow link 310b may automatically rotate relative to distal shoulder link 308b in a counter-clockwise direction about axis Q4 at joint 322b, while the stages of platform 200 automatically move base portion 302b in a downward direction along the Z axis relative to platform 200 via vertical extenders 206b and in an inward direction along the X axis relative to platform 200 via horizontal extenders 208b. As will be understood by a person having ordinary skill in the art, the system may programmed to execute the movements described above in an order and manner that avoids potential collisions between robot arms 300a, 300b and components of platform 200, e.g., lighthouse 203, each other, and/or other objects in the vicinity, e.g., via depth data obtained by the optical scanners.

Figure 45B:
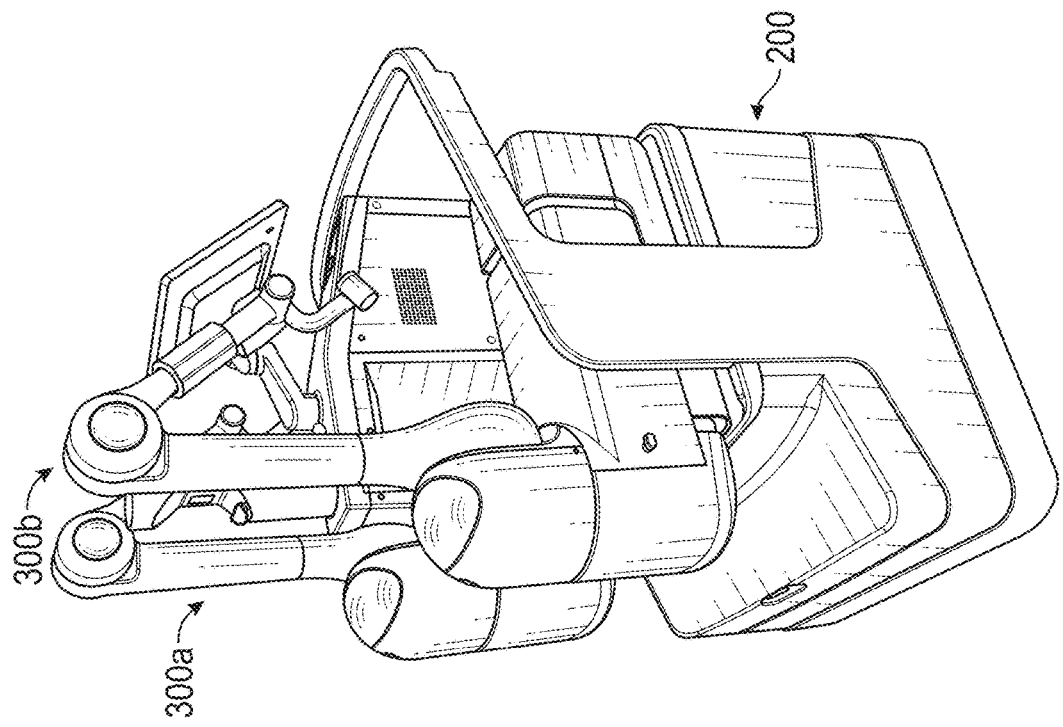
FIGS. 45A-45D illustrate the co-manipulation surgical system in another exemplary preset stow configuration.
Figure 45A:
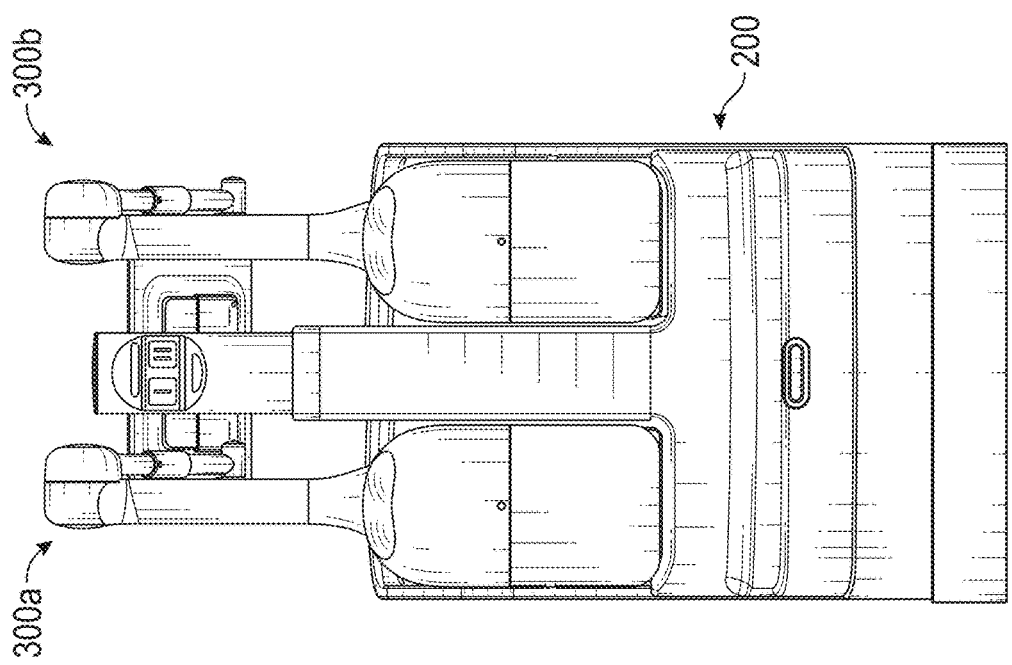
Figure 45D:
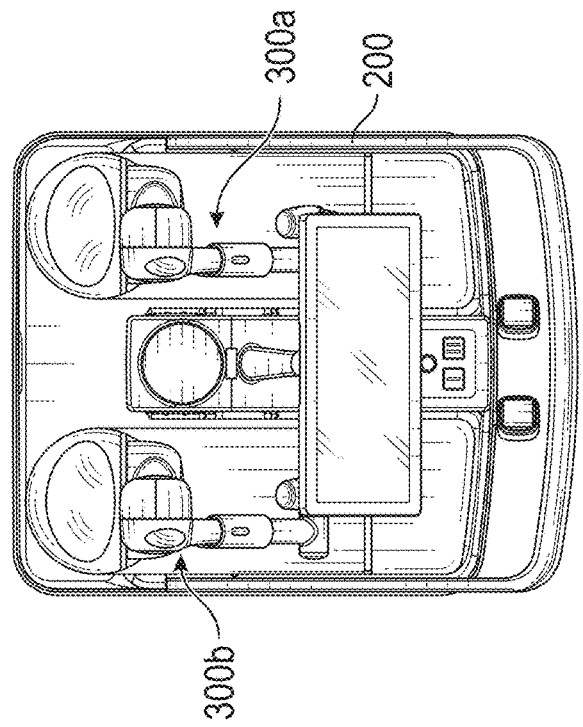
Figure 45C:
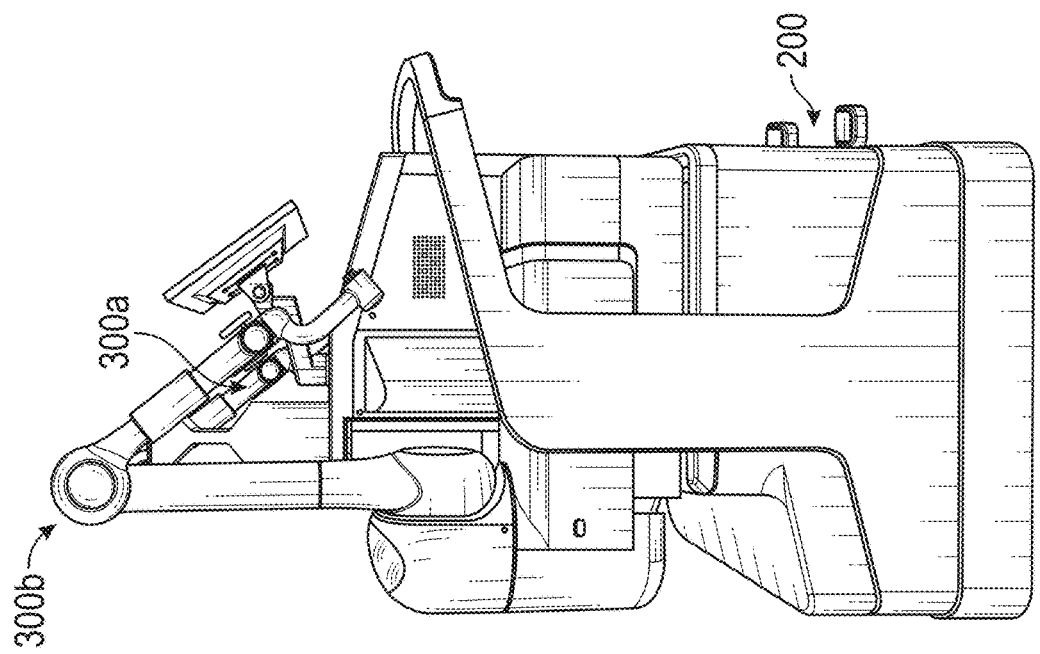

FIGS. 45A to 45D illustrate robot arms 300a, 300b in an alternative exemplary stow configuration where robot arms 300a, 300b including base portions 302a, 302b and shoulder portions 304a, 304b are within the footprint of platform 200. Preferably, in this stow configuration, the entirety of robot arms 300a, 300b including base portions 302a, 302b and shoulder portions 304a, 304b are fully and completely within the footprint of platform 200, as shown in FIG. 45D. As shown in FIGS. 45A to 45D, in this stow configuration, base portions 302a, 302b, shoulder portions 304a, 304b, and robot arms 300a, 300b have an identical configuration and orientation relative to platform 200. As will be understood by a person having ordinary skill in the art, the system may programmed to execute the requisite movements of the stages and robot arms in an order and manner to achieve the desired stow configuration that avoids potential collisions between robot arms 300a, 300b and components of platform 200, e.g., lighthouse 203, each other, and/or other objects in the vicinity, e.g., via depth data obtained by the optical scanners. For example, the stages may first automatically move base portion 302a in an upward direction along the Z axis relative to platform 200 via vertical extenders 206a and in an outward direction along the X axis relative to platform 200 via horizontal extenders 208a, prior to rotation of shoulder portion 304a relative to base portion 302a in a counter-clockwise direction about axis Q1 at joint 303a and rotation of distal shoulder link 308a relative to proximal shoulder link 306a in a counter-clockwise direction about axis Q3 at joint 320a, such that robot arm 300a, e.g., elbow link 310a, clears lighthouse 203 during the respective rotations.

Figure 46A:
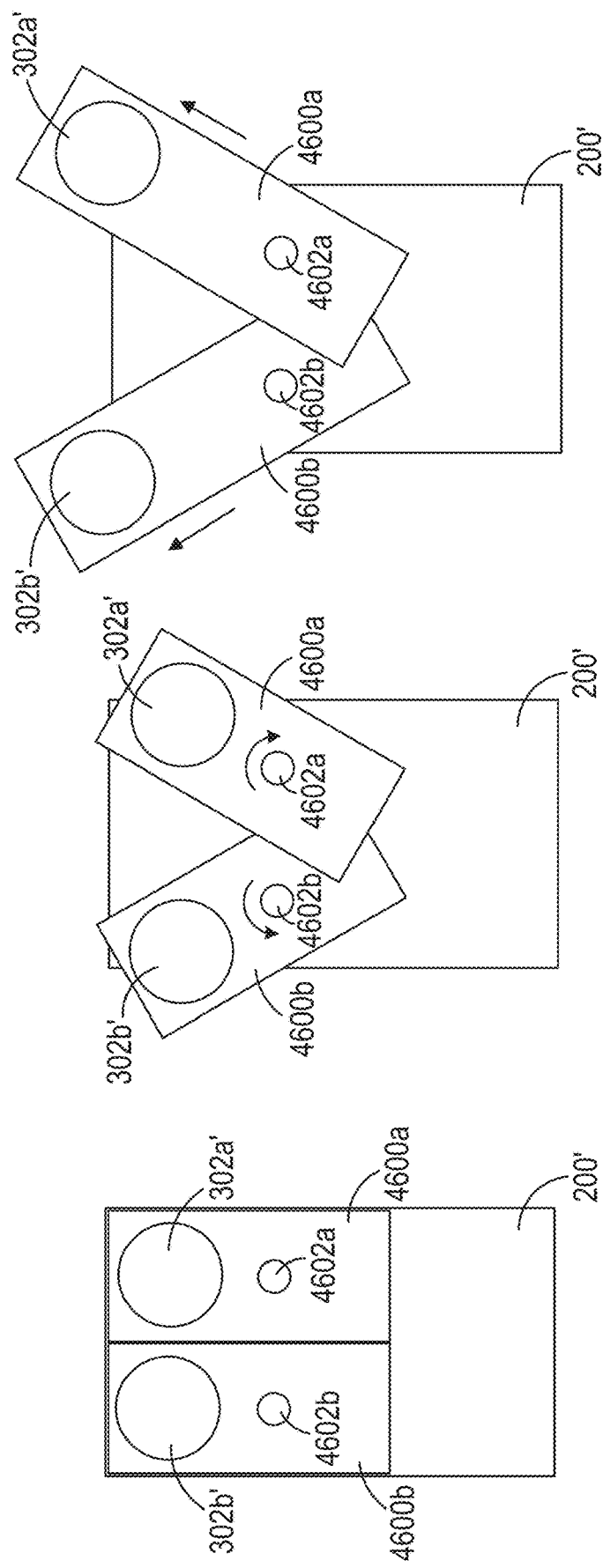
FIGS. 46A and 46B illustrate alternative exemplary co-manipulation surgical system platforms having a rotatable stage assembly constructed in accordance with the principles of the present disclosure.

As described above, in some embodiments, the stages may be rotatable relative to the platform to thereby cause the robot arms to rotate towards or away from each other, e.g., along a horizontal plane defined by the x-axis and the y-axis. Accordingly, in some embodiments, the platform 200 may have a smaller footprint, such that the robot arms may be entirely within the footprint of the platform in the stow mode, and the stages may be actuated to rotate and extend the base portions of the robot arms away from each other along the horizontal plane to achieve a spaced apart configuration generally provided by the wider footprint platform. FIG. 46A illustrates platform 200', which may be constructed similar to platform 200, except that platform 200' has a more narrow footprint than platform 200. As shown in FIG. 46A, platform 200' may include stage 4600a coupled to base portion 302a' of a first robot arm (not shown), which corresponds to base portion 302a of robot arm 300a, and stage 4600b coupled to base portion 302b' of a second robot arm (not shown), which corresponds to base portion 302b of robot arm 300b. Stages 4600a, 4600b may include horizontal and vertical extenders for moving base portions 302a', 302b' toward/away and up/down relative to platform 200', as described above. In addition, stages 4600a, 4600b are configured to rotate about joints 4602a, 4602b of platform 200', respectively, to thereby rotate base portions 302a', 302b' toward/away from each other. As shown in FIG. 46A, stages 4600a, 4600b may transition between a stow configuration where stages 4600a, 4600b, and accordingly the robot arms coupled thereto, are within the footprint of platform 200', and an extended configuration where stages 4600a, 4600b rotate in opposite directions away from each other about joints 4602a, 4602b, respectively, and further may extend base portions 302a', 302b' along the horizontal direction away from platform 200', such that base portions 302a', 302b' are spaced apart from each other a distance similar to base portions 302a, 302b of platform 200 in a operation-ready configuration. As will be understood by a person having ordinary skill in the art, the proximal portions of stages 4600a, 4600b may be configured such that during rotation of stages 4600a, 4600b, the respective proximal portions of stages 4600a, 4600b may overlap (from a top view) without colliding within one another. For example, stages 4600a, 4600b may include a vertical separation from one another that permits unobstructed overlap during rotation.

Figure 46B:
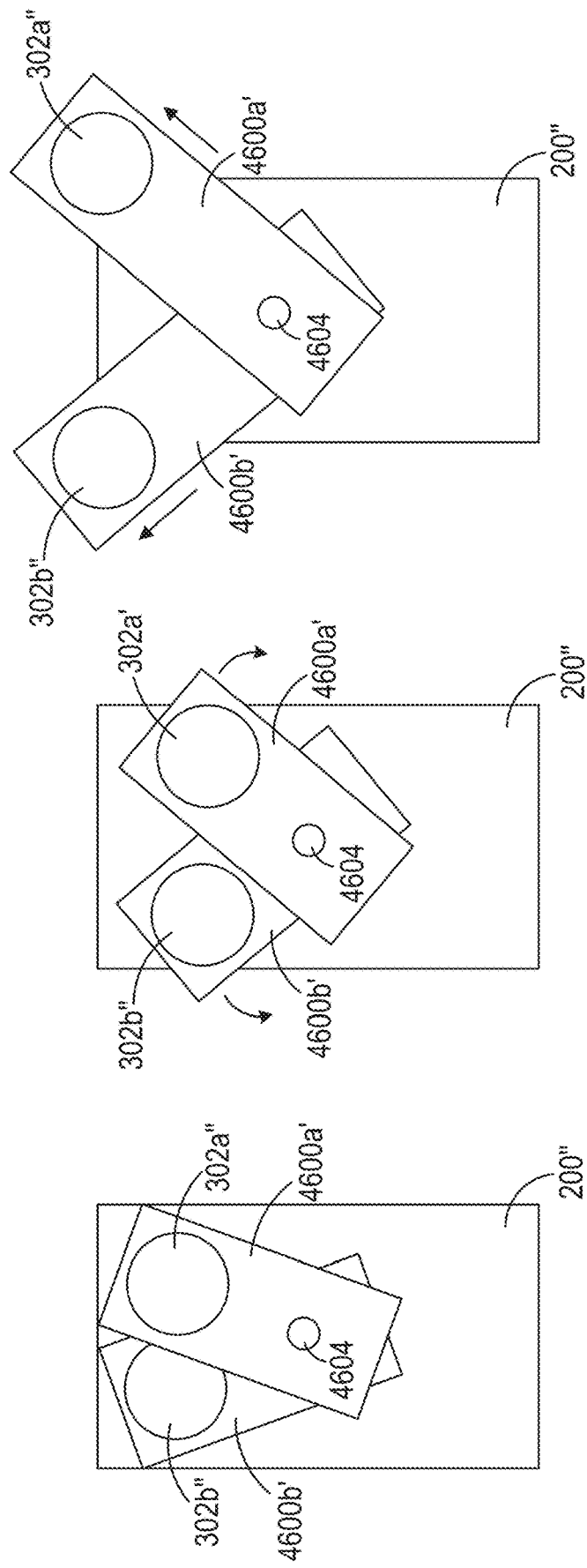

Referring now to FIG. 46B, platform 200" may be constructed similar to platform 200', except that the center of rotation of stages 4600a', 4600b' are coaxial about joint 4604 of platform 200". As shown in FIG. 46B, stages 4600a', 4600b' may transition between a stow configuration where stages 4600a', 4600b', and accordingly the robot arms coupled thereto, are within the footprint of platform 200", and an extended configuration where stages 4600a', 4600b' rotate in opposite directions away from each other about joint 4604, respectively, and further may extend base portions 302a", 302b" along the horizontal direction away from platform 200", such that base portions 302a", 302b" are spaced apart from each other a distance similar to base portions 302a, 302b of platform 200 in a operation-ready configuration. As will be understood by a person having ordinary skill in the art, the system may include a coaxial rotation mechanism configured to transmit torque to each of stages 4600a', 4600b' independently.

Some implementations of the systems described herein may be configured to be controlled or manipulated remotely, e.g., via joystick or other suitable remote control device, computer vision algorithm, force measuring algorithm, and/or by other means. However, in a preferred embodiment, the systems described herein operate without any telemetry, e.g., the robot arm is not teleoperated via a remote surgeon console separate from the robot arm, but instead the robot arm moves in response to movement applied to the surgical instrument coupled thereto. Any robot-assisted movements applied to the surgical instrument by the system, e.g., in the robotic assist mode, are not responsive to user input received at a remote surgeon console.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A method for assisting with laparoscopic surgery using a robot arm comprising a proximal end, a distal end configured to be removably coupled a surgical instrument, a plurality of links, and a plurality of joints between the proximal end and the distal end, the method comprising:
   causing, via a controller operatively coupled to the robot arm, the robot arm to switch to a passive mode responsive to determining that movement of the robot arm due to movement at a handle of the surgical instrument is less than a predetermined amount for at least a predetermined dwell time period, the controller configured to cause the robot arm to maintain a static position in the passive mode;
   applying, via the controller, gravity compensation to the robot arm to compensate for gravity of the surgical instrument;
   calculating, via the controller during application of the gravity compensation, a hold force required to maintain the distal end of the robot arm in a static position in the passive mode;
   establishing, via the controller, a baseline hold force based on the hold force; and
   applying, via the controller, a breakaway force threshold to the robot arm based on the baseline hold force, the breakaway force threshold being a predetermined amount of force required to be applied to the robot arm to cause the robot arm to exit the passive mode.

2. The method of claim 1, wherein a magnitude of the breakaway force threshold is equal in every direction relative to the baseline hold force.

3. The method of claim 1, wherein a total amount of force required to be applied to the robot arm in a direction to cause the robot arm to exit the passive mode is a sum of the baseline hold force and the breakaway force threshold in the direction.

4. The method of claim 1, wherein calculating the hold force required to maintain the distal end of the robot arm in the static position in the passive mode comprises continuously calculating, via the controller, the hold force required to maintain the distal end of the robot arm in the static position in the passive mode.

5. The method of claim 4, further comprising determining, via the controller, that the surgical instrument is in contact with one or more anatomical structures in the passive mode if the hold force gradually increases over time.

6. The method of claim 1, wherein calculating the hold force required to maintain the distal end of the robot arm in the static position in the passive mode comprises calculating, via the controller, the hold force required to maintain the distal end of the robot arm in the static position in the passive mode when one or more external forces are applied to the surgical instrument by one or more anatomical structures having an unknown mass.

7. The method of claim 1, wherein calculating the hold force required to maintain the distal end of the robot arm in the static position in the passive mode comprises determining, via the controller, a force required to be applied to the distal end of the robot arm to move the distal end of the robot arm from a current position to the static position.

8. The method of claim 1, further comprising:
causing, via the controller, the robot arm to automatically switch to a co-manipulation mode responsive to determining that the hold force required to maintain the distal end of the robot arm in the static position exceeds the breakaway force threshold,
wherein the robot arm is permitted to be freely moveable in the co-manipulation mode responsive to movement at the handle of the surgical instrument, while the gravity compensation is applied to the robot arm to compensate for gravity of the surgical instrument in the co-manipulation mode.

9. The method of claim 1, wherein calculating the hold force required to maintain the distal end of the robot arm in the static position in the passive mode comprises sensing, via the controller, a force applied at the distal end of the robot arm.

10. The method of claim 9, wherein sensing the force applied at the distal end of the robot arm comprises measuring, via the controller, current of a plurality of motors operatively coupled to at least some joints of the plurality of joints.

11. The method of claim 1, wherein applying gravity compensation to the robot arm to compensate for gravity of the surgical instrument comprises applying, via the controller, torque to at least some joints of the plurality of joints of the robot arm.

12. The method of claim 1, wherein establishing the baseline hold force based on the hold force comprises establishing, via the controller, the baseline hold force after a predetermined time period upon initiation of the passive mode.

13. The method of claim 12, further comprising:
applying, via the controller, a high breakaway force threshold to the robot arm during the predetermined time period, the high breakaway force threshold greater than the breakaway force threshold; and
causing, via the controller if the hold force required to maintain the distal end of the robot arm in the static position exceeds the high breakaway force threshold during the predetermined time period, the robot arm to exit the passive mode.

14. The method of claim 13, wherein the high breakaway force threshold is selected to prevent inadvertent disengagement of the robot arm from passive mode in response to inadvertent forces applied at the distal end of the robot arm during the predetermined time period.

15. The method of claim 12, further comprising:
applying, via the controller, an initial breakaway force threshold to the robot arm during the predetermined time period;
applying, via the controller if force applied at the distal end of the robot arm exceeds the initial breakaway force threshold during the predetermined time period, a high breakaway force threshold during the predetermined time period, the high breakaway force threshold greater than the breakaway force threshold; and
causing, via the controller if the hold force required to maintain the distal end of the robot arm in the static position exceeds the high breakaway force threshold during the predetermined time period, the robot arm to exit the passive mode.

16. The method of claim 12, further comprising:
applying, via the controller, if the hold force fluctuates after the predetermined time period upon initiation of the passive mode such that the baseline hold force cannot be established based on the calculated hold force, a default breakaway force threshold to the robot arm; and
causing, via the controller if the hold force required to maintain the distal end of the robot arm in the static position exceeds the default breakaway force threshold, the robot arm to exit the passive mode.

17. The method of claim 16, further comprising selecting, via the controller, the default breakaway force threshold from between a default high breakaway force threshold and a default low breakaway force threshold based on user input via a graphical user interface operatively coupled to the controller.

18. The method of claim 17, further comprising adjusting, via the controller, at least one of the default high breakaway force threshold or the default low breakaway force threshold based on user input via the graphical user interface.

19. The method of claim 1, wherein applying gravity compensation to the robot arm to compensate for gravity of the surgical instrument comprises applying, via the controller, the gravity compensation to the robot arm to compensate for gravity of the surgical instrument based on an estimated instrument parameter associated with the surgical instrument.

20. The method of claim 19, further comprising:
determining, via the controller, a calibrated instrument parameter for the surgical instrument based on the hold force; and
applying, via the controller, an adjusted gravity compensation to the robot arm based on the calibrated instrument parameter.

21. The method of claim 20, wherein establishing the baseline hold force based on the hold force comprises establishing, via the controller, the baseline hold force based on the hold force required to maintain the distal end of the robot arm in the static position in the passive mode upon application of the adjusted gravity compensation to the robot arm.

22. The method of claim 20, wherein the calibrated instrument parameter is selected such that, during application of the adjusted gravity compensation, the hold force is adjusted within a predetermined range associated with a known parameter of the surgical instrument.

\* \* \* \* \*